(12) United States Patent
Muir et al.

(10) Patent No.: US 12,297,472 B2
(45) Date of Patent: *May 13, 2025

(54) SPLIT INTEINS WITH EXCEPTIONAL SPLICING ACTIVITY

(71) Applicant: THE TRUSTEES OF PRINCETON UNIVERSITY, Princeton, NJ (US)

(72) Inventors: Tom W. Muir, Princeton, NJ (US); Adam J. Stevens, Princeton, NJ (US); Neel H. Shah, Berkeley, CA (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 186 days.

This patent is subject to a terminal disclaimer.

(21) Appl. No.: 17/363,698

(22) Filed: Jun. 30, 2021

(65) Prior Publication Data
US 2021/0371467 A1   Dec. 2, 2021

Related U.S. Application Data

(63) Continuation of application No. 16/073,602, filed as application No. PCT/US2017/015455 on Jan. 27, 2017, now Pat. No. 11,142,550.

(60) Provisional application No. 62/288,661, filed on Jan. 29, 2016.

(51) Int. Cl.
| | | |
|---|---|---|
| C12N 9/00 | (2006.01) | |
| C07K 14/00 | (2006.01) | |
| C07K 14/32 | (2006.01) | |
| C07K 16/28 | (2006.01) | |
| C12N 15/62 | (2006.01) | |

(52) U.S. Cl.
CPC .............. *C12N 9/93* (2013.01); *C07K 14/001* (2013.01); *C07K 14/32* (2013.01); *C07K 16/2851* (2013.01); *C12N 15/62* (2013.01); *C07K 2319/21* (2013.01); *C07K 2319/30* (2013.01); *C07K 2319/92* (2013.01)

(58) Field of Classification Search
CPC .. A61K 47/6803; C07K 14/001; C07K 14/32; C07K 16/2851; C07K 2319/21; C07K 2319/30; C07K 2319/92; C12N 15/62; C12N 9/50; C12N 9/93
See application file for complete search history.

(56) References Cited

U.S. PATENT DOCUMENTS

| | | | | |
|---|---|---|---|---|
| 11,142,550 | B2 * | 10/2021 | Muir | .................... C07K 14/001 |
| 2015/0344549 | A1 * | 12/2015 | Muir | ...................... C12P 21/02 |
| | | | | 435/183 |

FOREIGN PATENT DOCUMENTS

| | | |
|---|---|---|
| CN | 104053779 A | 9/2014 |
| JP | 2014-528720 A1 | 10/2014 |
| JP | 2015-522020 A1 | 8/2015 |

(Continued)

OTHER PUBLICATIONS

Stevens et al., Design of a Split Intein with Exceptional Protein Splicing Activity. J Am Chem Soc. Feb. 24, 2016;138(7):2162-5, and Supplemental S1-S53. doi: 10.1021/jacs.5b13528. Epub Feb. 8, 2016. PMID: 26854538; PMCID: PMC4894280 (Year: 2016).*

(Continued)

*Primary Examiner* — Randall L Beane
(74) *Attorney, Agent, or Firm* — Kramer & Amado, P.C.

(57) ABSTRACT

Embodiments of the present invention relate to inteins, split inteins, compositions comprising inteins and methods for use of these.

23 Claims, 36 Drawing Sheets
Specification includes a Sequence Listing.

(56) References Cited

FOREIGN PATENT DOCUMENTS

| WO | 2013045632 A1 | 4/2013 |
|---|---|---|
| WO | 2014004336 A2 | 1/2014 |
| WO | 2014004336 A3 | 1/2014 |

OTHER PUBLICATIONS

Stevens et al., A promiscuous split intein with expanded protein engineering applications. Proc Natl Acad Sci U S A. Aug. 8, 2017; 114(32):8538-8543 and Suppl. S1-S67, doi: 10.1073/pnas. 1701083114. Epub Jul. 24, 2017. PMID: 28739907; PMCID: PMC5559002 (Year: 2017).*

National Intellectual Property Administration, PRC Translation by Jeekal & Partners re: Chinese Application No. 2017800212670, dated Apr. 23, 2021, 3 pgs.

National Intellectual Property Administration, PRC Search Report re: Chinese Application No. 2017800212670, 4 pgs.

Toshio Yamasaki et al., Intein Mediated Ligation of Protein. Fragments, Biophysics, 1999, vol. 39, pp. 182-184.

English translation of Toshio Yamasaki et al., Biophysics, 1999, vol. 39, pp. 182-184.

Shah et al., Ultrafast Protein Splicing is Common among Cyanobacterial Split Inteins: Implications for Protein Engineering, Journal of the American Chemical Society, vol. 134: 11338-11341, and Supp. pp. S2-S52 (Jun. 26, 2012) (Year: 2012).

Livingstone et al., Protein sequence alignments: a strategy for the hierarchical analysis of residue conservation, Cabios, vol. 9(6): 745-756 (1993) (Year: 1993).

Volkmann et al., Protein trans-splicing and its use in structural biology: opportunities and limitations, Mol Biosyst, vol. 6 ( 11) :2110-2 ( Nov. 2010) (Year: 2010).

Yifeng Li, Split-inteins and their bioapplications, Biotechnol. Lett., vol. 37:2121-2137 (Jul. 8, 2015) (Year: 2015).

Altschul, et al., "Basic Local Alignment Search Tool", J. Mol. Biol. (1990) 215, 403-410.

Amitai, et al., "Modulation of intein activity by its neighboring extein substrates", PNAS, Jul. 7, 2009, vol. 106, No. 27, 11005-11010.

Aranko, "Intermolecular domain swapping induces intein-mediated protein alternative splicing", Nature Chemical Biology—Aug. 2013.

Barbuto, et al., "Induction of innate and adaptive immunity by delivery of poli dA:dT to dendritic cells", Nat. Chem. Biol. Apr. 2013; 9 (4): 250-256.

Carvajal-Vallejos, et al., "Unprecedented Rates and Efficiencies Revealed for New Natural Split Inteins form Metagenomic Sources", The Journal of Biological Chemistry, vol. 287, No. 34, pp. 28686-28696 (Aug. 17, 2012).

Cheriyan, et al., "Faster Protein Splicing with the Nostoc punctiforme DnaE Intein Using Non-native Extein Residues", The Journal of Biological Chemistry, vol. 288, No. 9, pp. 6202-6211 (Mar. 1, 2013).

Dearden, et al., "A conserved threonine spring-loads precursor for intein splicing", Protein Science 2013, vol. 22:557-563.

Du, et al., "Highly Conserved Histidine Plays a Dual Catalytic Role in Protein Splicing: a pKa Shift Mechanism", J. Am. Chem. Soc., Aug. 19, 2009, 131(32): 11581-11589.

Grigoriev, et al., "The Genome Portal of the Department of Energy Joint Genome Institute", Nucleic Acids Research, 2012, vol. 40, Database issue, published online Nov. 22, 2011.

Iwai, et al., "Highly efficient protein trans-splicing by a naturally split DnaE intein from Nostoc punctiforme", FEBS Letters 580 (2006) 1853-1858.

Lehmann, et al., "From DNA sequence to improved functionality: using protein sequence comparisons to rapidly design a thermostable consensus phytase", Protein Engineering, vol. 13, No. 1, pp. 49-57, 2000.

Mohlmann, et al., "Site-specific modficiation of ED-B-targeting antibody using intein-fusion technology", BMC Biotechnology 2011, 11:76.

Pietrokovski, et al., "Conserved sequence features of inteins (protein introns) and their use in identifying new inteins and related proteins", Protein Science (1994) 3:2340-2350.

Shah, et al., "Asymmetric Peptide Dendrimers are Effective Linkers for Antibody-Mediated Delivery of Diverse Payloads to B Cells in Vitro and in Vivo", Pharm. Res., May 22, 2014, 11 pages.

Shah, et al., "Extein Residues Play an Intimate Role in the Rate Limiting Step of Protein Trans-Splicing", Journal of the American Chemical Society, Mar. 18, 2013, pp. 1-19, downloaded from http://pubs.acs.org on Mar. 20, 2013.

Shah, et al., "Inteins: nature's gift to protein chemists", Chem. Sci. 2014, 5, 446.

Shah, et al., "Naturally Split Inteins Assemble through a "Capture and Collapse" Mechanism", Journal of the American Chemical Society, 2013, 135, 18673-18681.

Shah, et al., "Ultrafast Protein Splicing is Common among Cyanobacterial Split Inteins: Implications for Protein Engineering", Journal of the American Chemical Society 2012, 134, 11338-11341.

Steipe, "Consensus-Based Engineering of Protein Stability: From Intrabodies to Thermostable Enzymes", Applications: Optimization and Screening, Methods in Enzymology, vol. 388, pp. 176-186.

Stevens, et al., "Design of a Split Intein with Exceptional Protein Splicing Activity", Journal of American Chemical Society 2016, 138, 2162-2165.

Tatusova, et al., "RefSeq microbial genomes database: new representation and annotation strategy", Nucleic Acids Research, 2014, vol. 42, Database Issue D553-D559, published online Dec. 6, 2013.

Vila-Perello, et al., "Streamlined Expressed Protein Ligation Using Split Inteins", Journal of American Chemical Society 2013, 135, 286-292.

Wu, "Conserved residues that modulate protein trans-splicing of Npu DnaE split intein", Biochem. J. (2014) 461, 247-255.

Wu, et al., "Protein trans-splicing by a split intein encoded in a split DnaE gene of Synechocystis sp. PCC6803", Proc. Natl. Acad. Sci. USA, vol. 95, pp. 9226-9231, Aug. 1998.

Zettler, et al., "The naturally split Npu DnaE intein exhibits an extraordinarily high rate in the protein trans-splicing reaction", FEBS Letters 583 (2009) 909-914.

Vivien Schutz, et al., "Click-Tag and Amine-Tag: Chemical Tag Approaches for Efficient Protein Labeling In Vitro and on Live Cells using the Naturally Split Npu DnaE Intein," Angew. Chem. Int. Ed. 2014, 53, 4113-4117; 5 pgs.

Neel H. Shah, et al., "Kinetic Control of One-Pot Trans-Splicing Reactions by Using a Wild-Type and Designed Split Intein," NIH Public Access Author Manuscript; Angew Chem Int Ed Engl. Jul. 11, 2011; 12 pgs.

Henning D. Mootz, et al., "Conditional Protein Splicing: A New Tool to Control Protein Structure and Function in Vitro and in Vivo," 2003 American Chemical Society; 9 pgs.

Glen P. Liszczak, et al., Genomic Targeting of Epigenetic Probes using a Chemically Tailored Cas9 System; PNAS—Jan. 24, 2017; vol. 114, No. 4; 6 pgs.

Steve W. Lockless, et al., "Traceless Protein Splicing Utilizing Evolved Split Inteins," PNAS—Jul. 7, 2009; vol. 106, No. 27; 6 pgs.

Jesper S. Oeemig, et al., "Solution Structure of DnaE intein from Nostoc Punctiforme: Structural Basis for the Design of a New Split Intein Suitable for Site-specific Chemical Modification," Federation of European Biochemical Societies; 2009; 6 pgs.

Yael David, et al., "Chemical Tagging and Customizing of Cellular Chromatin States Using Ultrafast Trans-splicing Inteins," Nat Chem., May 2015, 7(5). pp. 394-402, doi: 10.1038/nchem.2224.

Joachim Zettler, et al., "The Naturally Split Npu DnaE Intein Exhibits an Extraordinarily High Rate in the Protein Trans-Splicing Reaction," FEBS Letters 583, 2009, pp. 909-914.

Hideo Iwai, et al., "Highly Efficient Protein Trans-Splicing By a Naturally Split DnaE Intein from Nostoc Punctiforme," FEBS Letters 580, 2006, pp. 1853-1858.

(56) References Cited

OTHER PUBLICATIONS

Neel H. Shah, et al., "Ultrafast Protein Splicing is Common Among Cyanobacterial Split Inteins: Implications for Protein Engineering," J Am Chem Soc., Jul. 18, 2012, 134 (28), pp. 11338-11341, doi: 10.1021/ja303226x.

Adam J. Stevens, et al., "A Promiscuous Split Intein with Expanded Protein Engineering Applications," PNAS, vol. 114, No. 32, Aug. 8, 2017, pp. 8538-8543.

\* cited by examiner

N-Inteins

```
                              10                  20                  30                  40              50
                              |                   |                   |                   |               |
NspPCC73102/1-137    CLSYETE-ILTVEYGLLPIGKIVEKRIECTVYSVDNNGNIYTQPVAQWHDR
CthPCC7203/1-137     CLSYDTEILTVEYGAIPIGKIVEERIECTVYSVDNNGFIYTQPIAQWHNR
NspCCY9414/1-137     CLSYDTEILTVEYGYIPIGEIVEKAIECSVYSVDNNGNVYTQPIAQWHNR
AcyPCC7122/1-137     CLSYDTEVLTVEYGFIPIGEIVEKRIECSI-FSVDKNGNVYTQPIAQWHNR
CspPCC7507/1-137     CLSYDTEVLTVEYGLLPIGEIVEKRIECRVFSVDNHGNVYTQPIAQWHNR
NspPCC7524/1-137     CLSYDTEILTVEYGLIPIGEIVEKRIECSLFSVASNGIVYTQPIAQWHNR
Naz0708/1-137        CLSYKTEVLTVEYGLIPIGEIVEKRIECSVFSVDENCNIYTQPIAQWHNR
NspPCC7120/1-137     CLSYDTEVLTV-YGFVPIGEIVEKGIECSVFSINNNGIVYTQPIAQWHHR
AvaATCC29413/1-137   CLSYDTEVLTVEYGFVPIGEIVDKGIECSVFSIDSNGIVYTQPIAQWHDR
PspPCC7327/1-135     CLSYDTKILTVEYGAMPIGKIVEEQIDCTVYTVNQNGFVYTQPIAQWHYR
CspPCC7424/1-135     CLSYETQIMTVEYGLMPIGKIVEEQIDCTVYTVNKNGFVYTQPIAQWHHR
CspPCC7822/1-134     CLSYDTEVLTVEYGPMPIGEIVEEKQIECTVYTVDKNGLVYTQPIAQWHNR
NspPCC7107/1-137     CLSYDTQVLTVEYGLVPIGEIVEEKGIECSVFTIDDGHCYVYTQAIAQWHHR
Tbol/cb1/1-136       CLSYDTEILTVEYGFLPIGEIVEKQIECAVYSVDGNGNIYTQSIAQWHNR
Aov/1-136            CLSADTEILTVEYGPMAICKIVEEKIECRVYSVDNSNGYIYTQSIAQWHRR
OmvPCC7112/1-137     CLSYDTKILTVEYCFLIPICKIVEEKIDCTVYSVDVNGNVYSQPIAQWHNR
RspPCC7116/1-135     CLSYDTEVLTEEFCLIPICKIVEEKIDCTVYSVDVNGNVYSQPIAQWHNR
TerMS101/1-137       CLTYETEIMTVEYGPLPICEIVEYRIECTVYTVDKNGYIYTQPIAQWHNR
MspPCC7113/1-137     CLSYDSEILTVEYGLMPIGEIVEEGIECNVYTVNQNGFIYPQAIAQWHHR
ScyPCC7437/1-137     CLSYDTEILTVEYGAMPIGKIVKEEQILCSVFSVDEQCNVYTQPIAQWHER
CspPCC6303/1-137     CLSYDTEILTWEYCFLKICEIVEEQICTVYSVDQYGFVYTQAIAQWHDR
Gst/1-134            CLSYDTEVLTVEYCVLPICKIVEEQIQCTVYSVDQYGFVYTQAIAQWHDR
```

FIG. 7A.1

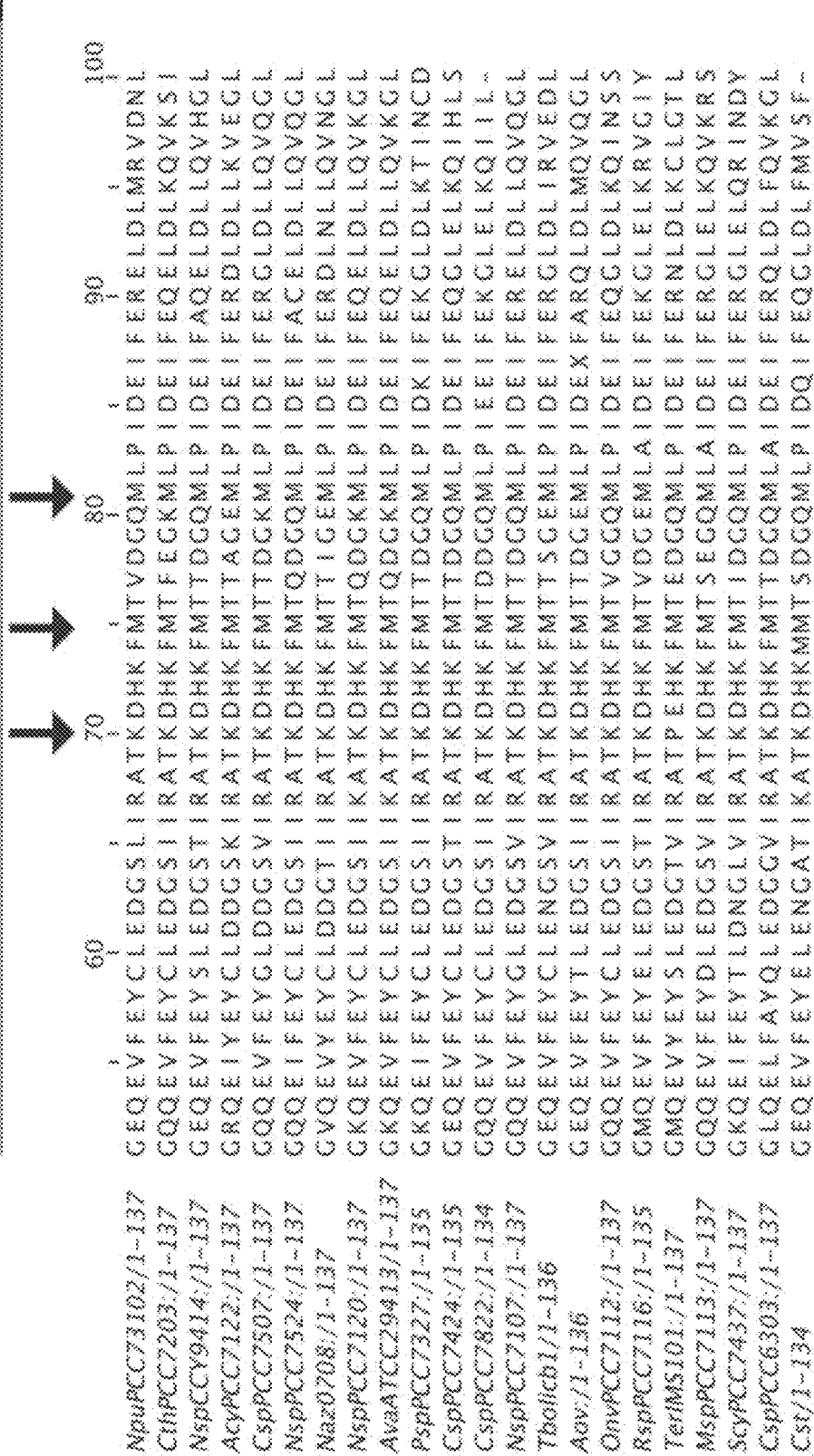
FIG. 7A.2

FIG. 7A.3

N-Inteins

|  | 10 | 20 | 30 | 40 | 50 |
|---|---|---|---|---|---|
| CspATCC51142/1-134 | CLSYDTEILTVEYGPMP | ICKIVEEN | NCTVYTVDPNGFVYTQAI | AQWHYR |
| CspPCC8801/1-134 | CLSYDTEILTVEYGAIP | ICKVVEEN | IDCTVYTVDKNGFVYTQNI | AQWHLR |
| Asp/1-136 | CLSYDTEILTVEYGFLE | IGEIVEKQ | IECKVYTIDSNGMLYTQSI | AQWHNR |
| Aha/1-137 | CLSYDTEIWTVEYGAMP | ICKIVEEK | IECSVYTVDENGFVYTQPI | AQWHPR |
| HspPCC7418/1-137 | CLSYDTEIWTVEYGAMP | ICKIVEEK | IECSVYTVDENGFVYTQPI | AQWHPR |
| CapPCC10605/1-137 | CLSYDTKVLTVEYGPLP | ICKINCQV | YSVDKNGFIYTQNI | AQWHDR |
| Cat/1-133 | CLSYNTEVLTVEYGPLP | ICKVVQEN | IRCRVYTTNDQGLIYTQAI | AQWHNR |
| Olc/1-137 | CLSYDTEVLTVEYGPLP | ICKVVDEQ | IHCRVYSVDENGFVYTQAI | AQWHDR |
| Cen/1-137 | CLSYDTEVLTVEYGPLP | ICRMVEES | LDCTVYTVDKNGFVYTQSI | QQWHSR |
| SspPCC7502/1-133 | CLGYDTPVLTVEYGFMP | ICKIVEEN | IQCHVYSVDQNGLVFTQAI | AQWHNR |
| DsaPCC8305/1-134 | CLSYDTEVLTEEYGAIP | ICKIVEEK | IECSVYTVDENGFIYSQPI | AQWHPR |
| CstPCC7417/1-137 | CLSYDTEILTVEYGFIP | ICKIVEEN | INCSVYSVDNHGNVYTQPI | AQWHNR |
| SspPCC6803/1-137 | CLSFGTEILTVEYGPLP | ICKIVSEE | INCSVYSVDPEGRVYTQAI | AQWHDR |
| GspPCC7407/1-137 | CLSYETPVMTVEYGPLP | ICKIVEEQ | LDCTVYSVDEQGHVYTQPV | AQWHHR |
| SspPCC6714/1-137 | CLSFDAEILTVEYGPLS | ICKIVCEE | INCSVYSVDPQGRIYTQAI | AQWHDR |
| MaePCC7806/1-135 | CLGGETLLILTEEYGLLP | IAKIVSEE | VNCTVYTVDKNGHVYSQPI | SQWHER |
| MaeNIES843/1-135 | CLGGETLILTEEYGLLP | IAKIVSEE | INCTVYTVDQNGFVYSQPI | SQWHER |
| AmaMBIC11017/1-137 | CLSYDTPVLTLEYGWLP | IGQVVQEQ | IECQVFSINERGHLYTQPI | VEQWHHR |
| LspPCC7376/1-137 | CLDGETPIVTVEYGVLP | IREIVEKE | LLCSVYSIDENGFVYTQPV | EQWHQR |
| SelPCC301/1-137 | CLAADTEVLTVEYGPLP | IAICKLVEEN | IRCQVYCCNPDGVIYSQPI | GQWHQR |
| SspPCC6312/1-137 | CLSADTELYTVEYGWLP | ICRLVEEQ | IECQVLSVNAHCHVYSQPI | AQWHRR |
| Tel/1-137 | CLSGETAVMTVEYGAVP | IRRLVQER | LSCHVYSLDGQGHLYTQPI | AQWHFQ |

FIG. 7B.1

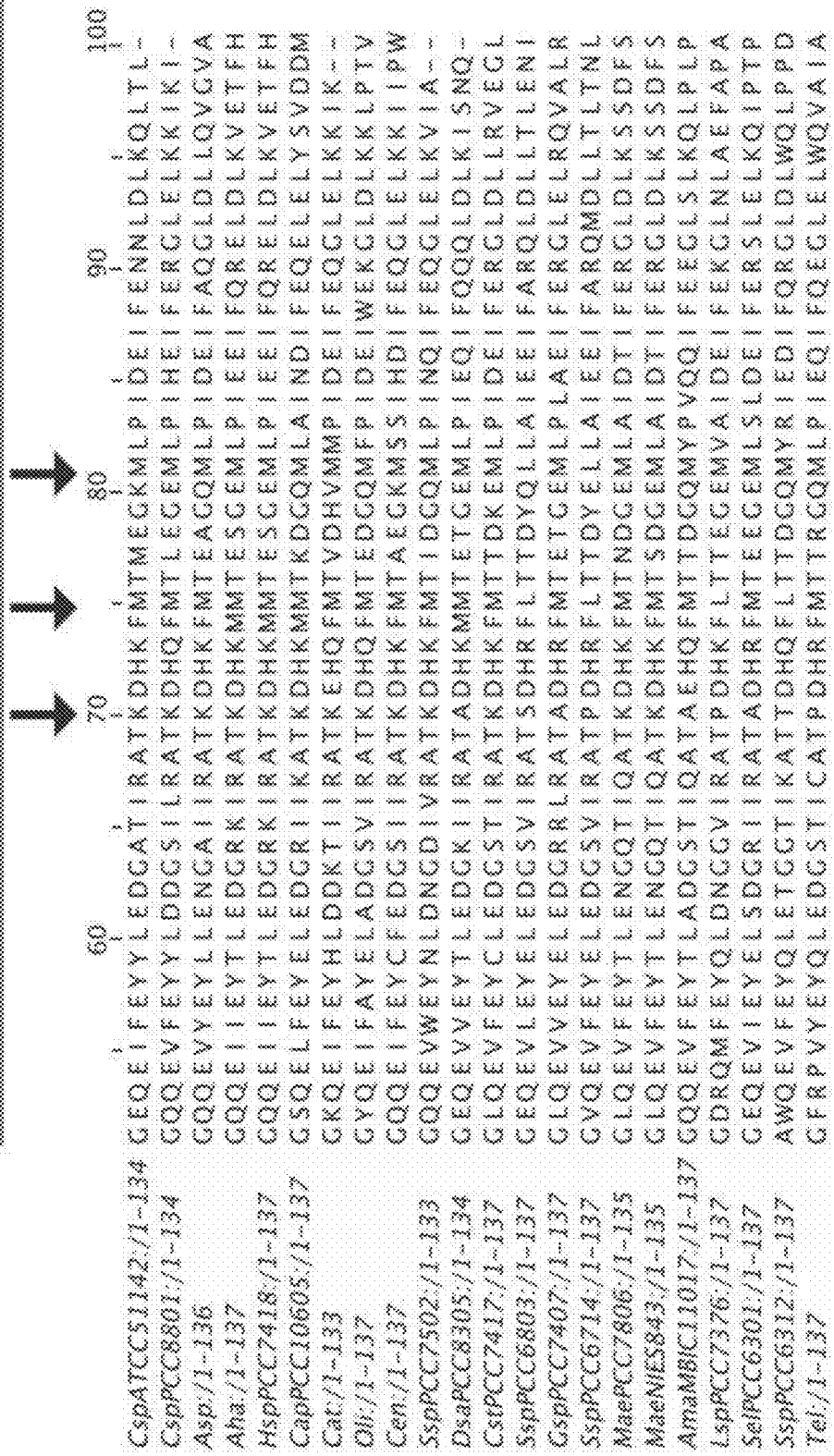
FIG. 7B.2

FIG. 7B.3

N-Inteins

| | 10 | 20 | 30 | 40 | 50 |
|---|---|---|---|---|---|
| Tsp/1-137 | CLSGETAVMTVEYGAVP | IRRLVQERLTCHVYSLDAQGHLYTQP | IAQWHFQ |
| Tvu/1-137 | CLSGETAVMTVEYGAIP | IRRLVQERLICQVYSLDPQGHLYTQP | IAQWHFQ |
| SspPCC7002/1-137 | CLAGGTPVVTVEYGVLP | IQTIVEQELLCHVYSVDAQGLIYAQL | IEQWHQR |
| ShoPCC7110/1-136 | CLSYDTEVLTAEYGFLP | ICKIVEKAIECTVYSVDNDGNIYTQP | IAQWHDR |
| WinUHHT291/1-136 | CLSYDTEILTVEYGFLP | IGEIVEKRIECTVYTVDTNGYVYTQA | IAQWHNR |
| FspPCC9605/1-136 | CLSYDTEVLTVEYGFLP | IGEIVEKGIECSVYTVDSNGNVYTQT | IAQWHNR |
| MrePCC10914/1-137 | CLSYDTEVLTVEYGFLP | IGEIVEKSIECSVYTVDSNGNVYTQI | IAQWHNR |
| ShoUTEX2349/1-137 | CLSYNSEVLTVEYGFLP | IGEIVEKGIECSVYSVDSYGKIYTQV | IAQWHNR |
| AspPCC7108/1-137 | CLSSDTEVLTVEYGLIP | IEEIVEKRIDCSVFSVDKNGNIYTQP | IAQWHDR |
| FspPCC9339/1-137 | CLSYDTEVLTVEYGFLP | IGEIVEKRIECTVYTVDNHGNIYSQP | IAQWHNR |
| Csp336/1-137 | CLSYDTEIFFTVEYGFLP | IGEIVEKRLECTVLTVDNHGNIYSQP | IAQWHNR |
| FthPCC7521/1-136 | CLSYETEILTVEYGFLS | IGEIVEKRIECSVYTVDNNGYVCTQT | IAQWHEQ |
| CyaPCC7702/1-137 | CLSYDTEILTVEYGFLP | IGEIVEKRIECTVYTVDSNGYIYTQP | IAQWHNR |
| FspPCC9431/1-136 | CLSYDTEVLTVEYGFLP | IGEIVEKRIECTVYTVDTNGYVYTQA | IAQWHNR |
| FmuPCC7414/1-137 | CLSYDTEVLTVEYGFLP | IGEIVEKRTIECNVFTVDSNGYVYTQP | IAQWHNR |
| FmuPCC73103/1-137 | CLSYDTEVLTVEYGAIP | IGKVDEKIECTVYSVDKNGLIYTQP | IAQWHNR |
| Lae/1-137 | CLSYKTQVLTVEYGLLA | IGEIVEKNIECSVFSVDIHGNVYTQP | IAQWHHR |
| MspPCC7126/1-135 | CLSYDTEILTVEYGALP | ICKIVENQMICSVYSIDNNGYIYIQP | IAQWHNR |
| Lsp/1-137 | CLSYDTEVLTVEYGAMY | ICKIVEKQIECTVYSVDENGYVYTQP | IAQWHNR |
| CwaWH8501/1-137 | CLSYDTEILTVEYGAVA | IGEIVEKQIECTVYSVDENGYVYTQP | IAQWHNR |
| CchPCC7420/1-135 | CLSYDTQVLTVEYGAMY | ICKIVEEKINCTVYTVDKNGFVYTQT | IAQWHNR |
| CspPCC6712/1-133 | CLSYDTEVLTVEYGAIP | ICKIVEEKIACNVYSVDKNGFVYTQP | IAQYHDR |

FIG. 7C.1

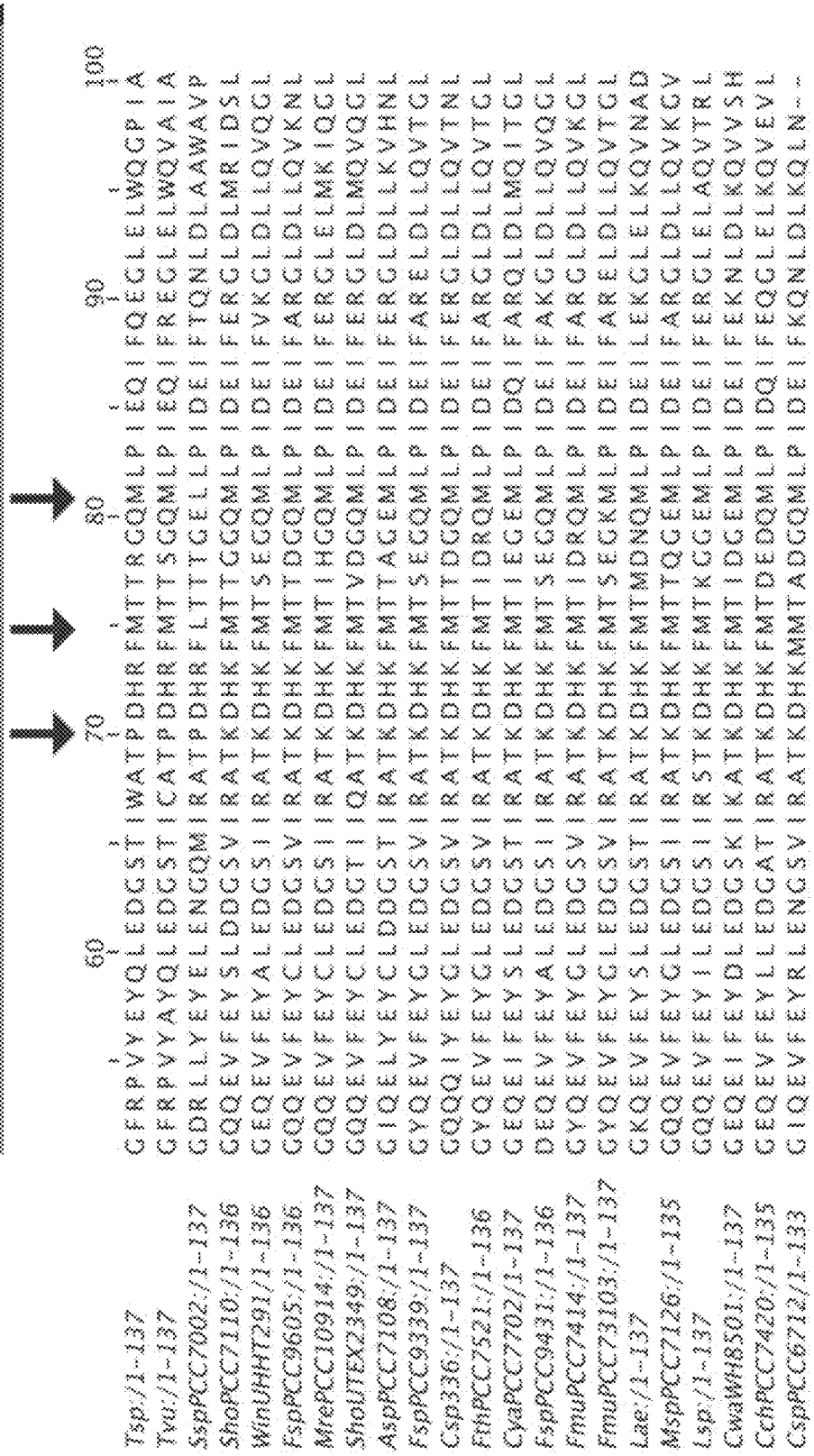
FIG. 7C.2

C-Inteins

| | 110 | 120 | 130 | |
|---|---|---|---|---|
| Tsp/1-137 | PSCKIVCRQLVGWQAVYDIGVARDHNFLLANGAIAAN |
| Tvu/1-137 | PPCKIVGRRLVGWQAVYDIGLAGDHNFLLANGAIAAN |
| SspPCC7002/1-137 | DSVKIIRRKFIGHAPTYDIGLSQDHNFLCQGLIAAN |
| ShoPCC7110/1-136 | P-VKILTRKSIGKQTYDIGVEQNHNFVIKNGLVASN |
| WmUHHT291/1-136 | P-VKIITRKFLGIQNVYDIGVEQNHNFVIKNGLVASN |
| FspPCC9605/1-136 | P-VKIVTRRPLGTQNVYDIGVESDHNFVTRDGFIASN |
| MrePCC10914/1-137 | PEAKITRKSLGTQNVYDIGVERDHNFVMKNGLIASN |
| ShoUTEX2349/1-137 | PQVKIITRNYVGKENVYDIGVSSDHNFVMKNGLIASN |
| AspPCC7108/1-137 | VNVKIVTRRLLGIQNYYDIGVEQNHNFAIKNGLVASN |
| FspPCC9339/1-137 | DNVKVITRKLADTENVYDIGVENHHNFLIKNGLVASN |
| Csp336/1-137 | P-VKIITRKSLGTQNVYDIGVERDHNF--IKNGFVASN |
| FthPCC7521/1-136 | PQVKISTKKSLGKQKVYDIGVEQNHNFVIKNGLVASN |
| CyaPCC7702/1-137 | P-VKIVTRKFLGIQNVYDIGVEQNHNFVIKNGLVASN |
| FspPCC9431/1-136 | PEVKIITRQSLGTQNVYDIGVEQNHNFVIKNGLVASN |
| FmuPCC7414/1-137 | INVKIVTRKFLGIQNVYDIGVETDHNFLLANGSVASN |
| FmuPCC73103/1-137 | SVVKIVSRKSLDSQTVYDIGVEQDHNFLLANGSVASN |
| Lae/1-137 | --VKIITRKYIGKENVYDIGVKQDHNFAIKNGLIAAN |
| MspPCC7126/1-135 | EQVKIISRRSVGVQSVYDIGVKQDHNFLRNGLIASN |
| Lsp/1-137 | PDVKIIGCRSLGTQKVYDIGVERDHNFLLANGSIASN |
| CwaWH8501/1-137 | --VKIICRKPLGTQPVYDIGVAKDHNFLFNGLVASN |
| CchPCC7420/1-135 | --VKIISRQSLGKQSVFDIGVAKDHNFLLANGLVASN |
| CspPCC6712/1-133 | | | | |

FIG. 7C.3

N-Inteins

```
                           10         20         30         40         50
                           |          |          |          |          |
AfuNES81/1-132      CLSYDTE-LTVEYGFLQIGEIVEKQ-LECKVYTVDSNGLLYTQS-IAQWHNR
Rbr/1-137           CLSYETEVLTLEYGFLPIGEIVDKQMVCTVFSVNDSGNVYTQPICQWHDR
CspCCy0110/1-134    CLSYDTE-LTVEYGAMPIGKIVEENINCSVYTVNKNGFVYTQS-IAQWHHR
XspPCC7305/1-135    CLSADTEVLTVEYGCAISIGKIVEERIECTVYSVDANCFVYTQEIAQWHNR
PspPCC7319/1-135    CLSYDTE-IYTVEYGCALPIGKIVESRIKCTVLTYDKNGLVYSQPIVQWHDR
CraCS505/1-137      CLSYETEVLTLEYGCFVPIGEIVNKQMVCTVFSLNDSGNVYTQPICQWHDR
SmaPCC6313/1-129    CLTYDTLVLTVEYGCPVPIGKLVEAQINCQVYSVDANGFIYTQAIAQWHDR
SsuPCC9445/1-131    CLSYDTKI-ITVEEYGCLLPIAKIVSEEINCTVYSVDPNGFIYTQPIAQWHQR
MaePCC9807/1-135    CLGGETLI-ITEEYGCALPIGEIVEKRINCHVYTRAESCFFYIQSIEQWHER
MspGL/1-130         CLSYDTEVLTLKYGCALPLEIGEIVEEQIACHVYSVDANGFVYTQPIAQWHSR
LspPCC6406/1-136    CLSADTQLLTVEYGCPLEIGEIVEEQIECQVFSINERCHLYTQPIAQWHDR
AspCCMEE5410/1-132  CLSYDTPVLTLEYGCWLPIGQVVQEQIECQVFSINERCHLYTQPIAQWHDR
ChePCC6308/1-133    CLSYDTEVLTVEFGAIPMGKIVEAKRIPCHVFSVDKNGFIYTQNIAQWHDR
NroPCC7104/1-133    CLSADTELLTLEYGCPLTIGEIVAKRIPCHVFSVDESGYVYTQPVAQWHER
RlaKORDI51-2/1-137  CLSYDTEVLTVEYGCPLAIGTIVSERLACTVYTVDRSGFLYAQAISQWHER
CfrPCC9212/1-136    CLSYDTAI-LTVEHGCPMSIGEIVEKGILEVTVYTVDSNCYIYTQPIAQWHNR
RinHH01/1-137       CLSYDTQI-LTVEHGPMSIGEIVEKCLECHVYTVNKNGNICIQTITQWHFR
SspPCC7117/1-137    CLACDTPVVTVEYGCVLPIQTIVEQELLCQVYSVDAQGLIYTQPIEQWHNR
SspPCC8807/1-137    CLACDTPVVTVEYGCVLPIQTIVEQELLCHVYSVDAQGLIYTQPIEQWHQR
SspNKBG042902/1-137 CLACDTPVVTVEYGCVLPIQTIVEQELLCHVYSVDAQGLIYTQPIEQWHQR
SspNKBG15041/1-129  CLACGTPVVTVEYGCVLPIRTIVDQELLCHVYSLDPQGFIYAQPVEQWHHR
SspPCC73109/1-130   CLACGTPVVTVEYGCVLPIQTIVEELLCHVYSVDAQGLIYTQPIEQWHQR
```

FIG. 7D.1

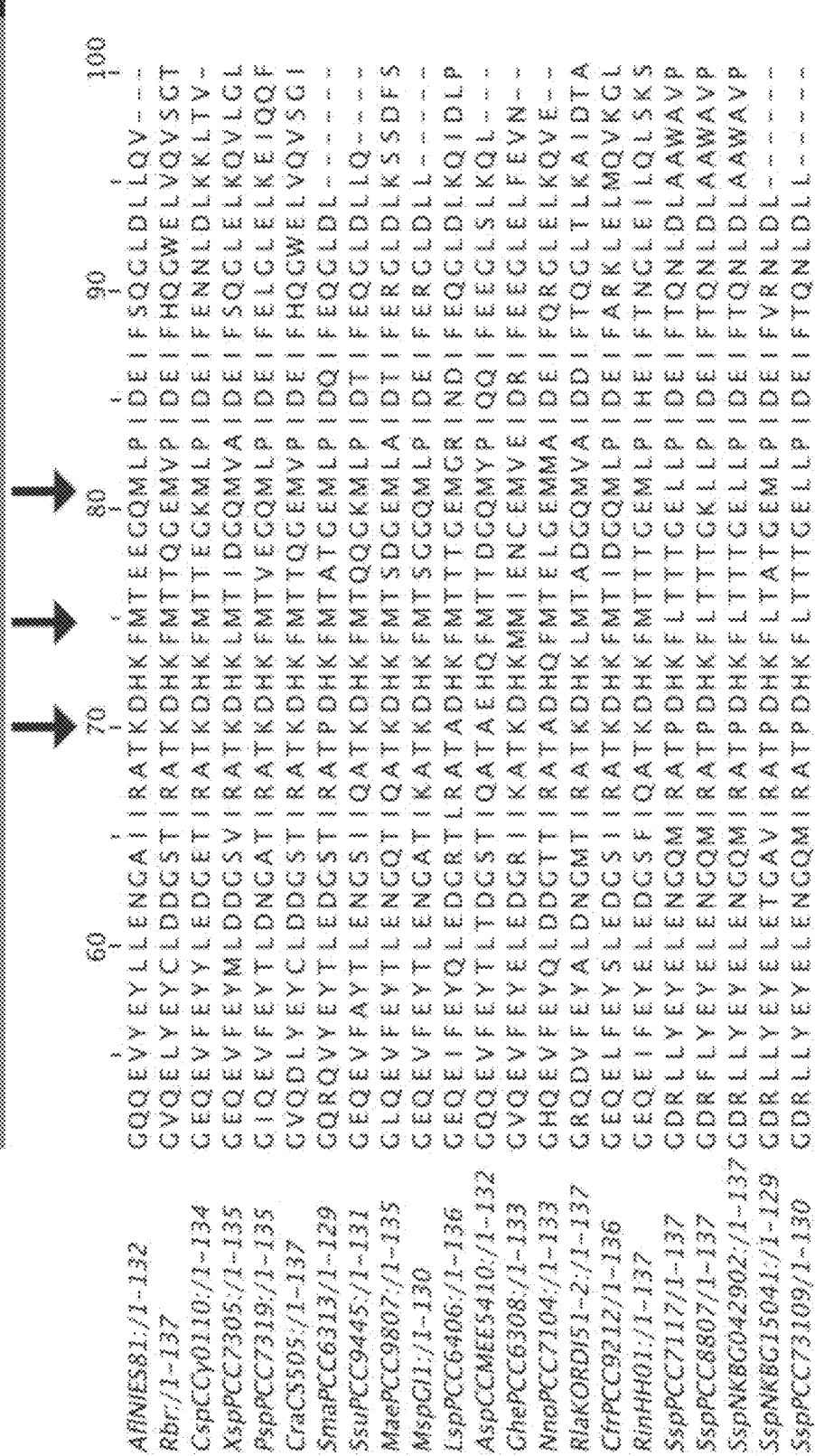
FIG. 7D.2

FIG. 7D.3

N-Inteins

| | | 10 | 20 | 30 | 40 | 50 |
|---|---|---|---|---|---|---|
| SspPCC7003/1-130 | - | CLAGDTPVTVEYGVLP | IQT IVEQELLCHVY | SVDAQGLIYTQP | IEQWHKR |
| CspPCC8802/1-134 | | CLSYDTE I LTVEYGA I P | ICKVVEEN IDCTVYT | VDKNGFVYTQN | IAQWHLR |
| SelPCC7942/1-137 | | CLAADTEVLTVEYGP I A | IGKLVEEN IRCQVYC | CNPDGY IYSQP | IGQWHQR |
| CtrPCC6912/1-137 | | CLSYDTA I LTVEYGFLP | IGE IVEKG IECTVYT | VDSNGY IYTQP | IAQWHNR |
| CspATCC51472/1-132 | | CLSYDTE I I TVEYGPMP | IGK IVEEN INCTVYT | VDPNGFVYTQA | IAQWHYR |
| Lma/1-132 | | CLSYDTE I LTVEYGP I A | ICE IVEKG IPCTVYS | VDSNGYVYTQP | IAQWHNR |
| CspESFC/1-137 | | CLSYDTEVLTVEYGAVP | IGKLVEEKLNCSVYT | VDPNGY IYAQL | IAQWHDR |
| SspPCC7002/1-129 | | CLAGGTPVTVEYGVLP | IQT IVEQELLCHVY | SVDAQGL IYAQL | IEQWHQR |
| AmaMBIC11017/1-132 | | CLSYDTP I LLEEYGWLP | IGQVVQEQ IECQVF | S INERGHLYTQP | ISQWHER |
| Mae905/1-129 | | CLGGETL I LTEEYGCLLP | IAK IVSEEVNCTVY | SVDKNGFVYSQP | IAQWHHR |
| AcJAWQC910F/1-125 | | CLSYDTE I LTVEYGFLE | IGE IVEKQ IECKVYT | VDSNG I LYTQP | IAQWHHR |
| AcJAWQC931C/1-125 | | CLSYDTE I LTVEYGFLE | IGE IVEKQ IECRVYT | VDSNG I LYTQP | IAQWHHR |
| CspUCYN/1-124 | | CLSYDTKVLTVEYGPLP | IGKVVQEN IRCRVYT | NDQGL IYTQP | IAQWHYR |
| Pst/1-129 | | CLSYDTEVLTVEYGL I P | ISK IVEEK IECTVYT | VNNQGYVYTQP | IAQWHNR |
| PlaCYA98/1-129 | | CLSYDTE I LTVEYGLMP | ICK IVKEK IECTVYT | VNNQGYVYTQP | IAQWHHR |
| FdiUTEX481/1-137 | | CLSYDTEVLTVEYGL IP | ICE IVEKR LECSVY | SVD INCNVYTQP | IAQWHHR |
| Pxt585/1-129 | | CLSYDTE I LTVEYGL IP | ISK IVEEK IECTVYT | VNNQGYVYTQP | IAQWHNR |

FIG. 7E.1

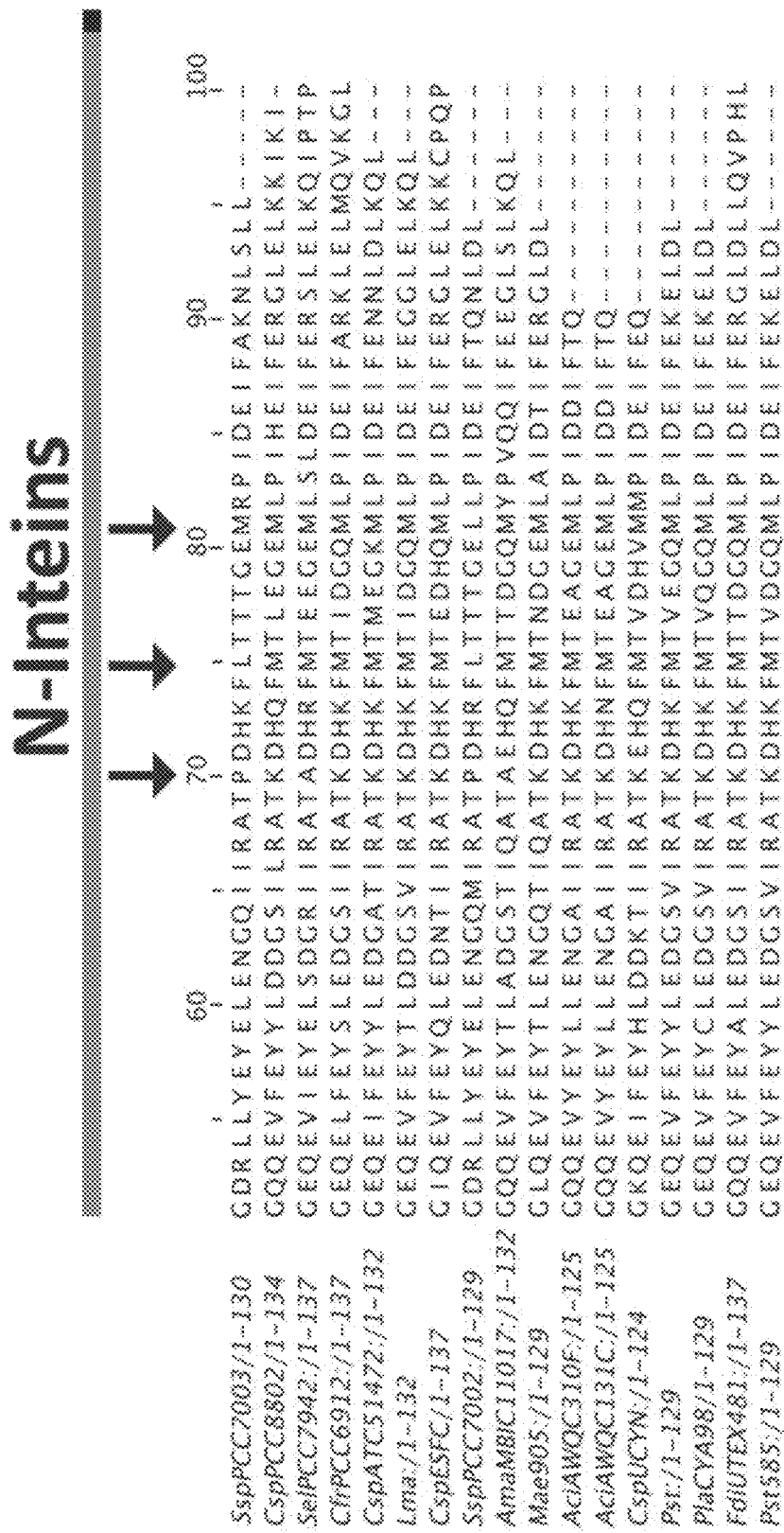
FIG. 7E.2

C-Inteins

```
SspPCC7003/1-130      --VKI IRRKFVGHAPTYDIGLSQDHNFLLGQGLIAAN-
CspPCC8802/1-134      --VKIVSYRSLGKQFYYDIGVAQDHNFLLANGSIASN
SelPCC7942/1-137      LLVKIVRRRSLGVQPVYDLGVATVHNFVLANGLVASN
CfrPCC6912/1-137      PEVKIIAKKSLGTQNVYDIGVERDHNFVIKNGLVASN
CspATCS1472/1-132     --VKIIGRQSLGVQKVYDIGVEKEHNFLLHNGLIASN
Lma/1-132             --VKIISRKSLGTQPVYDIGVKDDHNFI-LANGMVASN
CspESFC/1-137         QQVKIIRRRSLGFQPVYDIGLEQDHNFLLNQGAIASN
SspPCC7002/1-129      --VKIIRRKFIGHAPTYDIGLSQDHNFLLGQGLIAAN-
AmaMBIC11017/1-132    --VKIIQRRSLGLQSVYDIGLAQDHNFVMANGWVAAN
Mae9005/1-129         --VKIISRQSLCRKPVYDIGVERDHNFLLCNGLIASN
AciAWQC310F/1-125     --VKIISRTYVGQANVYDIGVENDHNFVIKNGFVAAN
AciAWQC131C/1-125     --VKIISRKYVCQANVYDIGVENDHNFVLSNGLIASN
CspUCYN/1-124         --KIIISRKSLGMHEVFDIGLEKDHNFVLSNGLVASN
Pst/1-129             --VKIISRKSLGTQPVYDIGVQEDHNFLLNNGLVASN
PlaCYA98/1-129        --VKIISRKSLGTQPVYDIGVQEDHNFLLNNGLIAAN
FdiUTEX481/1-137      PEVKIVTRRAIGAANVYDIGVEQDHNFAIKNGLIAAN
PstS85/1-129          --VKIISRKSLGTQPVYDIGVQEDHNFVLNNGLVASN
```

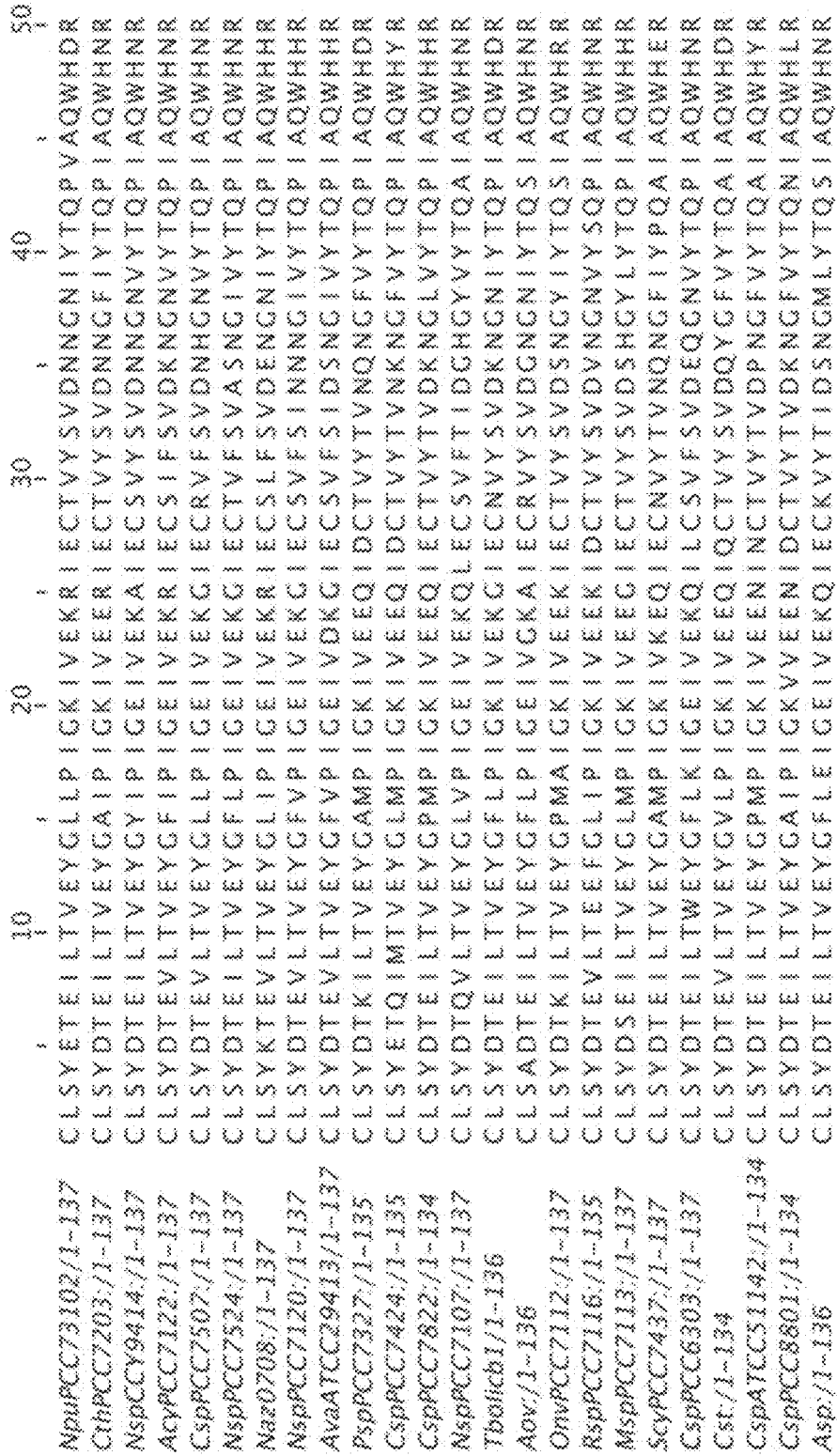
FIG. 7F.1

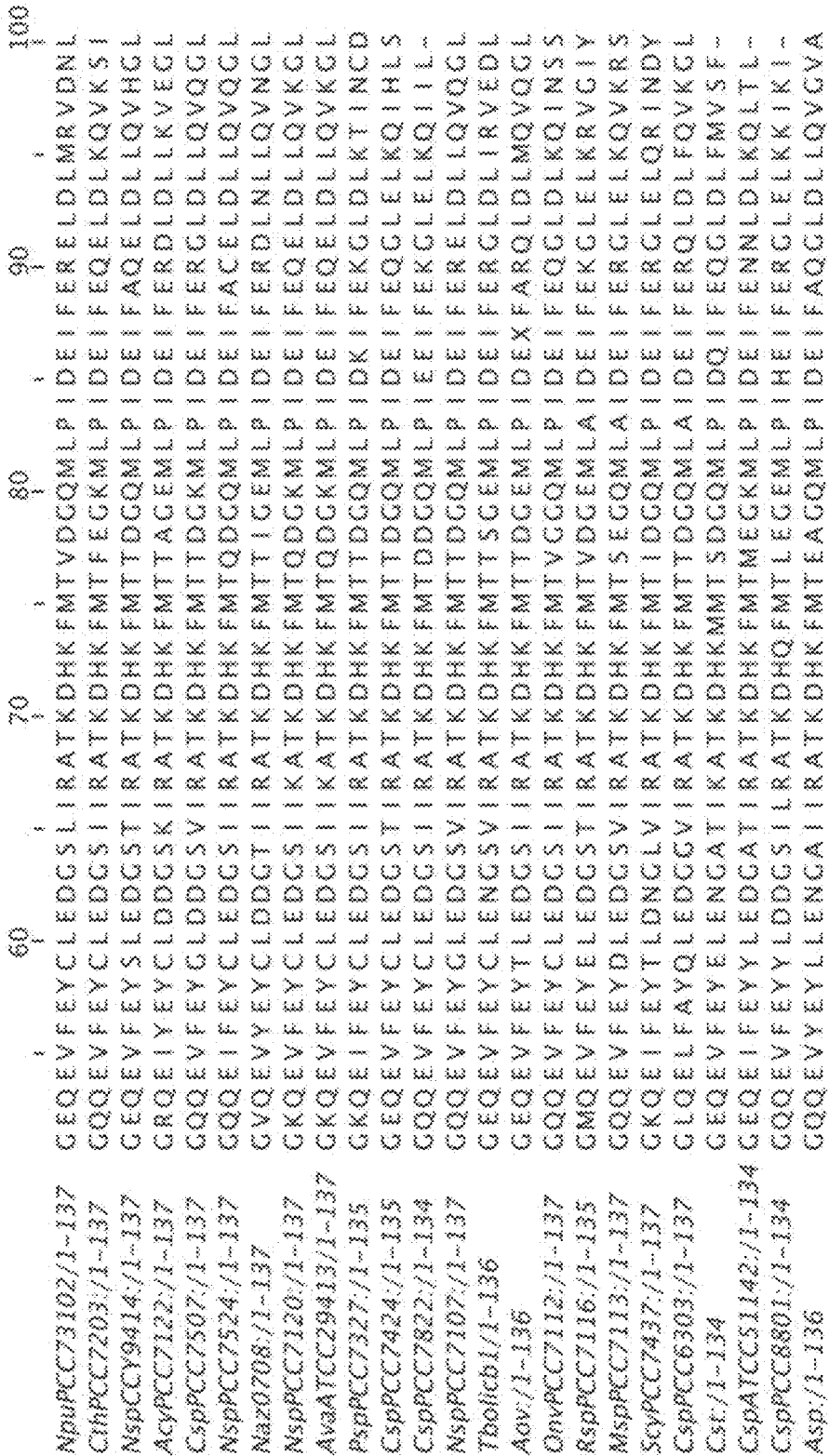
FIG. 7F.2

FIG. 7F.3

N-Inteins

| | 10 | 20 | 30 | 40 | 50 |
|---|---|---|---|---|---|
| Aha/1-137 | CLSYDTEIWTVEYGCAMPIGKIVEEKIECSVYTVDENGFVYTQPIAQWHPR |
| HspPCC7418/1-137 | CLSYDTEIWTVEYGCAMPIGKIVEEKIECSVYTVDENGFVYTQPIAQWHPR |
| CapPCC10605/1-137 | CLSYDTELLTVEYGCAISIGKIVEEKINCQVYSVDKNGFIYTQNIAQWHNR |
| Cat/1-133 | CLSYDTKVLTVEYGCPLPIGKIVEEKINCRVYTTNDQGLIYTQPIAQWHNR |
| Oli/1-137 | CLSYNTEVLTVEYGCPLPIGKIVDEQIHCRVYSVDENGFVYTQAIAQWHDR |
| Cen/1-137 | CLSYDTEVLTVEYGCAIPIGCRMVEESLDCTVYTVDKNGFVYTQSIQWHSR |
| SspPCC7502/1-133 | CLGYDTPVLTVEYGCMPIGKIVEEKIQCHVYSVDQNGLIYTQPIAQWHNR |
| CspUCYN/1-124 | CLSYDTKVLTVEYGCPLPIGKIVKVQENIRCRVYTTNDQGLIYTQPIAQWHNR |
| Pst/1-129 | CLSYDTEVLTVEYGCLIPISKIVEEKIECTVYTVNNQGYVYTQPIAQWHNR |
| PlaCVA98/1-129 | CLSYDTEVLTVEYGCLMPICKIVKEKIECTVYTVNNQGYVYTQPIAQWHNR |
| Pst585/1-129 | CLSYDTEILTVEYGCLIPISKIVEEKIDCTVYTVDKNGFVYTQPIAQWHLR |
| CspPCC8802/1-134 | CLSYDTAILTVEYGCAIPIGKIVEENIDCTVYTVDPNGFVYTQNIAQWHNR |
| CffPCC6912/1-137 | CLSYDTEILTVEYGCPMPICKIVEENINCTVYTVDPNGCYIYTQAIAQWHNR |
| CspATCS1472/1-132 | CLSYDTEVLTVEYGCAVPICKIVEEKLNCSVYTVDPNGYIYTQPIAQWHNR |
| Lma/1-132 | CLGETLLTEEYGLLPIAGEIVEEKGIECTVYTVDRSCFLYAQAISQWHER |
| CopESFC/1-137 | CLSYDTEVLTVEYGCAVPICKIVEEKLNCSVYTVDPNGFVYSQPISQWHER |
| Mae9405/1-129 | CLGGETLLTEEYGLLPIAKIVSEEVNCTVYSVDKNGFVYSQPISQWHER |
| RlaKORDI51-2/1-137 | CLSYDTEVLTVEYGCLLPIAKIVSEERLACTVYTVDRSCFLYAQAISQWHER |
| CffPCC9212/1-136 | CLSYDTEVLTVEYGCLLPIVEKGIVEKGIECTVYTVDSNGYIYTQPIAQWHDR |
| RmHH01/1-137 | CLSYDTQILTVEHGPMSIGEIVEKCLEHCVYTVNKNGNICIQTITQWHFR |
| GheCCC6308/1-133 | CLSYDTEVLTVEFGCAIPMGKIVEERLNCQVYSVDKNGFIYTQNIAQWHDR |
| SsuPCC9445/1-131 | CLSYDTKIITVEYGCAIAICTIVEQCLHCHVYSVDPNGFIYTQPIAQWHQR |
| MaePCC9807/1-135 | CLGGETLLTEEYGLLKYGCALPIGKIAKIVSEEINCVYTRAESCFFYIQSIEQWHDR |
| MspG1/1-130 | CLSYDTEVLTILKYGCALPIGKIVEKRINCHVYTRAEINCHVYTRAIECTVYSVDNDGNIYTQPIAQWHDR |
| ShoPCC7110/1-136 | CLSYDTEVLTAEYGFLPIGKIVEKAIECTVYSVDNDGNIYTQPIAQWHDR |

FIG. 7G.1

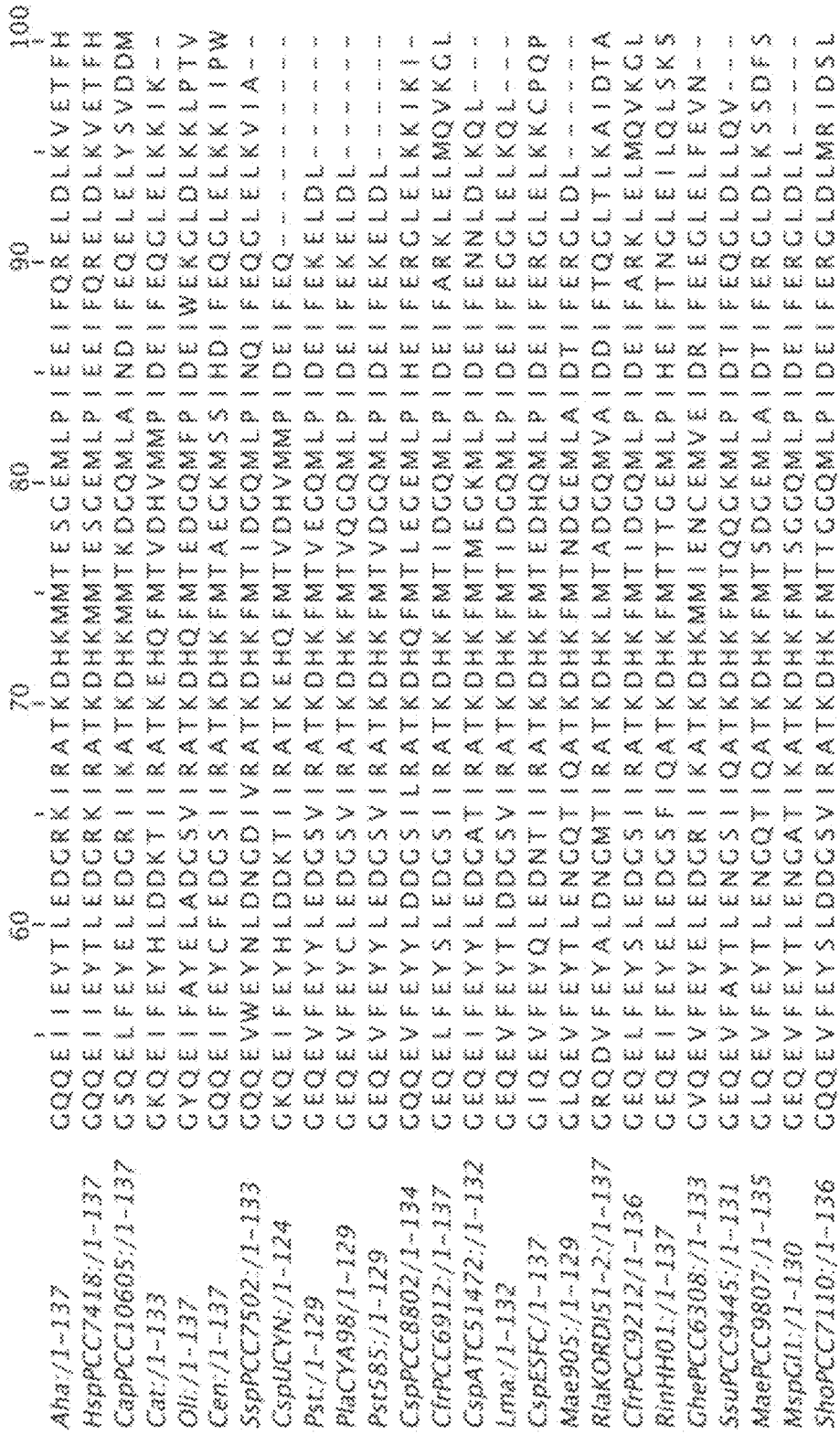
FIG. 7G.2

C-Inteins

| | 110 | 120 | 130 | |
|---|---|---|---|---|
| Aha/1-137 | EMVKIIKRQSLGRQNVYDVCVETDHNFVLANGCVASN |
| HspPCC7418/1-137 | EMVKIIKRQSLGRQNVYDICVETDHNFVLANGCVASN |
| CapPCC10605/1-137 | GVVKIVKRRSLGVQPVYDIGVEKDHNFILANGLVASN |
| Cra/1-133 | - - LKIIRRKSLGMHEVFDIGLEKDHNFVLSNGLIASN |
| Oli/1-137 | QDVKIVRRQSLGVQNVYDIGVEKDHNFLLASGEIASN |
| Cen/1-137 | SGAKIISCKRSLGKQSVYDIGVVQDHNFILANGVVASN |
| SspPCC7502/1-133 | - - IKIIVSCKPLRVQTVYDIGVEKDHNFVLSNGLVASN |
| CspUCYN/1-124 | - - VKIIRRKSLGTQPVYDIGLEKDHNFVLSNGLIASN |
| Pse/1-129 | - - VKIISRKSLGTQPVYDIGVQEDHNFVLNNGLVASN |
| PlaCYA98/1-129 | - - VKIISRKSLGTQPVYDIGVQEDHNFLLNNGLVASN |
| Pst585/1-129 | - - VKIIVSYRSLGKQFVYDIGVAQDHNFLLANGSIASN |
| CspPCC8802/1-134 | PEVKIIAKKSLGTQNVYDIGVEKEHNFVIKNGLVASN |
| CfrPCC6912/1-137 | - - IKIIGRQSLGTQPVYDIGVKDDHNFILEQDHNFLLGNGLVASN |
| CspATC51472/1-132 | - - VKIISRKSLGRKPVYDIGVARDHNFLLANGAIASN |
| Lma/1-132 | QQVKIIRRRSLGVQHVYDIGVAHVYDIGVARDHNFVIKNGLVASN |
| CspESFC/1-137 | - - VKIISRQSLGVQHVYDIGVARDHNFVIKNGLVASN |
| Mae9055/1-129 | AFMKIVSRKSLGVQHVYDIGVARDHNFVIKNGLVASN |
| RlaKORDJ51-2/1-137 | P - VKIIAKKSLGTQKVYDIGVNDDHNFALSNSFIASN |
| CfrPCC9212/1-136 | LLVKILARRSISSQQVYDIGVEKDHNFLLANGLVASN |
| RimHH01/1-137 | - - VKILKRRSLGVRPVYDIGVEKDHNFLLANGLVASN |
| GhePCC6308/1-133 | - - IKIIKRTSLGVRPVYDIGVIQDHNFLLCNGLIASN |
| SsuPCC9445/1-131 | - - VKIISRQFLGRKPVYDIGVEKDHNFLLANGCTVASN |
| MaePCC9807/1-135 | - - VKIVSRKSLGKQPVYDLGVAKDHNFLLANGCTVASN |
| MspGI1/1-130 | - - VKIIVSRKSIGKQTVYDIGVERDHNFVIKNGLVASN |
| ShoPCC7110/1-136 | P - VKILTRKSIGKQTVYDIGVERDHNFVIKNGLVASN |

FIG. 7G.3

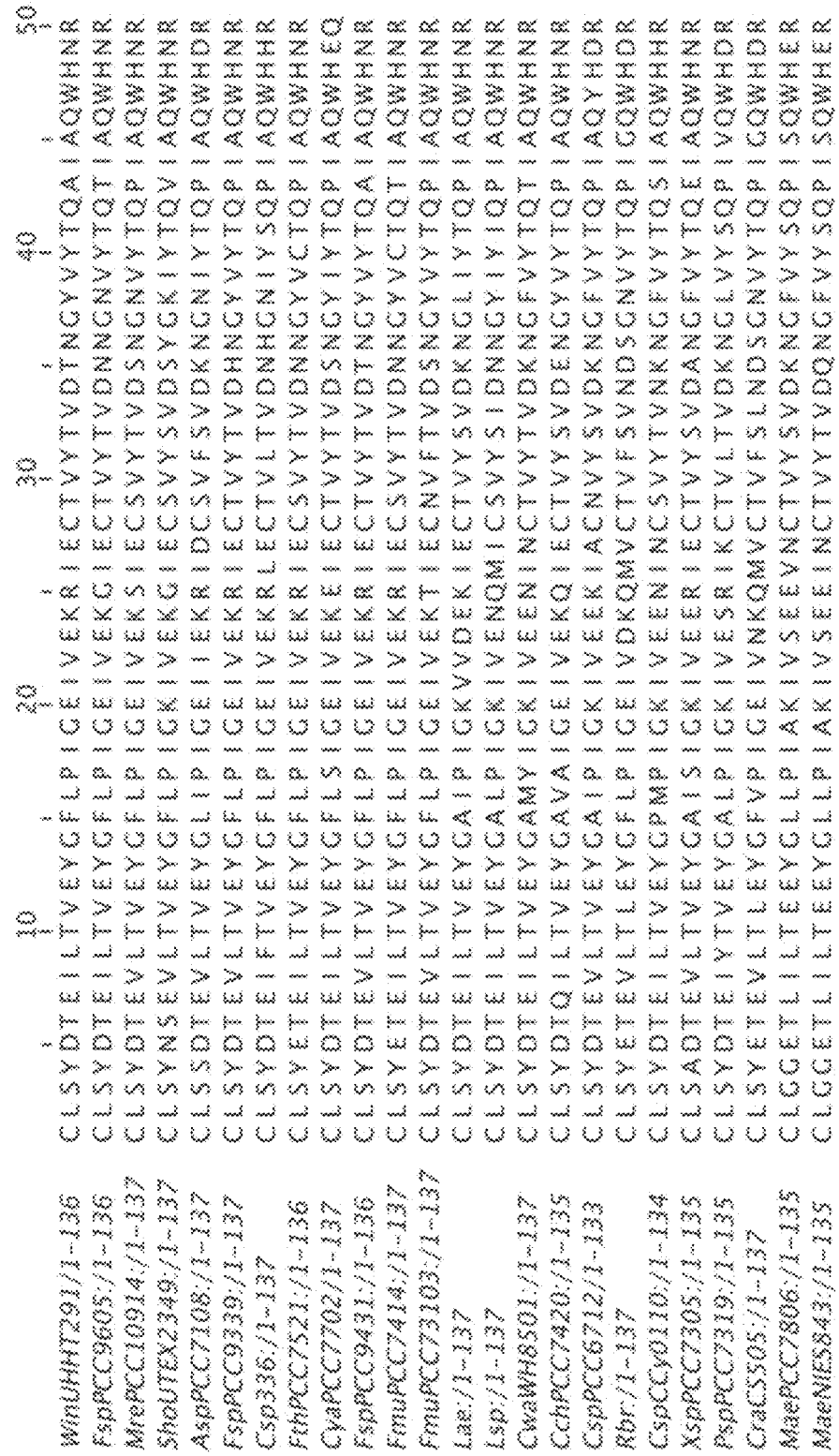
FIG. 7H.1

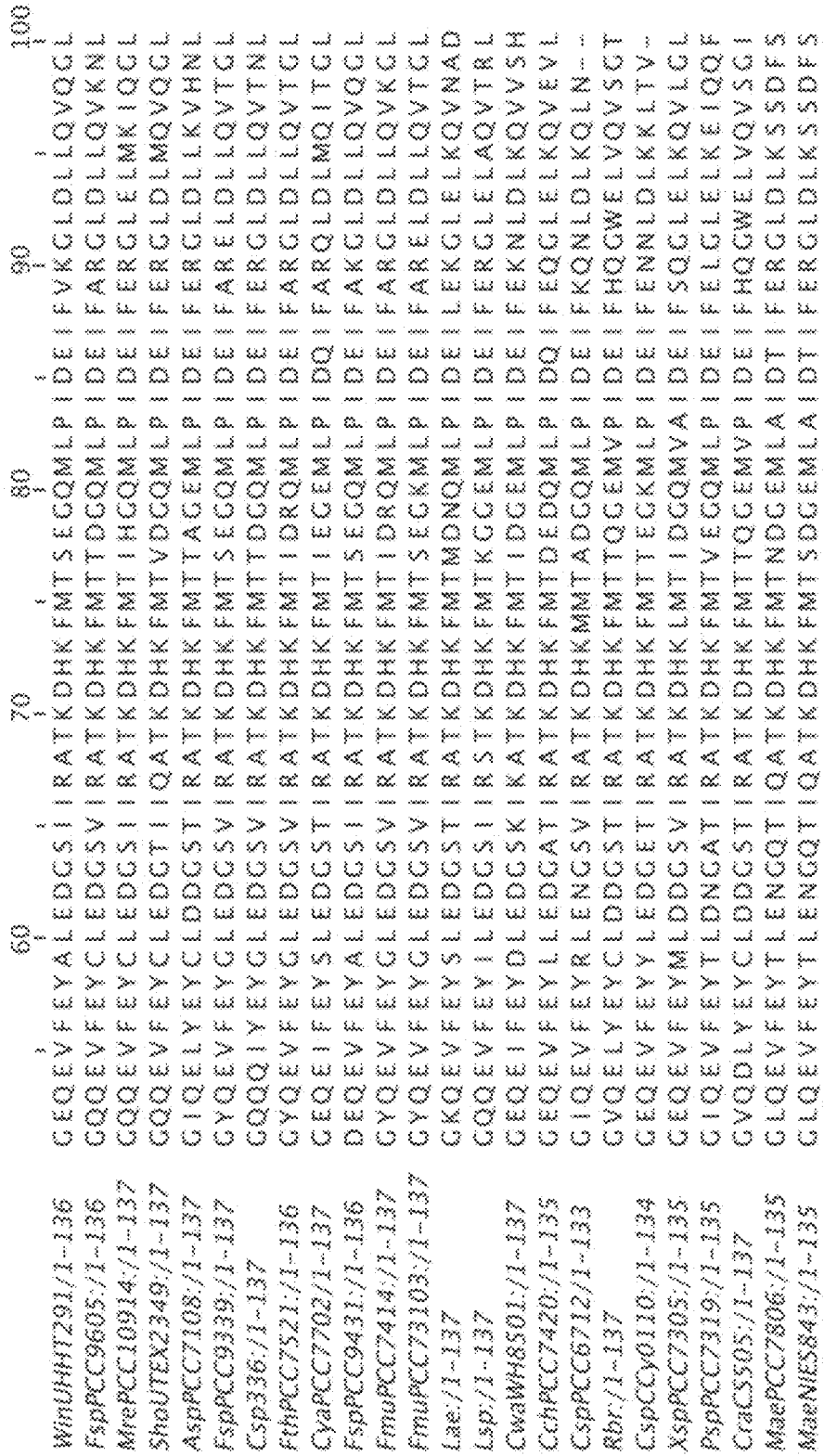
FIG. 7H.2

C-inteins

```
                          110                120                130
WinJHHT291/1-136    P--VKIITRKFLGIQNVYDIGVEQNHNFVIKNGLVASN
FspPCC9605/1-136    P--VKIVTRRPLGTQNVYDIGVESDHNFVIKNGLVASN
MrePCC10914/1-137   PEAKIITRKSLGTQNVYDIGVERDHNFVTRDGFIASN
ShoJTEX2349/1-137   PDVKIITRKSLGTQNVYDIGVSSDHNFVMKNGLIASN
AspPCC7108/1-137    PQVKIITRNYVGKENVYDIGVERDHNFAIKNGLIASN
FspPCC9339/1-137    VNVKIVTRRLLGIQNVYDIGVEQNHNFVIKNGLVASN
Csp336/1-137        DNVKVITRKLADTENVYDIGVENHHNFLIKNGLVASN
FthPCC7521/1-136    P--VKIITRKSLGTQNVYDIGVEQNHNFVIKNGLVASN
CyaPCC7702/1-137    PQVKISTKKSLGKQKVYDIGVVRDHNFI-IKNGFVASN
FspPCC9431/1-136    P--VKIVTRKFLGIQNVYDIGVEQNHNFVIKNGLVASN
FmuPCC7414/1-137    PEVKIITRQSLGTQNVYDIGVETDHNFLLANGSVASN
FmuPCC73103/1-137   INVKIVTRKFLGIQNVYDIGVKQDHNFFLRNGLIASN
Lae/1-137           SVVKIVSRKSLDSQTVYDIGVEKDHNFLLANGSIASN
Lsp/1-137           EQVKIISRRSVGVQSVYDIGVEKDHNFLLFNGSVASN
CwaWH8501/1-137     PDVKIIGCRSLGTQKVYDIGVEKDHNFLLANGLVASN
CchPCC7420/1-135    I--VKIIGRKPLGTQPYYDIGVAKDHNFLLANGLVASN
CspPCC6712/1-133    I--VKIISRQSLGKQSVFDIGVAKDHNFIIKNGLVASN
Rbr/1-137           MNVKIVSRRYLGKADVYDIGVAKDHNFIIKNGLVASN
CspCCY0110/1-134    I--VKIIERRSLGKQNVYDIGVEKDHNFLLSNNLIASN
XspPCC7305/1-135    I--VKIVSRKSLGTQTVYDLGVARDHNFLLANGTVASN
PspPCC7319/1-135    I--VKIISRQSLGKQSVYDIGVAKDHNFLLANGMVASN
CraCS505/1-137      SKVKIVSRRYLGKADVYDIGVAKDHNFIIKNGLVASN
MaePCC7806/1-135    I--VKIISRQSLGRKPVYDIGVEKDHNFLLGNGLIASN
MaeNIES843/1-135    I--VKIICRQSLGRKPVYDIGVEKDHNFLLGNGLIASN
```

FIG. 7H.3

SEQUENCE LISTING

```
<160> NUMBER OF SEQ ID NOS: 499

<210> SEQ ID NO 1
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Cys Leu Ser Tyr Asp Thr Glu Ile Leu Thr Val Glu Tyr Gly Phe Leu
1               5                   10                  15

Pro Ile Gly Lys Ile Val Glu Glu Arg Ile Glu Cys Thr Val Tyr Thr
            20                  25                  30

Val Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu
                85                  90

<210> SEQ ID NO 2
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Leu Ser Tyr Asp Thr Glu Ile Leu Thr Val Glu Tyr Gly Phe Leu
1               5                   10                  15

Pro Ile Gly Lys Ile Val Glu Glu Arg Ile Glu Cys Thr Val Tyr Thr
            20                  25                  30

Val Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Lys Gln
                85                  90                  95

Val Asp Gly Leu Pro
            100

<210> SEQ ID NO 3
<211> LENGTH: 35
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 3

Val Lys Ile Ile Ser Arg Lys Ser Leu Gly Thr Gln Asn Val Tyr Asp
1               5                   10                  15

Ile Gly Val Glu Lys Asp His Asn Phe Leu Leu Lys Asn Gly Leu Val
            20                  25                  30

Ala Ser Asn
        35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Val Lys Ile Ile Ser Arg Lys Ser Leu Gly Thr Gln Asn Val Tyr
1               5                   10                  15

Asp Ile Gly Val Glu Lys Asp His Asn Phe Leu Leu Lys Asn Gly Leu
            20                  25                  30

Val Ala Ser Asn
        35

<210> SEQ ID NO 5
<211> LENGTH: 102
<212> TYPE: PRT
<213> ORGANISM: Nostoc punctiforme

<400> SEQUENCE: 5

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100

<210> SEQ ID NO 6
<211> LENGTH: 35
<212> TYPE: PRT
<213> ORGANISM: Nostoc punctiforme

<400> SEQUENCE: 6

Ile Lys Ile Ala Thr Arg Lys Tyr Leu Gly Lys Gln Asn Val Tyr Asp
1               5                   10                  15

Ile Gly Val Glu Arg Asp His Asn Phe Ala Leu Lys Asn Gly Phe Ile
            20                  25                  30

Ala Ser Asn
        35

<210> SEQ ID NO 7
<211> LENGTH: 102
<212> TYPE: PRT
<213> ORGANISM: Chroococcidiopsis thermalis

<400> SEQUENCE: 7

Cys Leu Ser Tyr Asp Thr Glu Ile Leu Thr Val Glu Tyr Gly Ala Ile
1               5                   10                  15

Pro Ile Gly Lys Ile Val Glu Glu Arg Ile Glu Cys Thr Val Tyr Ser
            20                  25                  30

Val Asp Asn Asn Gly Phe Ile Tyr Thr Gln Pro Ile Ala Gln Trp His
        35                  40                  45

Asn Arg Gly Gln Gln Glu Val Phe Glu Tyr Cys Leu Glu Asp Gly Ser
    50                  55                  60

Ile Ile Arg Ala Thr Lys Asp His Lys Phe Met Thr Phe Glu Gly Lys
65                  70                  75                  80

Met Leu Pro Ile Asp Glu Ile Phe Glu Gln Glu Leu Asp Leu Lys Gln
                85                  90                  95

Val Lys Ser Ile Gln Asn
            100

<210> SEQ ID NO 8
<211> LENGTH: 35
<212> TYPE: PRT
<213> ORGANISM: Chroococcidiopsis thermalis

<400> SEQUENCE: 8

Val Lys Ile Ile Ser Arg Lys Ser Leu Gly Ile Gln Pro Val Tyr Asp
1               5                   10                  15

Ile Gly Val Glu Arg Asp His Lys Phe Val Leu Lys Asn Gly Leu Val
            20                  25                  30

Ala Ser Asn
        35

<210> SEQ ID NO 9
<211> LENGTH: 102
<212> TYPE: PRT
<213> ORGANISM: Nodularia spumigena

<400> SEQUENCE: 9

Cys Leu Ser Tyr Asp Thr Glu Ile Leu Thr Val Glu Tyr Gly Tyr Ile
1               5                   10                  15

Pro Ile Gly Glu Ile Val Glu Lys Ala Ile Glu Cys Ser Val Tyr Ser
            20                  25                  30

Val Asp Asn Asn Gly Asn Val Tyr Thr Gln Pro Ile Ala Gln Trp His
        35                  40                  45

Asn Arg Gly Glu Gln Glu Val Phe Glu Tyr Ser Leu Glu Asp Gly Ser
    50                  55                  60

Thr Ile Arg Ala Thr Lys Asp His Lys Phe Met Thr Thr Asp Gly Gln
65                  70                  75                  80

Met Leu Pro Ile Asp Glu Ile Phe Ala Gln Glu Leu Asp Leu Leu Gln
                85                  90                  95

Val His Gly Leu Pro Lys
            100

<210> SEQ ID NO 10
<211> LENGTH: 35
<212> TYPE: PRT

<213> ORGANISM: Nodularia spumigena

<400> SEQUENCE: 10

Val Lys Ile Thr Ala Arg Lys Phe Val Gly Arg Glu Asn Val Tyr Asp
1               5                   10                  15

Ile Gly Val Glu Arg Tyr His Asn Phe Ala Ile Lys Asn Gly Leu Ile
            20                  25                  30

Ala Ser Asn
        35

<210> SEQ ID NO 11
<211> LENGTH: 102
<212> TYPE: PRT
<213> ORGANISM: Anabaena cylindrica

<400> SEQUENCE: 11

Cys Leu Ser Tyr Asp Thr Glu Val Leu Thr Val Glu Tyr Gly Phe Ile
1               5                   10                  15

Pro Ile Gly Glu Ile Val Glu Lys Arg Ile Glu Cys Ser Ile Phe Ser
            20                  25                  30

Val Asp Lys Asn Gly Asn Val Tyr Thr Gln Pro Ile Ala Gln Trp His
        35                  40                  45

Asn Arg Gly Arg Gln Glu Ile Tyr Glu Tyr Cys Leu Asp Asp Gly Ser
    50                  55                  60

Lys Ile Arg Ala Thr Lys Asp His Lys Phe Met Thr Thr Ala Gly Glu
65                  70                  75                  80

Met Leu Pro Ile Asp Glu Ile Phe Glu Arg Asp Leu Asp Leu Leu Lys
                85                  90                  95

Val Glu Gly Leu Pro Glu
            100

<210> SEQ ID NO 12
<211> LENGTH: 35
<212> TYPE: PRT
<213> ORGANISM: Anabaena cylindrica

<400> SEQUENCE: 12

Val Lys Ile Ile Ser Arg Gln Tyr Leu Gly Gln Ala Asp Val Tyr Asp
1               5                   10                  15

Ile Gly Val Glu Glu Asp His Asn Phe Ala Ile Lys Asn Gly Phe Ile
            20                  25                  30

Ala Ser Asn
        35

<210> SEQ ID NO 13
<211> LENGTH: 102
<212> TYPE: PRT
<213> ORGANISM: Calothrix sp.

<400> SEQUENCE: 13

Cys Leu Ser Tyr Asp Thr Glu Val Leu Thr Val Glu Tyr Gly Leu Leu
1               5                   10                  15

Pro Ile Gly Glu Ile Val Glu Lys Gly Ile Glu Cys Arg Val Phe Ser
            20                  25                  30

Val Asp Asn His Gly Asn Val Tyr Thr Gln Pro Ile Ala Gln Trp His
        35                  40                  45

Asn Arg Gly Gln Gln Glu Val Phe Glu Tyr Gly Leu Asp Asp Gly Ser
    50                  55                  60

Val Ile Arg Ala Thr Lys Asp His Lys Phe Met Thr Thr Asp Gly Lys
65                  70                  75                  80

Met Leu Pro Ile Asp Glu Ile Phe Glu Arg Gly Leu Asp Leu Leu Gln
                85                  90                  95

Val Gln Gly Leu Pro Glu
            100

<210> SEQ ID NO 14
<211> LENGTH: 35
<212> TYPE: PRT
<213> ORGANISM: Calothrix sp.

<400> SEQUENCE: 14

Val Lys Val Ile Thr Arg Lys Tyr Ile Gly Lys Glu Asn Val Tyr Asp
1               5                   10                  15

Ile Gly Val Glu Leu Asp His Asn Phe Ala Ile Arg Asn Gly Leu Val
            20                  25                  30

Ala Ser Asn
        35

<210> SEQ ID NO 15
<211> LENGTH: 102
<212> TYPE: PRT
<213> ORGANISM: Nostoc sp.

<400> SEQUENCE: 15

Cys Leu Ser Tyr Asp Thr Glu Ile Leu Thr Val Glu Tyr Gly Phe Leu
1               5                   10                  15

Pro Ile Gly Glu Ile Val Glu Lys Gly Ile Glu Cys Thr Val Phe Ser
            20                  25                  30

Val Ala Ser Asn Gly Ile Val Tyr Thr Gln Pro Ile Ala Gln Trp His
        35                  40                  45

Asn Arg Gly Gln Gln Glu Ile Phe Glu Tyr Cys Leu Glu Asp Gly Ser
    50                  55                  60

Ile Ile Arg Ala Thr Lys Asp His Lys Phe Met Thr Gln Asp Gly Gln
65                  70                  75                  80

Met Leu Pro Ile Asp Glu Ile Phe Ala Cys Glu Leu Asp Leu Leu Gln
                85                  90                  95

Val Gln Gly Leu Pro Glu
            100

<210> SEQ ID NO 16
<211> LENGTH: 35
<212> TYPE: PRT
<213> ORGANISM: Nostoc sp.

<400> SEQUENCE: 16

Val Lys Val Val Thr Arg Lys Tyr Ile Gly Lys Glu Asn Val Tyr Asp
1               5                   10                  15

Ile Gly Val Glu Arg Asp His Asn Phe Val Ile Arg Asn Gly Leu Val
            20                  25                  30

Ala Ser Asn
        35

<210> SEQ ID NO 17
<211> LENGTH: 102
<212> TYPE: PRT
<213> ORGANISM: Nostoc azollae

<400> SEQUENCE: 17

Cys Leu Ser Tyr Lys Thr Glu Val Leu Thr Val Glu Tyr Gly Leu Ile
1               5                   10                  15

Pro Ile Gly Glu Ile Val Glu Lys Arg Ile Glu Cys Ser Leu Phe Ser
                20                  25                  30

Val Asp Glu Asn Gly Asn Ile Tyr Thr Gln Pro Ile Ala Gln Trp His
            35                  40                  45

His Arg Gly Val Gln Glu Val Tyr Glu Tyr Cys Leu Asp Asp Gly Thr
        50                  55                  60

Ile Ile Arg Ala Thr Lys Asp His Lys Phe Met Thr Thr Ile Gly Glu
65                  70                  75                  80

Met Leu Pro Ile Asp Glu Ile Phe Glu Arg Asp Leu Asn Leu Leu Gln
                85                  90                  95

Val Asn Gly Leu Pro Thr
            100

<210> SEQ ID NO 18
<211> LENGTH: 35
<212> TYPE: PRT
<213> ORGANISM: Nostoc azollae

<400> SEQUENCE: 18

Val Lys Ile Ile Ser Arg Gln Phe Leu Gly Pro Ala Asn Val Tyr Asp
1               5                   10                  15

Ile Gly Val Ala Gln Asp His Asn Phe Ala Ile Lys Asn Gly Leu Ile
                20                  25                  30

Ala Ser Asn
        35

<210> SEQ ID NO 19
<211> LENGTH: 102
<212> TYPE: PRT
<213> ORGANISM: Nostoc sp.

<400> SEQUENCE: 19

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
                20                  25                  30

Ile Asn Asn Asn Gly Ile Val Tyr Thr Gln Pro Ile Ala Gln Trp His
            35                  40                  45

His Arg Gly Lys Gln Glu Val Phe Glu Tyr Cys Leu Glu Asp Gly Ser
        50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 20
<211> LENGTH: 35
<212> TYPE: PRT
<213> ORGANISM: Nostoc sp.

<400> SEQUENCE: 20

Ile Lys Ile Ala Ser Arg Lys Phe Leu Gly Val Glu Asn Val Tyr Asp
1               5                   10                  15

```
Ile Gly Val Arg Arg Asp His Asn Phe Phe Ile Lys Asn Gly Leu Ile
            20                  25                  30

Ala Ser Asn
        35

<210> SEQ ID NO 21
<211> LENGTH: 102
<212> TYPE: PRT
<213> ORGANISM: Anabaena variabilis

<400> SEQUENCE: 21

Cys Leu Ser Tyr Asp Thr Glu Val Leu Thr Val Glu Tyr Gly Phe Val
1               5                   10                  15

Pro Ile Gly Glu Ile Val Asp Lys Gly Ile Glu Cys Ser Val Phe Ser
            20                  25                  30

Ile Asp Ser Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 22
<211> LENGTH: 35
<212> TYPE: PRT
<213> ORGANISM: Anabaena variabilis

<400> SEQUENCE: 22

Ile Lys Ile Ala Ser Arg Lys Phe Leu Gly Val Glu Asn Val Tyr Asp
1               5                   10                  15

Ile Gly Val Gly Arg Asp His Asn Phe Phe Val Lys Asn Gly Leu Ile
            20                  25                  30

Ala Ser Asn
        35

<210> SEQ ID NO 23
<211> LENGTH: 100
<212> TYPE: PRT
<213> ORGANISM: Pleurocapsa sp.

<400> SEQUENCE: 23

Cys Leu Ser Tyr Asp Thr Lys Ile Leu Thr Val Glu Tyr Gly Ala Met
1               5                   10                  15

Pro Ile Gly Lys Ile Val Glu Glu Gln Ile Asp Cys Thr Val Tyr Thr
            20                  25                  30

Val Asn Gln Asn Gly Phe Val Tyr Thr Gln Pro Ile Ala Gln Trp His
        35                  40                  45

Asp Arg Gly Lys Gln Glu Ile Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Lys Ile Phe Glu Lys Gly Leu Asp Leu Lys Thr
                85                  90                  95

Ile Asn Cys Asp
```

<210> SEQ ID NO 24
<211> LENGTH: 35
<212> TYPE: PRT
<213> ORGANISM: Pleurocapsa sp.

<400> SEQUENCE: 24

Val Lys Ile Leu Ser Arg Lys Ser Leu Gly Ile Gln Ser Val Tyr Asp
1               5                   10                  15

Ile Gly Val Glu Lys Asp His Asn Phe Leu Leu Ala Asn Gly Leu Val
            20                  25                  30

Ala Ser Asn
        35

<210> SEQ ID NO 25
<211> LENGTH: 100
<212> TYPE: PRT
<213> ORGANISM: Cyanothece sp.

<400> SEQUENCE: 25

Cys Leu Ser Tyr Glu Thr Gln Ile Met Thr Val Glu Tyr Gly Leu Met
1               5                   10                  15

Pro Ile Gly Lys Ile Val Glu Glu Ile Asp Cys Thr Val Tyr Thr
            20                  25                  30

Val Asn Lys Asn Gly Phe Val Tyr Thr Gln Pro Ile Ala Gln Trp His
            35                  40                  45

Tyr Arg Gly Glu Gln Glu Val Phe Glu Tyr Cys Leu Glu Asp Gly Ser
        50                  55                  60

Thr Ile Arg Ala Thr Lys Asp His Lys Phe Met Thr Thr Asp Gly Gln
65                  70                  75                  80

Met Leu Pro Ile Asp Glu Ile Phe Glu Gln Gly Leu Glu Leu Lys Gln
                85                  90                  95

Ile His Leu Ser
            100

<210> SEQ ID NO 26
<211> LENGTH: 35
<212> TYPE: PRT
<213> ORGANISM: Cyanothece sp.

<400> SEQUENCE: 26

Val Lys Ile Ile Ser Arg Gln Ser Leu Gly Ile Gln Pro Val Tyr Asp
1               5                   10                  15

Ile Gly Val Glu Lys Asp His Asn Phe Leu Ile Ser Asp Gly Leu Ile
            20                  25                  30

Ala Ser Asn
        35

<210> SEQ ID NO 27
<211> LENGTH: 99
<212> TYPE: PRT
<213> ORGANISM: Cyanothece sp.

<400> SEQUENCE: 27

Cys Leu Ser Tyr Asp Thr Glu Ile Leu Thr Val Glu Tyr Gly Pro Met
1               5                   10                  15

Pro Ile Gly Lys Ile Val Glu Glu Gln Ile Glu Cys Thr Val Tyr Thr
            20                  25                  30

```
Val Asp Lys Asn Gly Leu Val Tyr Thr Gln Pro Ile Ala Gln Trp His
        35                  40                  45

His Arg Gly Gln Gln Glu Val Phe Glu Tyr Cys Leu Glu Asp Gly Ser
 50                  55                  60

Ile Ile Arg Ala Thr Lys Asp His Lys Phe Met Thr Asp Asp Gly Gln
 65                  70                  75                  80

Met Leu Pro Ile Glu Glu Ile Phe Lys Gly Leu Glu Leu Lys Gln
                 85                  90                  95

Ile Ile Leu

<210> SEQ ID NO 28
<211> LENGTH: 35
<212> TYPE: PRT
<213> ORGANISM: Cyanothece sp.

<400> SEQUENCE: 28

Val Lys Ile Ile Ser Arg Gln Leu Ala Gly Asn Gln Thr Val Tyr Asp
 1               5                  10                  15

Leu Gly Val Glu Lys Asp His Asn Phe Leu Leu Ala Asn Gly Leu Ile
                 20                  25                  30

Ala Ser Asn
        35

<210> SEQ ID NO 29
<211> LENGTH: 102
<212> TYPE: PRT
<213> ORGANISM: Nostoc sp.

<400> SEQUENCE: 29

Cys Leu Ser Tyr Asp Thr Gln Val Leu Thr Val Glu Tyr Gly Leu Val
 1               5                  10                  15

Pro Ile Gly Glu Ile Val Glu Lys Gln Leu Glu Cys Ser Val Phe Thr
                 20                  25                  30

Ile Asp Gly His Gly Tyr Val Tyr Thr Gln Ala Ile Ala Gln Trp His
        35                  40                  45

Asn Arg Gly Gln Gln Glu Val Phe Glu Tyr Gly Leu Glu Asp Gly Ser
 50                  55                  60

Val Ile Arg Ala Thr Lys Asp His Lys Phe Met Thr Thr Asp Gly Gln
 65                  70                  75                  80

Met Leu Pro Ile Asp Glu Ile Phe Glu Arg Glu Leu Asp Leu Leu Gln
                 85                  90                  95

Val Gln Gly Leu Arg Trp
                100

<210> SEQ ID NO 30
<211> LENGTH: 35
<212> TYPE: PRT
<213> ORGANISM: Nostoc sp.

<400> SEQUENCE: 30

Val Lys Ile Ile Thr Arg Lys Tyr Ile Gly Gln Ala Asn Val Tyr Asp
 1               5                  10                  15

Ile Gly Val Ala Gln Asp His Asn Phe Val Ile Glu Asn Arg Leu Ile
                 20                  25                  30

Ala Ser Asn
        35

<210> SEQ ID NO 31
```

```
<211> LENGTH: 101
<212> TYPE: PRT
<213> ORGANISM: Tolypothrix bouteillei

<400> SEQUENCE: 31

Cys Leu Ser Tyr Asp Thr Glu Ile Leu Thr Val Glu Tyr Gly Phe Leu
1               5                   10                  15

Pro Ile Gly Lys Ile Val Glu Lys Gly Ile Glu Cys Asn Val Tyr Ser
            20                  25                  30

Val Asp Lys Asn Gly Asn Ile Tyr Thr Gln Pro Ile Ala Gln Trp His
        35                  40                  45

Asp Arg Gly Glu Gln Glu Val Phe Glu Tyr Cys Leu Glu Asn Gly Ser
    50                  55                  60

Val Ile Arg Ala Thr Lys Asp His Lys Phe Met Thr Thr Ser Gly Glu
65                  70                  75                  80

Met Leu Pro Ile Asp Glu Ile Phe Glu Arg Gly Leu Asp Leu Ile Arg
                85                  90                  95

Val Glu Asp Leu Pro
            100

<210> SEQ ID NO 32
<211> LENGTH: 35
<212> TYPE: PRT
<213> ORGANISM: Tolypothrix bouteillei

<400> SEQUENCE: 32

Val Lys Ile Leu Thr Arg Lys Ser Ile Gly Lys Gln Thr Val Tyr Asp
1               5                   10                  15

Ile Gly Val Glu Arg Asp His Asn Phe Val Ile Lys Asn Gly Ser Val
            20                  25                  30

Ala Ser Asn
        35

<210> SEQ ID NO 33
<211> LENGTH: 101
<212> TYPE: PRT
<213> ORGANISM: Aphanizomenon ovalisporum
<220> FEATURE:
<221> NAME/KEY: MOD_RES
<222> LOCATION: (87)..(87)
<223> OTHER INFORMATION: Any amino acid

<400> SEQUENCE: 33

Cys Leu Ser Ala Asp Thr Glu Ile Leu Thr Val Glu Tyr Gly Phe Leu
1               5                   10                  15

Pro Ile Gly Glu Ile Val Gly Lys Ala Ile Glu Cys Arg Val Tyr Ser
            20                  25                  30

Val Asp Gly Asn Gly Asn Ile Tyr Thr Gln Ser Ile Ala Gln Trp His
        35                  40                  45

Asn Arg Gly Glu Gln Glu Val Phe Glu Tyr Thr Leu Glu Asp Gly Ser
    50                  55                  60

Ile Ile Arg Ala Thr Lys Asp His Lys Phe Met Thr Thr Asp Gly Glu
65                  70                  75                  80

Met Leu Pro Ile Asp Glu Xaa Phe Ala Arg Gln Leu Asp Leu Met Gln
                85                  90                  95

Val Gln Gly Leu His
            100

<210> SEQ ID NO 34
```

```
<211> LENGTH: 35
<212> TYPE: PRT
<213> ORGANISM: Aphanizomenon ovalisporum

<400> SEQUENCE: 34

Val Lys Ile Thr Ala Arg Lys Phe Val Gly Arg Glu Asn Val Tyr Asp
1               5                   10                  15

Ile Gly Val Glu His His His Asn Phe Ala Ile Lys Asn Gly Leu Ile
            20                  25                  30

Ala Ser Asn
        35

<210> SEQ ID NO 35
<211> LENGTH: 102
<212> TYPE: PRT
<213> ORGANISM: Oscillatoria nigro-viridis

<400> SEQUENCE: 35

Cys Leu Ser Tyr Asp Thr Lys Ile Leu Thr Val Glu Tyr Gly Pro Met
1               5                   10                  15

Ala Ile Gly Lys Ile Val Glu Glu Lys Ile Glu Cys Thr Val Tyr Ser
            20                  25                  30

Val Asp Ser Asn Gly Tyr Ile Tyr Thr Gln Ser Ile Ala Gln Trp His
        35                  40                  45

Arg Arg Gly Gln Gln Glu Val Phe Glu Tyr Cys Leu Glu Asp Gly Ser
    50                  55                  60

Ile Ile Arg Ala Thr Lys Asp His Lys Phe Met Thr Val Gly Gly Gln
65                  70                  75                  80

Met Leu Pro Ile Asp Glu Ile Phe Glu Gln Gly Leu Asp Leu Lys Gln
                85                  90                  95

Ile Asn Ser Ser Ser Asp
            100

<210> SEQ ID NO 36
<211> LENGTH: 35
<212> TYPE: PRT
<213> ORGANISM: Oscillatoria nigro-viridis

<400> SEQUENCE: 36

Val Lys Ile Ile Ser Arg Lys Ser Leu Gly Thr Gln Glu Val Tyr Asp
1               5                   10                  15

Ile Gly Val Glu Arg Glu His Asn Phe Ile Leu Glu Asn Ser Leu Val
            20                  25                  30

Ala Ser Asn
        35

<210> SEQ ID NO 37
<211> LENGTH: 100
<212> TYPE: PRT
<213> ORGANISM: Rivularia sp.

<400> SEQUENCE: 37

Cys Leu Ser Tyr Asp Thr Glu Val Leu Thr Glu Glu Phe Gly Leu Ile
1               5                   10                  15

Pro Ile Gly Lys Ile Val Glu Glu Lys Ile Asp Cys Thr Val Tyr Ser
            20                  25                  30

Val Asp Val Asn Gly Asn Val Tyr Ser Gln Pro Ile Ala Gln Trp His
        35                  40                  45

Asn Arg Gly Met Gln Glu Val Phe Glu Tyr Glu Leu Glu Asp Gly Ser
```

```
                50             55             60
Thr Ile Arg Ala Thr Lys Asp His Lys Phe Met Thr Val Asp Gly Glu
 65                 70                 75                 80

Met Leu Ala Ile Asp Glu Ile Phe Glu Lys Gly Leu Glu Leu Lys Arg
                 85                 90                 95

Val Gly Ile Tyr
            100

<210> SEQ ID NO 38
<211> LENGTH: 35
<212> TYPE: PRT
<213> ORGANISM: Rivularia sp.

<400> SEQUENCE: 38

Val Lys Ile Ile Ser Arg Lys Val Leu Lys Thr Glu Asn Val Tyr Asp
 1               5                  10                 15

Ile Gly Leu Glu Gly Asp His Asn Phe Ile Ile Lys Asp Gly Leu Ile
                20                 25                 30

Ala Ser Asn
        35

<210> SEQ ID NO 39
<211> LENGTH: 102
<212> TYPE: PRT
<213> ORGANISM: Trichodesmium erythraeum

<400> SEQUENCE: 39

Cys Leu Thr Tyr Glu Thr Glu Ile Met Thr Val Glu Tyr Gly Pro Leu
 1               5                  10                 15

Pro Ile Gly Lys Ile Val Glu Tyr Arg Ile Glu Cys Thr Val Tyr Thr
                20                 25                 30

Val Asp Lys Asn Gly Tyr Ile Tyr Thr Gln Pro Ile Ala Gln Trp His
                35                 40                 45

Asn Arg Gly Met Gln Glu Val Tyr Glu Tyr Ser Leu Glu Asp Gly Thr
     50                 55                 60

Val Ile Arg Ala Thr Pro Glu His Lys Phe Met Thr Glu Asp Gly Gln
 65                 70                 75                 80

Met Leu Pro Ile Asp Glu Ile Phe Glu Arg Asn Leu Asp Leu Lys Cys
                 85                 90                 95

Leu Gly Thr Leu Glu Leu
            100

<210> SEQ ID NO 40
<211> LENGTH: 35
<212> TYPE: PRT
<213> ORGANISM: Trichodesmium erythraeum

<400> SEQUENCE: 40

Val Lys Ile Val Ser Arg Lys Leu Ala Lys Thr Glu Asn Val Tyr Asp
 1               5                  10                 15

Ile Gly Val Thr Lys Asp His Asn Phe Val Leu Ala Asn Gly Leu Ile
                20                 25                 30

Ala Ser Asn
        35

<210> SEQ ID NO 41
<211> LENGTH: 102
<212> TYPE: PRT
<213> ORGANISM: Microcoleus sp.
```

<400> SEQUENCE: 41

Cys Leu Ser Tyr Asp Ser Glu Ile Leu Thr Val Glu Tyr Gly Leu Met
1               5                   10                  15

Pro Ile Gly Lys Ile Val Glu Glu Gly Ile Glu Cys Thr Val Tyr Ser
            20                  25                  30

Val Asp Ser His Gly Tyr Leu Tyr Thr Gln Pro Ile Ala Gln Trp His
        35                  40                  45

His Arg Gly Gln Gln Glu Val Phe Glu Tyr Asp Leu Glu Asp Gly Ser
    50                  55                  60

Val Ile Arg Ala Thr Lys Asp His Lys Phe Met Thr Ser Glu Gly Gln
65                  70                  75                  80

Met Leu Ala Ile Asp Glu Ile Phe Glu Arg Gly Leu Glu Leu Lys Gln
                85                  90                  95

Val Lys Arg Ser Gln Pro
            100

<210> SEQ ID NO 42
<211> LENGTH: 35
<212> TYPE: PRT
<213> ORGANISM: Microcoleus sp.

<400> SEQUENCE: 42

Val Lys Ile Val Arg Arg Lys Ser Leu Gly Ile Gln Thr Val Tyr Asp
1               5                   10                  15

Ile Gly Val Glu Arg Asp His Asn Phe Leu Leu Ala Asn Gly Leu Val
            20                  25                  30

Ala Ser Asn
        35

<210> SEQ ID NO 43
<211> LENGTH: 102
<212> TYPE: PRT
<213> ORGANISM: Stanieria cyanosphaera

<400> SEQUENCE: 43

Cys Leu Ser Tyr Asp Thr Glu Ile Leu Thr Val Glu Tyr Gly Ala Met
1               5                   10                  15

Pro Ile Gly Lys Ile Val Lys Glu Gln Ile Glu Cys Asn Val Tyr Thr
            20                  25                  30

Val Asn Gln Asn Gly Phe Ile Tyr Pro Gln Ala Ile Ala Gln Trp His
        35                  40                  45

Glu Arg Gly Lys Gln Glu Ile Phe Glu Tyr Thr Leu Asp Asn Gly Leu
    50                  55                  60

Val Ile Arg Ala Thr Lys Asp His Lys Phe Met Thr Ile Asp Gly Gln
65                  70                  75                  80

Met Leu Pro Ile Asp Glu Ile Phe Glu Arg Gly Leu Glu Leu Gln Arg
                85                  90                  95

Ile Asn Asp Tyr Ser Asn
            100

<210> SEQ ID NO 44
<211> LENGTH: 35
<212> TYPE: PRT
<213> ORGANISM: Stanieria cyanosphaera

<400> SEQUENCE: 44

Val Lys Ile Val Ser Arg Lys Ser Leu Gly Lys Gln Pro Val Tyr Asp

```
                1               5                  10                 15
Ile Gly Val Thr Lys Asp His Asn Phe Leu Leu Ser Asn Gly Val Val
                20                 25                 30

Ala Ser Asn
        35

<210> SEQ ID NO 45
<211> LENGTH: 102
<212> TYPE: PRT
<213> ORGANISM: Calothrix sp.

<400> SEQUENCE: 45

Cys Leu Ser Tyr Asp Thr Glu Ile Leu Thr Trp Glu Tyr Gly Phe Leu
1               5                  10                 15

Lys Ile Gly Glu Ile Val Glu Lys Gln Ile Leu Cys Ser Val Phe Ser
                20                 25                 30

Val Asp Glu Gln Gly Asn Val Tyr Thr Gln Pro Ile Ala Gln Trp His
            35                 40                 45

Asn Arg Gly Leu Gln Glu Leu Phe Ala Tyr Gln Leu Glu Asp Gly Gly
        50                 55                 60

Val Ile Arg Ala Thr Lys Asp His Lys Phe Met Thr Thr Asp Gly Gln
65                  70                 75                  80

Met Leu Ala Ile Asp Glu Ile Phe Glu Arg Gln Leu Asp Leu Phe Gln
                85                 90                 95

Val Lys Gly Leu Pro Glu
            100

<210> SEQ ID NO 46
<211> LENGTH: 35
<212> TYPE: PRT
<213> ORGANISM: Calothrix sp.

<400> SEQUENCE: 46

Val Lys Ile Ile Ser Arg Lys Val Leu Lys Thr Glu Asn Val Tyr Asp
1               5                  10                 15

Ile Gly Leu Glu Gly Asp His Asn Phe Ile Ile Lys Asp Gly Leu Ile
                20                 25                 30

Ala Ser Asn
        35

<210> SEQ ID NO 47
<211> LENGTH: 99
<212> TYPE: PRT
<213> ORGANISM: Cyanobacterium stanieri

<400> SEQUENCE: 47

Cys Leu Ser Tyr Asp Thr Glu Val Leu Thr Val Glu Tyr Gly Val Leu
1               5                  10                 15

Pro Ile Gly Lys Ile Val Glu Glu Gln Ile Gln Cys Thr Val Tyr Ser
                20                 25                 30

Val Asp Gln Tyr Gly Phe Val Tyr Thr Gln Ala Ile Ala Gln Trp His
            35                 40                 45

Asp Arg Gly Glu Gln Glu Val Phe Glu Tyr Glu Leu Glu Asn Gly Ala
        50                 55                 60

Thr Ile Lys Ala Thr Lys Asp His Lys Met Met Thr Ser Asp Gly Gln
65                  70                 75                  80

Met Leu Pro Ile Asp Gln Ile Phe Glu Gln Gly Leu Asp Leu Phe Met
                85                 90                 95
```

Val Ser Phe

<210> SEQ ID NO 48
<211> LENGTH: 35
<212> TYPE: PRT
<213> ORGANISM: Cyanobacterium stanieri

<400> SEQUENCE: 48

Val Lys Ile Val Lys Arg Arg Ser His Gly Ile Gln Lys Val Tyr Asp
1               5                   10                  15

Ile Gly Val Ala Lys Asp His Asn Phe Leu Leu His Asn Gly Leu Val
                20                  25                  30

Ala Ser Asn
        35

<210> SEQ ID NO 49
<211> LENGTH: 99
<212> TYPE: PRT
<213> ORGANISM: Cyanothece sp.

<400> SEQUENCE: 49

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Thr Val Tyr Thr
                20                  25                  30

Val Asp Pro Asn Gly Phe Val Tyr Thr Gln Ala Ile Ala Gln Trp His
            35                  40                  45

Tyr Arg Gly Glu Gln Glu Ile Phe Glu Tyr Tyr Leu Glu Asp Gly Ala
        50                  55                  60

Thr Ile Arg Ala Thr Lys Asp His Lys Phe Met Thr Met Glu Gly Lys
65                  70                  75                  80

Met Leu Pro Ile Asp Glu Ile Phe Glu Asn Asn Leu Asp Leu Lys Gln
                85                  90                  95

Leu Thr Leu

<210> SEQ ID NO 50
<211> LENGTH: 35
<212> TYPE: PRT
<213> ORGANISM: Cyanothece sp.

<400> SEQUENCE: 50

Val Lys Ile Ile Gly Arg Gln Ser Leu Gly Val Gln Lys Val Tyr Asp
1               5                   10                  15

Ile Gly Val Glu Lys Glu His Asn Phe Leu Leu His Asn Gly Leu Ile
                20                  25                  30

Ala Ser Asn
        35

<210> SEQ ID NO 51
<211> LENGTH: 99
<212> TYPE: PRT
<213> ORGANISM: Cyanothece sp.

<400> SEQUENCE: 51

Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
                20                  25                  30

```
Val Asp Lys Asn Gly Phe Val Tyr Thr Gln Asn Ile Ala Gln Trp His
         35                  40                  45

Leu Arg Gly Gln Gln Glu Val Phe Glu Tyr Tyr Leu Asp Asp Gly Ser
 50                  55                  60

Ile Leu Arg Ala Thr Lys Asp His Gln Phe Met Thr Leu Gly Glu
 65                  70                  75                  80

Met Leu Pro Ile His Glu Ile Phe Glu Arg Gly Leu Glu Leu Lys Lys
                 85                  90                  95

Ile Lys Ile

<210> SEQ ID NO 52
<211> LENGTH: 35
<212> TYPE: PRT
<213> ORGANISM: Cyanothece sp.

<400> SEQUENCE: 52

Val Lys Ile Val Ser Tyr Arg Ser Leu Gly Lys Gln Phe Val Tyr Asp
 1               5                  10                  15

Ile Gly Val Ala Gln Asp His Asn Phe Leu Leu Ala Asn Gly Ser Ile
                 20                  25                  30

Ala Ser Asn
         35

<210> SEQ ID NO 53
<211> LENGTH: 101
<212> TYPE: PRT
<213> ORGANISM: Anabaena sp.

<400> SEQUENCE: 53

Cys Leu Ser Tyr Asp Thr Glu Ile Leu Thr Val Glu Tyr Gly Phe Leu
 1               5                  10                  15

Glu Ile Gly Glu Ile Val Glu Lys Gln Ile Glu Cys Lys Val Tyr Thr
                 20                  25                  30

Ile Asp Ser Asn Gly Met Leu Tyr Thr Gln Ser Ile Ala Gln Trp His
         35                  40                  45

Asn Arg Gly Gln Gln Glu Val Tyr Glu Tyr Leu Leu Glu Asn Gly Ala
 50                  55                  60

Ile Ile Arg Ala Thr Lys Asp His Lys Phe Met Thr Glu Ala Gly Gln
 65                  70                  75                  80

Met Leu Pro Ile Asp Glu Ile Phe Ala Gln Gly Leu Asp Leu Leu Gln
                 85                  90                  95

Val Gly Val Ala Glu
            100

<210> SEQ ID NO 54
<211> LENGTH: 35
<212> TYPE: PRT
<213> ORGANISM: Anabaena sp.

<400> SEQUENCE: 54

Val Lys Ile Val Ser Arg Thr Tyr Val Gly Gln Ala Asn Val Tyr Asp
 1               5                  10                  15

Ile Gly Val Glu Ser Asp His Asn Phe Val Ile Lys Asn Gly Phe Ile
                 20                  25                  30

Ala Ser Asn
         35

<210> SEQ ID NO 55
```

-continued

```
<211> LENGTH: 102
<212> TYPE: PRT
<213> ORGANISM: Aphanothece halophytica

<400> SEQUENCE: 55

Cys Leu Ser Tyr Asp Thr Glu Ile Trp Thr Val Glu Tyr Gly Ala Met
1               5                   10                  15

Pro Ile Gly Lys Ile Val Glu Lys Ile Glu Cys Ser Val Tyr Thr
                20                  25                  30

Val Asp Glu Asn Gly Phe Val Tyr Thr Gln Pro Ile Ala Gln Trp His
            35                  40                  45

Pro Arg Gly Gln Gln Glu Ile Ile Glu Tyr Thr Leu Glu Asp Gly Arg
50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met
            100

<210> SEQ ID NO 56
<211> LENGTH: 35
<212> TYPE: PRT
<213> ORGANISM: Aphanothece halophytica

<400> SEQUENCE: 56

Val Lys Ile Ile Lys Arg Gln Ser Leu Gly Arg Gln Asn Val Tyr Asp
1               5                   10                  15

Val Cys Val Glu Thr Asp His Asn Phe Val Leu Ala Asn Gly Cys Val
                20                  25                  30

Ala Ser Asn
        35

<210> SEQ ID NO 57
<211> LENGTH: 102
<212> TYPE: PRT
<213> ORGANISM: Halothece sp.

<400> SEQUENCE: 57

Cys Leu Ser Tyr Asp Thr Glu Ile Trp Thr Val Glu Tyr Gly Ala Met
1               5                   10                  15

Pro Ile Gly Lys Ile Val Glu Lys Ile Glu Cys Ser Val Tyr Thr
                20                  25                  30

Val Asp Glu Asn Gly Phe Val Tyr Thr Gln Pro Ile Ala Gln Trp His
            35                  40                  45

Pro Arg Gly Gln Gln Glu Ile Ile Glu Tyr Thr Leu Glu Asp Gly Arg
50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met
            100

<210> SEQ ID NO 58
<211> LENGTH: 35
<212> TYPE: PRT
<213> ORGANISM: Halothece sp.
```

```
<400> SEQUENCE: 58

Val Lys Ile Ile Lys Arg Gln Ser Leu Gly Arg Gln Asn Val Tyr Asp
1               5                   10                  15

Ile Gly Val Glu Thr Asp His Asn Phe Val Leu Ala Asn Gly Cys Val
            20                  25                  30

Ala Ser Asn
        35

<210> SEQ ID NO 59
<211> LENGTH: 102
<212> TYPE: PRT
<213> ORGANISM: Cyanobacterium aponinum

<400> SEQUENCE: 59

Cys Leu Ser Tyr Asp Thr Glu Ile Leu Thr Val Glu Tyr Gly Ala Ile
1               5                   10                  15

Ser Ile Gly Lys Ile Val Glu Lys Ile Asn Cys Gln Val Tyr Ser
            20                  25                  30

Val Asp Lys Asn Gly Phe Ile Tyr Thr Gln Asn Ile Ala Gln Trp His
            35                  40                  45

Asp Arg Gly Ser Gln Glu Leu Phe Glu Tyr Glu Leu Glu Asp Gly Arg
        50                  55                  60

Ile Ile Lys Ala Thr Lys Asp His Lys Met Met Thr Lys Asp Gly Gln
65                  70                  75                  80

Met Leu Ala Ile Asn Asp Ile Phe Gln Glu Leu Glu Leu Tyr Ser
                85                  90                  95

Val Asp Asp Met Gly Val
            100

<210> SEQ ID NO 60
<211> LENGTH: 35
<212> TYPE: PRT
<213> ORGANISM: Cyanobacterium aponinum

<400> SEQUENCE: 60

Val Lys Ile Val Lys Arg Arg Ser Leu Gly Val Gln Pro Val Tyr Asp
1               5                   10                  15

Ile Gly Val Glu Lys Asp His Asn Phe Ile Leu Ala Asn Gly Leu Val
            20                  25                  30

Ala Ser Asn
        35

<210> SEQ ID NO 61
<211> LENGTH: 98
<212> TYPE: PRT
<213> ORGANISM: Unknown
<220> FEATURE:
<223> OTHER INFORMATION: Description of Unknown:
      Candidatus Atelocyanobacterium thalassa isolate sequence

<400> SEQUENCE: 61

Cys Leu Ser Tyr Asp Thr Lys Val Leu Thr Val Glu Tyr Gly Pro Leu
1               5                   10                  15

Pro Ile Gly Lys Val Val Gln Glu Asn Ile Arg Cys Arg Val Tyr Thr
            20                  25                  30

Thr Asn Asp Gln Gly Leu Ile Tyr Thr Gln Pro Ile Ala Gln Trp His
        35                  40                  45

Asn Arg Gly Lys Gln Glu Ile Phe Glu Tyr His Leu Asp Asp Lys Thr
    50                  55                  60
```

```
Ile Ile Arg Ala Thr Lys Glu His Gln Phe Met Thr Val Asp His Val
 65                  70                  75                  80

Met Met Pro Ile Asp Glu Ile Phe Glu Gln Gly Leu Glu Leu Lys Lys
                 85                  90                  95

Ile Lys

<210> SEQ ID NO 62
<211> LENGTH: 35
<212> TYPE: PRT
<213> ORGANISM: Unknown
<220> FEATURE:
<223> OTHER INFORMATION: Description of Unknown:
      Candidatus Atelocyanobacterium thalassa isolate sequence

<400> SEQUENCE: 62

Leu Lys Ile Ile Arg Arg Lys Ser Leu Gly Met His Glu Val Phe Asp
  1               5                  10                  15

Ile Gly Leu Glu Lys Asp His Asn Phe Val Leu Ser Asn Gly Leu Ile
                 20                  25                  30

Ala Ser Asn
         35

<210> SEQ ID NO 63
<211> LENGTH: 102
<212> TYPE: PRT
<213> ORGANISM: Oscillatoria limnetica

<400> SEQUENCE: 63

Cys Leu Ser Tyr Asn Thr Glu Val Leu Thr Val Glu Tyr Gly Pro Leu
  1               5                  10                  15

Pro Ile Gly Lys Ile Val Asp Glu Gln Ile His Cys Arg Val Tyr Ser
                 20                  25                  30

Val Asp Glu Asn Gly Phe Val Tyr Thr Gln Ala Ile Ala Gln Trp His
                 35                  40                  45

Asp Arg Gly Tyr Gln Glu Ile Phe Ala Tyr Glu Leu Ala Asp Gly Ser
         50                  55                  60

Val Ile Arg Ala Thr Lys Asp His Gln Phe Met Thr Glu Asp Gly Gln
 65                  70                  75                  80

Met Phe Pro Ile Asp Glu Ile Trp Glu Lys Gly Leu Asp Leu Lys Lys
                 85                  90                  95

Leu Pro Thr Val Gln Asp
            100

<210> SEQ ID NO 64
<211> LENGTH: 35
<212> TYPE: PRT
<213> ORGANISM: Oscillatoria limnetica

<400> SEQUENCE: 64

Val Lys Ile Val Arg Arg Gln Ser Leu Gly Val Gln Asn Val Tyr Asp
  1               5                  10                  15

Ile Gly Val Glu Lys Asp His Asn Phe Leu Leu Ala Ser Gly Glu Ile
                 20                  25                  30

Ala Ser Asn
         35

<210> SEQ ID NO 65
<211> LENGTH: 102
<212> TYPE: PRT
```

```
<213> ORGANISM: Unknown
<220> FEATURE:
<223> OTHER INFORMATION: Description of Unknown:
      Cyanobacterium endosymbiont of Epithemia turgida sequence

<400> SEQUENCE: 65

Cys Leu Ser Tyr Asp Thr Glu Val Leu Thr Val Glu Tyr Gly Ala Ile
1               5                   10                  15

Pro Ile Gly Arg Met Val Glu Glu Ser Leu Asp Cys Thr Val Tyr Thr
            20                  25                  30

Val Asp Lys Asn Gly Phe Val Tyr Thr Gln Ser Ile Gln Gln Trp His
        35                  40                  45

Ser Arg Gly Gln Gln Glu Ile Phe Glu Tyr Cys Phe Glu Asp Gly Ser
50                  55                  60

Ile Ile Arg Ala Thr Lys Asp His Lys Phe Met Thr Ala Glu Gly Lys
65                  70                  75                  80

Met Ser Ser Ile His Asp Ile Phe Glu Gln Gly Leu Glu Leu Lys Lys
                85                  90                  95

Ile Ile Pro Trp Ser Gly
            100

<210> SEQ ID NO 66
<211> LENGTH: 35
<212> TYPE: PRT
<213> ORGANISM: Unknown
<220> FEATURE:
<223> OTHER INFORMATION: Description of Unknown:
      Cyanobacterium endosymbiont of Epithemia turgida sequence

<400> SEQUENCE: 66

Ala Lys Ile Ile Ser Cys Lys Ser Leu Gly Lys Gln Ser Val Tyr Asp
1               5                   10                  15

Ile Gly Val Val Gln Asp His Asn Phe Leu Ala Asn Gly Val Val
            20                  25                  30

Ala Ser Asn
        35

<210> SEQ ID NO 67
<211> LENGTH: 98
<212> TYPE: PRT
<213> ORGANISM: Synechococcus sp.

<400> SEQUENCE: 67

Cys Leu Gly Tyr Asp Thr Pro Val Leu Thr Val Glu Tyr Gly Phe Met
1               5                   10                  15

Pro Ile Gly Lys Ile Val Glu Glu Lys Ile Gln Cys His Val Tyr Ser
            20                  25                  30

Val Asp Gln Asn Gly Leu Val Phe Thr Gln Ala Ile Ala Gln Trp His
        35                  40                  45

Asn Arg Gly Gln Gln Glu Val Trp Glu Tyr Asn Leu Asp Asn Gly Asp
50                  55                  60

Ile Val Arg Ala Thr Lys Asp His Lys Phe Met Thr Ile Asp Gly Gln
65                  70                  75                  80

Met Leu Pro Ile Asn Gln Ile Phe Glu Gln Gly Leu Glu Leu Lys Val
                85                  90                  95

Ile Ala

<210> SEQ ID NO 68
<211> LENGTH: 35
```

```
<212> TYPE: PRT
<213> ORGANISM: Synechococcus sp.

<400> SEQUENCE: 68

Val Lys Ile Val Ser Cys Lys Pro Leu Arg Val Gln Thr Val Tyr Asp
1               5                   10                  15

Ile Gly Val Glu Lys Asp His Asn Phe Ile Leu Asp Asn Gly Leu Val
            20                  25                  30

Ala Ser Asn
        35

<210> SEQ ID NO 69
<211> LENGTH: 99
<212> TYPE: PRT
<213> ORGANISM: Dactylococcopsis salina

<400> SEQUENCE: 69

Cys Leu Ser Tyr Asp Thr Glu Val Leu Thr Glu Glu Tyr Gly Ala Ile
1               5                   10                  15

Pro Ile Gly Lys Ile Val Glu Glu Arg Met Asn Cys His Val Tyr Ser
            20                  25                  30

Val Asp Glu Asn Gly Phe Ile Tyr Ser Gln Pro Ile Ala Gln Trp His
        35                  40                  45

Pro Arg Gly Glu Gln Glu Val Val Glu Tyr Thr Leu Glu Asp Gly Lys
    50                  55                  60

Ile Ile Arg Ala Thr Ala Asp His Lys Met Met Thr Glu Thr Gly Glu
65                  70                  75                  80

Met Leu Pro Ile Glu Gln Ile Phe Gln Gln Leu Asp Leu Lys Ile
                85                  90                  95

Ser Asn Gln

<210> SEQ ID NO 70
<211> LENGTH: 35
<212> TYPE: PRT
<213> ORGANISM: Dactylococcopsis salina

<400> SEQUENCE: 70

Val Lys Ile Ile Asn Arg Gln Ser Leu Gly Lys Gln Thr Val Tyr Asp
1               5                   10                  15

Ile Gly Val Glu Lys Asp His Asn Phe Ile Leu Gly Asn Gly Leu Val
            20                  25                  30

Ala Ser Asn
        35

<210> SEQ ID NO 71
<211> LENGTH: 102
<212> TYPE: PRT
<213> ORGANISM: Cylindrospermum stagnale

<400> SEQUENCE: 71

Cys Leu Ser Tyr Asp Thr Glu Ile Leu Thr Val Glu Tyr Gly Phe Ile
1               5                   10                  15

Pro Ile Gly Glu Ile Val Glu Lys Arg Ile Glu Cys Ser Val Tyr Ser
            20                  25                  30

Val Asp Asn His Gly Asn Val Tyr Thr Gln Pro Ile Ala Gln Trp His
        35                  40                  45

Asn Arg Gly Leu Gln Glu Val Phe Glu Tyr Cys Leu Glu Asp Gly Ser
    50                  55                  60
```

Thr Ile Arg Ala Thr Lys Asp His Lys Phe Met Thr Thr Asp Lys Glu
65                  70                  75                  80

Met Leu Pro Ile Asp Glu Ile Phe Glu Arg Gly Leu Asp Leu Leu Arg
                85                  90                  95

Val Glu Gly Leu Pro Ile
            100

<210> SEQ ID NO 72
<211> LENGTH: 35
<212> TYPE: PRT
<213> ORGANISM: Cylindrospermum stagnale

<400> SEQUENCE: 72

Val Lys Ile Ile Met Arg Ser Tyr Val Gly Arg Glu Asn Val Tyr Asp
1               5                   10                  15

Ile Gly Val Glu Arg Asp His Asn Phe Val Ala Lys Asn Gly Leu Ile
            20                  25                  30

Ala Ala Asn
        35

<210> SEQ ID NO 73
<211> LENGTH: 102
<212> TYPE: PRT
<213> ORGANISM: Synechocystis sp.

<400> SEQUENCE: 73

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gly Leu Asp Leu Leu Thr
                85                  90                  95

Leu Glu Asn Ile Lys Gln
            100

<210> SEQ ID NO 74
<211> LENGTH: 35
<212> TYPE: PRT
<213> ORGANISM: Synechocystis sp.

<400> SEQUENCE: 74

Val Lys Val Ile Gly Arg Arg Ser Leu Gly Val Gln Arg Ile Phe Asp
1               5                   10                  15

Ile Gly Leu Pro Gln Asp His Asn Phe Leu Leu Ala Asn Gly Ala Ile
            20                  25                  30

Ala Ala Asn
        35

<210> SEQ ID NO 75
<211> LENGTH: 102
<212> TYPE: PRT
<213> ORGANISM: Geitlerinema sp.

<400> SEQUENCE: 75

```
Cys Leu Ser Tyr Glu Thr Pro Val Met Thr Val Glu Tyr Gly Pro Leu
1               5                   10                  15

Pro Ile Gly Arg Ile Val Glu Glu Gln Leu Asp Cys Thr Val Tyr Ser
            20                  25                  30

Val Asp Glu Gln Gly His Val Tyr Thr Gln Pro Val Ala Gln Trp His
                35                  40                  45

His Arg Gly Leu Gln Glu Val Val Glu Tyr Glu Leu Glu Asp Gly Arg
        50                  55                  60

Arg Leu Arg Ala Thr Ala Asp His Arg Phe Met Thr Glu Thr Gly Glu
65                  70                  75                  80

Met Leu Pro Leu Ala Glu Ile Phe Glu Arg Gly Leu Glu Leu Arg Gln
                85                  90                  95

Val Ala Leu Arg Val Pro
            100
```

<210> SEQ ID NO 76
<211> LENGTH: 35
<212> TYPE: PRT
<213> ORGANISM: Geitlerinema sp.

<400> SEQUENCE: 76

```
Val Lys Ile Val Ser Arg Arg Ser Leu Gly Met Gln Leu Val Tyr Asp
1               5                   10                  15

Ile Gly Val Ala Ala Asp His Asn Phe Val Leu Ala Asp Gly Leu Ile
            20                  25                  30

Ala Ala Asn
        35
```

<210> SEQ ID NO 77
<211> LENGTH: 102
<212> TYPE: PRT
<213> ORGANISM: Synechocystis sp.

<400> SEQUENCE: 77

```
Cys Leu Ser Phe Asp Ala Glu Ile Leu Thr Val Glu Tyr Gly Pro Leu
1               5                   10                  15

Ser Ile Gly Lys Ile Val Gly Glu Glu Ile Asn Cys Ser Val Tyr Ser
            20                  25                  30

Val Asp Pro Gln Gly Arg Ile Tyr Thr Gln Ala Ile Ala Gln Trp His
                35                  40                  45

Asp Arg Gly Val Gln Glu Val Phe Glu Tyr Glu Leu Glu Asp Gly Ser
        50                  55                  60

Val Ile Arg Ala Thr Pro Asp His Arg Phe Leu Thr Thr Asp Tyr Glu
65                  70                  75                  80

Leu Leu Ala Ile Glu Glu Ile Phe Ala Arg Gln Met Asp Leu Leu Thr
                85                  90                  95

Leu Thr Asn Leu Lys Leu
            100
```

<210> SEQ ID NO 78
<211> LENGTH: 35
<212> TYPE: PRT
<213> ORGANISM: Synechocystis sp.

<400> SEQUENCE: 78

```
Val Lys Val Val Arg Arg Ser Leu Gly Met His Arg Val Phe Asp
1               5                   10                  15
```

Ile Gly Leu Ala Gln Asp His Asn Phe Leu Leu Ala Asn Gly Ala Ile
            20                  25                  30

Ala Ala Asn
        35

<210> SEQ ID NO 79
<211> LENGTH: 100
<212> TYPE: PRT
<213> ORGANISM: Microcystis aeruginosa

<400> SEQUENCE: 79

Cys Leu Gly Gly Glu Thr Leu Ile Leu Thr Glu Glu Tyr Gly Leu Leu
1               5                   10                  15

Pro Ile Ala Lys Ile Val Ser Glu Glu Val Asn Cys Thr Val Tyr Ser
            20                  25                  30

Val Asp Lys Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Asn Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser
        100

<210> SEQ ID NO 80
<211> LENGTH: 35
<212> TYPE: PRT
<213> ORGANISM: Microcystis aeruginosa

<400> SEQUENCE: 80

Val Lys Ile Ile Ser Arg Gln Ser Leu Gly Arg Lys Pro Val Tyr Asp
1               5                   10                  15

Ile Gly Val Glu Lys Asp His Asn Phe Leu Leu Gly Asn Gly Leu Ile
            20                  25                  30

Ala Ser Asn
        35

<210> SEQ ID NO 81
<211> LENGTH: 100
<212> TYPE: PRT
<213> ORGANISM: Microcystis aeruginosa

<400> SEQUENCE: 81

Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Cys Thr Val Tyr Thr
            20                  25                  30

Val Asp Gln Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser

<210> SEQ ID NO 82
<211> LENGTH: 35
<212> TYPE: PRT
<213> ORGANISM: Microcystis aeruginosa

<400> SEQUENCE: 82

Val Lys Ile Ile Gly Arg Gln Ser Leu Gly Arg Lys Pro Val Tyr Asp
1               5                   10                  15

Ile Gly Val Glu Lys Asp His Asn Phe Leu Leu Gly Asn Gly Leu Ile
            20                  25                  30

Ala Ser Asn
        35

<210> SEQ ID NO 83
<211> LENGTH: 102
<212> TYPE: PRT
<213> ORGANISM: Acaryochloris marina

<400> SEQUENCE: 83

Cys Leu Ser Tyr Asp Thr Pro Val Leu Thr Leu Glu Tyr Gly Trp Leu
1               5                   10                  15

Pro Ile Gly Gln Val Val Gln Glu Gln Ile Glu Cys Gln Val Phe Ser
            20                  25                  30

Ile Asn Glu Arg Gly His Leu Tyr Thr Gln Pro Ile Ala Gln Trp His
        35                  40                  45

His Arg Gly Gln Gln Glu Val Phe Glu Tyr Thr Leu Ala Asp Gly Ser
    50                  55                  60

Thr Ile Gln Ala Thr Ala Glu His Gln Phe Met Thr Thr Asp Gly Gln
65                  70                  75                  80

Met Tyr Pro Val Gln Gln Ile Phe Glu Glu Gly Leu Ser Leu Lys Gln
                85                  90                  95

Leu Pro Leu Pro Trp Gln
            100

<210> SEQ ID NO 84
<211> LENGTH: 35
<212> TYPE: PRT
<213> ORGANISM: Acaryochloris marina

<400> SEQUENCE: 84

Val Lys Ile Ile Gln Arg Arg Ser Leu Gly Leu Gln Ser Val Tyr Asp
1               5                   10                  15

Ile Gly Leu Ala Gln Asp His Asn Phe Val Met Ala Asn Gly Trp Val
            20                  25                  30

Ala Ala Asn
        35

<210> SEQ ID NO 85
<211> LENGTH: 102
<212> TYPE: PRT
<213> ORGANISM: Leptolyngbya sp.

<400> SEQUENCE: 85

Cys Leu Asp Gly Glu Thr Pro Ile Val Thr Val Glu Tyr Gly Val Leu
1               5                   10                  15

Pro Ile Arg Glu Ile Val Glu Lys Glu Leu Leu Cys Ser Val Tyr Ser
            20                  25                  30

```
Ile Asp Glu Asn Gly Phe Val Tyr Thr Gln Pro Val Glu Gln Trp His
            35                  40                  45

Gln Arg Gly Asp Arg Gln Met Phe Glu Tyr Gln Leu Asp Asn Gly Gly
 50                      55                  60

Val Ile Arg Ala Thr Pro Asp His Lys Phe Leu Thr Thr Glu Gly Glu
 65                  70                  75                  80

Met Val Ala Ile Asp Glu Ile Phe Glu Lys Gly Leu Asn Leu Ala Glu
                 85                  90                  95

Phe Ala Pro Ala Asp Leu
                100

<210> SEQ ID NO 86
<211> LENGTH: 35
<212> TYPE: PRT
<213> ORGANISM: Leptolyngbya sp.

<400> SEQUENCE: 86

Val Lys Ile Leu Arg Arg His Ser Ile Gly Lys Ala Lys Thr Tyr Asp
 1               5                  10                  15

Ile Gly Val Ser Lys Asn His Asn Phe Leu Leu Ala Asn Gly Leu Phe
                 20                  25                  30

Ala Ser Asn
        35

<210> SEQ ID NO 87
<211> LENGTH: 102
<212> TYPE: PRT
<213> ORGANISM: Synechococcus elongatus

<400> SEQUENCE: 87

Cys Leu Ala Ala Asp Thr Glu Val Leu Thr Val Glu Tyr Gly Pro Ile
 1               5                  10                  15

Ala Ile Gly Lys Leu Val Glu Glu Asn Ile Arg Cys Gln Val Tyr Cys
                 20                  25                  30

Cys Asn Pro Asp Gly Tyr Ile Tyr Ser Gln Pro Ile Gly Gln Trp His
            35                  40                  45

Gln Arg Gly Glu Gln Glu Val Ile Glu Tyr Glu Leu Ser Asp Gly Arg
 50                      55                  60

Ile Ile Arg Ala Thr Ala Asp His Arg Phe Met Thr Glu Glu Gly Glu
 65                  70                  75                  80

Met Leu Ser Leu Asp Glu Ile Phe Glu Arg Ser Leu Glu Leu Lys Gln
                 85                  90                  95

Ile Pro Thr Pro Leu Leu
                100

<210> SEQ ID NO 88
<211> LENGTH: 35
<212> TYPE: PRT
<213> ORGANISM: Synechococcus elongatus

<400> SEQUENCE: 88

Val Lys Ile Val Arg Arg Ser Leu Gly Val Gln Pro Val Tyr Asp
 1               5                  10                  15

Leu Gly Val Ala Thr Val His Asn Phe Val Leu Ala Asn Gly Leu Val
                 20                  25                  30

Ala Ser Asn
        35
```

-continued

```
<210> SEQ ID NO 89
<211> LENGTH: 102
<212> TYPE: PRT
<213> ORGANISM: Synechococcus sp.

<400> SEQUENCE: 89

Cys Leu Ser Ala Asp Thr Glu Leu Tyr Thr Val Glu Tyr Gly Trp Leu
1               5                   10                  15

Pro Ile Gly Arg Leu Val Glu Glu Gln Ile Glu Cys Gln Val Leu Ser
            20                  25                  30

Val Asn Ala His Gly His Val Tyr Ser Gln Pro Ile Ala Gln Trp His
        35                  40                  45

Arg Arg Ala Trp Gln Glu Val Phe Glu Tyr Gln Leu Glu Thr Gly Gly
    50                  55                  60

Thr Ile Lys Ala Thr Thr Asp His Gln Phe Leu Thr Thr Asp Gly Gln
65                  70                  75                  80

Met Tyr Arg Ile Glu Asp Ile Phe Gln Arg Gly Leu Asp Leu Trp Gln
                85                  90                  95

Leu Pro Pro Asp Arg Phe
            100

<210> SEQ ID NO 90
<211> LENGTH: 35
<212> TYPE: PRT
<213> ORGANISM: Synechococcus sp.

<400> SEQUENCE: 90

Val Lys Ile Ile Ser Arg Cys Ser Leu Gly Ile Gln Pro Val Tyr Asp
1               5                   10                  15

Ile Gly Val Ala Gln Asp His Asn Phe Val Ile Arg Gly Gly Leu Val
            20                  25                  30

Ala Ser Asn
        35

<210> SEQ ID NO 91
<211> LENGTH: 102
<212> TYPE: PRT
<213> ORGANISM: Thermosynechococcus elongatus

<400> SEQUENCE: 91

Cys Leu Ser Gly Glu Thr Ala Val Met Thr Val Glu Tyr Gly Ala Val
1               5                   10                  15

Pro Ile Arg Arg Leu Val Gln Glu Arg Leu Ser Cys His Val Tyr Ser
            20                  25                  30

Leu Asp Gly Gln Gly His Leu Tyr Thr Gln Pro Ile Ala Gln Trp His
        35                  40                  45

Phe Gln Gly Phe Arg Pro Val Tyr Glu Tyr Gln Leu Glu Asp Gly Ser
    50                  55                  60

Thr Ile Cys Ala Thr Pro Asp His Arg Phe Met Thr Thr Arg Gly Gln
65                  70                  75                  80

Met Leu Pro Ile Glu Gln Ile Phe Gln Glu Gly Leu Glu Leu Trp Gln
                85                  90                  95

Val Ala Ile Ala Pro Arg
            100

<210> SEQ ID NO 92
<211> LENGTH: 35
<212> TYPE: PRT
<213> ORGANISM: Thermosynechococcus elongatus
```

<400> SEQUENCE: 92

Gly Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Asn
        35

<210> SEQ ID NO 93
<211> LENGTH: 102
<212> TYPE: PRT
<213> ORGANISM: Thermosynechococcus sp.

<400> SEQUENCE: 93

Cys Leu Ser Gly Glu Thr Ala Val Met Thr Val Glu Tyr Gly Ala Val
1               5                   10                  15

Pro Ile Arg Arg Leu Val Gln Glu Arg Leu Thr Cys His Val Tyr Ser
            20                  25                  30

Leu Asp Ala Gln Gly His Leu Tyr Thr Gln Pro Ile Ala Gln Trp His
        35                  40                  45

Phe Gln Gly Phe Arg Pro Val Tyr Glu Tyr Gln Leu Glu Asp Gly Ser
    50                  55                  60

Thr Ile Trp Ala Thr Pro Asp His Arg Phe Met Thr Thr Arg Gly Gln
65                  70                  75                  80

Met Leu Pro Ile Glu Gln Ile Phe Gln Glu Gly Leu Glu Leu Trp Gln
                85                  90                  95

Gly Pro Ile Ala Pro Ser
            100

<210> SEQ ID NO 94
<211> LENGTH: 35
<212> TYPE: PRT
<213> ORGANISM: Thermosynechococcus sp.

<400> SEQUENCE: 94

Cys Lys Ile Val Gly Arg Gln Leu Val Gly Trp Gln Ala Val Tyr Asp
1               5                   10                  15

Ile Gly Val Ala Arg Asp His Asn Phe Leu Leu Ala Asn Gly Ala Ile
            20                  25                  30

Ala Ala Asn
        35

<210> SEQ ID NO 95
<211> LENGTH: 102
<212> TYPE: PRT
<213> ORGANISM: Thermosynechococcus vulcanus

<400> SEQUENCE: 95

Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
            20                  25                  30

Leu Asp Pro Gln Gly His Leu Tyr Thr Gln Pro Ile Ala Gln Trp His
        35                  40                  45

Phe Gln Gly Phe Arg Pro Val Tyr Ala Tyr Gln Leu Glu Asp Gly Ser
    50                  55                  60

Thr Ile Cys Ala Thr Pro Asp His Arg Phe Met Thr Thr Ser Gly Gln

```
                65                  70                  75                  80
Met Leu Pro Ile Glu Gln Ile Phe Arg Glu Gly Leu Glu Leu Trp Gln
                    85                  90                  95

Val Ala Ile Ala Pro Pro
                100

<210> SEQ ID NO 96
<211> LENGTH: 35
<212> TYPE: PRT
<213> ORGANISM: Thermosynechococcus vulcanus

<400> SEQUENCE: 96

Cys Lys Ile Val Gly Arg Arg Leu Val Gly Trp Gln Ala Val Tyr Asp
1               5                   10                  15

Ile Gly Leu Ala Gly Asp His Asn Phe Leu Ala Asn Gly Ala Ile
            20                  25                  30

Ala Ala Asn
        35

<210> SEQ ID NO 97
<211> LENGTH: 102
<212> TYPE: PRT
<213> ORGANISM: Synechococcus sp.

<400> SEQUENCE: 97

Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                    85                  90                  95

Trp Ala Val Pro Asp Ser
                100

<210> SEQ ID NO 98
<211> LENGTH: 35
<212> TYPE: PRT
<213> ORGANISM: Synechococcus sp.

<400> SEQUENCE: 98

Val Lys Ile Ile Arg Arg Lys Phe Ile Gly His Ala Pro Thr Tyr Asp
1               5                   10                  15

Ile Gly Leu Ser Gln Asp His Asn Phe Leu Gly Gln Gly Leu Ile
            20                  25                  30

Ala Ala Asn
        35

<210> SEQ ID NO 99
<211> LENGTH: 101
<212> TYPE: PRT
<213> ORGANISM: Scytonema hofmanni

<400> SEQUENCE: 99
```

```
Cys Leu Ser Tyr Asp Thr Glu Val Leu Thr Ala Glu Tyr Gly Phe Leu
1               5                   10                  15

Pro Ile Gly Lys Ile Val Glu Lys Ala Ile Glu Cys Thr Val Tyr Ser
            20                  25                  30

Val Asp Asn Asp Gly Asn Ile Tyr Thr Gln Pro Ile Ala Gln Trp His
        35                  40                  45

Asp Arg Gly Gln Gln Glu Val Phe Glu Tyr Ser Leu Asp Asp Gly Ser
    50                  55                  60

Val Ile Arg Ala Thr Lys Asp His Lys Phe Met Thr Thr Gly Gly Gln
65                  70                  75                  80

Met Leu Pro Ile Asp Glu Ile Phe Glu Arg Gly Leu Asp Leu Met Arg
                85                  90                  95

Ile Asp Ser Leu Pro
            100
```

<210> SEQ ID NO 100
<211> LENGTH: 35
<212> TYPE: PRT
<213> ORGANISM: Scytonema hofmanni

<400> SEQUENCE: 100

```
Val Lys Ile Leu Thr Arg Lys Ser Ile Gly Lys Gln Thr Val Tyr Asp
1               5                   10                  15

Ile Gly Val Glu Arg Asp His Asn Phe Val Ile Lys Asn Gly Leu Val
            20                  25                  30

Ala Ser Asn
        35
```

<210> SEQ ID NO 101
<211> LENGTH: 101
<212> TYPE: PRT
<213> ORGANISM: Westiella intricata

<400> SEQUENCE: 101

```
Cys Leu Ser Tyr Asp Thr Glu Ile Leu Thr Val Glu Tyr Gly Phe Leu
1               5                   10                  15

Pro Ile Gly Glu Ile Val Glu Lys Arg Ile Glu Cys Thr Val Tyr Thr
            20                  25                  30

Val Asp Thr Asn Gly Tyr Val Tyr Thr Gln Ala Ile Ala Gln Trp His
        35                  40                  45

Asn Arg Gly Glu Gln Glu Val Phe Glu Tyr Ala Leu Glu Asp Gly Ser
    50                  55                  60

Ile Ile Arg Ala Thr Lys Asp His Lys Phe Met Thr Ser Glu Gly Gln
65                  70                  75                  80

Met Leu Pro Ile Asp Glu Ile Phe Val Lys Gly Leu Asp Leu Leu Gln
                85                  90                  95

Val Gln Gly Leu Pro
            100
```

<210> SEQ ID NO 102
<211> LENGTH: 35
<212> TYPE: PRT
<213> ORGANISM: Westiella intricata

<400> SEQUENCE: 102

```
Val Lys Ile Ile Thr Arg Lys Phe Leu Gly Ile Gln Asn Val Tyr Asp
1               5                   10                  15

Ile Gly Val Glu Gln Asn His Asn Phe Val Ile Lys Asn Gly Leu Val
```

```
                      20                  25                  30

Ala Ser Asn
        35

<210> SEQ ID NO 103
<211> LENGTH: 101
<212> TYPE: PRT
<213> ORGANISM: Fischerella sp.

<400> SEQUENCE: 103

Cys Leu Ser Tyr Asp Thr Glu Ile Leu Thr Val Glu Tyr Gly Phe Leu
1               5                  10                  15

Pro Ile Gly Glu Ile Val Glu Lys Gly Ile Glu Cys Thr Val Tyr Thr
                20                  25                  30

Val Asp Asn Asn Gly Asn Val Tyr Thr Gln Thr Ile Ala Gln Trp His
            35                  40                  45

Asn Arg Gly Gln Gln Glu Val Phe Glu Tyr Cys Leu Glu Asp Gly Ser
        50                  55                  60

Val Ile Arg Ala Thr Lys Asp His Lys Phe Met Thr Thr Asp Gly Gln
65                  70                  75                  80

Met Leu Pro Ile Asp Glu Ile Phe Ala Arg Gly Leu Asp Leu Leu Gln
                85                  90                  95

Val Lys Asn Leu Pro
            100

<210> SEQ ID NO 104
<211> LENGTH: 35
<212> TYPE: PRT
<213> ORGANISM: Fischerella sp.

<400> SEQUENCE: 104

Val Lys Ile Val Thr Arg Arg Pro Leu Gly Thr Gln Asn Val Tyr Asp
1               5                  10                  15

Ile Gly Val Glu Ser Asp His Asn Phe Val Ile Lys Asn Gly Leu Val
                20                  25                  30

Ala Ser Asn
        35

<210> SEQ ID NO 105
<211> LENGTH: 102
<212> TYPE: PRT
<213> ORGANISM: Mastigocladopsis repens

<400> SEQUENCE: 105

Cys Leu Ser Tyr Asp Thr Glu Val Leu Thr Val Glu Tyr Gly Phe Leu
1               5                  10                  15

Pro Ile Gly Glu Ile Val Glu Lys Ser Ile Glu Cys Ser Val Tyr Thr
                20                  25                  30

Val Asp Ser Asn Gly Asn Val Tyr Thr Gln Pro Ile Ala Gln Trp His
            35                  40                  45

Asn Arg Gly Gln Gln Glu Val Phe Glu Tyr Cys Leu Glu Asp Gly Ser
        50                  55                  60

Ile Ile Arg Ala Thr Lys Asp His Lys Phe Met Thr Ile His Gly Gln
65                  70                  75                  80

Met Leu Pro Ile Asp Glu Ile Phe Glu Arg Gly Leu Glu Leu Met Lys
                85                  90                  95

Ile Gln Gly Leu Pro Glu
            100
```

<210> SEQ ID NO 106
<211> LENGTH: 35
<212> TYPE: PRT
<213> ORGANISM: Mastigocladopsis repens

<400> SEQUENCE: 106

Ala Lys Ile Ile Thr Arg Lys Ser Leu Gly Thr Gln Asn Val Tyr Asp
1               5                   10                  15

Ile Gly Val Glu Arg Asp His Asn Phe Val Thr Arg Asp Gly Phe Ile
            20                  25                  30

Ala Ser Asn
        35

<210> SEQ ID NO 107
<211> LENGTH: 102
<212> TYPE: PRT
<213> ORGANISM: Scytonema hofmanni

<400> SEQUENCE: 107

Cys Leu Ser Tyr Asn Ser Glu Val Leu Thr Val Glu Tyr Gly Phe Leu
1               5                   10                  15

Pro Ile Gly Lys Ile Val Glu Lys Gly Ile Glu Cys Ser Val Tyr Ser
            20                  25                  30

Val Asp Ser Tyr Gly Lys Ile Tyr Thr Gln Val Ile Ala Gln Trp His
        35                  40                  45

Asn Arg Gly Gln Gln Glu Val Phe Glu Tyr Cys Leu Glu Asp Gly Thr
    50                  55                  60

Ile Ile Gln Ala Thr Lys Asp His Lys Phe Met Thr Val Asp Gly Gln
65                  70                  75                  80

Met Leu Pro Ile Asp Glu Ile Phe Glu Arg Gly Leu Asp Leu Met Gln
                85                  90                  95

Val Gln Gly Leu Pro Asp
            100

<210> SEQ ID NO 108
<211> LENGTH: 35
<212> TYPE: PRT
<213> ORGANISM: Scytonema hofmanni

<400> SEQUENCE: 108

Val Lys Ile Ile Thr Arg Lys Ser Leu Gly Thr Gln Asn Val Tyr Asp
1               5                   10                  15

Ile Gly Val Ser Ser Asp His Asn Phe Val Met Lys Asn Gly Leu Ile
            20                  25                  30

Ala Ser Asn
        35

<210> SEQ ID NO 109
<211> LENGTH: 102
<212> TYPE: PRT
<213> ORGANISM: Anabaena sp.

<400> SEQUENCE: 109

Cys Leu Ser Ser Asp Thr Glu Val Leu Thr Val Glu Tyr Gly Leu Ile
1               5                   10                  15

Pro Ile Gly Glu Ile Ile Glu Lys Arg Ile Asp Cys Ser Val Phe Ser
            20                  25                  30

Val Asp Lys Asn Gly Asn Ile Tyr Thr Gln Pro Ile Ala Gln Trp His

```
                35                  40                  45
Asp Arg Gly Ile Gln Glu Leu Tyr Glu Tyr Cys Leu Asp Asp Gly Ser
         50                  55                  60

Thr Ile Arg Ala Thr Lys Asp His Lys Phe Met Thr Thr Ala Gly Glu
 65                  70                  75                  80

Met Leu Pro Ile Asp Glu Ile Phe Glu Arg Gly Leu Asp Leu Leu Lys
                 85                  90                  95

Val His Asn Leu Pro Gln
                100

<210> SEQ ID NO 110
<211> LENGTH: 35
<212> TYPE: PRT
<213> ORGANISM: Anabaena sp.

<400> SEQUENCE: 110

Val Lys Ile Ile Thr Arg Asn Tyr Val Gly Lys Glu Asn Val Tyr Asp
 1               5                  10                  15

Ile Gly Val Glu Arg Asp His Asn Phe Ala Ile Lys Asn Gly Leu Ile
                20                  25                  30

Ala Ser Asn
         35

<210> SEQ ID NO 111
<211> LENGTH: 102
<212> TYPE: PRT
<213> ORGANISM: Fischerella sp.

<400> SEQUENCE: 111

Cys Leu Ser Tyr Asp Thr Glu Val Leu Thr Val Glu Tyr Gly Phe Leu
 1               5                  10                  15

Pro Ile Gly Glu Ile Val Glu Lys Arg Ile Glu Cys Thr Val Tyr Thr
                20                  25                  30

Val Asp His Asn Gly Tyr Val Tyr Thr Gln Pro Ile Ala Gln Trp His
                 35                  40                  45

Asn Arg Gly Tyr Gln Glu Val Phe Glu Tyr Gly Leu Glu Asp Gly Ser
         50                  55                  60

Val Ile Arg Ala Thr Lys Asp His Lys Phe Met Thr Ser Glu Gly Gln
 65                  70                  75                  80

Met Leu Pro Ile Asp Glu Ile Phe Ala Arg Glu Leu Asp Leu Leu Gln
                 85                  90                  95

Val Thr Gly Leu Val Asn
                100

<210> SEQ ID NO 112
<211> LENGTH: 35
<212> TYPE: PRT
<213> ORGANISM: Fischerella sp.

<400> SEQUENCE: 112

Val Lys Ile Val Thr Arg Arg Leu Leu Gly Ile Gln Asn Val Tyr Asp
 1               5                  10                  15

Ile Gly Val Glu Gln Asn His Asn Phe Val Ile Lys Asn Gly Leu Val
                20                  25                  30

Ala Ser Asn
         35

<210> SEQ ID NO 113
```

```
<211> LENGTH: 102
<212> TYPE: PRT
<213> ORGANISM: Calothrix sp.

<400> SEQUENCE: 113

Cys Leu Ser Tyr Asp Thr Glu Ile Phe Thr Val Glu Tyr Gly Phe Leu
1               5                   10                  15

Pro Ile Gly Glu Ile Val Glu Lys Arg Leu Glu Cys Thr Val Leu Thr
            20                  25                  30

Val Asp Asn His Gly Asn Ile Tyr Ser Gln Pro Ile Ala Gln Trp His
        35                  40                  45

His Arg Gly Gln Gln Gln Ile Tyr Glu Tyr Gly Leu Glu Asp Gly Ser
    50                  55                  60

Val Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Leu Gln
                85                  90                  95

Val Thr Asn Leu Asp Asn
            100

<210> SEQ ID NO 114
<211> LENGTH: 35
<212> TYPE: PRT
<213> ORGANISM: Calothrix sp.

<400> SEQUENCE: 114

Val Lys Val Ile Thr Arg Lys Leu Ala Asp Thr Glu Asn Val Tyr Asp
1               5                   10                  15

Ile Gly Val Glu Asn His His Asn Phe Leu Ile Lys Asn Gly Leu Val
            20                  25                  30

Ala Ser Asn
        35

<210> SEQ ID NO 115
<211> LENGTH: 101
<212> TYPE: PRT
<213> ORGANISM: Fischerella thermalis

<400> SEQUENCE: 115

Cys Leu Ser Tyr Glu Thr Glu Ile Leu Thr Val Glu Tyr Gly Phe Leu
1               5                   10                  15

Pro Ile Gly Glu Ile Val Glu Lys Arg Ile Glu Cys Ser Val Tyr Thr
            20                  25                  30

Val Asp Asn Asn Gly Tyr Val Cys Thr Gln Pro Ile Ala Gln Trp His
        35                  40                  45

Asn Arg Gly Tyr Gln Glu Val Phe Glu Tyr Gly Leu Glu Asp Gly Ser
    50                  55                  60

Val Ile Arg Ala Thr Lys Asp His Lys Phe Met Thr Ile Asp Arg Gln
65                  70                  75                  80

Met Leu Pro Ile Asp Glu Ile Phe Ala Arg Gly Leu Asp Leu Leu Gln
                85                  90                  95

Val Thr Gly Leu Pro
            100

<210> SEQ ID NO 116
<211> LENGTH: 35
<212> TYPE: PRT
<213> ORGANISM: Fischerella thermalis
```

```
<400> SEQUENCE: 116

Val Lys Ile Ile Thr Arg Lys Ser Leu Gly Thr Gln Asn Val Tyr Asp
1               5                   10                  15

Ile Gly Val Glu Gln Asn His Asn Phe Val Ile Lys Asn Gly Leu Val
            20                  25                  30

Ala Ser Asn
        35

<210> SEQ ID NO 117
<211> LENGTH: 102
<212> TYPE: PRT
<213> ORGANISM: Cyanobacterium sp.

<400> SEQUENCE: 117

Cys Leu Ser Tyr Asp Thr Glu Ile Leu Thr Val Glu Tyr Gly Phe Leu
1               5                   10                  15

Ser Ile Gly Glu Ile Val Glu Lys Glu Ile Glu Cys Thr Val Tyr Thr
            20                  25                  30

Val Asp Ser Asn Gly Tyr Ile Tyr Thr Gln Pro Ile Ala Gln Trp His
        35                  40                  45

Glu Gln Gly Glu Gln Ile Phe Glu Tyr Ser Leu Glu Asp Gly Ser
    50                  55                  60

Thr Ile Arg Ala Thr Lys Asp His Lys Phe Met Thr Ile Glu Gly Glu
65                  70                  75                  80

Met Leu Pro Ile Asp Gln Ile Phe Ala Arg Gln Leu Asp Leu Met Gln
                85                  90                  95

Ile Thr Gly Leu Pro Gln
            100

<210> SEQ ID NO 118
<211> LENGTH: 35
<212> TYPE: PRT
<213> ORGANISM: Cyanobacterium sp.

<400> SEQUENCE: 118

Val Lys Ile Ser Thr Lys Lys Ser Leu Gly Lys Gln Lys Val Tyr Asp
1               5                   10                  15

Ile Gly Val Val Arg Asp His Asn Phe Ile Ile Lys Asn Gly Phe Val
            20                  25                  30

Ala Ser Asn
        35

<210> SEQ ID NO 119
<211> LENGTH: 101
<212> TYPE: PRT
<213> ORGANISM: Fischerella sp.

<400> SEQUENCE: 119

Cys Leu Ser Tyr Asp Thr Glu Val Leu Thr Val Glu Tyr Gly Phe Leu
1               5                   10                  15

Pro Ile Gly Glu Ile Val Glu Lys Arg Ile Glu Cys Thr Val Tyr Thr
            20                  25                  30

Val Asp Thr Asn Gly Tyr Val Tyr Thr Gln Ala Ile Ala Gln Trp His
        35                  40                  45

Asn Arg Asp Glu Gln Glu Val Phe Glu Tyr Ala Leu Glu Asp Gly Ser
    50                  55                  60

Ile Ile Arg Ala Thr Lys Asp His Lys Phe Met Thr Ser Glu Gly Gln
65                  70                  75                  80
```

```
Met Leu Pro Ile Asp Glu Ile Phe Ala Lys Gly Leu Asp Leu Leu Gln
                85                  90                  95

Val Gln Gly Leu Pro
            100

<210> SEQ ID NO 120
<211> LENGTH: 35
<212> TYPE: PRT
<213> ORGANISM: Fischerella sp.

<400> SEQUENCE: 120

Val Lys Ile Val Thr Arg Lys Phe Leu Gly Ile Gln Asn Val Tyr Asp
1               5                   10                  15

Ile Gly Val Glu Gln Asn His Asn Phe Val Ile Lys Asn Gly Leu Val
            20                  25                  30

Ala Ser Asn
        35

<210> SEQ ID NO 121
<211> LENGTH: 102
<212> TYPE: PRT
<213> ORGANISM: Fischerella muscicola

<400> SEQUENCE: 121

Cys Leu Ser Tyr Glu Thr Glu Ile Leu Thr Val Glu Tyr Gly Phe Leu
1               5                   10                  15

Pro Ile Gly Glu Ile Val Glu Lys Arg Ile Glu Cys Ser Val Tyr Thr
            20                  25                  30

Val Asp Asn Asn Gly Tyr Val Cys Thr Gln Thr Ile Ala Gln Trp His
            35                  40                  45

Asn Arg Gly Tyr Gln Glu Val Phe Glu Tyr Gly Leu Glu Asp Gly Ser
        50                  55                  60

Val Ile Arg Ala Thr Lys Asp His Lys Phe Met Thr Ile Asp Arg Gln
65                  70                  75                  80

Met Leu Pro Ile Asp Glu Ile Phe Ala Arg Gly Leu Asp Leu Leu Gln
                85                  90                  95

Val Lys Gly Leu Pro Glu
            100

<210> SEQ ID NO 122
<211> LENGTH: 35
<212> TYPE: PRT
<213> ORGANISM: Fischerella muscicola

<400> SEQUENCE: 122

Val Lys Ile Ile Thr Arg Gln Ser Leu Gly Thr Gln Asn Val Tyr Asp
1               5                   10                  15

Ile Gly Val Glu Gln Asn His Asn Phe Val Ile Lys Asn Gly Leu Val
            20                  25                  30

Ala Ser Asn
        35

<210> SEQ ID NO 123
<211> LENGTH: 102
<212> TYPE: PRT
<213> ORGANISM: Fischerella muscicola

<400> SEQUENCE: 123

Cys Leu Ser Tyr Asp Thr Glu Val Leu Thr Val Glu Tyr Gly Phe Leu
```

```
                1               5                  10                  15
            Pro Ile Gly Glu Ile Val Glu Lys Thr Ile Glu Cys Asn Val Phe Thr
                                20                  25                  30

Val Asp Ser Asn Gly Tyr Val Tyr Thr Gln Pro Ile Ala Gln Trp His
                        35                  40                  45

Asn Arg Gly Tyr Gln Glu Val Phe Glu Tyr Gly Leu Glu Asp Gly Ser
                    50                  55                  60

Val Ile Arg Ala Thr Lys Asp His Lys Phe Met Thr Ser Glu Gly Lys
            65                  70                  75                  80

Met Leu Pro Ile Asp Glu Ile Phe Ala Arg Glu Leu Asp Leu Leu Gln
                                85                  90                  95

Val Thr Gly Leu Ile Asn
                        100

<210> SEQ ID NO 124
<211> LENGTH: 35
<212> TYPE: PRT
<213> ORGANISM: Fischerella muscicola

<400> SEQUENCE: 124

Val Lys Ile Val Thr Arg Lys Phe Leu Gly Ile Gln Asn Val Tyr Asp
            1               5                  10                  15

Ile Gly Val Glu Gln Asn His Asn Phe Val Ile Lys Asn Gly Leu Val
                        20                  25                  30

Ala Ser Asn
                    35

<210> SEQ ID NO 125
<211> LENGTH: 102
<212> TYPE: PRT
<213> ORGANISM: Lyngbya aestuarii

<400> SEQUENCE: 125

Cys Leu Ser Tyr Asp Thr Glu Ile Leu Thr Val Glu Tyr Gly Ala Ile
            1               5                  10                  15

Pro Ile Gly Lys Val Val Asp Glu Lys Ile Glu Cys Thr Val Tyr Ser
                                20                  25                  30

Val Asp Lys Asn Gly Leu Ile Tyr Thr Gln Pro Ile Ala Gln Trp His
                        35                  40                  45

Asn Arg Gly Lys Gln Glu Val Phe Glu Tyr Ser Leu Glu Asp Gly Ser
                    50                  55                  60

Thr Ile Arg Ala Thr Lys Asp His Lys Phe Met Thr Met Asp Asn Gln
            65                  70                  75                  80

Met Leu Pro Ile Asp Glu Ile Leu Glu Lys Gly Leu Glu Leu Lys Gln
                                85                  90                  95

Val Asn Ala Asp Ser Val
                        100

<210> SEQ ID NO 126
<211> LENGTH: 35
<212> TYPE: PRT
<213> ORGANISM: Lyngbya aestuarii

<400> SEQUENCE: 126

Val Lys Ile Val Ser Arg Lys Ser Leu Asp Ser Gln Thr Val Tyr Asp
            1               5                  10                  15

Ile Gly Val Glu Thr Asp His Asn Phe Leu Leu Ala Asn Gly Ser Val
                        20                  25                  30
```

Ala Ser Asn
        35

<210> SEQ ID NO 127
<211> LENGTH: 100
<212> TYPE: PRT
<213> ORGANISM: Microchaete sp.

<400> SEQUENCE: 127

Cys Leu Ser Tyr Lys Thr Gln Val Leu Thr Val Glu Tyr Gly Leu Leu
1               5                   10                  15

Ala Ile Gly Glu Ile Val Glu Lys Asn Ile Glu Cys Ser Val Phe Ser
            20                  25                  30

Val Asp Ile His Gly Asn Val Tyr Thr Gln Pro Ile Ala Gln Trp His
        35                  40                  45

His Arg Gly Gln Gln Glu Val Phe Glu Tyr Gly Leu Glu Asp Gly Ser
    50                  55                  60

Ile Ile Arg Ala Thr Lys Asp His Lys Phe Met Thr Thr Gln Gly Glu
65                  70                  75                  80

Met Leu Pro Ile Asp Glu Ile Phe Ala Arg Gly Leu Asp Leu Leu Gln
                85                  90                  95

Val Lys Gly Val
        100

<210> SEQ ID NO 128
<211> LENGTH: 35
<212> TYPE: PRT
<213> ORGANISM: Microchaete sp.

<400> SEQUENCE: 128

Val Lys Ile Ile Thr Arg Lys Tyr Ile Gly Lys Glu Asn Val Tyr Asp
1               5                   10                  15

Ile Gly Val Glu Gln Asp His Asn Phe Ala Ile Lys Asn Gly Leu Ile
            20                  25                  30

Ala Ala Asn
        35

<210> SEQ ID NO 129
<211> LENGTH: 102
<212> TYPE: PRT
<213> ORGANISM: Leptolyngbya sp.

<400> SEQUENCE: 129

Cys Leu Ser Tyr Asp Thr Glu Ile Leu Thr Val Glu Tyr Gly Ala Leu
1               5                   10                  15

Pro Ile Gly Lys Ile Val Glu Asn Gln Met Ile Cys Ser Val Tyr Ser
            20                  25                  30

Ile Asp Asn Asn Gly Tyr Ile Tyr Ile Gln Pro Ile Ala Gln Trp His
        35                  40                  45

Asn Arg Gly Gln Gln Glu Val Phe Glu Tyr Ile Leu Glu Asp Gly Ser
    50                  55                  60

Ile Ile Arg Ser Thr Lys Asp His Lys Phe Met Thr Lys Gly Gly Glu
65                  70                  75                  80

Met Leu Pro Ile Asp Glu Ile Phe Glu Arg Gly Leu Glu Leu Ala Gln
                85                  90                  95

Val Thr Arg Leu Glu Gln
        100

<210> SEQ ID NO 130
<211> LENGTH: 35
<212> TYPE: PRT
<213> ORGANISM: Leptolyngbya sp.

<400> SEQUENCE: 130

Val Lys Ile Ile Ser Arg Arg Ser Val Gly Val Gln Ser Val Tyr Asp
1               5                   10                  15

Ile Gly Val Lys Gln Asp His Asn Phe Phe Leu Arg Asn Gly Leu Ile
            20                  25                  30

Ala Ser Asn
        35

<210> SEQ ID NO 131
<211> LENGTH: 102
<212> TYPE: PRT
<213> ORGANISM: Crocosphaera watsonii

<400> SEQUENCE: 131

Cys Leu Ser Tyr Asp Thr Glu Ile Leu Thr Val Glu Tyr Gly Ala Met
1               5                   10                  15

Tyr Ile Gly Lys Ile Val Glu Glu Asn Ile Asn Cys Thr Val Tyr Thr
            20                  25                  30

Val Asp Lys Asn Gly Phe Val Tyr Thr Gln Thr Ile Ala Gln Trp His
        35                  40                  45

Asn Arg Gly Glu Gln Glu Ile Phe Gly Tyr Asp Leu Glu Asp Gly Ser
    50                  55                  60

Lys Ile Lys Ala Thr Lys Asp His Lys Phe Met Thr Ile Asp Gly Glu
65                  70                  75                  80

Met Leu Pro Ile Asp Glu Ile Phe Glu Lys Asn Leu Asp Leu Lys Gln
                85                  90                  95

Val Val Ser His Pro Asp
            100

<210> SEQ ID NO 132
<211> LENGTH: 35
<212> TYPE: PRT
<213> ORGANISM: Crocosphaera watsonii

<400> SEQUENCE: 132

Val Lys Ile Ile Gly Cys Arg Ser Leu Gly Thr Gln Lys Val Tyr Asp
1               5                   10                  15

Ile Gly Val Glu Lys Asp His Asn Phe Leu Leu Ala Asn Gly Ser Ile
            20                  25                  30

Ala Ser Asn
        35

<210> SEQ ID NO 133
<211> LENGTH: 100
<212> TYPE: PRT
<213> ORGANISM: Coleofasciculus chthonoplastes

<400> SEQUENCE: 133

Cys Leu Ser Tyr Asp Thr Gln Ile Leu Thr Val Glu Tyr Gly Ala Val
1               5                   10                  15

Ala Ile Gly Glu Ile Val Glu Lys Gln Ile Glu Cys Thr Val Tyr Ser
            20                  25                  30

Val Asp Glu Asn Gly Tyr Val Tyr Thr Gln Pro Ile Ala Gln Trp His
        35                  40                  45

Asn Arg Gly Glu Gln Glu Val Phe Glu Tyr Leu Leu Glu Asp Gly Ala
            50                  55                  60

Thr Ile Arg Ala Thr Lys Asp His Lys Phe Met Thr Asp Glu Asp Gln
 65                  70                  75                  80

Met Leu Pro Ile Asp Gln Ile Phe Glu Gln Gly Leu Glu Leu Lys Gln
                    85                  90                  95

Val Glu Val Leu
            100

<210> SEQ ID NO 134
<211> LENGTH: 35
<212> TYPE: PRT
<213> ORGANISM: Coleofasciculus chthonoplastes

<400> SEQUENCE: 134

Val Lys Ile Ile Gly Arg Lys Pro Leu Gly Thr Gln Pro Val Tyr Asp
 1               5                  10                  15

Ile Gly Val Glu Arg Asp His Asn Phe Leu Leu Phe Asn Gly Ser Val
                20                  25                  30

Ala Ser Asn
        35

<210> SEQ ID NO 135
<211> LENGTH: 98
<212> TYPE: PRT
<213> ORGANISM: Chroococcidiopsis sp.

<400> SEQUENCE: 135

Cys Leu Ser Tyr Asp Thr Glu Val Leu Thr Val Glu Tyr Gly Ala Ile
 1               5                  10                  15

Pro Ile Gly Lys Ile Val Glu Glu Lys Ile Ala Cys Asn Val Tyr Ser
                20                  25                  30

Val Asp Lys Asn Gly Phe Val Tyr Thr Gln Pro Ile Ala Gln Tyr His
            35                  40                  45

Asp Arg Gly Ile Gln Glu Val Phe Glu Tyr Arg Leu Glu Asn Gly Ser
        50                  55                  60

Val Ile Arg Ala Thr Lys Asp His Lys Met Met Thr Ala Asp Gly Gln
 65                  70                  75                  80

Met Leu Pro Ile Asp Glu Ile Phe Lys Gln Asn Leu Asp Leu Lys Gln
                85                  90                  95

Leu Asn

<210> SEQ ID NO 136
<211> LENGTH: 35
<212> TYPE: PRT
<213> ORGANISM: Chroococcidiopsis sp.

<400> SEQUENCE: 136

Val Lys Ile Ile Ser Arg Gln Ser Leu Gly Lys Gln Ser Val Phe Asp
 1               5                  10                  15

Ile Gly Val Ala Lys Asp His Asn Phe Leu Leu Ala Asn Gly Leu Val
                20                  25                  30

Ala Ser Asn
        35

<210> SEQ ID NO 137
<211> LENGTH: 97
<212> TYPE: PRT

<213> ORGANISM: Aphanizomenon flos-aquae

<400> SEQUENCE: 137

Cys Leu Ser Tyr Asp Thr Glu Ile Leu Thr Val Glu Tyr Gly Phe Leu
1               5                   10                  15

Gln Ile Gly Glu Ile Val Glu Lys Gln Ile Glu Cys Lys Val Tyr Thr
            20                  25                  30

Val Asp Ser Asn Gly Ile Leu Tyr Thr Gln Ser Ile Ala Gln Trp His
        35                  40                  45

Asn Arg Gly Gln Gln Glu Val Tyr Glu Tyr Leu Leu Glu Asn Gly Ala
    50                  55                  60

Ile Ile Arg Ala Thr Lys Asp His Lys Phe Met Thr Glu Glu Gly Gln
65                  70                  75                  80

Met Leu Pro Ile Asp Glu Ile Phe Ser Gln Gly Leu Asp Leu Leu Gln
                85                  90                  95

Val

<210> SEQ ID NO 138
<211> LENGTH: 35
<212> TYPE: PRT
<213> ORGANISM: Aphanizomenon flos-aquae

<400> SEQUENCE: 138

Val Lys Ile Ile Ser Arg Thr Tyr Val Gly Gln Ala Asn Val Tyr Asp
1               5                   10                  15

Ile Gly Val Glu Asn Asp His Asn Phe Val Ile Lys Asn Gly Phe Ile
            20                  25                  30

Ala Ala Asn
        35

<210> SEQ ID NO 139
<211> LENGTH: 102
<212> TYPE: PRT
<213> ORGANISM: Raphidiopsis brookii

<400> SEQUENCE: 139

Cys Leu Ser Tyr Glu Thr Glu Val Leu Thr Leu Glu Tyr Gly Phe Leu
1               5                   10                  15

Pro Ile Gly Glu Ile Val Asp Lys Gln Met Val Cys Thr Val Phe Ser
            20                  25                  30

Val Asn Asp Ser Gly Asn Val Tyr Thr Gln Pro Ile Gly Gln Trp His
        35                  40                  45

Asp Arg Gly Val Gln Glu Leu Tyr Glu Tyr Cys Leu Asp Asp Gly Ser
    50                  55                  60

Thr Ile Arg Ala Thr Lys Asp His Lys Phe Met Thr Thr Gln Gly Glu
65                  70                  75                  80

Met Val Pro Ile Asp Glu Ile Phe His Gln Gly Trp Glu Leu Val Gln
                85                  90                  95

Val Ser Gly Thr Met Asn
        100

<210> SEQ ID NO 140
<211> LENGTH: 35
<212> TYPE: PRT
<213> ORGANISM: Raphidiopsis brookii

<400> SEQUENCE: 140

Val Lys Ile Val Ser Arg Arg Tyr Leu Gly Lys Ala Asp Val Tyr Asp

```
                1               5                   10                  15

Ile Gly Val Ala Lys Asp His Asn Phe Ile Ile Lys Asn Gly Leu Val
                20                  25                  30

Ala Ser Asn
        35

<210> SEQ ID NO 141
<211> LENGTH: 99
<212> TYPE: PRT
<213> ORGANISM: Cyanothece sp.

<400> SEQUENCE: 141

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Ser Val Tyr Thr
                20                  25                  30

Val Asn Lys Asn Gly Phe Val Tyr Thr Gln Ser Ile Ala Gln Trp His
                35                  40                  45

His Arg Gly Glu Gln Glu Val Phe Glu Tyr Tyr Leu Glu Asp Gly Glu
        50                  55                  60

Thr Ile Arg Ala Thr Lys Asp His Lys Phe Met Thr Thr Glu Gly Lys
65                  70                  75                  80

Met Leu Pro Ile Asp Glu Ile Phe Glu Asn Asn Leu Asp Leu Lys Lys
                85                  90                  95

Leu Thr Val

<210> SEQ ID NO 142
<211> LENGTH: 35
<212> TYPE: PRT
<213> ORGANISM: Cyanothece sp.

<400> SEQUENCE: 142

Val Lys Ile Ile Glu Arg Arg Ser Leu Gly Lys Gln Asn Val Tyr Asp
1               5                   10                  15

Ile Gly Val Glu Lys Asp His Asn Phe Leu Leu Ser Asn Asn Leu Ile
                20                  25                  30

Ala Ser Asn
        35

<210> SEQ ID NO 143
<211> LENGTH: 100
<212> TYPE: PRT
<213> ORGANISM: Xenococcus sp.

<400> SEQUENCE: 143

Cys Leu Ser Ala Asp Thr Glu Val Leu Thr Val Glu Tyr Gly Ala Ile
1               5                   10                  15

Ser Ile Gly Lys Ile Val Glu Glu Arg Ile Glu Cys Thr Val Tyr Ser
                20                  25                  30

Val Asp Ala Asn Gly Phe Val Tyr Thr Gln Glu Ile Ala Gln Trp His
                35                  40                  45

Asn Arg Gly Glu Gln Glu Val Phe Glu Tyr Met Leu Asp Asp Gly Ser
        50                  55                  60

Val Ile Arg Ala Thr Lys Asp His Lys Leu Met Thr Ile Asp Gly Gln
65                  70                  75                  80

Met Val Ala Ile Asp Glu Ile Phe Ser Gln Gly Leu Glu Leu Lys Gln
                85                  90                  95
```

-continued

Val Leu Gly Leu
            100

<210> SEQ ID NO 144
<211> LENGTH: 35
<212> TYPE: PRT
<213> ORGANISM: Xenococcus sp.

<400> SEQUENCE: 144

Val Lys Ile Val Ser Arg Lys Ser Leu Gly Thr Gln Thr Val Tyr Asp
1               5                   10                  15

Leu Gly Val Ala Arg Asp His Asn Phe Leu Ala Asn Gly Thr Val
            20                  25                  30

Ala Ser Asn
        35

<210> SEQ ID NO 145
<211> LENGTH: 100
<212> TYPE: PRT
<213> ORGANISM: Pleurocapsa sp.

<400> SEQUENCE: 145

Cys Leu Ser Tyr Asp Thr Glu Ile Tyr Thr Val Glu Tyr Gly Ala Leu
1               5                   10                  15

Pro Ile Gly Lys Ile Val Glu Ser Arg Ile Lys Cys Thr Val Leu Thr
            20                  25                  30

Val Asp Lys Asn Gly Leu Val Tyr Ser Gln Pro Ile Val Gln Trp His
            35                  40                  45

Asp Arg Gly Ile Gln Glu Val Phe Glu Tyr Thr Leu Asp Asn Gly Ala
50                  55                  60

Thr Ile Arg Ala Thr Lys Asp His Lys Phe Met Thr Val Glu Gly Gln
65                  70                  75                  80

Met Leu Pro Ile Asp Glu Ile Phe Glu Leu Gly Leu Glu Leu Lys Glu
                85                  90                  95

Ile Gln Gln Phe
            100

<210> SEQ ID NO 146
<211> LENGTH: 35
<212> TYPE: PRT
<213> ORGANISM: Pleurocapsa sp.

<400> SEQUENCE: 146

Val Lys Ile Ile Ser Arg Gln Ser Leu Gly Lys Gln Ser Val Tyr Asp
1               5                   10                  15

Ile Gly Val Ala Lys Asp His Asn Phe Leu Ala Asn Gly Met Val
            20                  25                  30

Ala Ser Asn
        35

<210> SEQ ID NO 147
<211> LENGTH: 102
<212> TYPE: PRT
<213> ORGANISM: Cylindrospermopsis raciborskii

<400> SEQUENCE: 147

Cys Leu Ser Tyr Glu Thr Glu Val Leu Thr Leu Glu Tyr Gly Phe Val
1               5                   10                  15

Pro Ile Gly Glu Ile Val Asn Lys Gln Met Val Cys Thr Val Phe Ser
            20                  25                  30

```
Leu Asn Asp Ser Gly Asn Val Tyr Thr Gln Pro Ile Gly Gln Trp His
        35                  40                  45

Asp Arg Gly Val Gln Asp Leu Tyr Glu Tyr Cys Leu Asp Asp Gly Ser
 50                  55                  60

Thr Ile Arg Ala Thr Lys Asp His Lys Phe Met Thr Thr Gln Gly Glu
 65                  70                  75                  80

Met Val Pro Ile Asp Glu Ile Phe His Gln Gly Trp Glu Leu Val Gln
                 85                  90                  95

Val Ser Gly Ile Ser Lys
                100

<210> SEQ ID NO 148
<211> LENGTH: 35
<212> TYPE: PRT
<213> ORGANISM: Cylindrospermopsis raciborskii

<400> SEQUENCE: 148

Val Lys Ile Val Ser Arg Arg Tyr Leu Gly Lys Ala Asp Val Tyr Asp
 1               5                  10                  15

Ile Gly Val Ala Lys Asp His Asn Phe Ile Ile Lys Asn Gly Leu Val
                20                  25                  30

Ala Ser Asn
        35

<210> SEQ ID NO 149
<211> LENGTH: 94
<212> TYPE: PRT
<213> ORGANISM: Spirulina major

<400> SEQUENCE: 149

Cys Leu Thr Tyr Asp Thr Leu Val Leu Thr Val Glu Tyr Gly Pro Val
 1               5                  10                  15

Pro Ile Gly Lys Leu Val Glu Ala Gln Ile Asn Cys Gln Val Tyr Ser
                20                  25                  30

Val Asp Ala Asn Gly Phe Ile Tyr Thr Gln Ala Ile Ala Gln Trp His
        35                  40                  45

Asp Arg Gly Gln Arg Gln Val Tyr Glu Tyr Thr Leu Glu Asp Gly Ser
 50                  55                  60

Thr Ile Arg Ala Thr Pro Asp His Lys Phe Met Thr Ala Thr Gly Glu
 65                  70                  75                  80

Met Leu Pro Ile Asp Gln Ile Phe Glu Gln Gly Leu Asp Leu
                 85                  90

<210> SEQ ID NO 150
<211> LENGTH: 35
<212> TYPE: PRT
<213> ORGANISM: Spirulina major

<400> SEQUENCE: 150

Val Lys Ile Ile His Arg Arg Ala Leu Pro Pro Gln Ser Val Tyr Asp
 1               5                  10                  15

Ile Gly Val Glu Arg Asp His Asn Phe Leu Leu Pro Ser Gly Trp Val
                20                  25                  30

Ala Ser Asn
        35

<210> SEQ ID NO 151
<211> LENGTH: 96
```

```
<212> TYPE: PRT
<213> ORGANISM: Spirulina subsalsa

<400> SEQUENCE: 151

Cys Leu Ser Tyr Asp Thr Lys Ile Ile Thr Val Glu Tyr Gly Ala Ile
1               5                   10                  15

Ala Ile Gly Thr Ile Val Glu Gln Gly Leu His Cys His Val Tyr Ser
            20                  25                  30

Val Asp Pro Asn Gly Phe Ile Tyr Thr Gln Pro Ile Ala Gln Trp His
        35                  40                  45

Gln Arg Gly Glu Gln Glu Val Phe Ala Tyr Thr Leu Glu Asn Gly Ser
    50                  55                  60

Ile Ile Gln Ala Thr Lys Asp His Lys Phe Met Thr Gln Gln Gly Lys
65                  70                  75                  80

Met Leu Pro Ile Asp Thr Ile Phe Glu Gln Gly Leu Asp Leu Leu Gln
                85                  90                  95

<210> SEQ ID NO 152
<211> LENGTH: 35
<212> TYPE: PRT
<213> ORGANISM: Spirulina subsalsa

<400> SEQUENCE: 152

Val Lys Ile Ile Lys Arg Thr Ser Leu Gly Val Arg Pro Val Tyr Asp
1               5                   10                  15

Ile Gly Val Ile Gln Asp His Asn Phe Leu Glu Asn Gly Leu Val
            20                  25                  30

Ala Ser Asn
        35

<210> SEQ ID NO 153
<211> LENGTH: 100
<212> TYPE: PRT
<213> ORGANISM: Microcystis aeruginosa

<400> SEQUENCE: 153

Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Cys Thr Val Tyr Ser
            20                  25                  30

Val Asp Lys Asn Gly Phe Ile Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser
        100

<210> SEQ ID NO 154
<211> LENGTH: 35
<212> TYPE: PRT
<213> ORGANISM: Microcystis aeruginosa

<400> SEQUENCE: 154

Val Lys Ile Ile Ser Arg Gln Phe Leu Gly Arg Lys Pro Val Tyr Asp
1               5                   10                  15
```

```
Ile Gly Val Glu Lys Asp His Asn Phe Leu Leu Gly Asn Gly Leu Ile
            20                  25                  30

Ala Ser Asn
        35

<210> SEQ ID NO 155
<211> LENGTH: 95
<212> TYPE: PRT
<213> ORGANISM: Myxosarcina sp.

<400> SEQUENCE: 155

Cys Leu Ser Tyr Asp Thr Glu Val Leu Thr Leu Lys Tyr Gly Ala Leu
1               5                   10                  15

Pro Ile Gly Glu Ile Val Glu Lys Arg Ile Asn Cys His Val Tyr Thr
            20                  25                  30

Arg Ala Glu Ser Gly Phe Phe Tyr Ile Gln Ser Ile Glu Gln Trp His
        35                  40                  45

Asp Arg Gly Glu Gln Glu Val Phe Glu Tyr Thr Leu Glu Asn Gly Ala
    50                  55                  60

Thr Ile Lys Ala Thr Lys Asp His Lys Phe Met Thr Ser Gly Gly Gln
65                  70                  75                  80

Met Leu Pro Ile Asp Glu Ile Phe Glu Arg Gly Leu Asp Leu Leu
                85                  90                  95

<210> SEQ ID NO 156
<211> LENGTH: 35
<212> TYPE: PRT
<213> ORGANISM: Myxosarcina sp.

<400> SEQUENCE: 156

Val Lys Ile Val Ser Arg Lys Ser Leu Gly Lys Gln Pro Val Tyr Asp
1               5                   10                  15

Leu Gly Val Ala Lys Asp His Asn Phe Leu Leu Ala Asn Gly Thr Val
            20                  25                  30

Ala Ser Asn
        35

<210> SEQ ID NO 157
<211> LENGTH: 101
<212> TYPE: PRT
<213> ORGANISM: Leptolyngbya sp.

<400> SEQUENCE: 157

Cys Leu Ser Ala Asp Thr Gln Leu Leu Thr Val Glu Tyr Gly Pro Leu
1               5                   10                  15

Glu Ile Gly Arg Ile Val Glu Glu Gln Ile Ala Cys His Val Tyr Ser
            20                  25                  30

Val Asp Ala Asn Gly Phe Val Tyr Thr Gln Pro Ile Ala Gln Trp His
        35                  40                  45

Ser Arg Gly Glu Gln Glu Ile Phe Glu Tyr Gln Leu Glu Asp Gly Arg
    50                  55                  60

Thr Leu Arg Ala Thr Ala Asp His Lys Phe Met Thr Thr Thr Gly Glu
65                  70                  75                  80

Met Gly Arg Ile Asn Asp Ile Phe Glu Gln Gly Leu Asp Leu Lys Gln
                85                  90                  95

Ile Asp Leu Pro Gln
            100
```

<210> SEQ ID NO 158
<211> LENGTH: 35
<212> TYPE: PRT
<213> ORGANISM: Leptolyngbya sp.

<400> SEQUENCE: 158

Val Lys Val Val Ser Arg Gln Ser Leu Gly Val Gln Pro Val Tyr Asp
1               5                   10                  15

Ile Gly Val Ala Thr Asp His Asn Phe Leu Leu Ala Asp Gly Leu Val
                20                  25                  30

Ala Ser Asn
        35

<210> SEQ ID NO 159
<211> LENGTH: 97
<212> TYPE: PRT
<213> ORGANISM: Acaryochloris sp.

<400> SEQUENCE: 159

Cys Leu Ser Tyr Asp Thr Pro Val Leu Thr Leu Glu Tyr Gly Trp Leu
1               5                   10                  15

Pro Ile Gly Gln Val Val Gln Glu Gln Ile Glu Cys Gln Val Phe Ser
                20                  25                  30

Ile Asn Glu Arg Gly His Leu Tyr Thr Gln Pro Ile Ala Gln Trp His
            35                  40                  45

His Arg Gly Gln Gln Glu Val Phe Glu Tyr Thr Leu Thr Asp Gly Ser
        50                  55                  60

Thr Ile Gln Ala Thr Ala Glu His Gln Phe Met Thr Thr Asp Gly Gln
65                  70                  75                  80

Met Tyr Pro Ile Gln Gln Ile Phe Glu Glu Gly Leu Ser Leu Lys Gln
                85                  90                  95

Leu

<210> SEQ ID NO 160
<211> LENGTH: 35
<212> TYPE: PRT
<213> ORGANISM: Acaryochloris sp.

<400> SEQUENCE: 160

Val Lys Ile Thr Gln Arg Arg Ser Leu Gly Leu Gln Ser Val Tyr Asp
1               5                   10                  15

Ile Gly Leu Ala Gln Asp His Asn Phe Val Ile Ala Asn Gly Trp Val
                20                  25                  30

Ala Ala Asn
        35

<210> SEQ ID NO 161
<211> LENGTH: 98
<212> TYPE: PRT
<213> ORGANISM: Geminocystis herdmanii

<400> SEQUENCE: 161

Cys Leu Ser Tyr Asp Thr Glu Val Leu Thr Val Glu Phe Gly Ala Ile
1               5                   10                  15

Pro Met Gly Lys Ile Val Glu Glu Arg Leu Asn Cys Gln Val Tyr Ser
                20                  25                  30

Val Asp Lys Asn Gly Phe Ile Tyr Thr Gln Asn Ile Ala Gln Trp His
            35                  40                  45

```
Asp Arg Gly Val Gln Glu Val Phe Glu Tyr Glu Leu Glu Asp Gly Arg
    50                  55                  60

Ile Ile Lys Ala Thr Lys Asp His Lys Met Met Ile Glu Asn Cys Glu
65                  70                  75                  80

Met Val Glu Ile Asp Arg Ile Phe Glu Glu Gly Leu Glu Leu Phe Glu
                85                  90                  95

Val Asn

<210> SEQ ID NO 162
<211> LENGTH: 35
<212> TYPE: PRT
<213> ORGANISM: Geminocystis herdmanii

<400> SEQUENCE: 162

Val Lys Ile Leu Lys Arg Arg Ser Ile Ser Gln Gln Val Tyr Asp
1               5                   10                  15

Ile Gly Val Glu Lys Asp His Asn Phe Leu Leu Ala Asn Gly Leu Val
                20                  25                  30

Ala Ser Asn
        35

<210> SEQ ID NO 163
<211> LENGTH: 98
<212> TYPE: PRT
<213> ORGANISM: Nodosilinea nodulosa

<400> SEQUENCE: 163

Cys Leu Ser Ala Asp Thr Glu Leu Leu Thr Leu Glu Tyr Gly Pro Leu
1               5                   10                  15

Thr Ile Gly Glu Ile Val Ala Lys Arg Ile Pro Cys His Val Phe Ser
                20                  25                  30

Val Asp Glu Ser Gly Tyr Val Tyr Thr Gln Pro Val Ala Gln Trp His
            35                  40                  45

Gln Arg Gly His Gln Glu Val Phe Glu Tyr Gln Leu Asp Asp Gly Thr
    50                  55                  60

Thr Ile Arg Ala Thr Ala Asp His Gln Phe Met Thr Glu Leu Gly Glu
65                  70                  75                  80

Met Met Ala Ile Asp Glu Ile Phe Gln Arg Gly Leu Glu Leu Lys Gln
                85                  90                  95

Val Glu

<210> SEQ ID NO 164
<211> LENGTH: 35
<212> TYPE: PRT
<213> ORGANISM: Nodosilinea nodulosa

<400> SEQUENCE: 164

Val Lys Ile Ile Ser Arg Gln Ser Leu Gly Val Gln Pro Val Tyr Asp
1               5                   10                  15

Ile Gly Val Ala Arg Asp His Asn Phe Leu Leu Ala Asp Gly Gln Val
                20                  25                  30

Ala Ser Asn
        35

<210> SEQ ID NO 165
<211> LENGTH: 102
<212> TYPE: PRT
<213> ORGANISM: Rubidibacter lacunae
```

```
<400> SEQUENCE: 165

Cys Leu Ser Tyr Asp Thr Glu Val Leu Thr Val Glu Tyr Gly Pro Leu
1               5                   10                  15

Ala Ile Gly Thr Ile Val Ser Glu Arg Leu Ala Cys Thr Val Tyr Thr
            20                  25                  30

Val Asp Arg Ser Gly Phe Leu Tyr Ala Gln Ala Ile Ser Gln Trp His
        35                  40                  45

Glu Arg Gly Arg Gln Asp Val Phe Glu Tyr Ala Leu Asp Asn Gly Met
    50                  55                  60

Thr Ile Arg Ala Thr Lys Asp His Lys Leu Met Thr Ala Asp Gly Gln
65                  70                  75                  80

Met Val Ala Ile Asp Asp Ile Phe Thr Gln Gly Leu Thr Leu Lys Ala
                85                  90                  95

Ile Asp Thr Ala Ala Phe
            100

<210> SEQ ID NO 166
<211> LENGTH: 35
<212> TYPE: PRT
<213> ORGANISM: Rubidibacter lacunae

<400> SEQUENCE: 166

Met Lys Ile Val Ser Arg Lys Ser Leu Gly Val Gln His Val Tyr Asp
1               5                   10                  15

Ile Gly Val Ala Arg Asp His Asn Phe Leu Ala Asn Gly Ala Ile
            20                  25                  30

Ala Ser Asn
        35

<210> SEQ ID NO 167
<211> LENGTH: 101
<212> TYPE: PRT
<213> ORGANISM: Chlorogloeopsis fritschii

<400> SEQUENCE: 167

Cys Leu Ser Tyr Asp Thr Ala Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Ser Asn Gly Tyr Ile Tyr Thr Gln Pro Ile Ala Gln Trp His
        35                  40                  45

Asn Arg Gly Glu Gln Glu Leu Phe Glu Tyr Ser Leu Glu Asp Gly Ser
    50                  55                  60

Ile Ile Arg Ala Thr Lys Asp His Lys Phe Met Thr Ile Asp Gly Gln
65                  70                  75                  80

Met Leu Pro Ile Asp Glu Ile Phe Ala Arg Lys Leu Glu Leu Met Gln
                85                  90                  95

Val Lys Gly Leu Pro
            100

<210> SEQ ID NO 168
<211> LENGTH: 35
<212> TYPE: PRT
<213> ORGANISM: Chlorogloeopsis fritschii

<400> SEQUENCE: 168

Val Lys Ile Ile Ala Lys Lys Ser Leu Gly Thr Gln Asn Val Tyr Asp
1               5                   10                  15
```

Ile Gly Val Glu Arg Asp His Asn Phe Val Ile Lys Asn Gly Leu Val
                20                  25                  30

Ala Ser Asn
        35

<210> SEQ ID NO 169
<211> LENGTH: 102
<212> TYPE: PRT
<213> ORGANISM: Richelia intracellularis

<400> SEQUENCE: 169

Cys Leu Ser Tyr Asp Thr Gln Ile Leu Thr Val Glu His Gly Pro Met
1               5                   10                  15

Ser Ile Gly Glu Ile Val Glu Lys Cys Leu Glu Cys His Val Tyr Thr
                20                  25                  30

Val Asn Lys Asn Gly Asn Ile Cys Ile Gln Thr Ile Thr Gln Trp His
            35                  40                  45

Phe Arg Gly Glu Gln Glu Ile Phe Glu Tyr Glu Leu Glu Asp Gly Ser
        50                  55                  60

Phe Ile Gln Ala Thr Lys Asp His Lys Phe Met Thr Thr Thr Gly Glu
65                  70                  75                  80

Met Leu Pro Ile His Glu Ile Phe Thr Asn Gly Leu Glu Ile Leu Gln
                85                  90                  95

Leu Ser Lys Ser Leu Leu
            100

<210> SEQ ID NO 170
<211> LENGTH: 35
<212> TYPE: PRT
<213> ORGANISM: Richelia intracellularis

<400> SEQUENCE: 170

Val Lys Ile Leu Ala Arg Lys Ser Leu Gly Thr Gln Lys Val Tyr Asp
1               5                   10                  15

Ile Gly Val Asn Asp Asp His Asn Phe Ala Leu Ser Asn Ser Phe Ile
                20                  25                  30

Ala Ser Asn
        35

<210> SEQ ID NO 171
<211> LENGTH: 102
<212> TYPE: PRT
<213> ORGANISM: Synechococcus sp.

<400> SEQUENCE: 171

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys Gln Val Tyr Ser
                20                  25                  30

Val Asp Ala Gln Gly Leu Ile Tyr Thr Gln Pro Ile Glu Gln Trp His
            35                  40                  45

Asn Arg Gly Asp Arg Leu Leu Tyr Glu Tyr Glu Leu Glu Asn Gly Gln
        50                  55                  60

Met Ile Arg Ala Thr Pro Asp His Lys Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

```
Trp Ala Val Pro Asp Ser
            100

<210> SEQ ID NO 172
<211> LENGTH: 35
<212> TYPE: PRT
<213> ORGANISM: Synechococcus sp.

<400> SEQUENCE: 172

Val Lys Ile Ile Arg Arg Lys Phe Ile Gly His Ala Pro Thr Tyr Asp
1               5                   10                  15

Ile Gly Leu Ser Gln Asp His Asn Phe Leu Gly Gln Gly Leu Ile
            20                  25                  30

Ala Ala Asn
        35

<210> SEQ ID NO 173
<211> LENGTH: 102
<212> TYPE: PRT
<213> ORGANISM: Synechococcus sp.

<400> SEQUENCE: 173

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Thr Gln Pro Ile Glu Gln Trp His
        35                  40                  45

Gln Arg Gly Asp Arg Phe Leu Tyr Glu Tyr Glu Leu Glu Asn Gly Gln
    50                  55                  60

Met Ile Arg Ala Thr Pro Asp His Lys Phe Leu Thr Thr Thr Gly Lys
65                  70                  75                  80

Leu Leu Pro Ile Asp Glu Ile Phe Thr Gln Asn Leu Asp Leu Ala Ala
                85                  90                  95

Trp Ala Val Pro Asp Ser
            100

<210> SEQ ID NO 174
<211> LENGTH: 35
<212> TYPE: PRT
<213> ORGANISM: Synechococcus sp.

<400> SEQUENCE: 174

Val Lys Ile Ile Arg Arg Lys Phe Ile Gly His Ala Pro Thr Tyr Asp
1               5                   10                  15

Ile Gly Leu Ser Gln Asp His Asn Phe Leu Gly Gln Gly Phe Ile
            20                  25                  30

Ala Ala Asn
        35

<210> SEQ ID NO 175
<211> LENGTH: 102
<212> TYPE: PRT
<213> ORGANISM: Synechococcus sp.

<400> SEQUENCE: 175

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30
```

```
Val Asp Ala Gln Gly Leu Ile Tyr Thr Gln Pro Ile Glu Gln Trp His
        35                  40                  45

Gln Arg Gly Asp Arg Leu Leu Tyr Glu Tyr Glu Leu Glu Asn Gly Gln
 50                  55                  60

Met Ile Arg Ala Thr Pro Asp His Lys Phe Leu Thr Thr Thr Gly Glu
 65                  70                  75                  80

Leu Leu Pro Ile Asp Glu Ile Phe Thr Gln Asn Leu Asp Leu Ala Ala
                85                  90                  95

Trp Ala Val Pro Asp Ser
                100
```

```
<210> SEQ ID NO 176
<211> LENGTH: 35
<212> TYPE: PRT
<213> ORGANISM: Synechococcus sp.

<400> SEQUENCE: 176
```

```
Val Lys Ile Leu Arg Arg Lys Phe Ile Gly Arg Ala Pro Thr Tyr Asp
 1               5                  10                  15

Ile Gly Leu Ser Gln Asp His Asn Phe Leu Leu Gly Gln Gly Leu Val
                20                  25                  30

Ala Ala Asn
        35
```

```
<210> SEQ ID NO 177
<211> LENGTH: 94
<212> TYPE: PRT
<213> ORGANISM: Synechococcus sp.

<400> SEQUENCE: 177
```

```
Cys Leu Ala Gly Asp Thr Pro Val Val Thr Val Glu Tyr Gly Val Leu
 1               5                  10                  15

Pro Ile Arg Thr Ile Val Asp Gln Glu Leu Leu Cys His Val Tyr Ser
                20                  25                  30

Leu Asp Pro Gln Gly Phe Ile Tyr Ala Gln Pro Val Glu Gln Trp His
        35                  40                  45

Arg Arg Gly Asp Arg Leu Leu Tyr Glu Tyr Glu Leu Glu Thr Gly Ala
 50                  55                  60

Val Ile Arg Ala Thr Pro Asp His Lys Phe Leu Thr Ala Thr Gly Glu
 65                  70                  75                  80

Met Leu Pro Ile Asp Glu Ile Phe Val Arg Asn Leu Asp Leu
                85                  90
```

```
<210> SEQ ID NO 178
<211> LENGTH: 35
<212> TYPE: PRT
<213> ORGANISM: Synechococcus sp.

<400> SEQUENCE: 178
```

```
Val Lys Ile Ile Arg Arg Asn Leu Ile Gly Glu Ala Ala Thr Tyr Asp
 1               5                  10                  15

Ile Gly Leu Gly Lys Asp His Asn Phe Leu Leu Gly Gln Gly Leu Ile
                20                  25                  30

Ala Ser Asn
        35
```

```
<210> SEQ ID NO 179
<211> LENGTH: 95
```

```
<212> TYPE: PRT
<213> ORGANISM: Synechococcus sp.

<400> SEQUENCE: 179

Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
                20                  25                  30

Val Asp Ala Gln Gly Leu Ile Tyr Thr Gln Pro Ile Glu Gln Trp His
            35                  40                  45

Gln Arg Gly Asp Arg Leu Leu Tyr Glu Tyr Glu Leu Glu Asn Gly Gln
        50                  55                  60

Met Ile Arg Ala Thr Pro Asp His Lys Phe Leu Thr Thr Thr Gly Glu
65                  70                  75                  80

Leu Leu Pro Ile Asp Glu Ile Phe Thr Gln Asn Leu Asp Leu Leu
                85                  90                  95

<210> SEQ ID NO 180
<211> LENGTH: 35
<212> TYPE: PRT
<213> ORGANISM: Synechococcus sp.

<400> SEQUENCE: 180

Val Lys Ile Ile Arg Arg Lys Phe Ile Gly His Ala Pro Thr Tyr Asp
1               5                   10                  15

Ile Gly Leu Ser Gln Asp His Asn Phe Leu Leu Gly Gln Gly Leu Ile
                20                  25                  30

Ala Ala Asn
        35

<210> SEQ ID NO 181
<211> LENGTH: 95
<212> TYPE: PRT
<213> ORGANISM: Synechococcus sp.

<400> SEQUENCE: 181

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys His Val Tyr Ser
                20                  25                  30

Val Asp Ala Gln Gly Leu Ile Tyr Thr Gln Pro Ile Glu Gln Trp His
            35                  40                  45

Lys Arg Gly Asp Arg Leu Leu Tyr Glu Tyr Glu Leu Glu Asn Gly Gln
        50                  55                  60

Ile Ile Arg Ala Thr Pro Asp His Lys Phe Leu Thr Thr Thr Gly Glu
65                  70                  75                  80

Met Arg Pro Ile Asp Glu Ile Phe Ala Lys Asn Leu Ser Leu Leu
                85                  90                  95

<210> SEQ ID NO 182
<211> LENGTH: 35
<212> TYPE: PRT
<213> ORGANISM: Synechococcus sp.

<400> SEQUENCE: 182

Val Lys Ile Ile Arg Arg Lys Phe Val Gly His Ala Pro Thr Tyr Asp
1               5                   10                  15

Ile Gly Leu Ser Gln Asp His Asn Phe Leu Leu Gly Gln Gly Leu Ile
                20                  25                  30
```

Ala Ala Asn
        35

<210> SEQ ID NO 183
<211> LENGTH: 99
<212> TYPE: PRT
<213> ORGANISM: Cyanothece sp.

<400> SEQUENCE: 183

Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
            20                  25                  30

Val Asp Lys Asn Gly Phe Val Tyr Thr Gln Asn Ile Ala Gln Trp His
        35                  40                  45

Leu Arg Gly Gln Gln Glu Val Phe Glu Tyr Tyr Leu Asp Asp Gly Ser
    50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Arg Gly Leu Glu Leu Lys Lys
                85                  90                  95

Ile Lys Ile

<210> SEQ ID NO 184
<211> LENGTH: 35
<212> TYPE: PRT
<213> ORGANISM: Cyanothece sp.

<400> SEQUENCE: 184

Val Lys Ile Val Ser Tyr Arg Ser Leu Gly Lys Gln Phe Val Tyr Asp
1               5                   10                  15

Ile Gly Val Ala Gln Asp His Asn Phe Leu Leu Ala Asn Gly Ser Ile
            20                  25                  30

Ala Ser Asn
        35

<210> SEQ ID NO 185
<211> LENGTH: 102
<212> TYPE: PRT
<213> ORGANISM: Synechococcus elongatus

<400> SEQUENCE: 185

Cys Leu Ala Ala Asp Thr Glu Val Leu Thr Val Glu Tyr Gly Pro Ile
1               5                   10                  15

Ala Ile Gly Lys Leu Val Glu Glu Asn Ile Arg Cys Gln Val Tyr Cys
            20                  25                  30

Cys Asn Pro Asp Gly Tyr Ile Tyr Ser Gln Pro Ile Gly Gln Trp His
        35                  40                  45

Gln Arg Gly Glu Gln Glu Val Ile Glu Tyr Leu Ser Asp Gly Arg
    50                  55                  60

Ile Ile Arg Ala Thr Ala Asp His Arg Phe Met Thr Glu Glu Gly Glu
65                  70                  75                  80

Met Leu Ser Leu Asp Glu Ile Phe Glu Arg Ser Leu Glu Leu Lys Gln
                85                  90                  95

Ile Pro Thr Pro Leu Leu
                100

<210> SEQ ID NO 186
<211> LENGTH: 35
<212> TYPE: PRT
<213> ORGANISM: Synechococcus elongatus

<400> SEQUENCE: 186

Val Lys Ile Val Arg Arg Ser Leu Gly Val Gln Pro Val Tyr Asp
1               5                   10                  15

Leu Gly Val Ala Thr Val His Asn Phe Val Leu Ala Asn Gly Leu Val
            20                  25                  30

Ala Ser Asn
        35

<210> SEQ ID NO 187
<211> LENGTH: 102
<212> TYPE: PRT
<213> ORGANISM: Chlorogloeposis fritschii

<400> SEQUENCE: 187

Cys Leu Ser Tyr Asp Thr Ala Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Ser Asn Gly Tyr Ile Tyr Thr Gln Pro Ile Ala Gln Trp His
        35                  40                  45

Asn Arg Gly Glu Gln Glu Leu Phe Glu Tyr Ser Leu Glu Asp Gly Ser
    50                  55                  60

Ile Ile Arg Ala Thr Lys Asp His Lys Phe Met Thr Ile Asp Gly Gln
65                  70                  75                  80

Met Leu Pro Ile Asp Glu Ile Phe Ala Arg Lys Leu Glu Leu Met Gln
                85                  90                  95

Val Lys Gly Leu Pro Glu
            100

<210> SEQ ID NO 188
<211> LENGTH: 35
<212> TYPE: PRT
<213> ORGANISM: Chlorogloeposis fritschii

<400> SEQUENCE: 188

Val Lys Ile Ile Ala Lys Lys Ser Leu Gly Thr Gln Asn Val Tyr Asp
1               5                   10                  15

Ile Gly Val Glu Arg Asp His Asn Phe Val Ile Lys Asn Gly Leu Val
            20                  25                  30

Ala Ser Asn
        35

<210> SEQ ID NO 189
<211> LENGTH: 97
<212> TYPE: PRT
<213> ORGANISM: Cyanothece sp.

<400> SEQUENCE: 189

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Thr Val Tyr Thr
            20                  25                  30

Val Asp Pro Asn Gly Phe Val Tyr Thr Gln Ala Ile Ala Gln Trp His
        35                  40                  45

```
Tyr Arg Gly Glu Gln Glu Ile Phe Glu Tyr Tyr Leu Glu Asp Gly Ala
        50                  55                  60

Thr Ile Arg Ala Thr Lys Asp His Lys Phe Met Thr Met Glu Gly Lys
 65                  70                  75                  80

Met Leu Pro Ile Asp Glu Ile Phe Glu Asn Asn Leu Asp Leu Lys Gln
                 85                  90                  95

Leu

<210> SEQ ID NO 190
<211> LENGTH: 35
<212> TYPE: PRT
<213> ORGANISM: Cyanothece sp.

<400> SEQUENCE: 190

Val Lys Ile Ile Gly Arg Gln Ser Leu Gly Val Gln Lys Val Tyr Asp
 1               5                  10                  15

Ile Gly Val Glu Lys Glu His Asn Phe Leu Leu His Asn Gly Leu Ile
                20                  25                  30

Ala Ser Asn
        35

<210> SEQ ID NO 191
<211> LENGTH: 97
<212> TYPE: PRT
<213> ORGANISM: Lyngbya majuscula

<400> SEQUENCE: 191

Cys Leu Ser Tyr Asp Thr Glu Ile Ile Thr Val Glu Tyr Gly Pro Ile
 1               5                  10                  15

Ala Ile Gly Glu Ile Val Glu Lys Gly Ile Pro Cys Thr Val Tyr Ser
                20                  25                  30

Val Asp Ser Asn Gly Tyr Val Tyr Thr Gln Pro Ile Ala Gln Trp His
             35                  40                  45

Asn Arg Gly Glu Gln Glu Val Phe Glu Tyr Thr Leu Asp Asp Gly Ser
         50                  55                  60

Val Ile Arg Ala Thr Lys Asp His Lys Phe Met Thr Ile Asp Gly Gln
 65                  70                  75                  80

Met Leu Pro Ile Asp Glu Ile Phe Glu Gly Gly Leu Glu Leu Lys Gln
                 85                  90                  95

Leu

<210> SEQ ID NO 192
<211> LENGTH: 35
<212> TYPE: PRT
<213> ORGANISM: Lyngbya majuscula

<400> SEQUENCE: 192

Val Lys Ile Ile Ser Arg Lys Ser Leu Gly Thr Gln Pro Val Tyr Asp
 1               5                  10                  15

Ile Gly Val Lys Asp Asp His Asn Phe Ile Leu Ala Asn Gly Met Val
                20                  25                  30

Ala Ser Asn
        35

<210> SEQ ID NO 193
<211> LENGTH: 102
<212> TYPE: PRT
<213> ORGANISM: Unknown
<220> FEATURE:
```

<223> OTHER INFORMATION: Description of Unknown: filamentous
      cyanobacterium ESFC-1 sequence

<400> SEQUENCE: 193

Cys Leu Ser Tyr Asp Thr Glu Val Leu Thr Val Glu Tyr Gly Ala Val
1               5                   10                  15

Pro Ile Gly Lys Leu Val Glu Lys Leu Asn Cys Ser Val Tyr Thr
            20                  25                  30

Val Asp Pro Asn Gly Tyr Ile Tyr Thr Gln Ala Ile Ala Gln Trp His
        35                  40                  45

Asp Arg Gly Ile Gln Glu Val Phe Glu Tyr Gln Leu Glu Asp Asn Thr
    50                  55                  60

Ile Ile Arg Ala Thr Lys Asp His Lys Phe Met Thr Glu Asp His Gln
65                  70                  75                  80

Met Leu Pro Ile Asp Glu Ile Phe Glu Arg Gly Leu Glu Leu Lys Lys
                85                  90                  95

Cys Pro Gln Pro Gln Gln
            100

<210> SEQ ID NO 194
<211> LENGTH: 35
<212> TYPE: PRT
<213> ORGANISM: Unknown
<220> FEATURE:
<223> OTHER INFORMATION: Description of Unknown: filamentous
      cyanobacterium ESFC-1 sequence

<400> SEQUENCE: 194

Val Lys Ile Ile Arg Arg Arg Ser Leu Gly Phe Gln Pro Val Tyr Asp
1               5                   10                  15

Ile Gly Leu Glu Gln Asp His Asn Phe Leu Leu Asn Gln Gly Ala Ile
            20                  25                  30

Ala Ser Asn
        35

<210> SEQ ID NO 195
<211> LENGTH: 94
<212> TYPE: PRT
<213> ORGANISM: Synechococcus sp.

<400> SEQUENCE: 195

Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu
                85                  90

<210> SEQ ID NO 196
<211> LENGTH: 35
<212> TYPE: PRT
<213> ORGANISM: Synechococcus sp.

<400> SEQUENCE: 196

```
Val Lys Ile Ile Arg Arg Lys Phe Ile Gly His Ala Pro Thr Tyr Asp
1               5                   10                  15

Ile Gly Leu Ser Gln Asp His Asn Phe Leu Leu Gly Gln Gly Leu Ile
                20                  25                  30

Ala Ala Asn
        35
```

<210> SEQ ID NO 197
<211> LENGTH: 97
<212> TYPE: PRT
<213> ORGANISM: Acaryochloris marina

<400> SEQUENCE: 197

```
Cys Leu Ser Tyr Asp Thr Pro Val Leu Thr Leu Glu Tyr Gly Trp Leu
1               5                   10                  15

Pro Ile Gly Gln Val Val Gln Glu Gln Ile Glu Cys Gln Val Phe Ser
                20                  25                  30

Ile Asn Glu Arg Gly His Leu Tyr Thr Gln Pro Ile Ala Gln Trp His
                35                  40                  45

His Arg Gly Gln Gln Glu Val Phe Glu Tyr Thr Leu Ala Asp Gly Ser
            50                  55                  60

Thr Ile Gln Ala Thr Ala Glu His Gln Phe Met Thr Thr Asp Gly Gln
65                  70                  75                  80

Met Tyr Pro Val Gln Gln Ile Phe Glu Glu Gly Leu Ser Leu Lys Gln
                85                  90                  95

Leu
```

<210> SEQ ID NO 198
<211> LENGTH: 35
<212> TYPE: PRT
<213> ORGANISM: Acaryochloris marina

<400> SEQUENCE: 198

```
Val Lys Ile Ile Gln Arg Arg Ser Leu Gly Leu Gln Ser Val Tyr Asp
1               5                   10                  15

Ile Gly Leu Ala Gln Asp His Asn Phe Val Met Ala Asn Gly Trp Val
                20                  25                  30

Ala Ala Asn
        35
```

<210> SEQ ID NO 199
<211> LENGTH: 94
<212> TYPE: PRT
<213> ORGANISM: Microcystis aeruginosa

<400> SEQUENCE: 199

```
Cys Leu Gly Gly Glu Thr Leu Ile Leu Thr Glu Glu Tyr Gly Leu Leu
1               5                   10                  15

Pro Ile Ala Lys Ile Val Ser Glu Glu Val Asn Cys Thr Val Tyr Ser
                20                  25                  30

Val Asp Lys Asn Gly Phe Val Tyr Ser Gln Pro Ile Ser Gln Trp His
            35                  40                  45

Glu Arg Gly Leu Gln Glu Val Phe Glu Tyr Thr Leu Glu Asn Gly Gln
            50                  55                  60

Thr Ile Gln Ala Thr Lys Asp His Lys Phe Met Thr Asn Asp Gly Glu
65                  70                  75                  80

Met Leu Ala Ile Asp Thr Ile Phe Glu Arg Gly Leu Asp Leu
```

```
<210> SEQ ID NO 200
<211> LENGTH: 35
<212> TYPE: PRT
<213> ORGANISM: Microcystis aeruginosa

<400> SEQUENCE: 200

Val Lys Ile Ile Ser Arg Gln Ser Leu Gly Arg Lys Pro Val Tyr Asp
1               5                   10                  15

Ile Gly Val Glu Lys Asp His Asn Phe Leu Leu Gly Asn Gly Leu Ile
                20                  25                  30

Ala Ser Asn
        35

<210> SEQ ID NO 201
<211> LENGTH: 90
<212> TYPE: PRT
<213> ORGANISM: Anabaena circinalis

<400> SEQUENCE: 201

Cys Leu Ser Tyr Asp Thr Glu Ile Leu Thr Val Glu Tyr Gly Phe Leu
1               5                   10                  15

Glu Ile Gly Glu Ile Val Glu Lys Gln Ile Glu Cys Lys Val Tyr Thr
                20                  25                  30

Val Asp Ser Asn Gly Ile Leu Tyr Thr Gln Pro Ile Ala Gln Trp His
            35                  40                  45

His Arg Gly Gln Gln Glu Val Tyr Glu Tyr Leu Leu Glu Asn Gly Ala
        50                  55                  60

Ile Ile Arg Ala Thr Lys Asp His Lys Phe Met Thr Glu Ala Gly Glu
65                  70                  75                  80

Met Leu Pro Ile Asp Asp Ile Phe Thr Gln
                85                  90

<210> SEQ ID NO 202
<211> LENGTH: 35
<212> TYPE: PRT
<213> ORGANISM: Anabaena circinalis

<400> SEQUENCE: 202

Val Lys Ile Ile Ser Arg Thr Tyr Val Gly Gln Ala Asn Val Tyr Asp
1               5                   10                  15

Ile Gly Val Glu Asn Asp His Asn Phe Val Ile Lys Asn Gly Phe Val
                20                  25                  30

Ala

```
Tyr Arg Gly Gln Gln Glu Val Tyr Glu Tyr Leu Leu Glu Asn Gly Ala
         50                  55                  60

Ile Ile Arg Ala Thr Lys Asp His Asn Phe Met Thr Glu Ala Gly Glu
 65                  70                  75                  80

Met Leu Pro Ile Asp Asp Ile Phe Thr Gln
                 85                  90

<210> SEQ ID NO 204
<211> LENGTH: 35
<212> TYPE: PRT
<213> ORGANISM: Anabaena circinalis

<400> SEQUENCE: 204

Ile Lys Ile Ile Ser Arg Lys Tyr Val Gly Gln Ala Asn Val Tyr Asp
 1               5                  10                  15

Ile Gly Val Glu Asn Asp His Asn Phe Val Ile Lys Asn Gly Phe Val
                 20                  25                  30

Ala Ala Asn
         35

<210> SEQ ID NO 205
<211> LENGTH: 90
<212> TYPE: PRT
<213> ORGANISM: Cyanobacterium sp.

<400> SEQUENCE: 205

Cys Leu Ser Tyr Asp Thr Lys Val Leu Thr Val Glu Tyr Gly Pro Leu
 1               5                  10                  15

Pro Ile Gly Lys Val Val Gln Glu Asn Ile Arg Cys Arg Val Tyr Thr
                 20                  25                  30

Thr Asn Asp Gln Gly Leu Ile Tyr Thr Gln Pro Ile Ala Gln Trp His
         35                  40                  45

Asn Arg Gly Lys Gln Glu Ile Phe Glu Tyr His Leu Asp Asp Lys Thr
 50                  55                  60

Ile Ile Arg Ala Thr Lys Glu His Gln Phe Met Thr Val Asp His Val
 65                  70                  75                  80

Met Met Pro Ile Asp Glu Ile Phe Glu Gln
                 85                  90

<210> SEQ ID NO 206
<211> LENGTH: 34
<212> TYPE: PRT
<213> ORGANISM: Cyanobacterium sp.

<400> SEQUENCE: 206

Lys Ile Ile Arg Arg Lys Ser Leu Gly Met His Glu Val Phe Asp Ile
 1               5                  10                  15

Gly Leu Glu Lys Asp His Asn Phe Val Leu Ser Asn Gly Leu Ile Ala
                 20                  25                  30

Ser Asn

<210> SEQ ID NO 207
<211> LENGTH: 94
<212> TYPE: PRT
<213> ORGANISM: Planktothrix sp.

<400> SEQUENCE: 207

Cys Leu Ser Tyr Asp Thr Glu Val Leu Thr Val Glu Tyr Gly Leu Ile
 1               5                  10                  15
```

```
Pro Ile Ser Lys Ile Val Glu Glu Lys Ile Glu Cys Thr Val Tyr Thr
            20                  25                  30

Val Asn Asn Gln Gly Tyr Val Tyr Thr Gln Pro Ile Ala Gln Trp His
        35                  40                  45

Asn Arg Gly Glu Gln Glu Val Phe Glu Tyr Tyr Leu Glu Asp Gly Ser
    50                  55                  60

Val Ile Arg Ala Thr Lys Asp His Lys Phe Met Thr Val Glu Gly Gln
65                  70                  75                  80

Met Leu Pro Ile Asp Glu Ile Phe Glu Lys Glu Leu Asp Leu
                85                  90

<210> SEQ ID NO 208
<211> LENGTH: 35
<212> TYPE: PRT
<213> ORGANISM: Planktothrix sp.

<400> SEQUENCE: 208

Val Lys Ile Ile Ser Arg Lys Ser Leu Gly Thr Gln Pro Val Tyr Asp
1               5                   10                  15

Ile Gly Val Gln Glu Asp His Asn Phe Val Leu Asn Asn Gly Leu Val
            20                  25                  30

Ala Ser Asn
        35

<210> SEQ ID NO 209
<211> LENGTH: 94
<212> TYPE: PRT
<213> ORGANISM: Planktothrix sp.

<400> SEQUENCE: 209

Cys Leu Ser Tyr Asp Thr Glu Ile Leu Thr Val Glu Tyr Gly Leu Met
1               5                   10                  15

Pro Ile Gly Lys Ile Val Lys Glu Lys Ile Glu Cys Thr Val Tyr Thr
            20                  25                  30

Val Asn Asn Gln Gly Tyr Val Tyr Thr Gln Pro Ile Ala Gln Trp His
        35                  40                  45

His Arg Gly Glu Gln Glu Val Phe Glu Tyr Cys Leu Glu Asp Gly Ser
    50                  55                  60

Val Ile Arg Ala Thr Lys Asp His Lys Phe Met Thr Val Gln Gly Gln
65                  70                  75                  80

Met Leu Pro Ile Asp Glu Ile Phe Glu Lys Glu Leu Asp Leu
                85                  90

<210> SEQ ID NO 210
<211> LENGTH: 35
<212> TYPE: PRT
<213> ORGANISM: Planktothrix sp.

<400> SEQUENCE: 210

Val Lys Ile Ile Ser Arg Lys Ser Leu Gly Thr Gln Pro Val Tyr Asp
1               5                   10                  15

Ile Gly Val Gln Glu Asp His Asn Phe Leu Leu Asn Asn Gly Leu Val
            20                  25                  30

Ala Ser Asn
        35

<210> SEQ ID NO 211
<211> LENGTH: 102
<212> TYPE: PRT
```

<213> ORGANISM: Fremyella diplosiphon

<400> SEQUENCE: 211

Cys Leu Ser Tyr Asp Thr Glu Val Leu Thr Val Glu Tyr Gly Leu Ile
1               5                   10                  15

Pro Ile Gly Glu Ile Val Glu Lys Arg Leu Glu Cys Ser Val Tyr Ser
            20                  25                  30

Val Asp Ile Asn Gly Asn Val Tyr Thr Gln Pro Ile Ala Gln Trp His
        35                  40                  45

His Arg Gly Gln Gln Glu Val Phe Glu Tyr Ala Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Leu Gln
                85                  90                  95

Val Pro His Leu Pro Glu
            100

<210> SEQ ID NO 212
<211> LENGTH: 35
<212> TYPE: PRT
<213> ORGANISM: Fremyella diplosiphon

<400> SEQUENCE: 212

Val Lys Ile Val Thr Arg Arg Ala Ile Gly Ala Ala Asn Val Tyr Asp
1               5                   10                  15

Ile Gly Val Glu Gln Asp His Asn Phe Ala Ile Lys Asn Gly Leu Ile
            20                  25                  30

Ala Ala Asn
        35

<210> SEQ ID NO 213
<211> LENGTH: 94
<212> TYPE: PRT
<213> ORGANISM: Planktothrix sp.

<400> SEQUENCE: 213

Cys Leu Ser Tyr Asp Thr Glu Ile Leu Thr Val Glu Tyr Gly Leu Ile
1               5                   10                  15

Pro Ile Ser Lys Ile Val Glu Leu Lys Ile Glu Cys Thr Val Tyr Thr
            20                  25                  30

Val Asn Asn Gln Gly Tyr Val Tyr Thr Gln Pro Ile Ala Gln Trp His
        35                  40                  45

Asn Arg Gly Glu Gln Glu Val Phe Glu Tyr Tyr Leu Glu Asp Gly Ser
    50                  55                  60

Val Ile Arg Ala Thr Lys Asp His Lys Phe Met Thr Val Asp Gly Gln
65                  70                  75                  80

Met Leu Pro Ile Asp Glu Ile Phe Glu Lys Glu Leu Asp Leu
                85                  90

<210> SEQ ID NO 214
<211> LENGTH: 35
<212> TYPE: PRT
<213> ORGANISM: Planktothrix sp.

<400> SEQUENCE: 214

Val Lys Ile Ile Ser Arg Lys Ser Leu Gly Thr Gln Pro Val Tyr Asp
1               5                   10                  15

Ile Gly Val Gln Glu Asp His Asn Phe Val Leu Asn Asn Gly Leu Val
            20                  25                  30

Ala Ser Asn
        35

<210> SEQ ID NO 215
<211> LENGTH: 102
<212> TYPE: PRT
<213> ORGANISM: Nostoc punctiforme

<400> SEQUENCE: 215

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100

<210> SEQ ID NO 216
<211> LENGTH: 35
<212> TYPE: PRT
<213> ORGANISM: Nostoc punctiforme

<400> SEQUENCE: 216

Ile Lys Ile Ala Thr Arg Lys Tyr Leu Gly Lys Gln Asn Val Tyr Asp
1               5                   10                  15

Ile Gly Val Glu Arg Asp His Asn Phe Ala Leu Lys Asn Gly Phe Ile
            20                  25                  30

Ala Ser Asn
        35

<210> SEQ ID NO 217
<211> LENGTH: 102
<212> TYPE: PRT
<213> ORGANISM: Chroococcidiopsis thermalis

<400> SEQUENCE: 217

Cys Leu Ser Tyr Asp Thr Glu Ile Leu Thr Val Glu Tyr Gly Ala Ile
1               5                   10                  15

Pro Ile Gly Lys Ile Val Glu Glu Arg Ile Glu Cys Thr Val Tyr Ser
            20                  25                  30

Val Asp Asn Asn Gly Phe Ile Tyr Thr Gln Pro Ile Ala Gln Trp His
        35                  40                  45

Asn Arg Gly Gln Gln Glu Val Phe Glu Tyr Cys Leu Glu Asp Gly Ser
    50                  55                  60

Ile Ile Arg Ala Thr Lys Asp His Lys Phe Met Thr Phe Glu Gly Lys
65                  70                  75                  80

Met Leu Pro Ile Asp Glu Ile Phe Glu Gln Glu Leu Asp Leu Lys Gln
                85                  90                  95

Val Lys Ser Ile Gln Asn

```
<210> SEQ ID NO 218
<211> LENGTH: 35
<212> TYPE: PRT
<213> ORGANISM: Chroococcidiopsis thermalis

<400> SEQUENCE: 218

Val Lys Ile Ile Ser Arg Lys Ser Leu Gly Ile Gln Pro Val Tyr Asp
1               5                   10                  15

Ile Gly Val Glu Arg Asp His Lys Phe Val Leu Lys Asn Gly Leu Val
            20                  25                  30

Ala Ser Asn
        35

<210> SEQ ID NO 219
<211> LENGTH: 102
<212> TYPE: PRT
<213> ORGANISM: Nodularia spumigena

<400> SEQUENCE: 219

Cys Leu Ser Tyr Asp Thr Glu Ile Leu Thr Val Glu Tyr Gly Tyr Ile
1               5                   10                  15

Pro Ile Gly Glu Ile Val Glu Lys Ala Ile Glu Cys Ser Val Tyr Ser
            20                  25                  30

Val Asp Asn Asn Gly Asn Val Tyr Thr Gln Pro Ile Ala Gln Trp His
        35                  40                  45

Asn Arg Gly Glu Gln Glu Val Phe Glu Tyr Ser Leu Glu Asp Gly Ser
    50                  55                  60

Thr Ile Arg Ala Thr Lys Asp His Lys Phe Met Thr Thr Asp Gly Gln
65                  70                  75                  80

Met Leu Pro Ile Asp Glu Ile Phe Ala Gln Glu Leu Asp Leu Leu Gln
                85                  90                  95

Val His Gly Leu Pro Lys
            100

<210> SEQ ID NO 220
<211> LENGTH: 35
<212> TYPE: PRT
<213> ORGANISM: Nodularia spumigena

<400> SEQUENCE: 220

Val Lys Ile Thr Ala Arg Lys Phe Val Gly Arg Glu Asn Val Tyr Asp
1               5                   10                  15

Ile Gly Val Glu Arg Tyr His Asn Phe Ala Ile Lys Asn Gly Leu Ile
            20                  25                  30

Ala Ser Asn
        35

<210> SEQ ID NO 221
<211> LENGTH: 102
<212> TYPE: PRT
<213> ORGANISM: Anabaena cylindrica

<400> SEQUENCE: 221

Cys Leu Ser Tyr Asp Thr Glu Val Leu Thr Val Glu Tyr Gly Phe Ile
1               5                   10                  15

Pro Ile Gly Glu Ile Val Glu Lys Arg Ile Glu Cys Ser Ile Phe Ser
            20                  25                  30
```

```
Val Asp Lys Asn Gly Asn Val Tyr Thr Gln Pro Ile Ala Gln Trp His
        35                  40                  45

Asn Arg Gly Arg Gln Glu Ile Tyr Glu Tyr Cys Leu Asp Asp Gly Ser
50                      55                  60

Lys Ile Arg Ala Thr Lys Asp His Lys Phe Met Thr Thr Ala Gly Glu
65                  70                  75                  80

Met Leu Pro Ile Asp Glu Ile Phe Glu Arg Asp Leu Asp Leu Leu Lys
                85                  90                  95

Val Glu Gly Leu Pro Glu
            100
```

<210> SEQ ID NO 222
<211> LENGTH: 35
<212> TYPE: PRT
<213> ORGANISM: Anabaena cylindrica

<400> SEQUENCE: 222

```
Val Lys Ile Ile Ser Arg Gln Tyr Leu Gly Gln Ala Asp Val Tyr Asp
1               5                   10                  15

Ile Gly Val Glu Glu Asp His Asn Phe Ala Ile Lys Asn Gly Phe Ile
                20                  25                  30

Ala Ser Asn
        35
```

<210> SEQ ID NO 223
<211> LENGTH: 102
<212> TYPE: PRT
<213> ORGANISM: Calothrix sp.

<400> SEQUENCE: 223

```
Cys Leu Ser Tyr Asp Thr Glu Val Leu Thr Val Glu Tyr Gly Leu Leu
1               5                   10                  15

Pro Ile Gly Glu Ile Val Glu Lys Gly Ile Glu Cys Arg Val Phe Ser
                20                  25                  30

Val Asp Asn His Gly Asn Val Tyr Thr Gln Pro Ile Ala Gln Trp His
        35                  40                  45

Asn Arg Gly Gln Gln Glu Val Phe Glu Tyr Gly Leu Asp Asp Gly Ser
50                      55                  60

Val Ile Arg Ala Thr Lys Asp His Lys Phe Met Thr Thr Asp Gly Lys
65                  70                  75                  80

Met Leu Pro Ile Asp Glu Ile Phe Glu Arg Gly Leu Asp Leu Leu Gln
                85                  90                  95

Val Gln Gly Leu Pro Glu
            100
```

<210> SEQ ID NO 224
<211> LENGTH: 35
<212> TYPE: PRT
<213> ORGANISM: Calothrix sp.

<400> SEQUENCE: 224

```
Val Lys Val Ile Thr Arg Lys Tyr Ile Gly Lys Glu Asn Val Tyr Asp
1               5                   10                  15

Ile Gly Val Glu Leu Asp His Asn Phe Ala Ile Arg Asn Gly Leu Val
                20                  25                  30

Ala Ser Asn
        35
```

<210> SEQ ID NO 225
<211> LENGTH: 102
<212> TYPE: PRT
<213> ORGANISM: Nostoc sp.

<400> SEQUENCE: 225

Cys Leu Ser Tyr Asp Thr Glu Ile Leu Thr Val Glu Tyr Gly Phe Leu
1               5                   10                  15

Pro Ile Gly Glu Ile Val Glu Lys Gly Ile Glu Cys Thr Val Phe Ser
            20                  25                  30

Val Ala Ser Asn Gly Ile Val Tyr Thr Gln Pro Ile Ala Gln Trp His
        35                  40                  45

Asn Arg Gly Gln Gln Glu Ile Phe Glu Tyr Cys Leu Glu Asp Gly Ser
    50                  55                  60

Ile Ile Arg Ala Thr Lys Asp His Lys Phe Met Thr Gln Asp Gly Gln
65                  70                  75                  80

Met Leu Pro Ile Asp Glu Ile Phe Ala Cys Glu Leu Asp Leu Leu Gln
                85                  90                  95

Val Gln Gly Leu Pro Glu
            100

<210> SEQ ID NO 226
<211> LENGTH: 35
<212> TYPE: PRT
<213> ORGANISM: Nostoc sp.

<400> SEQUENCE: 226

Val Lys Val Val Thr Arg Lys Tyr Ile Gly Lys Glu Asn Val Tyr Asp
1               5                   10                  15

Ile Gly Val Glu Arg Asp His Asn Phe Val Ile Arg Asn Gly Leu Val
            20                  25                  30

Ala Ser Asn
        35

<210> SEQ ID NO 227
<211> LENGTH: 102
<212> TYPE: PRT
<213> ORGANISM: Nostoc azollae

<400> SEQUENCE: 227

Cys Leu Ser Tyr Lys Thr Glu Val Leu Thr Val Glu Tyr Gly Leu Ile
1               5                   10                  15

Pro Ile Gly Glu Ile Val Glu Lys Arg Ile Glu Cys Ser Leu Phe Ser
            20                  25                  30

Val Asp Glu Asn Gly Asn Ile Tyr Thr Gln Pro Ile Ala Gln Trp His
        35                  40                  45

His Arg Gly Val Gln Glu Val Tyr Glu Tyr Cys Leu Asp Asp Gly Thr
    50                  55                  60

Ile Ile Arg Ala Thr Lys Asp His Lys Phe Met Thr Thr Ile Gly Glu
65                  70                  75                  80

Met Leu Pro Ile Asp Glu Ile Phe Glu Arg Asp Leu Asn Leu Leu Gln
                85                  90                  95

Val Asn Gly Leu Pro Thr
            100

<210> SEQ ID NO 228
<211> LENGTH: 35
<212> TYPE: PRT
<213> ORGANISM: Nostoc azollae

<400> SEQUENCE: 228

Val Lys Ile Ile Ser Arg Gln Phe Leu Gly Pro Ala Asn Val Tyr Asp
1               5                   10                  15

Ile Gly Val Ala Gln Asp His Asn Phe Ala Ile Lys Asn Gly Leu Ile
            20                  25                  30

Ala Ser Asn
        35

<210> SEQ ID NO 229
<211> LENGTH: 102
<212> TYPE: PRT
<213> ORGANISM: Nostoc sp.

<400> SEQUENCE: 229

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 230
<211> LENGTH: 35
<212> TYPE: PRT
<213> ORGANISM: Nostoc sp.

<400> SEQUENCE: 230

Ile Lys Ile Ala Ser Arg Lys Phe Leu Gly Val Glu Asn Val Tyr Asp
1               5                   10                  15

Ile Gly Val Arg Arg Asp His Asn Phe Phe Ile Lys Asn Gly Leu Ile
            20                  25                  30

Ala Ser Asn
        35

<210> SEQ ID NO 231
<211> LENGTH: 102
<212> TYPE: PRT
<213> ORGANISM: Anabaena variabilis

<400> SEQUENCE: 231

Cys Leu Ser Tyr Asp Thr Glu Val Leu Thr Val Glu Tyr Gly Phe Val
1               5                   10                  15

Pro Ile Gly Glu Ile Val Asp Lys Gly Ile Glu Cys Ser Val Phe Ser
            20                  25                  30

Ile Asp Ser Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys

```
                65                  70                  75                  80
Met Leu Pro Ile Asp Glu Ile Phe Glu Gln Glu Leu Asp Leu Leu Gln
                    85                  90                  95

Val Lys Gly Leu Pro Glu
            100

<210> SEQ ID NO 232
<211> LENGTH: 35
<212> TYPE: PRT
<213> ORGANISM: Anabaena variabilis

<400> SEQUENCE: 232

Ile Lys Ile Ala Ser Arg Lys Phe Leu Gly Val Glu Asn Val Tyr Asp
1               5                   10                  15

Ile Gly Val Gly Arg Asp His Asn Phe Phe Val Lys Asn Gly Leu Ile
                20                  25                  30

Ala Ser Asn
        35

<210> SEQ ID NO 233
<211> LENGTH: 100
<212> TYPE: PRT
<213> ORGANISM: Pleurocapsa sp.

<400> SEQUENCE: 233

Cys Leu Ser Tyr Asp Thr Lys Ile Leu Thr Val Glu Tyr Gly Ala Met
1               5                   10                  15

Pro Ile Gly Lys Ile Val Glu Glu Gln Ile Asp Cys Thr Val Tyr Thr
                20                  25                  30

Val Asn Gln Asn Gly Phe Val Tyr Thr Gln Pro Ile Ala Gln Trp His
            35                  40                  45

Asp Arg Gly Lys Gln Glu Ile Phe Glu Tyr Cys Leu Glu Asp Gly Ser
        50                  55                  60

Ile Ile Arg Ala Thr Lys Asp His Lys Phe Met Thr Thr Asp Gly Gln
65                  70                  75                  80

Met Leu Pro Ile Asp Lys Ile Phe Glu Lys Gly Leu Asp Leu Lys Thr
                85                  90                  95

Ile Asn Cys Asp
            100

<210> SEQ ID NO 234
<211> LENGTH: 35
<212> TYPE: PRT
<213> ORGANISM: Pleurocapsa sp.

<400> SEQUENCE: 234

Val Lys Ile Leu Ser Arg Lys Ser Leu Gly Ile Gln Ser Val Tyr Asp
1               5                   10                  15

Ile Gly Val Glu Lys Asp His Asn Phe Leu Leu Ala Asn Gly Leu Val
                20                  25                  30

Ala Ser Asn
        35

<210> SEQ ID NO 235
<211> LENGTH: 100
<212> TYPE: PRT
<213> ORGANISM: Cyanothece sp.

<400> SEQUENCE: 235
```

```
Cys Leu Ser Tyr Glu Thr Gln Ile Met Thr Val Glu Tyr Gly Leu Met
1               5                   10                  15

Pro Ile Gly Lys Ile Val Glu Glu Gln Ile Asp Cys Thr Val Tyr Thr
                20                  25                  30

Val Asn Lys Asn Gly Phe Val Tyr Thr Gln Pro Ile Ala Gln Trp His
            35                  40                  45

Tyr Arg Gly Glu Gln Glu Val Phe Glu Tyr Cys Leu Glu Asp Gly Ser
        50                  55                  60

Thr Ile Arg Ala Thr Lys Asp His Lys Phe Met Thr Thr Asp Gly Gln
65                  70                  75                  80

Met Leu Pro Ile Asp Glu Ile Phe Glu Gln Gly Leu Glu Leu Lys Gln
                85                  90                  95

Ile His Leu Ser
            100
```

<210> SEQ ID NO 236
<211> LENGTH: 35
<212> TYPE: PRT
<213> ORGANISM: Cyanothece sp.

<400> SEQUENCE: 236

```
Val Lys Ile Ile Ser Arg Gln Ser Leu Gly Ile Gln Pro Val Tyr Asp
1               5                   10                  15

Ile Gly Val Glu Lys Asp His Asn Phe Leu Ile Ser Asp Gly Leu Ile
                20                  25                  30

Ala Ser Asn
        35
```

<210> SEQ ID NO 237
<211> LENGTH: 99
<212> TYPE: PRT
<213> ORGANISM: Cyanothece sp.

<400> SEQUENCE: 237

```
Cys Leu Ser Tyr Asp Thr Glu Ile Leu Thr Val Glu Tyr Gly Pro Met
1               5                   10                  15

Pro Ile Gly Lys Ile Val Glu Glu Gln Ile Glu Cys Thr Val Tyr Thr
                20                  25                  30

Val Asp Lys Asn Gly Leu Val Tyr Thr Gln Pro Ile Ala Gln Trp His
            35                  40                  45

His Arg Gly Gln Gln Glu Val Phe Glu Tyr Cys Leu Glu Asp Gly Ser
        50                  55                  60

Ile Ile Arg Ala Thr Lys Asp His Lys Phe Met Thr Asp Asp Gly Gln
65                  70                  75                  80

Met Leu Pro Ile Glu Glu Ile Phe Glu Lys Gly Leu Glu Leu Lys Gln
                85                  90                  95

Ile Ile Leu
```

<210> SEQ ID NO 238
<211> LENGTH: 35
<212> TYPE: PRT
<213> ORGANISM: Cyanothece sp.

<400> SEQUENCE: 238

```
Val Lys Ile Ile Ser Arg Gln Leu Ala Gly Asn Gln Thr Val Tyr Asp
1               5                   10                  15

Leu Gly Val Glu Lys Asp His Asn Phe Leu Leu Ala Asn Gly Leu Ile
                20                  25                  30
```

Ala Ser Asn
        35

<210> SEQ ID NO 239
<211> LENGTH: 102
<212> TYPE: PRT
<213> ORGANISM: Nostoc sp.

<400> SEQUENCE: 239

Cys Leu Ser Tyr Asp Thr Gln Val Leu Thr Val Glu Tyr Gly Leu Val
1               5                   10                  15

Pro Ile Gly Glu Ile Val Glu Lys Gln Leu Glu Cys Ser Val Phe Thr
            20                  25                  30

Ile Asp Gly His Gly Tyr Val Tyr Thr Gln Ala Ile Ala Gln Trp His
        35                  40                  45

Asn Arg Gly Gln Gln Glu Val Phe Glu Tyr Gly Leu Glu Asp Gly Ser
    50                  55                  60

Val Ile Arg Ala Thr Lys Asp His Lys Phe Met Thr Thr Asp Gly Gln
65                  70                  75                  80

Met Leu Pro Ile Asp Glu Ile Phe Glu Arg Glu Leu Asp Leu Leu Gln
                85                  90                  95

Val Gln Gly Leu Arg Trp
            100

<210> SEQ ID NO 240
<211> LENGTH: 35
<212> TYPE: PRT
<213> ORGANISM: Nostoc sp.

<400> SEQUENCE: 240

Val Lys Ile Ile Thr Arg Lys Tyr Ile Gly Gln Ala Asn Val Tyr Asp
1               5                   10                  15

Ile Gly Val Ala Gln Asp His Asn Phe Val Ile Glu Asn Arg Leu Ile
            20                  25                  30

Ala Ser Asn
        35

<210> SEQ ID NO 241
<211> LENGTH: 101
<212> TYPE: PRT
<213> ORGANISM: Tolypothrix bouteillei

<400> SEQUENCE: 241

Cys Leu Ser Tyr Asp Thr Glu Ile Leu Thr Val Glu Tyr Gly Phe Leu
1               5                   10                  15

Pro Ile Gly Lys Ile Val Glu Lys Gly Ile Glu Cys Asn Val Tyr Ser
            20                  25                  30

Val Asp Lys Asn Gly Asn Ile Tyr Thr Gln Pro Ile Ala Gln Trp His
        35                  40                  45

Asp Arg Gly Glu Gln Glu Val Phe Glu Tyr Cys Leu Glu Asn Gly Ser
    50                  55                  60

Val Ile Arg Ala Thr Lys Asp His Lys Phe Met Thr Thr Ser Gly Glu
65                  70                  75                  80

Met Leu Pro Ile Asp Glu Ile Phe Glu Arg Gly Leu Asp Leu Ile Arg
                85                  90                  95

Val Glu Asp Leu Pro
            100

-continued

<210> SEQ ID NO 242
<211> LENGTH: 35
<212> TYPE: PRT
<213> ORGANISM: Tolypothrix bouteillei

<400> SEQUENCE: 242

Val Lys Ile Leu Thr Arg Lys Ser Ile Gly Lys Gln Thr Val Tyr Asp
1               5                   10                  15

Ile Gly Val Glu Arg Asp His Asn Phe Val Ile Lys Asn Gly Ser Val
            20                  25                  30

Ala Ser Asn
        35

<210> SEQ ID NO 243
<211> LENGTH: 101
<212> TYPE: PRT
<213> ORGANISM: Aphanizomenon ovalisporum
<220> FEATURE:
<221> NAME/KEY: MOD_RES
<222> LOCATION: (87)..(87)
<223> OTHER INFORMATION: Any amino acid

<400> SEQUENCE: 243

Cys Leu Ser Ala Asp Thr Glu Ile Leu Thr Val Glu Tyr Gly Phe Leu
1               5                   10                  15

Pro Ile Gly Glu Ile Val Gly Lys Ala Ile Glu Cys Arg Val Tyr Ser
            20                  25                  30

Val Asp Gly Asn Gly Asn Ile Tyr Thr Gln Ser Ile Ala Gln Trp His
        35                  40                  45

Asn Arg Gly Glu Gln Glu Val Phe Glu Tyr Thr Leu Glu Asp Gly Ser
    50                  55                  60

Ile Ile Arg Ala Thr Lys Asp His Lys Phe Met Thr Thr Asp Gly Glu
65                  70                  75                  80

Met Leu Pro Ile Asp Glu Xaa Phe Ala Arg Gln Leu Asp Leu Met Gln
                85                  90                  95

Val Gln Gly Leu His
            100

<210> SEQ ID NO 244
<211> LENGTH: 35
<212> TYPE: PRT
<213> ORGANISM: Aphanizomenon ovalisporum

<400> SEQUENCE: 244

Val Lys Ile Thr Ala Arg Lys Phe Val Gly Arg Glu Asn Val Tyr Asp
1               5                   10                  15

Ile Gly Val Glu His His His Asn Phe Ala Ile Lys Asn Gly Leu Ile
            20                  25                  30

Ala Ser Asn
        35

<210> SEQ ID NO 245
<211> LENGTH: 102
<212> TYPE: PRT
<213> ORGANISM: Oscillatoria nigro-viridis

<400> SEQUENCE: 245

Cys Leu Ser Tyr Asp Thr Lys Ile Leu Thr Val Glu Tyr Gly Pro Met
1               5                   10                  15

Ala Ile Gly Lys Ile Val Glu Glu Lys Ile Glu Cys Thr Val Tyr Ser

```
                    20                  25                  30

Val Asp Ser Asn Gly Tyr Ile Tyr Thr Gln Ser Ile Ala Gln Trp His
            35                  40                  45

Arg Arg Gly Gln Gln Glu Val Phe Glu Tyr Cys Leu Glu Asp Gly Ser
    50                  55                  60

Ile Ile Arg Ala Thr Lys Asp His Lys Phe Met Thr Val Gly Gly Gln
65                  70                  75                  80

Met Leu Pro Ile Asp Glu Ile Phe Glu Gln Gly Leu Asp Leu Lys Gln
                85                  90                  95

Ile Asn Ser Ser Ser Asp
            100
```

<210> SEQ ID NO 246
<211> LENGTH: 35
<212> TYPE: PRT
<213> ORGANISM: Oscillatoria nigro-viridis

<400> SEQUENCE: 246

```
Val Lys Ile Ile Ser Arg Lys Ser Leu Gly Thr Gln Glu Val Tyr Asp
1               5                   10                  15

Ile Gly Val Glu Arg Glu His Asn Phe Ile Leu Glu Asn Ser Leu Val
            20                  25                  30

Ala Ser Asn
        35
```

<210> SEQ ID NO 247
<211> LENGTH: 100
<212> TYPE: PRT
<213> ORGANISM: Rivularia sp.

<400> SEQUENCE: 247

```
Cys Leu Ser Tyr Asp Thr Glu Val Leu Thr Glu Glu Phe Gly Leu Ile
1               5                   10                  15

Pro Ile Gly Lys Ile Val Glu Glu Lys Ile Asp Cys Thr Val Tyr Ser
            20                  25                  30

Val Asp Val Asn Gly Asn Val Tyr Ser Gln Pro Ile Ala Gln Trp His
        35                  40                  45

Asn Arg Gly Met Gln Glu Val Phe Glu Tyr Glu Leu Glu Asp Gly Ser
    50                  55                  60

Thr Ile Arg Ala Thr Lys Asp His Lys Phe Met Thr Val Asp Gly Glu
65                  70                  75                  80

Met Leu Ala Ile Asp Glu Ile Phe Glu Lys Gly Leu Glu Leu Lys Arg
                85                  90                  95

Val Gly Ile Tyr
        100
```

<210> SEQ ID NO 248
<211> LENGTH: 35
<212> TYPE: PRT
<213> ORGANISM: Rivularia sp.

<400> SEQUENCE: 248

```
Val Lys Ile Ile Ser Arg Lys Val Leu Lys Thr Glu Asn Val Tyr Asp
1               5                   10                  15

Ile Gly Leu Glu Gly Asp His Asn Phe Ile Ile Lys Asp Gly Leu Ile
            20                  25                  30

Ala Ser Asn
        35
```

<210> SEQ ID NO 249
<211> LENGTH: 102
<212> TYPE: PRT
<213> ORGANISM: Microcoleus sp.

<400> SEQUENCE: 249

Cys Leu Ser Tyr Asp Ser Glu Ile Leu Thr Val Glu Tyr Gly Leu Met
1               5                   10                  15

Pro Ile Gly Lys Ile Val Glu Glu Ile Glu Cys Thr Val Tyr Ser
            20                  25                  30

Val Asp Ser His Gly Tyr Leu Tyr Thr Gln Pro Ile Ala Gln Trp His
        35                  40                  45

His Arg Gly Gln Gln Glu Val Phe Glu Tyr Asp Leu Glu Asp Gly Ser
    50                  55                  60

Val Ile Arg Ala Thr Lys Asp His Lys Phe Met Thr Ser Glu Gly Gln
65                  70                  75                  80

Met Leu Ala Ile Asp Glu Ile Phe Glu Arg Gly Leu Glu Leu Lys Gln
                85                  90                  95

Val Lys Arg Ser Gln Pro
            100

<210> SEQ ID NO 250
<211> LENGTH: 35
<212> TYPE: PRT
<213> ORGANISM: Microcoleus sp.

<400> SEQUENCE: 250

Val Lys Ile Val Arg Arg Lys Ser Leu Gly Ile Gln Thr Val Tyr Asp
1               5                   10                  15

Ile Gly Val Glu Arg Asp His Asn Phe Leu Leu Ala Asn Gly Leu Val
            20                  25                  30

Ala Ser Asn
        35

<210> SEQ ID NO 251
<211> LENGTH: 102
<212> TYPE: PRT
<213> ORGANISM: Stanieria cyanosphaera

<400> SEQUENCE: 251

Cys Leu Ser Tyr Asp Thr Glu Ile Leu Thr Val Glu Tyr Gly Ala Met
1               5                   10                  15

Pro Ile Gly Lys Ile Val Lys Glu Gln Ile Glu Cys Asn Val Tyr Thr
            20                  25                  30

Val Asn Gln Asn Gly Phe Ile Tyr Pro Gln Ala Ile Ala Gln Trp His
        35                  40                  45

Glu Arg Gly Lys Gln Glu Ile Phe Glu Tyr Thr Leu Asp Asn Gly Leu
    50                  55                  60

Val Ile Arg Ala Thr Lys Asp His Lys Phe Met Thr Ile Asp Gly Gln
65                  70                  75                  80

Met Leu Pro Ile Asp Glu Ile Phe Glu Arg Gly Leu Glu Leu Gln Arg
                85                  90                  95

Ile Asn Asp Tyr Ser Asn
            100

<210> SEQ ID NO 252
<211> LENGTH: 35

```
<212> TYPE: PRT
<213> ORGANISM: Stanieria cyanosphaera

<400> SEQUENCE: 252

Val Lys Ile Val Ser Arg Lys Ser Leu Gly Lys Gln Pro Val Tyr Asp
1               5                   10                  15

Ile Gly Val Thr Lys Asp His Asn Phe Leu Leu Ser Asn Gly Val Val
            20                  25                  30

Ala Ser Asn
        35

<210> SEQ ID NO 253
<211> LENGTH: 102
<212> TYPE: PRT
<213> ORGANISM: Calothrix sp.

<400> SEQUENCE: 253

Cys Leu Ser Tyr Asp Thr Glu Ile Leu Thr Trp Glu Tyr Gly Phe Leu
1               5                   10                  15

Lys Ile Gly Glu Ile Val Glu Lys Gln Ile Leu Cys Ser Val Phe Ser
            20                  25                  30

Val Asp Glu Gln Gly Asn Val Tyr Thr Gln Pro Ile Ala Gln Trp His
        35                  40                  45

Asn Arg Gly Leu Gln Glu Leu Phe Ala Tyr Gln Leu Glu Asp Gly Gly
    50                  55                  60

Val Ile Arg Ala Thr Lys Asp His Lys Phe Met Thr Thr Asp Gly Gln
65                  70                  75                  80

Met Leu Ala Ile Asp Glu Ile Phe Glu Arg Gln Leu Asp Leu Phe Gln
                85                  90                  95

Val Lys Gly Leu Pro Glu
            100

<210> SEQ ID NO 254
<211> LENGTH: 35
<212> TYPE: PRT
<213> ORGANISM: Calothrix sp.

<400> SEQUENCE: 254

Val Lys Ile Ile Ser Arg Lys Val Leu Lys Thr Glu Asn Val Tyr Asp
1               5                   10                  15

Ile Gly Leu Glu Gly Asp His Asn Phe Ile Ile Lys Asp Gly Leu Ile
            20                  25                  30

Ala Ser Asn
        35

<210> SEQ ID NO 255
<211> LENGTH: 99
<212> TYPE: PRT
<213> ORGANISM: Cyanobacterium stanieri

<400> SEQUENCE: 255

Cys Leu Ser Tyr Asp Thr Glu Val Leu Thr Val Glu Tyr Gly Val Leu
1               5                   10                  15

Pro Ile Gly Lys Ile Val Glu Glu Gln Ile Gln Cys Thr Val Tyr Ser
            20                  25                  30

Val Asp Gln Tyr Gly Phe Val Tyr Thr Gln Ala Ile Ala Gln Trp His
        35                  40                  45

Asp Arg Gly Glu Gln Glu Val Phe Glu Tyr Glu Leu Glu Asn Gly Ala
    50                  55                  60
```

```
Thr Ile Lys Ala Thr Lys Asp His Lys Met Met Thr Ser Asp Gly Gln
 65                  70                  75                  80

Met Leu Pro Ile Asp Gln Ile Phe Glu Gln Gly Leu Asp Leu Phe Met
                 85                  90                  95

Val Ser Phe

<210> SEQ ID NO 256
<211> LENGTH: 35
<212> TYPE: PRT
<213> ORGANISM: Cyanobacterium stanieri

<400> SEQUENCE: 256

Val Lys Ile Val Lys Arg Arg Ser His Gly Ile Gln Lys Val Tyr Asp
 1               5                  10                  15

Ile Gly Val Ala Lys Asp His Asn Phe Leu Leu His Asn Gly Leu Val
                 20                  25                  30

Ala Ser Asn
        35

<210> SEQ ID NO 257
<211> LENGTH: 99
<212> TYPE: PRT
<213> ORGANISM: Cyanothece sp.

<400> SEQUENCE: 257

Cys Leu Ser Tyr Asp Thr Glu Ile Leu Thr Val Glu Tyr Gly Pro Met
 1               5                  10                  15

Pro Ile Gly Lys Ile Val Glu Glu Asn Ile Asn Cys Thr Val Tyr Thr
                 20                  25                  30

Val Asp Pro Asn Gly Phe Val Tyr Thr Gln Ala Ile Ala Gln Trp His
                 35                  40                  45

Tyr Arg Gly Glu Gln Glu Ile Phe Glu Tyr Tyr Leu Glu Asp Gly Ala
             50                  55                  60

Thr Ile Arg Ala Thr Lys Asp His Lys Phe Met Thr Met Glu Gly Lys
 65                  70                  75                  80

Met Leu Pro Ile Asp Glu Ile Phe Glu Asn Asn Leu Asp Leu Lys Gln
                 85                  90                  95

Leu Thr Leu

<210> SEQ ID NO 258
<211> LENGTH: 35
<212> TYPE: PRT
<213> ORGANISM: Cyanothece sp.

<400> SEQUENCE: 258

Val Lys Ile Ile Gly Arg Gln Ser Leu Gly Val Gln Lys Val Tyr Asp
 1               5                  10                  15

Ile Gly Val Glu Lys Glu His Asn Phe Leu Leu His Asn Gly Leu Ile
                 20                  25                  30

Ala Ser Asn
        35

<210> SEQ ID NO 259
<211> LENGTH: 99
<212> TYPE: PRT
<213> ORGANISM: Cyanothece sp.

<400> SEQUENCE: 259
```

```
Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
            20                  25                  30

Val Asp Lys Asn Gly Phe Val Tyr Thr Gln Asn Ile Ala Gln Trp His
            35                  40                  45

Leu Arg Gly Gln Gln Glu Val Phe Glu Tyr Tyr Leu Asp Asp Gly Ser
        50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Arg Gly Leu Glu Leu Lys Lys
                85                  90                  95

Ile Lys Ile
```

<210> SEQ ID NO 260
<211> LENGTH: 35
<212> TYPE: PRT
<213> ORGANISM: Cyanothece sp.

<400> SEQUENCE: 260

```
Val Lys Ile Val Ser Tyr Arg Ser Leu Gly Lys Gln Phe Val Tyr Asp
1               5                   10                  15

Ile Gly Val Ala Gln Asp His Asn Phe Leu Leu Ala Asn Gly Ser Ile
            20                  25                  30

Ala Ser Asn
        35
```

<210> SEQ ID NO 261
<211> LENGTH: 101
<212> TYPE: PRT
<213> ORGANISM: Anabaena sp.

<400> SEQUENCE: 261

```
Cys Leu Ser Tyr Asp Thr Glu Ile Leu Thr Val Glu Tyr Gly Phe Leu
1               5                   10                  15

Glu Ile Gly Glu Ile Val Glu Lys Gln Ile Glu Cys Lys Val Tyr Thr
            20                  25                  30

Ile Asp Ser Asn Gly Met Leu Tyr Thr Gln Ser Ile Ala Gln Trp His
            35                  40                  45

Asn Arg Gly Gln Gln Glu Val Tyr Glu Tyr Leu Leu Glu Asn Gly Ala
        50                  55                  60

Ile Ile Arg Ala Thr Lys Asp His Lys Phe Met Thr Glu Ala Gly Gln
65                  70                  75                  80

Met Leu Pro Ile Asp Glu Ile Phe Ala Gln Gly Leu Asp Leu Leu Gln
                85                  90                  95

Val Gly Val Ala Glu
            100
```

<210> SEQ ID NO 262
<211> LENGTH: 35
<212> TYPE: PRT
<213> ORGANISM: Anabaena sp.

<400> SEQUENCE: 262

```
Val Lys Ile Val Ser Arg Thr Tyr Val Gly Gln Ala Asn Val Tyr Asp
1               5                   10                  15

Ile Gly Val Glu Ser Asp His Asn Phe Val Ile Lys Asn Gly Phe Ile
            20                  25                  30
```

Ala Ser Asn
        35

<210> SEQ ID NO 263
<211> LENGTH: 102
<212> TYPE: PRT
<213> ORGANISM: Aphanothece halophytica

<400> SEQUENCE: 263

Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Cys Ser Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
    50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met
            100

<210> SEQ ID NO 264
<211> LENGTH: 35
<212> TYPE: PRT
<213> ORGANISM: Aphanothece halophytica

<400> SEQUENCE: 264

Val Lys Ile Ile Lys Arg Gln Ser Leu Gly Arg Gln Asn Val Tyr Asp
1               5                   10                  15

Val Cys Val Glu Thr Asp His Asn Phe Val Leu Ala Asn Gly Cys Val
            20                  25                  30

Ala Ser Asn
        35

<210> SEQ ID NO 265
<211> LENGTH: 102
<212> TYPE: PRT
<213> ORGANISM: Halothece sp.

<400> SEQUENCE: 265

Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Cys Ser Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
    50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met
            100

<210> SEQ ID NO 266
<211> LENGTH: 35
<212> TYPE: PRT
<213> ORGANISM: Halothece sp.

<400> SEQUENCE: 266

Val Lys Ile Ile Lys Arg Gln Ser Leu Gly Arg Gln Asn Val Tyr Asp
1               5                   10                  15

Ile Gly Val Glu Thr Asp His Asn Phe Val Leu Ala Asn Gly Cys Val
            20                  25                  30

Ala Ser Asn
        35

<210> SEQ ID NO 267
<211> LENGTH: 102
<212> TYPE: PRT
<213> ORGANISM: Cyanobacterium aponinum

<400> SEQUENCE: 267

Cys Leu Ser Tyr Asp Thr Glu Ile Leu Thr Val Glu Tyr Gly Ala Ile
1               5                   10                  15

Ser Ile Gly Lys Ile Val Glu Glu Lys Ile Asn Cys Gln Val Tyr Ser
            20                  25                  30

Val Asp Lys Asn Gly Phe Ile Tyr Thr Gln Asn Ile Ala Gln Trp His
        35                  40                  45

Asp Arg Gly Ser Gln Glu Leu Phe Glu Tyr Glu Leu Glu Asp Gly Arg
    50                  55                  60

Ile Ile Lys Ala Thr Lys Asp His Lys Met Met Thr Lys Asp Gly Gln
65                  70                  75                  80

Met Leu Ala Ile Asn Asp Ile Phe Glu Gln Glu Leu Glu Leu Tyr Ser
                85                  90                  95

Val Asp Asp Met Gly Val
            100

<210> SEQ ID NO 268
<211> LENGTH: 35
<212> TYPE: PRT
<213> ORGANISM: Cyanobacterium aponinum

<400> SEQUENCE: 268

Val Lys Ile Val Lys Arg Arg Ser Leu Gly Val Gln Pro Val Tyr Asp
1               5                   10                  15

Ile Gly Val Glu Lys Asp His Asn Phe Ile Leu Ala Asn Gly Leu Val
            20                  25                  30

Ala Ser Asn
        35

<210> SEQ ID NO 269
<211> LENGTH: 98
<212> TYPE: PRT
<213> ORGANISM: Unknown
<220> FEATURE:
<223> OTHER INFORMATION: Description of Unknown:
      Candidatus Atelocyanobacterium thalassa isolate sequence

<400> SEQUENCE: 269

Cys Leu Ser Tyr Asp Thr Lys Val Leu Thr Val Glu Tyr Gly Pro Leu
1               5                   10                  15

Pro Ile Gly Lys Val Val Gln Glu Asn Ile Arg Cys Arg Val Tyr Thr
            20                  25                  30

```
Thr Asn Asp Gln Gly Leu Ile Tyr Thr Gln Pro Ile Ala Gln Trp His
        35                  40                  45

Asn Arg Gly Lys Gln Glu Ile Phe Glu Tyr His Leu Asp Asp Lys Thr
 50                  55                  60

Ile Ile Arg Ala Thr Lys Glu His Gln Phe Met Thr Val Asp His Val
 65                  70                  75                  80

Met Met Pro Ile Asp Glu Ile Phe Glu Gln Gly Leu Glu Leu Lys Lys
                 85                  90                  95

Ile Lys

<210> SEQ ID NO 270
<211> LENGTH: 35
<212> TYPE: PRT
<213> ORGANISM: Unknown
<220> FEATURE:
<223> OTHER INFORMATION: Description of Unknown:
      Candidatus Atelocyanobacterium thalassa isolate sequence

<400> SEQUENCE: 270

Leu Lys Ile Ile Arg Arg Lys Ser Leu Gly Met His Glu Val Phe Asp
 1               5                  10                  15

Ile Gly Leu Glu Lys Asp His Asn Phe Val Leu Ser Asn Gly Leu Ile
                 20                  25                  30

Ala Ser Asn
        35

<210> SEQ ID NO 271
<211> LENGTH: 102
<212> TYPE: PRT
<213> ORGANISM: Oscillatoria limnetica

<400> SEQUENCE: 271

Cys Leu Ser Tyr Asn Thr Glu Val Leu Thr Val Glu Tyr Gly Pro Leu
 1               5                  10                  15

Pro Ile Gly Lys Ile Val Asp Glu Gln Ile His Cys Arg Val Tyr Ser
                 20                  25                  30

Val Asp Glu Asn Gly Phe Val Tyr Thr Gln Ala Ile Ala Gln Trp His
        35                  40                  45

Asp Arg Gly Tyr Gln Glu Ile Phe Ala Tyr Glu Leu Ala Asp Gly Ser
 50                  55                  60

Val Ile Arg Ala Thr Lys Asp His Gln Phe Met Thr Glu Asp Gly Gln
 65                  70                  75                  80

Met Phe Pro Ile Asp Glu Ile Trp Glu Lys Gly Leu Asp Leu Lys Lys
                 85                  90                  95

Leu Pro Thr Val Gln Asp
        100

<210> SEQ ID NO 272
<211> LENGTH: 35
<212> TYPE: PRT
<213> ORGANISM: Oscillatoria limnetica

<400> SEQUENCE: 272

Val Lys Ile Val Arg Arg Gln Ser Leu Gly Val Gln Asn Val Tyr Asp
 1               5                  10                  15

Ile Gly Val Glu Lys Asp His Asn Phe Leu Leu Ala Ser Gly Glu Ile
                 20                  25                  30

Ala Ser Asn
```

<210> SEQ ID NO 273
<211> LENGTH: 102
<212> TYPE: PRT
<213> ORGANISM: Unknown
<220> FEATURE:
<223> OTHER INFORMATION: Description of Unknown:
      Cyanobacterium endosymbiont of Epithemia turgida sequence

<400> SEQUENCE: 273

Cys Leu Ser Tyr Asp Thr Glu Val Leu Thr Val Glu Tyr Gly Ala Ile
1               5                   10                  15

Pro Ile Gly Arg Met Val Glu Glu Ser Leu Asp Cys Thr Val Tyr Thr
            20                  25                  30

Val Asp Lys Asn Gly Phe Val Tyr Thr Gln Ser Ile Gln Gln Trp His
        35                  40                  45

Ser Arg Gly Gln Gln Glu Ile Phe Glu Tyr Cys Phe Glu Asp Gly Ser
    50                  55                  60

Ile Ile Arg Ala Thr Lys Asp His Lys Phe Met Thr Ala Glu Gly Lys
65                  70                  75                  80

Met Ser Ser Ile His Asp Ile Phe Glu Gln Gly Leu Glu Leu Lys Lys
                85                  90                  95

Ile Ile Pro Trp Ser Gly
            100

<210> SEQ ID NO 274
<211> LENGTH: 35
<212> TYPE: PRT
<213> ORGANISM: Unknown
<220> FEATURE:
<223> OTHER INFORMATION: Description of Unknown:
      Cyanobacterium endosymbiont of Epithemia turgida sequence

<400> SEQUENCE: 274

Ala Lys Ile Ile Ser Cys Lys Ser Leu Gly Lys Gln Ser Val Tyr Asp
1               5                   10                  15

Ile Gly Val Val Gln Asp His Asn Phe Leu Leu Ala Asn Gly Val Val
            20                  25                  30

Ala Ser Asn
        35

<210> SEQ ID NO 275
<211> LENGTH: 98
<212> TYPE: PRT
<213> ORGANISM: Synechococcus sp.

<400> SEQUENCE: 275

Cys Leu Gly Tyr Asp Thr Pro Val Leu Thr Val Glu Tyr Gly Phe Met
1               5                   10                  15

Pro Ile Gly Lys Ile Val Glu Glu Lys Ile Gln Cys His Val Tyr Ser
            20                  25                  30

Val Asp Gln Asn Gly Leu Val Phe Thr Gln Ala Ile Ala Gln Trp His
        35                  40                  45

Asn Arg Gly Gln Gln Glu Val Trp Glu Tyr Asn Leu Asp Asn Gly Asp
    50                  55                  60

Ile Val Arg Ala Thr Lys Asp His Lys Phe Met Thr Ile Asp Gly Gln
65                  70                  75                  80

Met Leu Pro Ile Asn Gln Ile Phe Glu Gln Gly Leu Glu Leu Lys Val
                85                  90                  95

```
Ile Ala

<210> SEQ ID NO 276
<211> LENGTH: 35
<212> TYPE: PRT
<213> ORGANISM: Synechococcus sp.

<400> SEQUENCE: 276

Val Lys Ile Val Ser Cys Lys Pro Leu Arg Val Gln Thr Val Tyr Asp
1               5                   10                  15

Ile Gly Val Glu Lys Asp His Asn Phe Ile Leu Asp Asn Gly Leu Val
            20                  25                  30

Ala Ser Asn
        35

<210> SEQ ID NO 277
<211> LENGTH: 90
<212> TYPE: PRT
<213> ORGANISM: Cyanobacterium sp.

<400> SEQUENCE: 277

Cys Leu Ser Tyr Asp Thr Lys Val Leu Thr Val Glu Tyr Gly Pro Leu
1               5                   10                  15

Pro Ile Gly Lys Val Val Gln Glu Asn Ile Arg Cys Arg Val Tyr Thr
            20                  25                  30

Thr Asn Asp Gln Gly Leu Ile Tyr Thr Gln Pro Ile Ala Gln Trp His
        35                  40                  45

Asn Arg Gly Lys Gln Glu Ile Phe Glu Tyr His Leu Asp Asp Lys Thr
    50                  55                  60

Ile Ile Arg Ala Thr Lys Glu His Gln Phe Met Thr Val Asp His Val
65                  70                  75                  80

Met Met Pro Ile Asp Glu Ile Phe Glu Gln
                85                  90

<210> SEQ ID NO 278
<211> LENGTH: 34
<212> TYPE: PRT
<213> ORGANISM: Cyanobacterium sp.

<400> SEQUENCE: 278

Lys Ile Ile Arg Arg Lys Ser Leu Gly Met His Glu Val Phe Asp Ile
1               5                   10                  15

Gly Leu Glu Lys Asp His Asn Phe Val Leu Ser Asn Gly Leu Ile Ala
            20                  25                  30

Ser Asn

<210> SEQ ID NO 279
<211> LENGTH: 94
<212> TYPE: PRT
<213> ORGANISM: Planktothrix sp.

<400> SEQUENCE: 279

Cys Leu Ser Tyr Asp Thr Glu Val Leu Thr Val Glu Tyr Gly Leu Ile
1               5                   10                  15

Pro Ile Ser Lys Ile Val Glu Glu Lys Ile Glu Cys Thr Val Tyr Thr
            20                  25                  30

Val Asn Asn Gln Gly Tyr Val Tyr Thr Gln Pro Ile Ala Gln Trp His
        35                  40                  45
```

Asn Arg Gly Glu Gln Glu Val Phe Glu Tyr Tyr Leu Glu Asp Gly Ser
            50                  55                  60

Val Ile Arg Ala Thr Lys Asp His Lys Phe Met Thr Val Glu Gly Gln
 65                  70                  75                  80

Met Leu Pro Ile Asp Glu Ile Phe Glu Lys Glu Leu Asp Leu
                 85                  90

<210> SEQ ID NO 280
<211> LENGTH: 35
<212> TYPE: PRT
<213> ORGANISM: Planktothrix sp.

<400> SEQUENCE: 280

Val Lys Ile Ile Ser Arg Lys Ser Leu Gly Thr Gln Pro Val Tyr Asp
 1               5                  10                  15

Ile Gly Val Gln Glu Asp His Asn Phe Val Leu Asn Asn Gly Leu Val
                20                  25                  30

Ala Ser Asn
        35

<210> SEQ ID NO 281
<211> LENGTH: 94
<212> TYPE: PRT
<213> ORGANISM: Planktothrix sp.

<400> SEQUENCE: 281

Cys Leu Ser Tyr Asp Thr Glu Ile Leu Thr Val Glu Tyr Gly Leu Met
 1               5                  10                  15

Pro Ile Gly Lys Ile Val Lys Glu Lys Ile Glu Cys Thr Val Tyr Thr
                20                  25                  30

Val Asn Asn Gln Gly Tyr Val Tyr Thr Gln Pro Ile Ala Gln Trp His
            35                  40                  45

His Arg Gly Glu Gln Glu Val Phe Glu Tyr Cys Leu Glu Asp Gly Ser
        50                  55                  60

Val Ile Arg Ala Thr Lys Asp His Lys Phe Met Thr Val Gln Gly Gln
 65                  70                  75                  80

Met Leu Pro Ile Asp Glu Ile Phe Glu Lys Glu Leu Asp Leu
                 85                  90

<210> SEQ ID NO 282
<211> LENGTH: 35
<212> TYPE: PRT
<213> ORGANISM: Planktothrix sp.

<400> SEQUENCE: 282

Val Lys Ile Ile Ser Arg Lys Ser Leu Gly Thr Gln Pro Val Tyr Asp
 1               5                  10                  15

Ile Gly Val Gln Glu Asp His Asn Phe Leu Leu Asn Asn Gly Leu Val
                20                  25                  30

Ala Ser Asn
        35

<210> SEQ ID NO 283
<211> LENGTH: 94
<212> TYPE: PRT
<213> ORGANISM: Planktothrix sp.

<400> SEQUENCE: 283

Cys Leu Ser Tyr Asp Thr Glu Ile Leu Thr Val Glu Tyr Gly Leu Ile
 1               5                  10                  15

```
Pro Ile Ser Lys Ile Val Glu Glu Lys Ile Glu Cys Thr Val Tyr Thr
             20                  25                  30

Val Asn Asn Gln Gly Tyr Val Tyr Thr Gln Pro Ile Ala Gln Trp His
         35                  40                  45

Asn Arg Gly Glu Gln Glu Val Phe Glu Tyr Tyr Leu Glu Asp Gly Ser
     50                  55                  60

Val Ile Arg Ala Thr Lys Asp His Lys Phe Met Thr Val Asp Gly Gln
 65                  70                  75                  80

Met Leu Pro Ile Asp Glu Ile Phe Lys Glu Leu Asp Leu
             85                  90
```

<210> SEQ ID NO 284
<211> LENGTH: 35
<212> TYPE: PRT
<213> ORGANISM: Planktothrix sp.

<400> SEQUENCE: 284

```
Val Lys Ile Ile Ser Arg Lys Ser Leu Gly Thr Gln Pro Val Tyr Asp
 1               5                  10                  15

Ile Gly Val Gln Glu Asp His Asn Phe Val Leu Asn Asn Gly Leu Val
             20                  25                  30

Ala Ser Asn
         35
```

<210> SEQ ID NO 285
<211> LENGTH: 99
<212> TYPE: PRT
<213> ORGANISM: Cyanothece sp.

<400> SEQUENCE: 285

```
Cys Leu Ser Tyr Asp Thr Glu Ile Leu Thr Val Glu Tyr Gly Ala Ile
 1               5                  10                  15

Pro Ile Gly Lys Val Val Glu Glu Asn Ile Asp Cys Thr Val Tyr Thr
             20                  25                  30

Val Asp Lys Asn Gly Phe Val Tyr Thr Gln Asn Ile Ala Gln Trp His
         35                  40                  45

Leu Arg Gly Gln Gln Glu Val Phe Glu Tyr Tyr Leu Asp Asp Gly Ser
     50                  55                  60

Ile Leu Arg Ala Thr Lys Asp His Gln Phe Met Thr Leu Glu Gly Glu
 65                  70                  75                  80

Met Leu Pro Ile His Glu Ile Phe Glu Arg Gly Leu Glu Leu Lys Lys
             85                  90                  95

Ile Lys Ile
```

<210> SEQ ID NO 286
<211> LENGTH: 35
<212> TYPE: PRT
<213> ORGANISM: Cyanothece sp.

<400> SEQUENCE: 286

```
Val Lys Ile Val Ser Tyr Arg Ser Leu Gly Lys Gln Phe Val Tyr Asp
 1               5                  10                  15

Ile Gly Val Ala Gln Asp His Asn Phe Leu Leu Ala Asn Gly Ser Ile
             20                  25                  30

Ala Ser Asn
         35
```

```
<210> SEQ ID NO 287
<211> LENGTH: 102
<212> TYPE: PRT
<213> ORGANISM: Chlorogloeposis fritschii

<400> SEQUENCE: 287

Cys Leu Ser Tyr Asp Thr Ala Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Ser Asn Gly Tyr Ile Tyr Thr Gln Pro Ile Ala Gln Trp His
        35                  40                  45

Asn Arg Gly Glu Gln Glu Leu Phe Glu Tyr Ser Leu Glu Asp Gly Ser
    50                  55                  60

Ile Ile Arg Ala Thr Lys Asp His Lys Phe Met Thr Ile Asp Gly Gln
65                  70                  75                  80

Met Leu Pro Ile Asp Glu Ile Phe Ala Arg Lys Leu Glu Leu Met Gln
                85                  90                  95

Val Lys Gly Leu Pro Glu
            100

<210> SEQ ID NO 288
<211> LENGTH: 35
<212> TYPE: PRT
<213> ORGANISM: Chlorogloeposis fritschii

<400> SEQUENCE: 288

Val Lys Ile Ile Ala Lys Lys Ser Leu Gly Thr Gln Asn Val Tyr Asp
1               5                   10                  15

Ile Gly Val Glu Arg Asp His Asn Phe Val Ile Lys Asn Gly Leu Val
            20                  25                  30

Ala Ser Asn
        35

<210> SEQ ID NO 289
<211> LENGTH: 97
<212> TYPE: PRT
<213> ORGANISM: Cyanothece sp.

<400> SEQUENCE: 289

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Thr Val Tyr Thr
            20                  25                  30

Val Asp Pro Asn Gly Phe Val Tyr Thr Gln Ala Ile Ala Gln Trp His
        35                  40                  45

Tyr Arg Gly Glu Gln Glu Ile Phe Glu Tyr Tyr Leu Glu Asp Gly Ala
    50                  55                  60

Thr Ile Arg Ala Thr Lys Asp His Lys Phe Met Thr Met Glu Gly Lys
65                  70                  75                  80

Met Leu Pro Ile Asp Glu Ile Phe Glu Asn Asn Leu Asp Leu Lys Gln
                85                  90                  95

Leu

<210> SEQ ID NO 290
<211> LENGTH: 35
<212> TYPE: PRT
<213> ORGANISM: Cyanothece sp.
```

-continued

```
<400> SEQUENCE: 290

Val Lys Ile Ile Gly Arg Gln Ser Leu Gly Val Gln Lys Val Tyr Asp
1               5                   10                  15

Ile Gly Val Glu Lys Glu His Asn Phe Leu His Asn Gly Leu Ile
            20                  25                  30

Ala Ser Asn
        35

<210> SEQ ID NO 291
<211> LENGTH: 97
<212> TYPE: PRT
<213> ORGANISM: Lyngbya majuscula

<400> SEQUENCE: 291

Cys Leu Ser Tyr Asp Thr Glu Ile Ile Thr Val Glu Tyr Gly Pro Ile
1               5                   10                  15

Ala Ile Gly Glu Ile Val Glu Lys Gly Ile Pro Cys Thr Val Tyr Ser
            20                  25                  30

Val Asp Ser Asn Gly Tyr Val Tyr Thr Gln Pro Ile Ala Gln Trp His
        35                  40                  45

Asn Arg Gly Glu Gln Glu Val Phe Glu Tyr Thr Leu Asp Asp Gly Ser
    50                  55                  60

Val Ile Arg Ala Thr Lys Asp His Lys Phe Met Thr Ile Asp Gly Gln
65                  70                  75                  80

Met Leu Pro Ile Asp Glu Ile Phe Gly Gly Leu Glu Leu Lys Gln
                85                  90                  95

Leu

<210> SEQ ID NO 292
<211> LENGTH: 35
<212> TYPE: PRT
<213> ORGANISM: Lyngbya majuscula

<400> SEQUENCE: 292

Val Lys Ile Ile Ser Arg Lys Ser Leu Gly Thr Gln Pro Val Tyr Asp
1               5                   10                  15

Ile Gly Val Lys Asp Asp His Asn Phe Ile Leu Ala Asn Gly Met Val
            20                  25                  30

Ala Ser Asn
        35

<210> SEQ ID NO 293
<211> LENGTH: 102
<212> TYPE: PRT
<213> ORGANISM: Unknown
<220> FEATURE:
<223> OTHER INFORMATION: Description of Unknown: filamentous
      cyanobacterium ESFC-1 sequence

<400> SEQUENCE: 293

Cys Leu Ser Tyr Asp Thr Glu Val Leu Thr Val Glu Tyr Gly Ala Val
1               5                   10                  15

Pro Ile Gly Lys Leu Val Glu Glu Lys Leu Asn Cys Ser Val Tyr Thr
            20                  25                  30

Val Asp Pro Asn Gly Tyr Ile Tyr Thr Gln Ala Ile Ala Gln Trp His
        35                  40                  45

Asp Arg Gly Ile Gln Glu Val Phe Glu Tyr Gln Leu Glu Asp Asn Thr
    50                  55                  60
```

```
Ile Ile Arg Ala Thr Lys Asp His Lys Phe Met Thr Glu Asp His Gln
 65                  70                  75                  80

Met Leu Pro Ile Asp Glu Ile Phe Glu Arg Gly Leu Glu Leu Lys Lys
                 85                  90                  95

Cys Pro Gln Pro Gln Gln
            100
```

<210> SEQ ID NO 294
<211> LENGTH: 35
<212> TYPE: PRT
<213> ORGANISM: Unknown
<220> FEATURE:
<223> OTHER INFORMATION: Description of Unknown: filamentous
      cyanobacterium ESFC-1 sequence

<400> SEQUENCE: 294

```
Val Lys Ile Ile Arg Arg Arg Ser Leu Gly Phe Gln Pro Val Tyr Asp
 1               5                  10                  15

Ile Gly Leu Glu Gln Asp His Asn Phe Leu Asn Gln Gly Ala Ile
                 20                  25                  30

Ala Ser Asn
        35
```

<210> SEQ ID NO 295
<211> LENGTH: 94
<212> TYPE: PRT
<213> ORGANISM: Microcystis aeruginosa

<400> SEQUENCE: 295

```
Cys Leu Gly Gly Glu Thr Leu Ile Leu Thr Glu Glu Tyr Gly Leu Leu
 1               5                  10                  15

Pro Ile Ala Lys Ile Val Ser Glu Glu Val Asn Cys Thr Val Tyr Ser
                 20                  25                  30

Val Asp Lys Asn Gly Phe Val Tyr Ser Gln Pro Ile Ser Gln Trp His
                 35                  40                  45

Glu Arg Gly Leu Gln Glu Val Phe Glu Tyr Thr Leu Glu Asn Gly Gln
 50                  55                  60

Thr Ile Gln Ala Thr Lys Asp His Lys Phe Met Thr Asn Asp Gly Glu
 65                  70                  75                  80

Met Leu Ala Ile Asp Thr Ile Phe Glu Arg Gly Leu Asp Leu
                 85                  90
```

<210> SEQ ID NO 296
<211> LENGTH: 35
<212> TYPE: PRT
<213> ORGANISM: Microcystis aeruginosa

<400> SEQUENCE: 296

```
Val Lys Ile Ile Ser Arg Gln Ser Leu Gly Arg Lys Pro Val Tyr Asp
 1               5                  10                  15

Ile Gly Val Glu Lys Asp His Asn Phe Leu Leu Gly Asn Gly Leu Ile
                 20                  25                  30

Ala Ser Asn
        35
```

<210> SEQ ID NO 297
<211> LENGTH: 102
<212> TYPE: PRT
<213> ORGANISM: Rubidibacter lacunae

<400> SEQUENCE: 297

Cys Leu Ser Tyr Asp Thr Glu Val Leu Thr Val Glu Tyr Gly Pro Leu
1               5                   10                  15

Ala Ile Gly Thr Ile Val Ser Glu Arg Leu Ala Cys Thr Val Tyr Thr
            20                  25                  30

Val Asp Arg Ser Gly Phe Leu Tyr Ala Gln Ala Ile Ser Gln Trp His
            35                  40                  45

Glu Arg Gly Arg Gln Asp Val Phe Glu Tyr Ala Leu Asp Asn Gly Met
        50                  55                  60

Thr Ile Arg Ala Thr Lys Asp His Lys Leu Met Thr Ala Asp Gly Gln
65              70                  75                  80

Met Val Ala Ile Asp Asp Ile Phe Thr Gln Gly Leu Thr Leu Lys Ala
                85                  90                  95

Ile Asp Thr Ala Ala Phe
            100

<210> SEQ ID NO 298
<211> LENGTH: 35
<212> TYPE: PRT
<213> ORGANISM: Rubidibacter lacunae

<400> SEQUENCE: 298

Met Lys Ile Val Ser Arg Lys Ser Leu Gly Val Gln His Val Tyr Asp
1               5                   10                  15

Ile Gly Val Ala Arg Asp His Asn Phe Leu Ala Asn Gly Ala Ile
            20                  25                  30

Ala Ser Asn
        35

<210> SEQ ID NO 299
<211> LENGTH: 101
<212> TYPE: PRT
<213> ORGANISM: Chlorogloeopsis fritschii

<400> SEQUENCE: 299

Cys Leu Ser Tyr Asp Thr Ala Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Ser Asn Gly Tyr Ile Tyr Thr Gln Pro Ile Ala Gln Trp His
            35                  40                  45

Asn Arg Gly Glu Gln Glu Leu Phe Glu Tyr Ser Leu Glu Asp Gly Ser
        50                  55                  60

Ile Ile Arg Ala Thr Lys Asp His Lys Phe Met Thr Ile Asp Gly Gln
65              70                  75                  80

Met Leu Pro Ile Asp Glu Ile Phe Ala Arg Lys Leu Glu Leu Met Gln
                85                  90                  95

Val Lys Gly Leu Pro
            100

<210> SEQ ID NO 300
<211> LENGTH: 35
<212> TYPE: PRT
<213> ORGANISM: Chlorogloeopsis fritschii

<400> SEQUENCE: 300

Val Lys Ile Ile Ala Lys Lys Ser Leu Gly Thr Gln Asn Val Tyr Asp
1               5                   10                  15

Ile Gly Val Glu Arg Asp His Asn Phe Val Ile Lys Asn Gly Leu Val
            20                  25                  30

Ala Ser Asn
        35

<210> SEQ ID NO 301
<211> LENGTH: 102
<212> TYPE: PRT
<213> ORGANISM: Richelia intracellularis

<400> SEQUENCE: 301

Cys Leu Ser Tyr Asp Thr Gln Ile Leu Thr Val Glu His Gly Pro Met
1               5                   10                  15

Ser Ile Gly Glu Ile Val Glu Lys Cys Leu Glu Cys His Val Tyr Thr
            20                  25                  30

Val Asn Lys Asn Gly Asn Ile Cys Ile Gln Thr Ile Thr Gln Trp His
        35                  40                  45

Phe Arg Gly Glu Gln Glu Ile Phe Glu Tyr Glu Leu Glu Asp Gly Ser
    50                  55                  60

Phe Ile Gln Ala Thr Lys Asp His Lys Phe Met Thr Thr Thr Gly Glu
65                  70                  75                  80

Met Leu Pro Ile His Glu Ile Phe Thr Asn Gly Leu Glu Ile Leu Gln
                85                  90                  95

Leu Ser Lys Ser Leu Leu
            100

<210> SEQ ID NO 302
<211> LENGTH: 35
<212> TYPE: PRT
<213> ORGANISM: Richelia intracellularis

<400> SEQUENCE: 302

Val Lys Ile Leu Ala Arg Lys Ser Leu Gly Thr Gln Lys Val Tyr Asp
1               5                   10                  15

Ile Gly Val Asn Asp Asp His Asn Phe Ala Leu Ser Asn Ser Phe Ile
            20                  25                  30

Ala Ser Asn
        35

<210> SEQ ID NO 303
<211> LENGTH: 98
<212> TYPE: PRT
<213> ORGANISM: Geminocystis herdmanii

<400> SEQUENCE: 303

Cys Leu Ser Tyr Asp Thr Glu Val Leu Thr Val Glu Phe Gly Ala Ile
1               5                   10                  15

Pro Met Gly Lys Ile Val Glu Glu Arg Leu Asn Cys Gln Val Tyr Ser
            20                  25                  30

Val Asp Lys Asn Gly Phe Ile Tyr Thr Gln Asn Ile Ala Gln Trp His
        35                  40                  45

Asp Arg Gly Val Gln Glu Val Phe Glu Tyr Glu Leu Glu Asp Gly Arg
    50                  55                  60

Ile Ile Lys Ala Thr Lys Asp His Lys Met Met Ile Glu Asn Cys Glu
65                  70                  75                  80

Met Val Glu Ile Asp Arg Ile Phe Glu Glu Gly Leu Glu Leu Phe Glu
                85                  90                  95

Val Asn

<210> SEQ ID NO 304
<211> LENGTH: 35
<212> TYPE: PRT
<213> ORGANISM: Geminocystis herdmanii

<400> SEQUENCE: 304

Val Lys Ile Leu Lys Arg Arg Ser Ile Ser Gln Gln Val Tyr Asp
1               5                   10                  15

Ile Gly Val Glu Lys Asp His Asn Phe Leu Leu Ala Asn Gly Leu Val
                20                  25                  30

Ala Ser Asn
        35

<210> SEQ ID NO 305
<211> LENGTH: 97
<212> TYPE: PRT
<213> ORGANISM: Spirulina subsalsa

<400> SEQUENCE: 305

Cys Leu Ser Tyr Asp Thr Lys Ile Ile Thr Val Glu Tyr Gly Ala Ile
1               5                   10                  15

Ala Ile Gly Thr Ile Val Glu Gln Gly Leu His Cys His Val Tyr Ser
                20                  25                  30

Val Asp Pro Asn Gly Phe Ile Tyr Thr Gln Pro Ile Ala Gln Trp His
            35                  40                  45

Gln Arg Gly Glu Gln Glu Val Phe Ala Tyr Thr Leu Glu Asn Gly Ser
        50                  55                  60

Ile Ile Gln Ala Thr Lys Asp His Lys Phe Met Thr Gln Gln Gly Lys
65                  70                  75                  80

Met Leu Pro Ile Asp Thr Ile Phe Glu Gln Gly Leu Asp Leu Leu Gln
                85                  90                  95

Val

<210> SEQ ID NO 306
<211> LENGTH: 34
<212> TYPE: PRT
<213> ORGANISM: Spirulina subsalsa

<400> SEQUENCE: 306

Lys Ile Ile Lys Arg Thr Ser Leu Gly Val Arg Pro Val Tyr Asp Ile
1               5                   10                  15

Gly Val Ile Gln Asp His Asn Phe Leu Leu Glu Asn Gly Leu Val Ala
                20                  25                  30

Ser Asn

<210> SEQ ID NO 307
<211> LENGTH: 100
<212> TYPE: PRT
<213> ORGANISM: Microcystis aeruginosa

<400> SEQUENCE: 307

Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Cys Thr Val Tyr Ser
                20                  25                  30

Val Asp Lys Asn Gly Phe Ile Tyr Ser Gln Pro Ile Ser Gln Trp His
            35                  40                  45

```
Glu Arg Gly Leu Gln Glu Val Phe Glu Tyr Thr Leu Glu Asn Gly Gln
 50                  55                  60

Thr Ile Gln Ala Thr Lys Asp His Lys Phe Met Thr Ser Asp Gly Glu
 65                  70                  75                  80

Met Leu Ala Ile Asp Thr Ile Phe Glu Arg Gly Leu Asp Leu Lys Ser
                 85                  90                  95

Ser Asp Phe Ser
            100
```

<210> SEQ ID NO 308
<211> LENGTH: 35
<212> TYPE: PRT
<213> ORGANISM: Microcystis aeruginosa

<400> SEQUENCE: 308

```
Val Lys Ile Ile Ser Arg Gln Phe Leu Gly Arg Lys Pro Val Tyr Asp
 1               5                  10                  15

Ile Gly Val Glu Lys Asp His Asn Phe Leu Gly Asn Gly Leu Ile
             20                  25                  30

Ala Ser Asn
         35
```

<210> SEQ ID NO 309
<211> LENGTH: 95
<212> TYPE: PRT
<213> ORGANISM: Myxosarcina sp.

<400> SEQUENCE: 309

```
Cys Leu Ser Tyr Asp Thr Glu Val Leu Thr Leu Lys Tyr Gly Ala Leu
 1               5                  10                  15

Pro Ile Gly Glu Ile Val Glu Lys Arg Ile Asn Cys His Val Tyr Thr
             20                  25                  30

Arg Ala Glu Ser Gly Phe Phe Tyr Ile Gln Ser Ile Glu Gln Trp His
             35                  40                  45

Asp Arg Gly Glu Gln Glu Val Phe Glu Tyr Thr Leu Glu Asn Gly Ala
 50                  55                  60

Thr Ile Lys Ala Thr Lys Asp His Lys Phe Met Thr Ser Gly Gly Gln
 65                  70                  75                  80

Met Leu Pro Ile Asp Glu Ile Phe Glu Arg Gly Leu Asp Leu Leu
                 85                  90                  95
```

<210> SEQ ID NO 310
<211> LENGTH: 35
<212> TYPE: PRT
<213> ORGANISM: Myxosarcina sp.

<400> SEQUENCE: 310

```
Val Lys Ile Val Ser Arg Lys Ser Leu Gly Lys Gln Pro Val Tyr Asp
 1               5                  10                  15

Leu Gly Val Ala Lys Asp His Asn Phe Leu Leu Ala Asn Gly Thr Val
             20                  25                  30

Ala Ser Asn
         35
```

<210> SEQ ID NO 311
<211> LENGTH: 101
<212> TYPE: PRT
<213> ORGANISM: Scytonema hofmanni

<400> SEQUENCE: 311

Cys Leu Ser Tyr Asp Thr Glu Val Leu Thr Ala Glu Tyr Gly Phe Leu
1               5                   10                  15

Pro Ile Gly Lys Ile Val Glu Lys Ala Ile Glu Cys Thr Val Tyr Ser
            20                  25                  30

Val Asp Asn Asp Gly Asn Ile Tyr Thr Gln Pro Ile Ala Gln Trp His
        35                  40                  45

Asp Arg Gly Gln Gln Glu Val Phe Glu Tyr Ser Leu Asp Asp Gly Ser
    50                  55                  60

Val Ile Arg Ala Thr Lys Asp His Lys Phe Met Thr Thr Gly Gly Gln
65                  70                  75                  80

Met Leu Pro Ile Asp Glu Ile Phe Glu Arg Gly Leu Asp Leu Met Arg
            85                  90                  95

Ile Asp Ser Leu Pro
            100

<210> SEQ ID NO 312
<211> LENGTH: 35
<212> TYPE: PRT
<213> ORGANISM: Scytonema hofmanni

<400> SEQUENCE: 312

Val Lys Ile Leu Thr Arg Lys Ser Ile Gly Lys Gln Thr Val Tyr Asp
1               5                   10                  15

Ile Gly Val Glu Arg Asp His Asn Phe Val Ile Lys Asn Gly Leu Val
            20                  25                  30

Ala Ser Asn
        35

<210> SEQ ID NO 313
<211> LENGTH: 101
<212> TYPE: PRT
<213> ORGANISM: Westiella intricata

<400> SEQUENCE: 313

Cys Leu Ser Tyr Asp Thr Glu Ile Leu Thr Val Glu Tyr Gly Phe Leu
1               5                   10                  15

Pro Ile Gly Glu Ile Val Glu Lys Arg Ile Glu Cys Thr Val Tyr Thr
            20                  25                  30

Val Asp Thr Asn Gly Tyr Val Tyr Thr Gln Ala Ile Ala Gln Trp His
        35                  40                  45

Asn Arg Gly Glu Gln Glu Val Phe Glu Tyr Ala Leu Glu Asp Gly Ser
    50                  55                  60

Ile Ile Arg Ala Thr Lys Asp His Lys Phe Met Thr Ser Glu Gly Gln
65                  70                  75                  80

Met Leu Pro Ile Asp Glu Ile Phe Val Lys Gly Leu Asp Leu Leu Gln
            85                  90                  95

Val Gln Gly Leu Pro
            100

<210> SEQ ID NO 314
<211> LENGTH: 35
<212> TYPE: PRT
<213> ORGANISM: Westiella intricata

<400> SEQUENCE: 314

Val Lys Ile Ile Thr Arg Lys Phe Leu Gly Ile Gln Asn Val Tyr Asp
1               5                   10                  15

```
Ile Gly Val Glu Gln Asn His Asn Phe Val Ile Lys Asn Gly Leu Val
            20                  25                  30

Ala Ser Asn
        35

<210> SEQ ID NO 315
<211> LENGTH: 101
<212> TYPE: PRT
<213> ORGANISM: Fischerella sp.

<400> SEQUENCE: 315

Cys Leu Ser Tyr Asp Thr Glu Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Asn Asn Gly Asn Val Tyr Thr Gln Thr Ile Ala Gln Trp His
        35                  40                  45

Asn Arg Gly Gln Gln Glu Val Phe Glu Tyr Cys Leu Glu Asp Gly Ser
    50                  55                  60

Val Ile Arg Ala Thr Lys Asp His Lys Phe Met Thr Thr Asp Gly Gln
65                  70                  75                  80

Met Leu Pro Ile Asp Glu Ile Phe Ala Arg Gly Leu Asp Leu Leu Gln
                85                  90                  95

Val Lys Asn Leu Pro
            100

<210> SEQ ID NO 316
<211> LENGTH: 35
<212> TYPE: PRT
<213> ORGANISM: Fischerella sp.

<400> SEQUENCE: 316

Val Lys Ile Val Thr Arg Arg Pro Leu Gly Thr Gln Asn Val Tyr Asp
1               5                   10                  15

Ile Gly Val Glu Ser Asp His Asn Phe Val Ile Lys Asn Gly Leu Val
            20                  25                  30

Ala Ser Asn
        35

<210> SEQ ID NO 317
<211> LENGTH: 102
<212> TYPE: PRT
<213> ORGANISM: Mastigocladopsis repens

<400> SEQUENCE: 317

Cys Leu Ser Tyr Asp Thr Glu Val Leu Thr Val Glu Tyr Gly Phe Leu
1               5                   10                  15

Pro Ile Gly Glu Ile Val Glu Lys Ser Ile Glu Cys Ser Val Tyr Thr
            20                  25                  30

Val Asp Ser Asn Gly Asn Val Tyr Thr Gln Pro Ile Ala Gln Trp His
        35                  40                  45

Asn Arg Gly Gln Gln Glu Val Phe Glu Tyr Cys Leu Glu Asp Gly Ser
    50                  55                  60

Ile Ile Arg Ala Thr Lys Asp His Lys Phe Met Thr Ile His Gly Gln
65                  70                  75                  80

Met Leu Pro Ile Asp Glu Ile Phe Glu Arg Gly Leu Glu Leu Met Lys
                85                  90                  95

Ile Gln Gly Leu Pro Glu
```

<210> SEQ ID NO 318
<211> LENGTH: 35
<212> TYPE: PRT
<213> ORGANISM: Mastigocladopsis repens

<400> SEQUENCE: 318

Ala Lys Ile Ile Thr Arg Lys Ser Leu Gly Thr Gln Asn Val Tyr Asp
1               5                   10                  15

Ile Gly Val Glu Arg Asp His Asn Phe Val Thr Arg Asp Gly Phe Ile
            20                  25                  30

Ala Ser Asn
        35

<210> SEQ ID NO 319
<211> LENGTH: 102
<212> TYPE: PRT
<213> ORGANISM: Scytonema hofmanni

<400> SEQUENCE: 319

Cys Leu Ser Tyr Asn Ser Glu Val Leu Thr Val Glu Tyr Gly Phe Leu
1               5                   10                  15

Pro Ile Gly Lys Ile Val Glu Lys Gly Ile Glu Cys Ser Val Tyr Ser
            20                  25                  30

Val Asp Ser Tyr Gly Lys Ile Tyr Thr Gln Val Ile Ala Gln Trp His
        35                  40                  45

Asn Arg Gly Gln Gln Glu Val Phe Glu Tyr Cys Leu Glu Asp Gly Thr
    50                  55                  60

Ile Ile Gln Ala Thr Lys Asp His Lys Phe Met Thr Val Asp Gly Gln
65                  70                  75                  80

Met Leu Pro Ile Asp Glu Ile Phe Glu Arg Gly Leu Asp Leu Met Gln
                85                  90                  95

Val Gln Gly Leu Pro Asp
            100

<210> SEQ ID NO 320
<211> LENGTH: 35
<212> TYPE: PRT
<213> ORGANISM: Scytonema hofmanni

<400> SEQUENCE: 320

Val Lys Ile Ile Thr Arg Lys Ser Leu Gly Thr Gln Asn Val Tyr Asp
1               5                   10                  15

Ile Gly Val Ser Ser Asp His Asn Phe Val Met Lys Asn Gly Leu Ile
            20                  25                  30

Ala Ser Asn
        35

<210> SEQ ID NO 321
<211> LENGTH: 102
<212> TYPE: PRT
<213> ORGANISM: Anabaena sp.

<400> SEQUENCE: 321

Cys Leu Ser Ser Asp Thr Glu Val Leu Thr Val Glu Tyr Gly Leu Ile
1               5                   10                  15

Pro Ile Gly Glu Ile Ile Glu Lys Arg Ile Asp Cys Ser Val Phe Ser
            20                  25                  30

Val Asp Lys Asn Gly Asn Ile Tyr Thr Gln Pro Ile Ala Gln Trp His
            35                  40                  45

Asp Arg Gly Ile Gln Glu Leu Tyr Glu Tyr Cys Leu Asp Asp Gly Ser
 50                  55                  60

Thr Ile Arg Ala Thr Lys Asp His Lys Phe Met Thr Thr Ala Gly Glu
 65                  70                  75                  80

Met Leu Pro Ile Asp Glu Ile Phe Glu Arg Gly Leu Asp Leu Leu Lys
                85                  90                  95

Val His Asn Leu Pro Gln
            100

<210> SEQ ID NO 322
<211> LENGTH: 35
<212> TYPE: PRT
<213> ORGANISM: Anabaena sp.

<400> SEQUENCE: 322

Val Lys Ile Ile Thr Arg Asn Tyr Val Gly Lys Glu Asn Val Tyr Asp
 1               5                  10                  15

Ile Gly Val Glu Arg Asp His Asn Phe Ala Ile Lys Asn Gly Leu Ile
                20                  25                  30

Ala Ser Asn
        35

<210> SEQ ID NO 323
<211> LENGTH: 102
<212> TYPE: PRT
<213> ORGANISM: Fischerella sp.

<400> SEQUENCE: 323

Cys Leu Ser Tyr Asp Thr Glu Val Leu Thr Val Glu Tyr Gly Phe Leu
 1               5                  10                  15

Pro Ile Gly Glu Ile Val Glu Lys Arg Ile Glu Cys Thr Val Tyr Thr
                20                  25                  30

Val Asp His Asn Gly Tyr Val Tyr Thr Gln Pro Ile Ala Gln Trp His
            35                  40                  45

Asn Arg Gly Tyr Gln Glu Val Phe Glu Tyr Gly Leu Glu Asp Gly Ser
 50                  55                  60

Val Ile Arg Ala Thr Lys Asp His Lys Phe Met Thr Ser Glu Gly Gln
 65                  70                  75                  80

Met Leu Pro Ile Asp Glu Ile Phe Ala Arg Glu Leu Asp Leu Leu Gln
                85                  90                  95

Val Thr Gly Leu Val Asn
            100

<210> SEQ ID NO 324
<211> LENGTH: 35
<212> TYPE: PRT
<213> ORGANISM: Fischerella sp.

<400> SEQUENCE: 324

Val Lys Ile Val Thr Arg Arg Leu Leu Gly Ile Gln Asn Val Tyr Asp
 1               5                  10                  15

Ile Gly Val Glu Gln Asn His Asn Phe Val Ile Lys Asn Gly Leu Val
                20                  25                  30

Ala Ser Asn
        35

```
<210> SEQ ID NO 325
<211> LENGTH: 102
<212> TYPE: PRT
<213> ORGANISM: Calothrix sp.

<400> SEQUENCE: 325

Cys Leu Ser Tyr Asp Thr Glu Ile Phe Thr Val Glu Tyr Gly Phe Leu
1               5                   10                  15

Pro Ile Gly Glu Ile Val Glu Lys Arg Leu Glu Cys Thr Val Leu Thr
            20                  25                  30

Val Asp Asn His Gly Asn Ile Tyr Ser Gln Pro Ile Ala Gln Trp His
        35                  40                  45

His Arg Gly Gln Gln Gln Ile Tyr Glu Tyr Gly Leu Glu Asp Gly Ser
    50                  55                  60

Val Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Leu Gln
                85                  90                  95

Val Thr Asn Leu Asp Asn
            100

<210> SEQ ID NO 326
<211> LENGTH: 35
<212> TYPE: PRT
<213> ORGANISM: Calothrix sp.

<400> SEQUENCE: 326

Val Lys Val Ile Thr Arg Lys Leu Ala Asp Thr Glu Asn Val Tyr Asp
1               5                   10                  15

Ile Gly Val Glu Asn His His Asn Phe Leu Ile Lys Asn Gly Leu Val
            20                  25                  30

Ala Ser Asn
        35

<210> SEQ ID NO 327
<211> LENGTH: 101
<212> TYPE: PRT
<213> ORGANISM: Fischerella thermalis

<400> SEQUENCE: 327

Cys Leu Ser Tyr Glu Thr Glu Ile Leu Thr Val Glu Tyr Gly Phe Leu
1               5                   10                  15

Pro Ile Gly Glu Ile Val Glu Lys Arg Ile Glu Cys Ser Val Tyr Thr
            20                  25                  30

Val Asp Asn Asn Gly Tyr Val Cys Thr Gln Pro Ile Ala Gln Trp His
        35                  40                  45

Asn Arg Gly Tyr Gln Glu Val Phe Glu Tyr Gly Leu Glu Asp Gly Ser
    50                  55                  60

Val Ile Arg Ala Thr Lys Asp His Lys Phe Met Thr Ile Asp Arg Gln
65                  70                  75                  80

Met Leu Pro Ile Asp Glu Ile Phe Ala Arg Gly Leu Asp Leu Leu Gln
                85                  90                  95

Val Thr Gly Leu Pro
            100

<210> SEQ ID NO 328
<211> LENGTH: 35
<212> TYPE: PRT
<213> ORGANISM: Fischerella thermalis
```

<400> SEQUENCE: 328

Val Lys Ile Ile Thr Arg Lys Ser Leu Gly Thr Gln Asn Val Tyr Asp
1               5                   10                  15

Ile Gly Val Glu Gln Asn His Asn Phe Val Ile Lys Asn Gly Leu Val
            20                  25                  30

Ala Ser Asn
        35

<210> SEQ ID NO 329
<211> LENGTH: 102
<212> TYPE: PRT
<213> ORGANISM: Unknown
<220> FEATURE:
<223> OTHER INFORMATION: Description of Unknown:
      cyanobacterium PCC 7702 Chl7702 sequence

<400> SEQUENCE: 329

Cys Leu Ser Tyr Asp Thr Glu Ile Leu Thr Val Glu Tyr Gly Phe Leu
1               5                   10                  15

Ser Ile Gly Glu Ile Val Glu Lys Glu Ile Glu Cys Thr Val Tyr Thr
            20                  25                  30

Val Asp Ser Asn Gly Tyr Ile Tyr Thr Gln Pro Ile Ala Gln Trp His
        35                  40                  45

Glu Gln Gly Glu Gln Ile Phe Glu Tyr Ser Leu Glu Asp Gly Ser
    50                  55                  60

Thr Ile Arg Ala Thr Lys Asp His Lys Phe Met Thr Ile Gly Glu
65                  70                  75                  80

Met Leu Pro Ile Asp Gln Ile Phe Ala Arg Gln Leu Asp Leu Met Gln
                85                  90                  95

Ile Thr Gly Leu Pro Gln
            100

<210> SEQ ID NO 330
<211> LENGTH: 35
<212> TYPE: PRT
<213> ORGANISM: Unknown
<220> FEATURE:
<223> OTHER INFORMATION: Description of Unknown:
      cyanobacterium PCC 7702 Chl7702 sequence

<400> SEQUENCE: 330

Val Lys Ile Ser Thr Lys Lys Ser Leu Gly Lys Gln Lys Val Tyr Asp
1               5                   10                  15

Ile Gly Val Val Arg Asp His Asn Phe Ile Ile Lys Asn Gly Phe Val
            20                  25                  30

Ala Ser Asn
        35

<210> SEQ ID NO 331
<211> LENGTH: 101
<212> TYPE: PRT
<213> ORGANISM: Fischerella sp.

<400> SEQUENCE: 331

Cys Leu Ser Tyr Asp Thr Glu Val Leu Thr Val Glu Tyr Gly Phe Leu
1               5                   10                  15

Pro Ile Gly Glu Ile Val Glu Lys Arg Ile Glu Cys Thr Val Tyr Thr
            20                  25                  30

Val Asp Thr Asn Gly Tyr Val Tyr Thr Gln Ala Ile Ala Gln Trp His

```
                35                  40                  45

Asn Arg Asp Glu Gln Glu Val Phe Glu Tyr Ala Leu Glu Asp Gly Ser
         50                  55                  60

Ile Ile Arg Ala Thr Lys Asp His Lys Phe Met Thr Ser Glu Gly Gln
 65                  70                  75                  80

Met Leu Pro Ile Asp Glu Ile Phe Ala Lys Gly Leu Asp Leu Leu Gln
                 85                  90                  95

Val Gln Gly Leu Pro
            100

<210> SEQ ID NO 332
<211> LENGTH: 35
<212> TYPE: PRT
<213> ORGANISM: Fischerella sp.

<400> SEQUENCE: 332

Val Lys Ile Val Thr Arg Lys Phe Leu Gly Ile Gln Asn Val Tyr Asp
 1               5                  10                  15

Ile Gly Val Glu Gln Asn His Asn Phe Val Ile Lys Asn Gly Leu Val
                20                  25                  30

Ala Ser Asn
         35

<210> SEQ ID NO 333
<211> LENGTH: 102
<212> TYPE: PRT
<213> ORGANISM: Fischerella muscicola

<400> SEQUENCE: 333

Cys Leu Ser Tyr Glu Thr Glu Ile Leu Thr Val Glu Tyr Gly Phe Leu
 1               5                  10                  15

Pro Ile Gly Glu Ile Val Glu Lys Arg Ile Glu Cys Ser Val Tyr Thr
                20                  25                  30

Val Asp Asn Asn Gly Tyr Val Cys Thr Gln Thr Ile Ala Gln Trp His
                35                  40                  45

Asn Arg Gly Tyr Gln Glu Val Phe Glu Tyr Gly Leu Glu Asp Gly Ser
         50                  55                  60

Val Ile Arg Ala Thr Lys Asp His Lys Phe Met Thr Ile Asp Arg Gln
 65                  70                  75                  80

Met Leu Pro Ile Asp Glu Ile Phe Ala Arg Gly Leu Asp Leu Leu Gln
                 85                  90                  95

Val Lys Gly Leu Pro Glu
            100

<210> SEQ ID NO 334
<211> LENGTH: 35
<212> TYPE: PRT
<213> ORGANISM: Fischerella muscicola

<400> SEQUENCE: 334

Val Lys Ile Ile Thr Arg Gln Ser Leu Gly Thr Gln Asn Val Tyr Asp
 1               5                  10                  15

Ile Gly Val Glu Gln Asn His Asn Phe Val Ile Lys Asn Gly Leu Val
                20                  25                  30

Ala Ser Asn
         35

<210> SEQ ID NO 335
```

```
<211> LENGTH: 102
<212> TYPE: PRT
<213> ORGANISM: Fischerella muscicola

<400> SEQUENCE: 335
```

Cys Leu Ser Tyr Asp Thr Glu Val Leu Thr Val Glu Tyr Gly Phe Leu
1               5                   10                  15

Pro Ile Gly Glu Ile Val Glu Lys Thr Ile Glu Cys Asn Val Phe Thr
            20                  25                  30

Val Asp Ser Asn Gly Tyr Val Tyr Thr Gln Pro Ile Ala Gln Trp His
        35                  40                  45

Asn Arg Gly Tyr Gln Glu Val Phe Glu Tyr Gly Leu Glu Asp Gly Ser
    50                  55                  60

Val Ile Arg Ala Thr Lys Asp His Lys Phe Met Thr Ser Glu Gly Lys
65                  70                  75                  80

Met Leu Pro Ile Asp Glu Ile Phe Ala Arg Glu Leu Asp Leu Leu Gln
                85                  90                  95

Val Thr Gly Leu Ile Asn
            100

```
<210> SEQ ID NO 336
<211> LENGTH: 35
<212> TYPE: PRT
<213> ORGANISM: Fischerella muscicola

<400> SEQUENCE: 336
```

Val Lys Ile Val Thr Arg Lys Phe Leu Gly Ile Gln Asn Val Tyr Asp
1               5                   10                  15

Ile Gly Val Glu Gln Asn His Asn Phe Val Ile Lys Asn Gly Leu Val
            20                  25                  30

Ala Ser Asn
        35

```
<210> SEQ ID NO 337
<211> LENGTH: 102
<212> TYPE: PRT
<213> ORGANISM: Lyngbya aestuarii

<400> SEQUENCE: 337
```

Cys Leu Ser Tyr Asp Thr Glu Ile Leu Thr Val Glu Tyr Gly Ala Ile
1               5                   10                  15

Pro Ile Gly Lys Val Val Asp Glu Lys Ile Glu Cys Thr Val Tyr Ser
            20                  25                  30

Val Asp Lys Asn Gly Leu Ile Tyr Thr Gln Pro Ile Ala Gln Trp His
        35                  40                  45

Asn Arg Gly Lys Gln Glu Val Phe Glu Tyr Ser Leu Glu Asp Gly Ser
    50                  55                  60

Thr Ile Arg Ala Thr Lys Asp His Lys Phe Met Thr Met Asp Asn Gln
65                  70                  75                  80

Met Leu Pro Ile Asp Glu Ile Leu Glu Lys Gly Leu Glu Leu Lys Gln
                85                  90                  95

Val Asn Ala Asp Ser Val
            100

```
<210> SEQ ID NO 338
<211> LENGTH: 35
<212> TYPE: PRT
<213> ORGANISM: Lyngbya aestuarii
```

-continued

```
<400> SEQUENCE: 338

Val Lys Ile Val Ser Arg Lys Ser Leu Asp Ser Gln Thr Val Tyr Asp
1               5                   10                  15

Ile Gly Val Glu Thr Asp His Asn Phe Leu Leu Ala Asn Gly Ser Val
                20                  25                  30

Ala Ser Asn
        35

<210> SEQ ID NO 339
<211> LENGTH: 102
<212> TYPE: PRT
<213> ORGANISM: Leptolyngbya sp.

<400> SEQUENCE: 339

Cys Leu Ser Tyr Asp Thr Glu Ile Leu Thr Val Glu Tyr Gly Ala Leu
1               5                   10                  15

Pro Ile Gly Lys Ile Val Glu Asn Gln Met Ile Cys Ser Val Tyr Ser
                20                  25                  30

Ile Asp Asn Asn Gly Tyr Ile Tyr Ile Gln Pro Ile Ala Gln Trp His
                35                  40                  45

Asn Arg Gly Gln Gln Glu Val Phe Glu Tyr Ile Leu Glu Asp Gly Ser
        50                  55                  60

Ile Ile Arg Ser Thr Lys Asp His Lys Phe Met Thr Lys Gly Gly Glu
65                  70                  75                  80

Met Leu Pro Ile Asp Glu Ile Phe Glu Arg Gly Leu Glu Leu Ala Gln
                85                  90                  95

Val Thr Arg Leu Glu Gln
            100

<210> SEQ ID NO 340
<211> LENGTH: 35
<212> TYPE: PRT
<213> ORGANISM: Leptolyngbya sp.

<400> SEQUENCE: 340

Val Lys Ile Ile Ser Arg Arg Ser Val Gly Val Gln Ser Val Tyr Asp
1               5                   10                  15

Ile Gly Val Lys Gln Asp His Asn Phe Phe Leu Arg Asn Gly Leu Ile
                20                  25                  30

Ala Ser Asn
        35

<210> SEQ ID NO 341
<211> LENGTH: 102
<212> TYPE: PRT
<213> ORGANISM: Crocosphaera watsonii

<400> SEQUENCE: 341

Cys Leu Ser Tyr Asp Thr Glu Ile Leu Thr Val Glu Tyr Gly Ala Met
1               5                   10                  15

Tyr Ile Gly Lys Ile Val Glu Glu Asn Ile Asn Cys Thr Val Tyr Thr
                20                  25                  30

Val Asp Lys Asn Gly Phe Val Tyr Thr Gln Thr Ile Ala Gln Trp His
                35                  40                  45

Asn Arg Gly Glu Gln Glu Ile Phe Glu Tyr Asp Leu Glu Asp Gly Ser
        50                  55                  60

Lys Ile Lys Ala Thr Lys Asp His Lys Phe Met Thr Ile Asp Gly Glu
65                  70                  75                  80
```

```
Met Leu Pro Ile Asp Glu Ile Phe Glu Lys Asn Leu Asp Leu Lys Gln
                85                  90                  95

Val Val Ser His Pro Asp
            100
```

<210> SEQ ID NO 342
<211> LENGTH: 35
<212> TYPE: PRT
<213> ORGANISM: Crocosphaera watsonii

<400> SEQUENCE: 342

```
Val Lys Ile Ile Gly Cys Arg Ser Leu Gly Thr Gln Lys Val Tyr Asp
1               5                   10                  15

Ile Gly Val Glu Lys Asp His Asn Phe Leu Leu Ala Asn Gly Ser Ile
            20                  25                  30

Ala Ser Asn
        35
```

<210> SEQ ID NO 343
<211> LENGTH: 100
<212> TYPE: PRT
<213> ORGANISM: Coleofasciculus chthonoplastes

<400> SEQUENCE: 343

```
Cys Leu Ser Tyr Asp Thr Gln Ile Leu Thr Val Glu Tyr Gly Ala Val
1               5                   10                  15

Ala Ile Gly Glu Ile Val Glu Lys Gln Ile Glu Cys Thr Val Tyr Ser
            20                  25                  30

Val Asp Glu Asn Gly Tyr Val Tyr Thr Gln Pro Ile Ala Gln Trp His
        35                  40                  45

Asn Arg Gly Glu Gln Glu Val Phe Glu Tyr Leu Leu Glu Asp Gly Ala
    50                  55                  60

Thr Ile Arg Ala Thr Lys Asp His Lys Phe Met Thr Asp Glu Asp Gln
65                  70                  75                  80

Met Leu Pro Ile Asp Gln Ile Phe Glu Gln Gly Leu Glu Leu Lys Gln
                85                  90                  95

Val Glu Val Leu
            100
```

<210> SEQ ID NO 344
<211> LENGTH: 35
<212> TYPE: PRT
<213> ORGANISM: Coleofasciculus chthonoplastes

<400> SEQUENCE: 344

```
Val Lys Ile Ile Gly Arg Lys Pro Leu Gly Thr Gln Pro Val Tyr Asp
1               5                   10                  15

Ile Gly Val Glu Arg Asp His Asn Phe Leu Leu Phe Asn Gly Ser Val
            20                  25                  30

Ala Ser Asn
        35
```

<210> SEQ ID NO 345
<211> LENGTH: 98
<212> TYPE: PRT
<213> ORGANISM: Chroococcidiopsis sp.

<400> SEQUENCE: 345

```
Cys Leu Ser Tyr Asp Thr Glu Val Leu Thr Val Glu Tyr Gly Ala Ile
```

```
                 1               5                  10                 15
            Pro Ile Gly Lys Ile Val Glu Glu Lys Ile Ala Cys Asn Val Tyr Ser
                         20                 25                 30

Val Asp Lys Asn Gly Phe Val Tyr Thr Gln Pro Ile Ala Gln Tyr His
                         35                 40                 45

Asp Arg Gly Ile Gln Glu Val Phe Glu Tyr Arg Leu Glu Asn Gly Ser
                         50                 55                 60

Val Ile Arg Ala Thr Lys Asp His Lys Met Met Thr Ala Asp Gly Gln
             65                 70                 75                 80

Met Leu Pro Ile Asp Glu Ile Phe Lys Gln Asn Leu Asp Leu Lys Gln
                              85                 90                 95

Leu Asn

<210> SEQ ID NO 346
            <211> LENGTH: 35
            <212> TYPE: PRT
            <213> ORGANISM: Chroococcidiopsis sp.

<400> SEQUENCE: 346

Val Lys Ile Ile Ser Arg Gln Ser Leu Gly Lys Gln Ser Val Phe Asp
             1               5                  10                 15

Ile Gly Val Ala Lys Asp His Asn Phe Leu Leu Ala Asn Gly Leu Val
                         20                 25                 30

Ala Ser Asn
                     35

<210> SEQ ID NO 347
            <211> LENGTH: 102
            <212> TYPE: PRT
            <213> ORGANISM: Raphidiopsis brookii

<400> SEQUENCE: 347

Cys Leu Ser Tyr Glu Thr Glu Val Leu Thr Leu Glu Tyr Gly Phe Leu
             1               5                  10                 15

Pro Ile Gly Glu Ile Val Asp Lys Gln Met Val Cys Thr Val Phe Ser
                         20                 25                 30

Val Asn Asp Ser Gly Asn Val Tyr Thr Gln Pro Ile Gly Gln Trp His
                         35                 40                 45

Asp Arg Gly Val Gln Glu Leu Tyr Glu Tyr Cys Leu Asp Asp Gly Ser
                         50                 55                 60

Thr Ile Arg Ala Thr Lys Asp His Lys Phe Met Thr Thr Gln Gly Glu
             65                 70                 75                 80

Met Val Pro Ile Asp Glu Ile Phe His Gln Gly Trp Glu Leu Val Gln
                              85                 90                 95

Val Ser Gly Thr Met Asn
                     100

<210> SEQ ID NO 348
            <211> LENGTH: 35
            <212> TYPE: PRT
            <213> ORGANISM: Raphidiopsis brookii

<400> SEQUENCE: 348

Val Lys Ile Val Ser Arg Arg Tyr Leu Gly Lys Ala Asp Val Tyr Asp
             1               5                  10                 15

Ile Gly Val Ala Lys Asp His Asn Phe Ile Ile Lys Asn Gly Leu Val
                         20                 25                 30
```

Ala Ser Asn
        35

<210> SEQ ID NO 349
<211> LENGTH: 99
<212> TYPE: PRT
<213> ORGANISM: Cyanothece sp.

<400> SEQUENCE: 349

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Ser Val Tyr Thr
            20                  25                  30

Val Asn Lys Asn Gly Phe Val Tyr Thr Gln Ser Ile Ala Gln Trp His
        35                  40                  45

His Arg Gly Glu Gln Glu Val Phe Glu Tyr Tyr Leu Glu Asp Gly Glu
    50                  55                  60

Thr Ile Arg Ala Thr Lys Asp His Lys Phe Met Thr Thr Glu Gly Lys
65                  70                  75                  80

Met Leu Pro Ile Asp Glu Ile Phe Glu Asn Asn Leu Asp Leu Lys Lys
                85                  90                  95

Leu Thr Val

<210> SEQ ID NO 350
<211> LENGTH: 35
<212> TYPE: PRT
<213> ORGANISM: Cyanothece sp.

<400> SEQUENCE: 350

Val Lys Ile Ile Glu Arg Arg Ser Leu Gly Lys Gln Asn Val Tyr Asp
1               5                   10                  15

Ile Gly Val Glu Lys Asp His Asn Phe Leu Ser Asn Asn Leu Ile
            20                  25                  30

Ala Ser Asn
        35

<210> SEQ ID NO 351
<211> LENGTH: 100
<212> TYPE: PRT
<213> ORGANISM: Xenococcus sp.

<400> SEQUENCE: 351

Cys Leu Ser Ala Asp Thr Glu Val Leu Thr Val Glu Tyr Gly Ala Ile
1               5                   10                  15

Ser Ile Gly Lys Ile Val Glu Glu Arg Ile Glu Cys Thr Val Tyr Ser
            20                  25                  30

Val Asp Ala Asn Gly Phe Val Tyr Thr Gln Glu Ile Ala Gln Trp His
        35                  40                  45

Asn Arg Gly Glu Gln Glu Val Phe Glu Tyr Met Leu Asp Asp Gly Ser
    50                  55                  60

Val Ile Arg Ala Thr Lys Asp His Lys Leu Met Thr Ile Asp Gly Gln
65                  70                  75                  80

Met Val Ala Ile Asp Glu Ile Phe Ser Gln Leu Glu Leu Lys Gln
                85                  90                  95

Val Leu Gly Leu
            100

<210> SEQ ID NO 352

```
<211> LENGTH: 35
<212> TYPE: PRT
<213> ORGANISM: Xenococcus sp.

<400> SEQUENCE: 352

Val Lys Ile Val Ser Arg Lys Ser Leu Gly Thr Gln Thr Val Tyr Asp
1               5                   10                  15

Leu Gly Val Ala Arg Asp His Asn Phe Leu Ala Asn Gly Thr Val
            20                  25                  30

Ala Ser Asn
        35

<210> SEQ ID NO 353
<211> LENGTH: 100
<212> TYPE: PRT
<213> ORGANISM: Pleurocapsa sp.

<400> SEQUENCE: 353

Cys Leu Ser Tyr Asp Thr Glu Ile Tyr Thr Val Glu Tyr Gly Ala Leu
1               5                   10                  15

Pro Ile Gly Lys Ile Val Glu Ser Arg Ile Lys Cys Thr Val Leu Thr
            20                  25                  30

Val Asp Lys Asn Gly Leu Val Tyr Ser Gln Pro Ile Val Gln Trp His
        35                  40                  45

Asp Arg Gly Ile Gln Glu Val Phe Glu Tyr Thr Leu Asp Asn Gly Ala
    50                  55                  60

Thr Ile Arg Ala Thr Lys Asp His Lys Phe Met Thr Val Glu Gly Gln
65                  70                  75                  80

Met Leu Pro Ile Asp Glu Ile Phe Glu Leu Gly Leu Glu Leu Lys Glu
                85                  90                  95

Ile Gln Gln Phe
        100

<210> SEQ ID NO 354
<211> LENGTH: 35
<212> TYPE: PRT
<213> ORGANISM: Pleurocapsa sp.

<400> SEQUENCE: 354

Val Lys Ile Ile Ser Arg Gln Ser Leu Gly Lys Gln Ser Val Tyr Asp
1               5                   10                  15

Ile Gly Val Ala Lys Asp His Asn Phe Leu Ala Asn Gly Met Val
            20                  25                  30

Ala Ser Asn
        35

<210> SEQ ID NO 355
<211> LENGTH: 102
<212> TYPE: PRT
<213> ORGANISM: Cylindrospermopsis raciborskii

<400> SEQUENCE: 355

Cys Leu Ser Tyr Glu Thr Glu Val Leu Thr Leu Glu Tyr Gly Phe Val
1               5                   10                  15

Pro Ile Gly Glu Ile Val Asn Lys Gln Met Val Cys Thr Val Phe Ser
            20                  25                  30

Leu Asn Asp Ser Gly Asn Val Tyr Thr Gln Pro Ile Gly Gln Trp His
        35                  40                  45

Asp Arg Gly Val Gln Asp Leu Tyr Glu Tyr Cys Leu Asp Asp Gly Ser
```

```
                50                  55                  60
Thr Ile Arg Ala Thr Lys Asp His Lys Phe Met Thr Thr Gln Gly Glu
 65                  70                  75                  80

Met Val Pro Ile Asp Glu Ile Phe His Gln Gly Trp Glu Leu Val Gln
                 85                  90                  95

Val Ser Gly Ile Ser Lys
            100

<210> SEQ ID NO 356
<211> LENGTH: 35
<212> TYPE: PRT
<213> ORGANISM: Cylindrospermopsis raciborskii

<400> SEQUENCE: 356

Val Lys Ile Val Ser Arg Arg Tyr Leu Gly Lys Ala Asp Val Tyr Asp
 1               5                  10                  15

Ile Gly Val Ala Lys Asp His Asn Phe Ile Ile Lys Asn Gly Leu Val
                20                  25                  30

Ala Ser Asn
        35

<210> SEQ ID NO 357
<211> LENGTH: 100
<212> TYPE: PRT
<213> ORGANISM: Microcystis aeruginosa

<400> SEQUENCE: 357

Cys Leu Gly Gly Glu Thr Leu Ile Leu Thr Glu Glu Tyr Gly Leu Leu
 1               5                  10                  15

Pro Ile Ala Lys Ile Val Ser Glu Glu Val Asn Cys Thr Val Tyr Ser
                20                  25                  30

Val Asp Lys Asn Gly Phe Val Tyr Ser Gln Pro Ile Ser Gln Trp His
                35                  40                  45

Glu Arg Gly Leu Gln Glu Val Phe Glu Tyr Thr Leu Glu Asn Gly Gln
             50                  55                  60

Thr Ile Gln Ala Thr Lys Asp His Lys Phe Met Thr Asn Asp Gly Glu
 65                  70                  75                  80

Met Leu Ala Ile Asp Thr Ile Phe Glu Arg Gly Leu Asp Leu Lys Ser
                 85                  90                  95

Ser Asp Phe Ser
            100

<210> SEQ ID NO 358
<211> LENGTH: 35
<212> TYPE: PRT
<213> ORGANISM: Microcystis aeruginosa

<400> SEQUENCE: 358

Val Lys Ile Ile Ser Arg Gln Ser Leu Gly Arg Lys Pro Val Tyr Asp
 1               5                  10                  15

Ile Gly Val Glu Lys Asp His Asn Phe Leu Leu Gly Asn Gly Leu Ile
                20                  25                  30

Ala Ser Asn
        35

<210> SEQ ID NO 359
<211> LENGTH: 100
<212> TYPE: PRT
<213> ORGANISM: Microcystis aeruginosa
```

<400> SEQUENCE: 359

Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Cys Thr Val Tyr Thr
                20                  25                  30

Val Asp Gln Asn Gly Phe Val Tyr Ser Gln Pro Ile Ser Gln Trp His
            35                  40                  45

Glu Arg Gly Leu Gln Glu Val Phe Glu Tyr Thr Leu Glu Asn Gly Gln
        50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser
            100

<210> SEQ ID NO 360
<211> LENGTH: 35
<212> TYPE: PRT
<213> ORGANISM: Microcystis aeruginosa

<400> SEQUENCE: 360

Val Lys Ile Ile Gly Arg Gln Ser Leu Gly Arg Lys Pro Val Tyr Asp
1               5                   10                  15

Ile Gly Val Glu Lys Asp His Asn Phe Leu Leu Gly Asn Gly Leu Ile
                20                  25                  30

Ala Ser Asn
        35

<210> SEQ ID NO 361
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
                20                  25                  30

Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
        50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
        130                 135                 140

```
Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
            165                 170                 175

Val Leu Glu Tyr Glu Leu Glu Asp Gly Ser Val Ile Arg Ala Thr Ser
            180                 185                 190

Asp His Arg Phe Leu Thr Thr Asp Tyr Gln Leu Leu Ala Ile Glu Glu
            195                 200                 205

Ile Phe Ala Arg Gln Leu Asp Leu Leu Thr Leu Glu Asn Ile Lys Gln
            210                 215                 220

Thr Glu Glu Ala Leu Asp Asn His Arg Leu Pro Phe Pro Leu Leu Asp
225                 230                 235                 240

Ala Gly Thr Ile Lys
            245

<210> SEQ ID NO 362
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Met Gly Ser Ser His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
            85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Ala Leu Ser Tyr Glu Thr
            115                 120                 125

Glu Ile Leu Thr Val Glu Tyr Gly Leu Leu Pro Ile Gly Lys Ile Val
130                 135                 140

Glu Lys Arg Ile Glu Cys Thr Val Tyr Ser Val Asp Asn Asn Gly Asn
145                 150                 155                 160

Ile Tyr Thr Gln Pro Val Ala Gln Trp His Asp Arg Gly Glu Gln Glu
            165                 170                 175

Val Phe Glu Tyr Cys Leu Glu Asp Gly Ser Leu Ile Arg Ala Thr Lys
            180                 185                 190

Asp His Lys Phe Met Thr Val Asp Gly Gln Met Leu Pro Ile Asp Glu
            195                 200                 205

Ile Phe Glu Arg Glu Leu Asp Leu Met Arg Val Asp Asn Leu Pro Asn
            210                 215                 220

<210> SEQ ID NO 363
<211> LENGTH: 240
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 363

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn Cys Ile Thr Gly Asp Ala Leu Val Ala Leu Pro Glu
        35                  40                  45

Gly Glu Ser Val Arg Ile Ala Asp Ile Val Pro Gly Ala Arg Pro Asn
    50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr
                85                  90                  95

Val Arg Thr Val Glu Gly Leu Arg Val Thr Gly Thr Ala Asn His Pro
            100                 105                 110

Leu Leu Cys Leu Val Asp Val Ala Gly Val Pro Thr Leu Leu Trp Lys
        115                 120                 125

Leu Ile Asp Glu Ile Lys Pro Gly Asp Tyr Ala Val Ile Gln Arg Ser
130                 135                 140

Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 364
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Ile Thr Gly Asp Ala Leu Val Ala Leu Pro Glu
        35                  40                  45

Gly Glu Ser Val Arg Ile Ala Asp Ile Val Pro Gly Ala Arg Pro Asn
    50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr
                85                  90                  95
```

Val Arg Thr Val Glu Gly Leu Arg Val Thr Gly Ala Asn His Pro
            100                 105                 110

Leu Leu Cys Leu Val Asp Val Ala Gly Val Pro Thr Leu Leu Trp Lys
        115                 120                 125

Leu Ile Asp Glu Ile Lys Pro Gly Asp Tyr Ala Val Ile Gln Arg Ser
    130                 135                 140

Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 365
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
    130                 135                 140

Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Leu Glu Tyr Glu Leu Glu Asp Gly Ser Val Ile Arg Ala Thr Ser
            180                 185                 190

Asp His Lys Phe Met Thr Thr Asp Gly Gln Met Leu Ala Ile Glu Glu
        195                 200                 205

Ile Phe Ala Arg Gln Leu Asp Leu Leu Thr Leu Glu Asn Ile Lys Gln

```
                  210                 215                 220

Thr Glu Glu Ala Leu Asp Asn His Arg Leu Pro Phe Pro Leu Leu Asp
225                 230                 235                 240

Ala Gly Thr Ile Lys
                245

<210> SEQ ID NO 366
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
                20                  25                  30

Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
130                 135                 140

Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Leu Glu Tyr Glu Leu Glu Asp Gly Ser Val Ile Arg Ala Thr Ser
            180                 185                 190

Asp His Lys Phe Leu Thr Thr Asp Tyr Gln Leu Leu Ala Ile Glu Glu
        195                 200                 205

Ile Phe Ala Arg Gln Leu Asp Leu Leu Thr Leu Glu Asn Ile Lys Gln
    210                 215                 220

Thr Glu Glu Ala Leu Asp Asn His Arg Leu Pro Phe Pro Leu Leu Asp
225                 230                 235                 240

Ala Gly Thr Ile Lys
                245

<210> SEQ ID NO 367
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Met Gly Ser Ser His His His His His His Gly Ser Gly Leu Val Pro
```

```
                1               5                   10                  15
        Arg Gly Ser Ala Ser Met Ser Asp Ser Glu Val Asn Gln Glu Ala Lys
                        20                  25                  30
        Pro Glu Val Lys Pro Glu Val Lys Pro Glu Thr His Ile Asn Leu Lys
                        35                  40                  45
        Val Ser Asp Gly Ser Ser Glu Ile Phe Phe Lys Ile Lys Lys Thr Thr
                50                  55                  60
        Pro Leu Arg Arg Leu Met Glu Ala Phe Ala Lys Arg Gln Gly Lys Glu
        65                  70                  75                  80
        Met Asp Ser Leu Arg Phe Leu Tyr Asp Gly Ile Arg Ile Gln Ala Asp
                        85                  90                  95
        Gln Thr Pro Glu Asp Leu Asp Met Glu Asp Asn Asp Ile Ile Glu Ala
                        100                 105                 110
        His Arg Glu Gln Ile Gly Gly Ala Glu Tyr Cys Leu Ser Phe Gly Thr
                        115                 120                 125
        Glu Ile Leu Thr Val Glu Tyr Gly Pro Leu Pro Ile Gly Lys Ile Val
                130                 135                 140
        Ser Glu Glu Ile Asn Cys Ser Val Tyr Ser Val Asp Pro Glu Gly Arg
        145                 150                 155                 160
        Val Tyr Thr Gln Ala Ile Ala Gln Trp His Asp Arg Gly Glu Gln Glu
                        165                 170                 175
        Val Leu Glu Tyr Glu Leu Glu Asp Gly Ser Val Ile Arg Ala Thr Ser
                        180                 185                 190
        Asp His Lys Phe Leu Thr Thr Asp Gly Gln Leu Leu Ala Ile Glu Glu
                        195                 200                 205
        Ile Phe Ala Arg Gln Leu Asp Leu Leu Thr Leu Glu Asn Ile Lys Gln
                210                 215                 220
        Thr Glu Glu Ala Leu Asp Asn His Arg Leu Pro Phe Pro Leu Leu Asp
        225                 230                 235                 240
        Ala Gly Thr Ile Lys
                        245

<210> SEQ ID NO 368
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Met Gly Ser Ser His His His His His His Gly Ser Gly Leu Val Pro
        1               5                   10                  15
        Arg Gly Ser Ala Ser Met Ser Asp Ser Glu Val Asn Gln Glu Ala Lys
                        20                  25                  30
        Pro Glu Val Lys Pro Glu Val Lys Pro Glu Thr His Ile Asn Leu Lys
                        35                  40                  45
        Val Ser Asp Gly Ser Ser Glu Ile Phe Phe Lys Ile Lys Lys Thr Thr
                50                  55                  60
        Pro Leu Arg Arg Leu Met Glu Ala Phe Ala Lys Arg Gln Gly Lys Glu
        65                  70                  75                  80
        Met Asp Ser Leu Arg Phe Leu Tyr Asp Gly Ile Arg Ile Gln Ala Asp
                        85                  90                  95
        Gln Thr Pro Glu Asp Leu Asp Met Glu Asp Asn Asp Ile Ile Glu Ala
                        100                 105                 110
```

His Arg Glu Gln Ile Gly Gly Ala Glu Tyr Cys Leu Ser Phe Gly Thr
            115                 120                 125

Glu Ile Leu Thr Val Glu Tyr Gly Pro Leu Pro Ile Gly Lys Ile Val
        130                 135                 140

Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Leu Glu Tyr Glu Leu Glu Asp Gly Ser Val Ile Arg Ala Thr Ser
            180                 185                 190

Asp His Lys Phe Leu Thr Thr Asp Gly Gln Met Leu Ala Ile Glu Glu
        195                 200                 205

Ile Phe Ala Arg Gln Leu Asp Leu Leu Thr Leu Glu Asn Ile Lys Gln
    210                 215                 220

Thr Glu Glu Ala Leu Asp Asn His Arg Leu Pro Phe Pro Leu Leu Asp
225                 230                 235                 240

Ala Gly Thr Ile Lys
                245

<210> SEQ ID NO 369
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
    130                 135                 140

Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Phe Glu Tyr Glu Leu Glu Asp Gly Ser Val Ile Arg Ala Thr Lys
            180                 185                 190

Asp His Arg Phe Leu Thr Thr Asp Tyr Gln Leu Leu Pro Ile Asp Glu
        195                 200                 205

Ile Phe Ala Arg Gln Leu Asp Leu Leu Thr Leu Glu Asn Ile Lys Gln
    210                 215                 220

Thr Glu Glu Ala Leu Asp Asn His Arg Leu Pro Phe Pro Leu Leu Asp
225                 230                 235                 240

Ala Gly Thr Ile Lys
                245

<210> SEQ ID NO 370
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
                20                  25                  30

Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
130                 135                 140

Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Leu Glu Tyr Glu Leu Glu Asp Gly Ser Val Ile Arg Ala Thr Ser
            180                 185                 190

Asp His Arg Phe Leu Thr Thr Asp Tyr Gln Leu Leu Pro Ile Glu Glu
        195                 200                 205

Ile Phe Ala Arg Gln Leu Asp Leu Leu Thr Leu Glu Asn Ile Lys Gln
    210                 215                 220

Thr Glu Glu Ala Leu Asp Asn His Arg Leu Pro Phe Pro Leu Leu Asp
225                 230                 235                 240

Ala Gly Thr Ile Lys
                245

<210> SEQ ID NO 371
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
 50                  55                  60

Pro Leu Arg Arg Leu Met Glu Ala Phe Ala Lys Arg Gln Gly Lys Glu
 65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
130                 135                 140

Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Leu Glu Tyr Glu Leu Glu Asp Gly Ser Val Ile Arg Ala Thr Lys
            180                 185                 190

Asp His Arg Phe Leu Thr Thr Asp Tyr Gln Leu Leu Pro Ile Glu Glu
        195                 200                 205

Ile Phe Ala Arg Gln Leu Asp Leu Leu Thr Leu Glu Asn Ile Lys Gln
        210                 215                 220

Thr Glu Glu Ala Leu Asp Asn His Arg Leu Pro Phe Pro Leu Leu Asp
225                 230                 235                 240

Ala Gly Thr Ile Lys
                245

<210> SEQ ID NO 372
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Met Gly Ser Ser His His His His His His Gly Ser Gly Leu Val Pro
 1               5                  10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
 50                  55                  60

Pro Leu Arg Arg Leu Met Glu Ala Phe Ala Lys Arg Gln Gly Lys Glu
 65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr

```
            115                 120                 125
Glu Ile Leu Thr Val Glu Tyr Gly Pro Leu Pro Ile Gly Lys Ile Val
        130                 135                 140

Ser Glu Glu Ile Asn Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Phe Glu Tyr Glu Leu Glu Asp Gly Ser Val Ile Arg Ala Thr Lys
            180                 185                 190

Asp His Arg Phe Leu Thr Thr Asp Tyr Gln Leu Leu Pro Ile Glu Glu
                195                 200                 205

Ile Phe Ala Arg Gln Leu Asp Leu Leu Thr Leu Glu Asn Ile Lys Gln
        210                 215                 220

Thr Glu Glu Ala Leu Asp Asn His Arg Leu Pro Phe Pro Leu Leu Asp
225                 230                 235                 240

Ala Gly Thr Ile Lys
                245

<210> SEQ ID NO 373
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
    130                 135                 140

Glu Lys Arg Ile Glu Cys Ser Val Tyr Ser Val Asp Pro Glu Gly Arg
145                 150                 155                 160

Val Tyr Thr Gln Ala Ile Ala Gln Trp His Asp Arg Gly Glu Gln Glu
                165                 170                 175

Val Leu Glu Tyr Glu Leu Glu Asp Gly Ser Val Ile Arg Ala Thr Ser
            180                 185                 190

Asp His Arg Phe Leu Thr Thr Asp Tyr Gln Leu Leu Ala Ile Glu Glu
        195                 200                 205

Ile Phe Ala Arg Gln Leu Asp Leu Leu Thr Leu Glu Asn Ile Lys Gln
    210                 215                 220
```

```
Thr Glu Glu Ala Leu Asp Asn His Arg Leu Pro Phe Pro Leu Leu Asp
225                 230                 235                 240

Ala Gly Thr Ile Lys
            245
```

<210> SEQ ID NO 374
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

```
Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Glu Tyr Cys Leu Ser Phe Gly Thr
        115                 120                 125

Glu Ile Leu Thr Val Glu Tyr Gly Pro Leu Pro Ile Gly Lys Ile Val
130                 135                 140

Ser Glu Glu Ile Asn Cys Ser Val Tyr Ser Val Asp Asn Asn Gly Asn
145                 150                 155                 160

Ile Tyr Thr Gln Ala Ile Ala Gln Trp His Asp Arg Gly Glu Gln Glu
                165                 170                 175

Val Leu Glu Tyr Glu Leu Glu Asp Gly Ser Val Ile Arg Ala Thr Ser
            180                 185                 190

Asp His Arg Phe Leu Thr Thr Asp Tyr Gln Leu Leu Ala Ile Glu Glu
        195                 200                 205

Ile Phe Ala Arg Gln Leu Asp Leu Leu Thr Leu Glu Asn Ile Lys Gln
210                 215                 220

Thr Glu Glu Ala Leu Asp Asn His Arg Leu Pro Phe Pro Leu Leu Asp
225                 230                 235                 240

Ala Gly Thr Ile Lys
            245
```

<210> SEQ ID NO 375
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

```
Met Ile Lys Ile Ala Thr Arg Arg Ser Leu Gly Val Gln Arg Ile Phe
1               5                   10                  15
```

Asp Ile Gly Leu Pro Gln Asp His Asn Phe Leu Leu Ala Asn Gly Ala
            20                  25                  30

Ile Ala Ala Asn Cys Ile Thr Gly Asp Ala Leu Val Ala Leu Pro Glu
        35                  40                  45

Gly Glu Ser Val Arg Ile Ala Asp Ile Val Pro Gly Ala Arg Pro Asn
    50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr
                85                  90                  95

Val Arg Thr Val Glu Gly Leu Arg Val Thr Gly Thr Ala Asn His Pro
            100                 105                 110

Leu Leu Cys Leu Val Asp Val Ala Gly Val Pro Thr Leu Leu Trp Lys
        115                 120                 125

Leu Ile Asp Glu Ile Lys Pro Gly Asp Tyr Ala Val Ile Gln Arg Ser
    130                 135                 140

Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 376
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Met Val Lys Val Ile Gly Arg Arg Ser Leu Gly Val Gln Asn Val Tyr
1               5                   10                  15

Asp Ile Gly Leu Pro Gln Asp His Asn Phe Leu Leu Ala Asn Gly Ala
            20                  25                  30

Ile Ala Ala Asn Cys Ile Thr Gly Asp Ala Leu Val Ala Leu Pro Glu
        35                  40                  45

Gly Glu Ser Val Arg Ile Ala Asp Ile Val Pro Gly Ala Arg Pro Asn
    50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr
                85                  90                  95

Val Arg Thr Val Glu Gly Leu Arg Val Thr Gly Thr Ala Asn His Pro
            100                 105                 110

Leu Leu Cys Leu Val Asp Val Ala Gly Val Pro Thr Leu Leu Trp Lys
        115                 120                 125

Leu Ile Asp Glu Ile Lys Pro Gly Asp Tyr Ala Val Ile Gln Arg Ser
    130                 135                 140

```
Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 377
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Met Val Lys Val Ile Gly Arg Arg Ser Leu Gly Val Gln Arg Ile Phe
1               5                   10                  15

Asp Ile Gly Val Glu Arg Asp His Asn Phe Leu Leu Ala Asn Gly Ala
                20                  25                  30

Ile Ala Ala Asn Cys Ile Thr Gly Asp Ala Leu Val Ala Leu Pro Glu
            35                  40                  45

Gly Glu Ser Val Arg Ile Ala Asp Ile Val Pro Gly Ala Arg Pro Asn
        50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr
                85                  90                  95

Val Arg Thr Val Glu Gly Leu Arg Val Thr Gly Thr Ala Asn His Pro
                100                 105                 110

Leu Leu Cys Leu Val Asp Val Ala Gly Val Pro Thr Leu Leu Trp Lys
            115                 120                 125

Leu Ile Asp Glu Ile Lys Pro Gly Asp Tyr Ala Val Ile Gln Arg Ser
        130                 135                 140

Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 378
<211> LENGTH: 240
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 378

Met Val Lys Val Ile Gly Arg Arg Ser Leu Gly Val Gln Arg Ile Phe
1               5                   10                  15

Asp Ile Gly Leu Pro Gln Asp His Asn Phe Ala Leu Lys Asn Gly Phe
            20                  25                  30

Ile Ala Ala Asn Cys Ile Thr Gly Asp Ala Leu Val Ala Leu Pro Glu
        35                  40                  45

Gly Glu Ser Val Arg Ile Ala Asp Ile Val Pro Gly Ala Arg Pro Asn
    50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr
                85                  90                  95

Val Arg Thr Val Glu Gly Leu Arg Val Thr Gly Thr Ala Asn His Pro
            100                 105                 110

Leu Leu Cys Leu Val Asp Val Ala Gly Val Pro Thr Leu Leu Trp Lys
        115                 120                 125

Leu Ile Asp Glu Ile Lys Pro Gly Asp Tyr Ala Val Ile Gln Arg Ser
130                 135                 140

Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 379
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ser Asn Cys Ile Thr Gly Asp Ala Leu Val Ala Leu Pro Glu
        35                  40                  45

Gly Glu Ser Val Arg Ile Ala Asp Ile Val Pro Gly Ala Arg Pro Asn
    50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr

```
                85                  90                  95
Val Arg Thr Val Glu Gly Leu Arg Val Thr Gly Thr Ala Asn His Pro
            100                 105                 110

Leu Leu Cys Leu Val Asp Val Ala Gly Val Pro Thr Leu Leu Trp Lys
        115                 120                 125

Leu Ile Asp Glu Ile Lys Pro Gly Asp Tyr Ala Val Ile Gln Arg Ser
130                 135                 140

Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 380
<211> LENGTH: 411
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Thr Gly Cys Cys Thr Gly Thr Cys Thr Thr Ala Cys Gly Ala Cys Ala
1               5                   10                  15

Cys Ala Gly Ala Gly Ala Thr Thr Cys Thr Gly Ala Cys Cys Gly Thr
            20                  25                  30

Thr Gly Ala Ala Thr Ala Thr Gly Gly Ala Thr Thr Cys Cys Thr Thr
        35                  40                  45

Cys Cys Thr Ala Thr Cys Gly Gly Thr Ala Ala Gly Ala Thr Cys Gly
    50                  55                  60

Thr Gly Gly Ala Gly Gly Ala Ala Cys Gly Gly Ala Thr Thr Gly Ala
65                  70                  75                  80

Ala Thr Gly Cys Ala Cys Ala Gly Thr Cys Thr Ala Thr Ala Cys Gly
                85                  90                  95

Gly Thr Ala Gly Ala Thr Ala Ala Ala Thr Gly Gly Cys Thr
            100                 105                 110

Thr Thr Gly Thr Gly Thr Ala Thr Ala Cys Ala Cys Ala Ala Cys Cys
        115                 120                 125

Thr Ala Thr Thr Gly Cys Thr Cys Ala Gly Thr Gly Gly Cys Ala Thr
    130                 135                 140

Ala Ala Cys Cys Gly Gly Gly Ala Gly Ala Ala Cys Ala Gly Gly
145                 150                 155                 160

Ala Ala Gly Thr Thr Thr Thr Cys Gly Ala Ala Thr Ala Cys Thr Gly
                165                 170                 175

Cys Thr Thr Ala Gly Ala Ala Gly Ala Cys Gly Gly Thr Thr Cys Gly
            180                 185                 190

Ala Thr Thr Ala Thr Cys Cys Gly Thr Cys Ala Ala Cys Gly Ala
        195                 200                 205
```

```
Ala Ala Gly Ala Thr Cys Ala Cys Ala Ala Thr Thr Ala Thr
    210                 215                 220

Gly Ala Cys Gly Ala Cys Cys Gly Ala Cys Gly Thr Cys Ala Gly
225                 230                 235                 240

Ala Thr Gly Thr Thr Ala Cys Cys Gly Ala Thr Thr Gly Ala Thr Gly
                245                 250                 255

Ala Gly Ala Thr Thr Thr Cys Gly Ala Ala Cys Gly Gly Gly Gly
                260                 265                 270

Gly Thr Thr Ala Gly Ala Cys Cys Thr Gly Ala Ala Ala Cys Ala Ala
                275                 280                 285

Gly Thr Thr Gly Ala Thr Gly Gly Thr Thr Thr Gly Cys Cys Gly Ala
290                 295                 300

Thr Gly Gly Thr Cys Ala Ala Gly Ala Thr Cys Ala Thr Thr Ala Gly
305                 310                 315                 320

Thr Cys Gly Thr Ala Ala Gly Ala Gly Thr Cys Thr Gly Gly Gly Cys
                325                 330                 335

Ala Cys Thr Cys Ala Ala Ala Ala Cys Gly Thr Cys Thr Ala Cys Gly
                340                 345                 350

Ala Thr Ala Thr Thr Gly Gly Ala Gly Thr Ala Gly Ala Ala Ala Ala
                355                 360                 365

Ala Gly Ala Thr Cys Ala Thr Ala Ala Thr Thr Thr Thr Thr Thr Gly
                370                 375                 380

Cys Thr Gly Ala Ala Gly Ala Ala Thr Gly Gly Cys Thr Gly Gly
385                 390                 395                 400

Thr Gly Gly Cys Cys Thr Cys Thr Ala Ala Cys
                405                 410
```

<210> SEQ ID NO 381
<211> LENGTH: 223
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 381

```
Met Gly Ser Ser His His His His His Gly Ser Gly Leu Val Pro
1               5                   10                  15

Arg Gly Ser Ala Ser Met Ser Asp Ser Glu Val Asn Gln Glu Ala Lys
                20                  25                  30

Pro Glu Val Lys Pro Glu Val Lys Pro Glu Thr His Ile Asn Leu Lys
                35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
                100                 105                 110

His Arg Glu Gln Ile Gly Gly Ala Glu Tyr Cys Leu Ser Tyr Asp Thr
                115                 120                 125

Glu Ile Leu Thr Val Glu Tyr Gly Phe Leu Pro Ile Gly Lys Ile Val
                130                 135                 140

Glu Glu Arg Ile Glu Cys Thr Val Tyr Thr Val Asp Lys Asn Gly Phe
145                 150                 155                 160
```

```
Val Tyr Thr Gln Pro Ile Ala Gln Trp His Asn Arg Gly Glu Gln Glu
                165                 170                 175

Val Phe Glu Tyr Cys Leu Glu Asp Gly Ser Ile Ile Arg Ala Thr Lys
            180                 185                 190

Asp His Lys Phe Met Thr Thr Asp Gly Gln Met Leu Pro Ile Asp Glu
        195                 200                 205

Ile Phe Glu Arg Gly Leu Asp Leu Lys Gln Val Asp Gly Leu Pro
    210                 215                 220

<210> SEQ ID NO 382
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Met Val Lys Ile Ile Ser Arg Lys Ser Leu Gly Thr Gln Asn Val Tyr
1               5                   10                  15

Asp Ile Gly Val Glu Lys Asp His Asn Phe Leu Leu Lys Asn Gly Leu
            20                  25                  30

Val Ala Ser Asn Cys Ile Thr Gly Asp Ala Leu Val Ala Leu Pro Glu
        35                  40                  45

Gly Glu Ser Val Arg Ile Ala Asp Ile Val Pro Gly Ala Arg Pro Asn
    50                  55                  60

Ser Asp Asn Ala Ile Asp Leu Lys Val Leu Asp Arg His Gly Asn Pro
65                  70                  75                  80

Val Leu Ala Asp Arg Leu Phe His Ser Gly Glu His Pro Val Tyr Thr
                85                  90                  95

Val Arg Thr Val Glu Gly Leu Arg Val Thr Gly Thr Ala Asn His Pro
            100                 105                 110

Leu Leu Cys Leu Val Asp Val Ala Gly Val Pro Thr Leu Leu Trp Lys
        115                 120                 125

Leu Ile Asp Glu Ile Lys Pro Gly Asp Tyr Ala Val Ile Gln Arg Ser
    130                 135                 140

Ala Phe Ser Val Asp Cys Ala Gly Phe Ala Arg Gly Lys Pro Glu Phe
145                 150                 155                 160

Ala Pro Thr Thr Tyr Thr Val Gly Val Pro Gly Leu Val Arg Phe Leu
                165                 170                 175

Glu Ala His His Arg Asp Pro Asp Ala Gln Ala Ile Ala Asp Glu Leu
            180                 185                 190

Thr Asp Gly Arg Phe Tyr Tyr Ala Lys Val Ala Ser Val Thr Asp Ala
        195                 200                 205

Gly Val Gln Pro Val Tyr Ser Leu Arg Val Asp Thr Ala Asp His Ala
    210                 215                 220

Phe Ile Thr Asn Gly Phe Val Ser His Ala His His His His His His
225                 230                 235                 240

<210> SEQ ID NO 383

<400> SEQUENCE: 383

000

<210> SEQ ID NO 384
<211> LENGTH: 299
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384
```

Met Glu Gln Lys Leu Ile Ser Glu Glu Asp Leu Ser His Ile Gln Arg
1               5                   10                  15

Glu Thr Ser Cys Ser Arg Pro Arg Leu Asn Ser Asn Met Asp Ala Asp
            20                  25                  30

Leu Tyr Gly Tyr Lys Trp Ala Arg Asp Asn Val Gly Gln Ser Gly Ala
        35                  40                  45

Thr Ile Tyr Arg Leu Tyr Gly Lys Pro Asp Ala Pro Glu Leu Phe Leu
    50                  55                  60

Lys His Gly Lys Gly Ser Val Ala Asn Asp Val Thr Asp Glu Met Val
65                  70                  75                  80

Arg Leu Asn Trp Leu Thr Glu Phe Met Pro Leu Pro Thr Ile Lys His
                85                  90                  95

Phe Ile Arg Thr Pro Asp Asp Ala Trp Leu Leu Thr Thr Ala Ile Pro
            100                 105                 110

Gly Lys Thr Ala Phe Gln Val Leu Glu Glu Tyr Pro Asp Ser Gly Glu
        115                 120                 125

Asn Ile Val Asp Ala Leu Ala Val Phe Leu Arg Arg Leu His Ser Ile
    130                 135                 140

Pro Val Cys Asn Cys Pro Phe Asn Ser Asp Arg Val Phe Arg Leu Ala
145                 150                 155                 160

Gln Ala Gln Ser Arg Met Asn Asn Gly Leu Val Asp Ala Ser Asp Phe
                165                 170                 175

Asp Asp Glu Arg Asn Gly Trp Pro Val Glu Gln Val Trp Lys Glu Met
            180                 185                 190

His Lys Leu Leu Pro Phe Cys Leu Ser Tyr Asp Thr Glu Ile Leu Thr
        195                 200                 205

Val Glu Tyr Gly Phe Leu Pro Ile Gly Lys Ile Val Glu Glu Arg Ile
    210                 215                 220

Glu Cys Thr Val Tyr Thr Val Asp Lys Asn Gly Phe Val Tyr Thr Gln
225                 230                 235                 240

Pro Ile Ala Gln Trp His Asn Arg Gly Glu Gln Glu Val Phe Glu Tyr
                245                 250                 255

Cys Leu Glu Asp Gly Ser Ile Ile Arg Ala Thr Lys Asp His Lys Phe
            260                 265                 270

Met Thr Thr Asp Gly Gln Met Leu Pro Ile Asp Glu Ile Phe Glu Arg
        275                 280                 285

Gly Leu Asp Leu Lys Gln Val Asp Gly Leu Pro
    290                 295

```
<210> SEQ ID NO 385
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Phe, Gly, Arg or Glu

<400> SEQUENCE: 385
```

```
Met Val Lys Ile Ile Ser Arg Lys Ser Leu Gly Thr Gln Asn Val Tyr
1               5                   10                  15

Asp Ile Gly Val Glu Lys Asp His Asn Phe Leu Leu Lys Asn Gly Leu
            20                  25                  30

Val Ala Ser Asn Cys Xaa Asn Ser Val Val Thr His Gly Asp Phe Ser
        35                  40                  45

Leu Asp Asn Leu Ile Phe Asp Glu Gly Lys Leu Ile Gly Cys Ile Asp
    50                  55                  60

Val Gly Arg Val Gly Ile Ala Asp Arg Tyr Gln Asp Leu Ala Ile Leu
65                  70                  75                  80

Trp Asn Cys Leu Gly Glu Phe Ser Pro Ser Leu Gln Lys Arg Leu Phe
                85                  90                  95

Gln Lys Tyr Gly Ile Asp Asn Pro Asp Met Asn Lys Leu Gln Phe His
            100                 105                 110

Leu Met Leu Asp Glu Phe Phe
        115
```

```

<210> SEQ ID NO 386
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Thr Gly Cys Cys Thr Gly Ala Gly Cys Thr Ala Cys Gly Ala Cys Ala
1               5                   10                  15

Cys Cys Gly Ala Gly Ala Thr Cys Cys Thr Gly Ala Cys Cys Gly Thr
            20                  25                  30

Gly Gly Ala Gly Thr Ala Cys Gly Gly Cys Thr Thr Cys Cys Thr Gly
        35                  40                  45

Cys Cys Cys Ala Thr Cys Gly Gly Cys Ala Ala Gly Ala Thr Cys Gly
    50                  55                  60

Thr Gly Gly Ala Gly Gly Ala Gly Cys Gly Cys Ala Thr Cys Gly Ala
65                  70                  75                  80

Gly Thr Gly Cys Ala Cys Cys Gly Thr Gly Thr Ala Cys Ala Cys Cys
                85                  90                  95

Gly Thr Gly Gly Ala Cys Ala Ala Gly Ala Ala Cys Gly Gly Cys Thr
            100                 105                 110

Thr Cys Gly Thr Gly Thr Ala Cys Ala Cys Cys Cys Ala Gly Cys Cys
        115                 120                 125

Cys Ala Thr Cys Gly Cys Cys Cys Ala Gly Thr Gly Gly Cys Ala Cys
    130                 135                 140

Ala Ala Cys Cys Gly Cys Gly Gly Cys Gly Ala Gly Cys Ala Gly Gly
145                 150                 155                 160

Ala Gly Gly Thr Gly Thr Thr Cys Gly Ala Gly Thr Ala Cys Thr Gly
                165                 170                 175

Cys Cys Thr Gly Gly Ala Gly Gly Ala Cys Gly Gly Cys Ala Gly Cys
            180                 185                 190

Ala Thr Cys Ala Thr Cys Cys Gly Cys Gly Cys Cys Ala Cys Cys Ala
        195                 200                 205

Ala Gly Gly Ala Cys Cys Ala Cys Ala Ala Gly Thr Thr Cys Ala Thr
    210                 215                 220

Gly Ala Cys Cys Ala Cys Cys Gly Ala Cys Gly Gly Cys Cys Ala Gly
```

-continued

```
              225                 230                 235                 240
        Ala Thr Gly Cys Thr Gly Cys Cys Ala Thr Cys Gly Ala Cys Gly
                        245                 250                 255

Ala Gly Ala Thr Cys Thr Thr Cys Gly Ala Cys Gly Cys Gly Gly
                        260                 265                 270

Cys Cys Thr Gly Gly Ala Cys Cys Thr Gly Ala Ala Gly Cys Ala Gly
                        275                 280                 285

Gly Thr Gly Gly Ala Cys Gly Gly Cys Thr Gly Cys Cys Gly
                290                 295                 300

Thr Gly Ala Ala Gly Ala Thr Cys Ala Thr Cys Ala Gly Cys Gly
        305                 310                 315                 320

Cys Ala Ala Gly Ala Gly Cys Cys Thr Gly Gly Cys Ala Cys Cys
                        325                 330                 335

Cys Ala Gly Ala Ala Cys Gly Thr Gly Thr Ala Cys Gly Ala Cys Ala
                        340                 345                 350

Thr Cys Gly Gly Cys Gly Thr Gly Gly Ala Gly Ala Gly Gly Ala
                        355                 360                 365

Cys Cys Ala Cys Ala Ala Cys Thr Thr Cys Thr Gly Cys Thr Gly
                        370                 375                 380

Ala Ala Gly Ala Ala Cys Gly Gly Cys Cys Thr Gly Gly Thr Gly Gly
        385                 390                 395                 400

Cys Cys Ala Gly Cys Ala Ala Cys
                        405

<210> SEQ ID NO 387
<211> LENGTH: 580
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Met Gly Trp Ser Cys Ile Ile Leu Phe Leu Val Ala Thr Ala Thr Gly
1               5                   10                  15

Val His Ser Glu Val Lys Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Asn Asp Phe Tyr Met Asn Trp Ile Arg Gln Pro Pro Gly Gln Ala Pro
        50                  55                  60

Glu Trp Leu Gly Val Ile Arg Asn Lys Gly Asn Gly Tyr Thr Thr Glu
65                  70                  75                  80

Val Asn Thr Ser Val Lys Gly Arg Phe Thr Ile Ser Arg Asp Asn Thr
                85                  90                  95

Gln Asn Ile Leu Tyr Leu Gln Met Asn Ser Leu Arg Ala Glu Asp Thr
            100                 105                 110

Ala Ile Tyr Tyr Cys Ala Arg Gly Gly Pro Tyr Tyr Ser Gly Asp
        115                 120                 125

Asp Ala Pro Tyr Trp Gly Gln Gly Val Met Val Thr Val Ser Ser Ala
    130                 135                 140

Thr Thr Lys Gly Pro Ser Val Tyr Pro Leu Ala Pro Gly Ser Ala Ala
145                 150                 155                 160

Gln Thr Asn Ser Met Val Thr Leu Gly Cys Leu Val Lys Gly Tyr Phe
                165                 170                 175
```

```
Pro Glu Pro Val Thr Val Thr Trp Asn Ser Gly Ser Leu Ser Ser Gly
            180                 185                 190

Val His Thr Phe Pro Ala Val Leu Gln Ser Asp Leu Tyr Thr Leu Ser
        195                 200                 205

Ser Ser Val Thr Val Pro Ser Ser Thr Trp Pro Ser Glu Thr Val Thr
    210                 215                 220

Cys Asn Val Ala His Pro Ala Ser Ser Thr Lys Val Asp Lys Lys Ile
225                 230                 235                 240

Val Pro Arg Asp Cys Gly Cys Lys Pro Cys Ile Cys Thr Val Pro Glu
            245                 250                 255

Val Ser Ser Val Phe Ile Phe Pro Pro Lys Pro Lys Asp Val Leu Thr
        260                 265                 270

Ile Thr Leu Thr Pro Lys Val Thr Cys Val Val Val Ala Ile Ser Lys
        275                 280                 285

Asp Asp Pro Glu Val Gln Phe Ser Trp Phe Val Asp Asp Val Glu Val
290                 295                 300

His Thr Ala Gln Thr Gln Pro Arg Glu Glu Gln Phe Asn Ser Thr Phe
305                 310                 315                 320

Arg Ser Val Ser Glu Leu Pro Ile Met His Gln Asp Trp Leu Asn Gly
            325                 330                 335

Lys Glu Phe Lys Cys Arg Val Asn Ser Ala Ala Phe Pro Ala Pro Ile
        340                 345                 350

Glu Lys Thr Ile Ser Lys Thr Lys Gly Arg Pro Lys Ala Pro Gln Val
        355                 360                 365

Tyr Thr Ile Pro Pro Pro Lys Glu Gln Met Ala Lys Asp Lys Val Ser
    370                 375                 380

Leu Thr Cys Met Ile Thr Asp Phe Phe Pro Glu Asp Ile Thr Val Glu
385                 390                 395                 400

Trp Gln Trp Asn Gly Gln Pro Ala Glu Asn Tyr Lys Asn Thr Gln Pro
            405                 410                 415

Ile Met Asp Thr Asp Gly Ser Tyr Phe Val Tyr Ser Lys Leu Asn Val
        420                 425                 430

Gln Lys Ser Asn Trp Glu Ala Gly Asn Thr Phe Thr Cys Ser Val Leu
        435                 440                 445

His Glu Gly Leu His Asn His His Thr Glu Lys Ser Leu Ser His Ser
    450                 455                 460

Pro Gly Lys Ala Ser Gly Gly Cys Leu Ser Tyr Asp Thr Glu Ile Leu
465                 470                 475                 480

Thr Val Glu Tyr Gly Phe Leu Pro Ile Gly Lys Ile Val Glu Glu Arg
            485                 490                 495

Ile Glu Cys Thr Val Tyr Thr Val Asp Lys Asn Gly Phe Val Tyr Thr
        500                 505                 510

Gln Pro Ile Ala Gln Trp His Asn Arg Gly Glu Gln Glu Val Phe Glu
        515                 520                 525

Tyr Cys Leu Glu Asp Gly Ser Ile Ile Arg Ala Thr Lys Asp His Lys
    530                 535                 540

Phe Met Thr Thr Asp Gly Gln Met Leu Pro Ile Asp Glu Ile Phe Glu
545                 550                 555                 560

Arg Gly Leu Asp Leu Lys Gln Val Asp Gly Leu Pro Gly His His His
            565                 570                 575

His His His Gly
            580
```

```
<210> SEQ ID NO 388
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Met Gly His His His His His Ser Gly Val Lys Ile Ile Ser Arg
1               5                   10                  15

Lys Ser Leu Gly Thr Gln Asn Val Tyr Asp Ile Gly Val Glu Lys Asp
            20                  25                  30

His Asn Phe Leu Leu Lys Asn Gly Leu Val Ala Ser Asn Cys Phe Asn
        35                  40                  45

Ser Gly Gly Cys Ile Thr Gly Asp Ala Leu Val Ala Leu Pro Glu Gly
    50                  55                  60

Glu Ser Val Arg Ile Ala Asp Ile Val Pro Gly Ala Arg Pro Asn Ser
65                  70                  75                  80

Asp Asn Ala Ile Asp Leu Lys Val Leu Asp Arg His Gly Asn Pro Val
                85                  90                  95

Leu Ala Asp Arg Leu Phe His Ser Gly Glu His Pro Val Tyr Thr Val
            100                 105                 110

Arg Thr Val Glu Gly Leu Arg Val Thr Gly Thr Ala Asn His Pro Leu
        115                 120                 125

Leu Cys Leu Val Asp Val Ala Gly Val Pro Thr Leu Leu Trp Lys Leu
    130                 135                 140

Ile Asp Glu Ile Lys Pro Gly Asp Tyr Ala Val Ile Gln Arg Ser Ala
145                 150                 155                 160

Phe Ser Val Asp Cys Ala Gly Phe Ala Arg Gly Lys Pro Glu Phe Ala
                165                 170                 175

Pro Thr Thr Tyr Thr Val Gly Val Pro Gly Leu Val Arg Phe Leu Glu
            180                 185                 190

Ala His His Arg Asp Pro Asp Ala Gln Ala Ile Ala Asp Glu Leu Thr
        195                 200                 205

Asp Gly Arg Phe Tyr Tyr Ala Lys Val Ala Ser Val Thr Asp Ala Gly
    210                 215                 220

Val Gln Pro Val Tyr Ser Leu Arg Val Asp Thr Ala Asp His Ala Phe
225                 230                 235                 240

Ile Thr Asn Gly Phe Val Ser His Ala His His His His His
                245                 250                 255

<210> SEQ ID NO 389
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Val Lys Ile Ile Ser Arg Lys Ser Leu Gly Thr Gln Asn Val Tyr Asp
1               5                   10                  15

Ile Gly Val Gly Glu Pro His Asn Phe Leu Leu Lys Asn Gly Leu Val
            20                  25                  30

Ala Ser Asn
        35
```

<210> SEQ ID NO 390
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 390

Cys Leu Ser Tyr Asp Thr Glu Ile Leu Thr Val Glu Tyr Gly Phe Leu
1               5                   10                  15

Pro Ile Gly Lys Ile Val Glu Glu Arg Ile Glu Cys Thr Val Tyr Thr
            20                  25                  30

Val Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Lys Gln
                85                  90                  95

Val Asp Gly Leu Pro Val Lys Ile Ile Ser Arg Lys Ser Leu Gly Thr
            100                 105                 110

Gln Asn Val Tyr Asp Ile Gly Val Glu Lys Asp His Asn Phe Leu Leu
        115                 120                 125

Lys Asn Gly Leu Val Ala Ser Asn
    130                 135

<210> SEQ ID NO 391
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 391

Cys Leu Ser Tyr Asp Thr Glu Ile Leu Thr Val Glu Tyr Gly Phe Leu
1               5                   10                  15

Pro Ile Gly Lys Ile Val Glu Glu Arg Ile Glu Cys Thr Val Tyr Thr
            20                  25                  30

Val Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Lys Gln
                85                  90                  95

Val Asp Gly Leu Pro Val Lys Ile Ile Ser Arg Lys Ser Leu Gly Thr
            100                 105                 110

Gln Asn Val Tyr Asp Ile Gly Val Gly Glu Pro His Asn Phe Leu Leu
        115                 120                 125

Lys Asn Gly Leu Val Ala Ser Asn
    130                 135

<210> SEQ ID NO 392
<211> LENGTH: 137
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 392

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn Ile Lys Ile Ala Thr Arg Lys Tyr Leu Gly
            100                 105                 110

Lys Gln Asn Val Tyr Asp Ile Gly Val Glu Arg Asp His Asn Phe Ala
        115                 120                 125

Leu Lys Asn Gly Phe Ile Ala Ser Asn
    130                 135

<210> SEQ ID NO 393
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Cys Leu Ser Tyr Asp Thr Glu Ile Leu Thr Val Glu Tyr Gly Phe Leu
1               5                   10                  15

Pro Ile Gly Lys Ile Val Glu Glu Arg Ile Glu Cys Asn Thr Tyr Ser
            20                  25                  30

Thr Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Lys Gln
                85                  90                  95

Val Asp Gly Leu Pro Val Lys Ile Ile Ser Arg Lys Ser Leu Gly Thr
            100                 105                 110

Gln Asn Val Tyr Asp Ile Gly Val Glu Lys Asp His Asn Phe Leu Leu
        115                 120                 125

Lys Asn Gly Leu Val Ala Ser Asn
    130                 135

<210> SEQ ID NO 394
<211> LENGTH: 137
<212> TYPE: PRT
<213> ORGANISM: Nostoc punctiform

<400> SEQUENCE: 394

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn Ile Lys Ile Ala Thr Arg Lys Tyr Leu Gly
            100                 105                 110

Lys Gln Asn Val Tyr Asp Ile Gly Val Glu Arg Asp His Asn Phe Ala
        115                 120                 125

Leu Lys Asn Gly Phe Ile Ala Ser Asn
    130                 135

<210> SEQ ID NO 395
<211> LENGTH: 137
<212> TYPE: PRT
<213> ORGANISM: Chroococcidiopsis thermalis

<400> SEQUENCE: 395

Cys Leu Ser Tyr Asp Thr Glu Ile Leu Thr Val Glu Tyr Gly Ala Ile
1               5                   10                  15

Pro Ile Gly Lys Ile Val Glu Glu Arg Ile Glu Cys Thr Val Tyr Ser
            20                  25                  30

Val Asp Asn Asn Gly Phe Ile Tyr Thr Gln Pro Ile Ala Gln Trp His
        35                  40                  45

Asn Arg Gly Gln Gln Glu Val Phe Glu Tyr Cys Leu Glu Asp Gly Ser
    50                  55                  60

Ile Ile Arg Ala Thr Lys Asp His Lys Phe Met Thr Phe Glu Gly Lys
65                  70                  75                  80

Met Leu Pro Ile Asp Glu Ile Phe Glu Gln Glu Leu Asp Leu Lys Gln
                85                  90                  95

Val Lys Ser Ile Gln Asn Val Lys Ile Ile Ser Arg Lys Ser Leu Gly
            100                 105                 110

Ile Gln Pro Val Tyr Asp Ile Gly Val Glu Arg Asp His Lys Phe Val
        115                 120                 125

Leu Lys Asn Gly Leu Val Ala Ser Asn
    130                 135

<210> SEQ ID NO 396
<211> LENGTH: 137
<212> TYPE: PRT
<213> ORGANISM: Nodularia spumigena

<400> SEQUENCE: 396

Cys Leu Ser Tyr Asp Thr Glu Ile Leu Thr Val Glu Tyr Gly Tyr Ile
1               5                   10                  15

Pro Ile Gly Glu Ile Val Glu Lys Ala Ile Glu Cys Ser Val Tyr Ser
            20                  25                  30

Val Asp Asn Asn Gly Asn Val Tyr Thr Gln Pro Ile Ala Gln Trp His
        35                  40                  45

```
Asn Arg Gly Glu Gln Glu Val Phe Glu Tyr Ser Leu Glu Asp Gly Ser
        50                  55                  60

Thr Ile Arg Ala Thr Lys Asp His Lys Phe Met Thr Thr Asp Gly Gln
 65                  70                  75                  80

Met Leu Pro Ile Asp Glu Ile Phe Ala Gln Glu Leu Asp Leu Leu Gln
                 85                  90                  95

Val His Gly Leu Pro Lys Val Lys Ile Thr Ala Arg Lys Phe Val Gly
            100                 105                 110

Arg Glu Asn Val Tyr Asp Ile Gly Val Glu Arg Tyr His Asn Phe Ala
            115                 120                 125

Ile Lys Asn Gly Leu Ile Ala Ser Asn
            130                 135

<210> SEQ ID NO 397
<211> LENGTH: 137
<212> TYPE: PRT
<213> ORGANISM: Anabaena cylindrica

<400> SEQUENCE: 397

Cys Leu Ser Tyr Asp Thr Glu Val Leu Thr Val Glu Tyr Gly Phe Ile
  1               5                  10                  15

Pro Ile Gly Glu Ile Val Glu Lys Arg Ile Glu Cys Ser Ile Phe Ser
                 20                  25                  30

Val Asp Lys Asn Gly Asn Val Tyr Thr Gln Pro Ile Ala Gln Trp His
             35                  40                  45

Asn Arg Gly Arg Gln Glu Ile Tyr Glu Tyr Cys Leu Asp Asp Gly Ser
        50                  55                  60

Lys Ile Arg Ala Thr Lys Asp His Lys Phe Met Thr Thr Ala Gly Glu
 65                  70                  75                  80

Met Leu Pro Ile Asp Glu Ile Phe Glu Arg Asp Leu Asp Leu Leu Lys
                 85                  90                  95

Val Glu Gly Leu Pro Glu Val Lys Ile Ile Ser Arg Gln Tyr Leu Gly
            100                 105                 110

Gln Ala Asp Val Tyr Asp Ile Gly Val Glu Glu Asp His Asn Phe Ala
            115                 120                 125

Ile Lys Asn Gly Phe Ile Ala Ser Asn
            130                 135

<210> SEQ ID NO 398
<211> LENGTH: 137
<212> TYPE: PRT
<213> ORGANISM: Calothrix sp.

<400> SEQUENCE: 398

Cys Leu Ser Tyr Asp Thr Glu Val Leu Thr Val Glu Tyr Gly Leu Leu
  1               5                  10                  15

Pro Ile Gly Glu Ile Val Glu Lys Gly Ile Glu Cys Arg Val Phe Ser
                 20                  25                  30

Val Asp Asn His Gly Asn Val Tyr Thr Gln Pro Ile Ala Gln Trp His
             35                  40                  45

Asn Arg Gly Gln Gln Glu Val Phe Glu Tyr Gly Leu Asp Asp Gly Ser
        50                  55                  60

Val Ile Arg Ala Thr Lys Asp His Lys Phe Met Thr Thr Asp Gly Lys
 65                  70                  75                  80

Met Leu Pro Ile Asp Glu Ile Phe Glu Arg Gly Leu Asp Leu Leu Gln
                 85                  90                  95
```

Val Gln Gly Leu Pro Glu Val Lys Val Ile Thr Arg Lys Tyr Ile Gly
            100                 105                 110

Lys Glu Asn Val Tyr Asp Ile Gly Val Glu Leu Asp His Asn Phe Ala
        115                 120                 125

Ile Arg Asn Gly Leu Val Ala Ser Asn
    130                 135

<210> SEQ ID NO 399
<211> LENGTH: 137
<212> TYPE: PRT
<213> ORGANISM: Nostoc sp.

<400> SEQUENCE: 399

Cys Leu Ser Tyr Asp Thr Glu Ile Leu Thr Val Glu Tyr Gly Phe Leu
1               5                   10                  15

Pro Ile Gly Glu Ile Val Glu Lys Gly Ile Glu Cys Thr Val Phe Ser
            20                  25                  30

Val Ala Ser Asn Gly Ile Val Tyr Thr Gln Pro Ile Ala Gln Trp His
        35                  40                  45

Asn Arg Gly Gln Gln Glu Ile Phe Glu Tyr Cys Leu Glu Asp Gly Ser
    50                  55                  60

Ile Ile Arg Ala Thr Lys Asp His Lys Phe Met Thr Gln Asp Gly Gln
65                  70                  75                  80

Met Leu Pro Ile Asp Glu Ile Phe Ala Cys Glu Leu Asp Leu Leu Gln
                85                  90                  95

Val Gln Gly Leu Pro Glu Val Lys Val Val Thr Arg Lys Tyr Ile Gly
            100                 105                 110

Lys Glu Asn Val Tyr Asp Ile Gly Val Glu Arg Asp His Asn Phe Val
        115                 120                 125

Ile Arg Asn Gly Leu Val Ala Ser Asn
    130                 135

<210> SEQ ID NO 400
<211> LENGTH: 137
<212> TYPE: PRT
<213> ORGANISM: Nostoc azollae

<400> SEQUENCE: 400

Cys Leu Ser Tyr Lys Thr Glu Val Leu Thr Val Glu Tyr Gly Leu Ile
1               5                   10                  15

Pro Ile Gly Glu Ile Val Glu Lys Arg Ile Glu Cys Ser Leu Phe Ser
            20                  25                  30

Val Asp Glu Asn Gly Asn Ile Tyr Thr Gln Pro Ile Ala Gln Trp His
        35                  40                  45

His Arg Gly Val Gln Glu Val Tyr Glu Tyr Cys Leu Asp Asp Gly Thr
    50                  55                  60

Ile Ile Arg Ala Thr Lys Asp His Lys Phe Met Thr Thr Ile Gly Glu
65                  70                  75                  80

Met Leu Pro Ile Asp Glu Ile Phe Glu Arg Asp Leu Asn Leu Leu Gln
                85                  90                  95

Val Asn Gly Leu Pro Thr Val Lys Ile Ile Ser Arg Gln Phe Leu Gly
            100                 105                 110

Pro Ala Asn Val Tyr Asp Ile Gly Val Ala Gln Asp His Asn Phe Ala
        115                 120                 125

Ile Lys Asn Gly Leu Ile Ala Ser Asn
    130                 135

<210> SEQ ID NO 401
<211> LENGTH: 137
<212> TYPE: PRT
<213> ORGANISM: Nostoc sp.

<400> SEQUENCE: 401

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu Ile Lys Ile Ala Ser Arg Lys Phe Leu Gly
            100                 105                 110

Val Glu Asn Val Tyr Asp Ile Gly Val Arg Arg Asp His Asn Phe Phe
        115                 120                 125

Ile Lys Asn Gly Leu Ile Ala Ser Asn
    130                 135

<210> SEQ ID NO 402
<211> LENGTH: 137
<212> TYPE: PRT
<213> ORGANISM: Anabaena variabilis

<400> SEQUENCE: 402

Cys Leu Ser Tyr Asp Thr Glu Val Leu Thr Val Glu Tyr Gly Phe Val
1               5                   10                  15

Pro Ile Gly Glu Ile Val Asp Lys Gly Ile Glu Cys Ser Val Phe Ser
            20                  25                  30

Ile Asp Ser Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu Ile Lys Ile Ala Ser Arg Lys Phe Leu Gly
            100                 105                 110

Val Glu Asn Val Tyr Asp Ile Gly Val Gly Arg Asp His Asn Phe Phe
        115                 120                 125

Val Lys Asn Gly Leu Ile Ala Ser Asn
    130                 135

<210> SEQ ID NO 403
<211> LENGTH: 135
<212> TYPE: PRT
<213> ORGANISM: Pleurocapsa sp.

<400> SEQUENCE: 403

```
Cys Leu Ser Tyr Asp Thr Lys Ile Leu Thr Val Glu Tyr Gly Ala Met
1               5                   10                  15

Pro Ile Gly Lys Ile Val Glu Glu Gln Ile Asp Cys Thr Val Tyr Thr
            20                  25                  30

Val Asn Gln Asn Gly Phe Val Tyr Thr Gln Pro Ile Ala Gln Trp His
        35                  40                  45

Asp Arg Gly Lys Gln Glu Ile Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Lys Ile Phe Glu Lys Gly Leu Asp Leu Lys Thr
                85                  90                  95

Ile Asn Cys Asp Val Lys Ile Leu Ser Arg Lys Ser Leu Gly Ile Gln
            100                 105                 110

Ser Val Tyr Asp Ile Gly Val Glu Lys Asp His Asn Phe Leu Leu Ala
        115                 120                 125

Asn Gly Leu Val Ala Ser Asn
    130                 135

<210> SEQ ID NO 404
<211> LENGTH: 135
<212> TYPE: PRT
<213> ORGANISM: Cyanothece sp.

<400> SEQUENCE: 404

Cys Leu Ser Tyr Glu Thr Gln Ile Met Thr Val Glu Tyr Gly Leu Met
1               5                   10                  15

Pro Ile Gly Lys Ile Val Glu Glu Gln Ile Asp Cys Thr Val Tyr Thr
            20                  25                  30

Val Asn Lys Asn Gly Phe Val Tyr Thr Gln Pro Ile Ala Gln Trp His
        35                  40                  45

Tyr Arg Gly Glu Gln Glu Val Phe Glu Tyr Cys Leu Glu Asp Gly Ser
    50                  55                  60

Thr Ile Arg Ala Thr Lys Asp His Lys Phe Met Thr Thr Asp Gly Gln
65                  70                  75                  80

Met Leu Pro Ile Asp Glu Ile Phe Glu Gln Gly Leu Glu Leu Lys Gln
                85                  90                  95

Ile His Leu Ser Val Lys Ile Ile Ser Arg Gln Ser Leu Gly Ile Gln
            100                 105                 110

Pro Val Tyr Asp Ile Gly Val Glu Lys Asp His Asn Phe Leu Ile Ser
        115                 120                 125

Asp Gly Leu Ile Ala Ser Asn
    130                 135

<210> SEQ ID NO 405
<211> LENGTH: 134
<212> TYPE: PRT
<213> ORGANISM: Cyanothece sp.

<400> SEQUENCE: 405

Cys Leu Ser Tyr Asp Thr Glu Ile Leu Thr Val Glu Tyr Gly Pro Met
1               5                   10                  15

Pro Ile Gly Lys Ile Val Glu Glu Gln Ile Glu Cys Thr Val Tyr Thr
            20                  25                  30

Val Asp Lys Asn Gly Leu Val Tyr Thr Gln Pro Ile Ala Gln Trp His
        35                  40                  45
```

```
His Arg Gly Gln Gln Glu Val Phe Glu Tyr Cys Leu Glu Asp Gly Ser
    50                  55                  60

Ile Ile Arg Ala Thr Lys Asp His Lys Phe Met Thr Asp Asp Gly Gln
65                  70                  75                  80

Met Leu Pro Ile Glu Glu Ile Phe Glu Lys Gly Leu Glu Leu Lys Gln
                85                  90                  95

Ile Ile Leu Val Lys Ile Ile Ser Arg Gln Leu Ala Gly Asn Gln Thr
                100                 105                 110

Val Tyr Asp Leu Gly Val Glu Lys Asp His Asn Phe Leu Leu Ala Asn
                115                 120                 125

Gly Leu Ile Ala Ser Asn
    130

<210> SEQ ID NO 406
<211> LENGTH: 137
<212> TYPE: PRT
<213> ORGANISM: Nostoc sp.

<400> SEQUENCE: 406

Cys Leu Ser Tyr Asp Thr Gln Val Leu Thr Val Glu Tyr Gly Leu Val
1               5                   10                  15

Pro Ile Gly Glu Ile Val Glu Lys Gln Leu Glu Cys Ser Val Phe Thr
                20                  25                  30

Ile Asp Gly His Gly Tyr Val Tyr Thr Gln Ala Ile Ala Gln Trp His
                35                  40                  45

Asn Arg Gly Gln Gln Glu Val Phe Glu Tyr Gly Leu Glu Asp Gly Ser
    50                  55                  60

Val Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Leu Gln
                85                  90                  95

Val Gln Gly Leu Arg Trp Val Lys Ile Ile Thr Arg Lys Tyr Ile Gly
                100                 105                 110

Gln Ala Asn Val Tyr Asp Ile Gly Val Ala Gln Asp His Asn Phe Val
                115                 120                 125

Ile Glu Asn Arg Leu Ile Ala Ser Asn
    130                 135

<210> SEQ ID NO 407
<211> LENGTH: 136
<212> TYPE: PRT
<213> ORGANISM: Tolypothrix bouteillei

<400> SEQUENCE: 407

Cys Leu Ser Tyr Asp Thr Glu Ile Leu Thr Val Glu Tyr Gly Phe Leu
1               5                   10                  15

Pro Ile Gly Lys Ile Val Glu Lys Gly Ile Glu Cys Asn Val Tyr Ser
                20                  25                  30

Val Asp Lys Asn Gly Asn Ile Tyr Thr Gln Pro Ile Ala Gln Trp His
                35                  40                  45

Asp Arg Gly Glu Gln Glu Val Phe Glu Tyr Cys Leu Glu Asn Gly Ser
    50                  55                  60

Val Ile Arg Ala Thr Lys Asp His Lys Phe Met Thr Thr Ser Gly Glu
65                  70                  75                  80

Met Leu Pro Ile Asp Glu Ile Phe Glu Arg Gly Leu Asp Leu Ile Arg
                85                  90                  95
```

Val Glu Asp Leu Pro Val Lys Ile Leu Thr Arg Lys Ser Ile Gly Lys
            100                 105                 110

Gln Thr Val Tyr Asp Ile Gly Val Glu Arg Asp His Asn Phe Val Ile
        115                 120                 125

Lys Asn Gly Ser Val Ala Ser Asn
    130                 135

<210> SEQ ID NO 408
<211> LENGTH: 136
<212> TYPE: PRT
<213> ORGANISM: Aphanizomenon ovalisporum
<220> FEATURE:
<221> NAME/KEY: MOD_RES
<222> LOCATION: (87)..(87)
<223> OTHER INFORMATION: Any amino acid

<400> SEQUENCE: 408

Cys Leu Ser Ala Asp Thr Glu Ile Leu Thr Val Glu Tyr Gly Phe Leu
1               5                   10                  15

Pro Ile Gly Glu Ile Val Gly Lys Ala Ile Glu Cys Arg Val Tyr Ser
            20                  25                  30

Val Asp Gly Asn Gly Asn Ile Tyr Thr Gln Ser Ile Ala Gln Trp His
        35                  40                  45

Asn Arg Gly Glu Gln Glu Val Phe Glu Tyr Thr Leu Glu Asp Gly Ser
    50                  55                  60

Ile Ile Arg Ala Thr Lys Asp His Lys Phe Met Thr Thr Asp Gly Glu
65                  70                  75                  80

Met Leu Pro Ile Asp Glu Xaa Phe Ala Arg Gln Leu Asp Leu Met Gln
                85                  90                  95

Val Gln Gly Leu His Val Lys Ile Thr Ala Arg Lys Phe Val Gly Arg
            100                 105                 110

Glu Asn Val Tyr Asp Ile Gly Val Glu His His Asn Phe Ala Ile
        115                 120                 125

Lys Asn Gly Leu Ile Ala Ser Asn
    130                 135

<210> SEQ ID NO 409
<211> LENGTH: 137
<212> TYPE: PRT
<213> ORGANISM: Oscillatoria nigro-viridis

<400> SEQUENCE: 409

Cys Leu Ser Tyr Asp Thr Lys Ile Leu Thr Val Glu Tyr Gly Pro Met
1               5                   10                  15

Ala Ile Gly Lys Ile Val Glu Glu Lys Ile Glu Cys Thr Val Tyr Ser
            20                  25                  30

Val Asp Ser Asn Gly Tyr Ile Tyr Thr Gln Ser Ile Ala Gln Trp His
        35                  40                  45

Arg Arg Gly Gln Gln Glu Val Phe Glu Tyr Cys Leu Glu Asp Gly Ser
    50                  55                  60

Ile Ile Arg Ala Thr Lys Asp His Lys Phe Met Thr Val Gly Gly Gln
65                  70                  75                  80

Met Leu Pro Ile Asp Glu Ile Phe Glu Gln Gly Leu Asp Leu Lys Gln
                85                  90                  95

Ile Asn Ser Ser Ser Asp Val Lys Ile Ser Arg Lys Ser Leu Gly
            100                 105                 110

Thr Gln Glu Val Tyr Asp Ile Gly Val Glu Arg Glu His Asn Phe Ile
        115                 120                 125

Leu Glu Asn Ser Leu Val Ala Ser Asn
    130                 135

<210> SEQ ID NO 410
<211> LENGTH: 135
<212> TYPE: PRT
<213> ORGANISM: Rivularia sp.

<400> SEQUENCE: 410

Cys Leu Ser Tyr Asp Thr Glu Val Leu Thr Glu Glu Phe Gly Leu Ile
1               5                   10                  15

Pro Ile Gly Lys Ile Val Glu Glu Lys Ile Asp Cys Thr Val Tyr Ser
            20                  25                  30

Val Asp Val Asn Gly Asn Val Tyr Ser Gln Pro Ile Ala Gln Trp His
        35                  40                  45

Asn Arg Gly Met Gln Glu Val Phe Glu Tyr Glu Leu Glu Asp Gly Ser
    50                  55                  60

Thr Ile Arg Ala Thr Lys Asp His Lys Phe Met Thr Val Asp Gly Glu
65                  70                  75                  80

Met Leu Ala Ile Asp Glu Ile Phe Glu Lys Gly Leu Glu Leu Lys Arg
                85                  90                  95

Val Gly Ile Tyr Val Lys Ile Ile Ser Arg Lys Val Leu Lys Thr Glu
            100                 105                 110

Asn Val Tyr Asp Ile Gly Leu Glu Gly Asp His Asn Phe Ile Ile Lys
        115                 120                 125

Asp Gly Leu Ile Ala Ser Asn
    130                 135

<210> SEQ ID NO 411
<211> LENGTH: 137
<212> TYPE: PRT
<213> ORGANISM: Trichodesmium erythraeum

<400> SEQUENCE: 411

Cys Leu Thr Tyr Glu Thr Glu Ile Met Thr Val Glu Tyr Gly Pro Leu
1               5                   10                  15

Pro Ile Gly Lys Ile Val Glu Tyr Arg Ile Glu Cys Thr Val Tyr Thr
            20                  25                  30

Val Asp Lys Asn Gly Tyr Ile Tyr Thr Gln Pro Ile Ala Gln Trp His
        35                  40                  45

Asn Arg Gly Met Gln Glu Val Tyr Glu Tyr Ser Leu Glu Asp Gly Thr
    50                  55                  60

Val Ile Arg Ala Thr Pro Glu His Lys Phe Met Thr Glu Asp Gly Gln
65                  70                  75                  80

Met Leu Pro Ile Asp Glu Ile Phe Glu Arg Asn Leu Asp Leu Lys Cys
                85                  90                  95

Leu Gly Thr Leu Glu Leu Val Lys Ile Val Ser Arg Lys Leu Ala Lys
            100                 105                 110

Thr Glu Asn Val Tyr Asp Ile Gly Val Thr Lys Asp His Asn Phe Val
        115                 120                 125

Leu Ala Asn Gly Leu Ile Ala Ser Asn
    130                 135

<210> SEQ ID NO 412
<211> LENGTH: 137
<212> TYPE: PRT
<213> ORGANISM: Microcoleus sp.

<400> SEQUENCE: 412

Cys Leu Ser Tyr Asp Ser Glu Ile Leu Thr Val Glu Tyr Gly Leu Met
1               5                   10                  15

Pro Ile Gly Lys Ile Val Glu Glu Gly Ile Glu Cys Thr Val Tyr Ser
            20                  25                  30

Val Asp Ser His Gly Tyr Leu Tyr Thr Gln Pro Ile Ala Gln Trp His
        35                  40                  45

His Arg Gly Gln Gln Glu Val Phe Glu Tyr Asp Leu Glu Asp Gly Ser
    50                  55                  60

Val Ile Arg Ala Thr Lys Asp His Lys Phe Met Thr Ser Glu Gly Gln
65                  70                  75                  80

Met Leu Ala Ile Asp Glu Ile Phe Glu Arg Gly Leu Glu Leu Lys Gln
                85                  90                  95

Val Lys Arg Ser Gln Pro Val Lys Ile Val Arg Arg Lys Ser Leu Gly
            100                 105                 110

Ile Gln Thr Val Tyr Asp Ile Gly Val Glu Arg Asp His Asn Phe Leu
        115                 120                 125

Leu Ala Asn Gly Leu Val Ala Ser Asn
    130                 135

<210> SEQ ID NO 413
<211> LENGTH: 137
<212> TYPE: PRT
<213> ORGANISM: Stanieria cyanosphaera

<400> SEQUENCE: 413

Cys Leu Ser Tyr Asp Thr Glu Ile Leu Thr Val Glu Tyr Gly Ala Met
1               5                   10                  15

Pro Ile Gly Lys Ile Val Lys Glu Gln Ile Glu Cys Asn Val Tyr Thr
            20                  25                  30

Val Asn Gln Asn Gly Phe Ile Tyr Pro Gln Ala Ile Ala Gln Trp His
        35                  40                  45

Glu Arg Gly Lys Gln Glu Ile Phe Glu Tyr Thr Leu Asp Asn Gly Leu
    50                  55                  60

Val Ile Arg Ala Thr Lys Asp His Lys Phe Met Thr Ile Asp Gly Gln
65                  70                  75                  80

Met Leu Pro Ile Asp Glu Ile Phe Glu Arg Gly Leu Glu Leu Gln Arg
                85                  90                  95

Ile Asn Asp Tyr Ser Asn Val Lys Ile Val Ser Arg Lys Ser Leu Gly
            100                 105                 110

Lys Gln Pro Val Tyr Asp Ile Gly Val Thr Lys Asp His Asn Phe Leu
        115                 120                 125

Leu Ser Asn Gly Val Val Ala Ser Asn
    130                 135

<210> SEQ ID NO 414
<211> LENGTH: 137
<212> TYPE: PRT
<213> ORGANISM: Calothrix sp.

<400> SEQUENCE: 414

Cys Leu Ser Tyr Asp Thr Glu Ile Leu Thr Trp Glu Tyr Gly Phe Leu
1               5                   10                  15

Lys Ile Gly Glu Ile Val Glu Lys Gln Ile Leu Cys Ser Val Phe Ser
            20                  25                  30

```
Val Asp Glu Gln Gly Asn Val Tyr Thr Gln Pro Ile Ala Gln Trp His
         35                  40                  45

Asn Arg Gly Leu Gln Glu Leu Phe Ala Tyr Gln Leu Glu Asp Gly Gly
 50                  55                  60

Val Ile Arg Ala Thr Lys Asp His Lys Phe Met Thr Thr Asp Gly Gln
 65                  70                  75                  80

Met Leu Ala Ile Asp Glu Ile Phe Glu Arg Gln Leu Asp Leu Phe Gln
                 85                  90                  95

Val Lys Gly Leu Pro Glu Val Lys Ile Ile Ser Arg Lys Val Leu Lys
                100                 105                 110

Thr Glu Asn Val Tyr Asp Ile Gly Leu Glu Gly Asp His Asn Phe Ile
            115                 120                 125

Ile Lys Asp Gly Leu Ile Ala Ser Asn
            130                 135

<210> SEQ ID NO 415
<211> LENGTH: 134
<212> TYPE: PRT
<213> ORGANISM: Cyanobacterium stanieri

<400> SEQUENCE: 415

Cys Leu Ser Tyr Asp Thr Glu Val Leu Thr Val Glu Tyr Gly Val Leu
 1               5                  10                  15

Pro Ile Gly Lys Ile Val Glu Glu Gln Ile Gln Cys Thr Val Tyr Ser
                 20                  25                  30

Val Asp Gln Tyr Gly Phe Val Tyr Thr Gln Ala Ile Ala Gln Trp His
             35                  40                  45

Asp Arg Gly Glu Gln Glu Val Phe Glu Tyr Glu Leu Glu Asn Gly Ala
 50                  55                  60

Thr Ile Lys Ala Thr Lys Asp His Lys Met Met Thr Ser Asp Gly Gln
 65                  70                  75                  80

Met Leu Pro Ile Asp Gln Ile Phe Glu Gln Gly Leu Asp Leu Phe Met
                 85                  90                  95

Val Ser Phe Val Lys Ile Val Lys Arg Arg Ser His Gly Ile Gln Lys
                100                 105                 110

Val Tyr Asp Ile Gly Val Ala Lys Asp His Asn Phe Leu His Asn
            115                 120                 125

Gly Leu Val Ala Ser Asn
            130

<210> SEQ ID NO 416
<211> LENGTH: 134
<212> TYPE: PRT
<213> ORGANISM: Cyanothece sp.

<400> SEQUENCE: 416

Cys Leu Ser Tyr Asp Thr Glu Ile Leu Thr Val Glu Tyr Gly Pro Met
 1               5                  10                  15

Pro Ile Gly Lys Ile Val Glu Glu Asn Ile Asn Cys Thr Val Tyr Thr
                 20                  25                  30

Val Asp Pro Asn Gly Phe Val Tyr Thr Gln Ala Ile Ala Gln Trp His
             35                  40                  45

Tyr Arg Gly Glu Gln Glu Ile Phe Glu Tyr Tyr Leu Glu Asp Gly Ala
 50                  55                  60

Thr Ile Arg Ala Thr Lys Asp His Lys Phe Met Thr Met Glu Gly Lys
 65                  70                  75                  80
```

```
Met Leu Pro Ile Asp Glu Ile Phe Glu Asn Asn Leu Asp Leu Lys Gln
                85                  90                  95

Leu Thr Leu Val Lys Ile Ile Gly Arg Gln Ser Leu Gly Val Gln Lys
            100                 105                 110

Val Tyr Asp Ile Gly Val Glu Lys Glu His Asn Phe Leu Leu His Asn
            115                 120                 125

Gly Leu Ile Ala Ser Asn
        130
```

<210> SEQ ID NO 417
<211> LENGTH: 134
<212> TYPE: PRT
<213> ORGANISM: Cyanothece sp.

<400> SEQUENCE: 417

```
Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
            20                  25                  30

Val Asp Lys Asn Gly Phe Val Tyr Thr Gln Asn Ile Ala Gln Trp His
            35                  40                  45

Leu Arg Gly Gln Gln Glu Val Phe Glu Tyr Tyr Leu Asp Asp Gly Ser
    50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Arg Gly Leu Glu Leu Lys Lys
                85                  90                  95

Ile Lys Ile Val Lys Ile Val Ser Tyr Arg Ser Leu Gly Lys Gln Phe
            100                 105                 110

Val Tyr Asp Ile Gly Val Ala Gln Asp His Asn Phe Leu Leu Ala Asn
            115                 120                 125

Gly Ser Ile Ala Ser Asn
        130
```

<210> SEQ ID NO 418
<211> LENGTH: 136
<212> TYPE: PRT
<213> ORGANISM: Anabaena sp.

<400> SEQUENCE: 418

```
Cys Leu Ser Tyr Asp Thr Glu Ile Leu Thr Val Glu Tyr Gly Phe Leu
1               5                   10                  15

Glu Ile Gly Glu Ile Val Glu Lys Gln Ile Glu Cys Lys Val Tyr Thr
            20                  25                  30

Ile Asp Ser Asn Gly Met Leu Tyr Thr Gln Ser Ile Ala Gln Trp His
            35                  40                  45

Asn Arg Gly Gln Gln Glu Val Tyr Glu Tyr Leu Leu Glu Asn Gly Ala
    50                  55                  60

Ile Ile Arg Ala Thr Lys Asp His Lys Phe Met Thr Glu Ala Gly Gln
65                  70                  75                  80

Met Leu Pro Ile Asp Glu Ile Phe Ala Gln Gly Leu Asp Leu Leu Gln
                85                  90                  95

Val Gly Val Ala Glu Val Lys Ile Val Ser Arg Thr Tyr Val Gly Gln
            100                 105                 110

Ala Asn Val Tyr Asp Ile Gly Val Glu Ser Asp His Asn Phe Val Ile
            115                 120                 125
```

```
Lys Asn Gly Phe Ile Ala Ser Asn
    130                 135
```

<210> SEQ ID NO 419
<211> LENGTH: 137
<212> TYPE: PRT
<213> ORGANISM: Aphanothece halophytica

<400> SEQUENCE: 419

```
Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Cys Ser Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
    50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met Val Lys Ile Ile Lys Arg Gln Ser Leu Gly
            100                 105                 110

Arg Gln Asn Val Tyr Asp Val Cys Val Glu Thr Asp His Asn Phe Val
        115                 120                 125

Leu Ala Asn Gly Cys Val Ala Ser Asn
    130                 135
```

<210> SEQ ID NO 420
<211> LENGTH: 137
<212> TYPE: PRT
<213> ORGANISM: Halothece sp.

<400> SEQUENCE: 420

```
Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Cys Ser Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
    50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Glu Leu Asp Leu Lys Val
                85                  90                  95

Glu Thr Phe His Glu Met Val Lys Ile Ile Lys Arg Gln Ser Leu Gly
            100                 105                 110

Arg Gln Asn Val Tyr Asp Ile Gly Val Glu Thr Asp His Asn Phe Val
        115                 120                 125

Leu Ala Asn Gly Cys Val Ala Ser Asn
    130                 135
```

<210> SEQ ID NO 421
<211> LENGTH: 137
<212> TYPE: PRT
<213> ORGANISM: Cyanobacterium aponinum

<400> SEQUENCE: 421

Cys Leu Ser Tyr Asp Thr Glu Ile Leu Thr Val Glu Tyr Gly Ala Ile
1               5                   10                  15

Ser Ile Gly Lys Ile Val Glu Glu Lys Ile Asn Cys Gln Val Tyr Ser
            20                  25                  30

Val Asp Lys Asn Gly Phe Ile Tyr Thr Gln Asn Ile Ala Gln Trp His
        35                  40                  45

Asp Arg Gly Ser Gln Glu Leu Phe Glu Tyr Glu Leu Glu Asp Gly Arg
    50                  55                  60

Ile Ile Lys Ala Thr Lys Asp His Lys Met Met Thr Lys Asp Gly Gln
65                  70                  75                  80

Met Leu Ala Ile Asn Asp Ile Phe Glu Gln Glu Leu Glu Leu Tyr Ser
                85                  90                  95

Val Asp Asp Met Gly Val Val Lys Ile Val Lys Arg Arg Ser Leu Gly
            100                 105                 110

Val Gln Pro Val Tyr Asp Ile Gly Val Glu Lys Asp His Asn Phe Ile
        115                 120                 125

Leu Ala Asn Gly Leu Val Ala Ser Asn
    130                 135

<210> SEQ ID NO 422
<211> LENGTH: 133
<212> TYPE: PRT
<213> ORGANISM: Unknown
<220> FEATURE:
<223> OTHER INFORMATION: Description of Unknown:
      Candidatus Atelocyanobacterium thalassa isolate sequence

<400> SEQUENCE: 422

Cys Leu Ser Tyr Asp Thr Lys Val Leu Thr Val Glu Tyr Gly Pro Leu
1               5                   10                  15

Pro Ile Gly Lys Val Val Gln Glu Asn Ile Arg Cys Arg Val Tyr Thr
            20                  25                  30

Thr Asn Asp Gln Gly Leu Ile Tyr Thr Gln Pro Ile Ala Gln Trp His
        35                  40                  45

Asn Arg Gly Lys Gln Glu Ile Phe Glu Tyr His Leu Asp Asp Lys Thr
    50                  55                  60

Ile Ile Arg Ala Thr Lys Glu His Gln Phe Met Thr Val Asp His Val
65                  70                  75                  80

Met Met Pro Ile Asp Glu Ile Phe Glu Gln Gly Leu Glu Leu Lys Lys
                85                  90                  95

Ile Lys Leu Lys Ile Ile Arg Arg Lys Ser Leu Gly Met His Glu Val
            100                 105                 110

Phe Asp Ile Gly Leu Glu Lys Asp His Asn Phe Val Leu Ser Asn Gly
        115                 120                 125

Leu Ile Ala Ser Asn
    130

<210> SEQ ID NO 423
<211> LENGTH: 137
<212> TYPE: PRT
<213> ORGANISM: Oscillatoria limnetica

<400> SEQUENCE: 423

Cys Leu Ser Tyr Asn Thr Glu Val Leu Thr Val Glu Tyr Gly Pro Leu
1               5                   10                  15

Pro Ile Gly Lys Ile Val Asp Glu Gln Ile His Cys Arg Val Tyr Ser

```
                20                  25                  30
Val Asp Glu Asn Gly Phe Val Tyr Thr Gln Ala Ile Ala Gln Trp His
            35                  40                  45

Asp Arg Gly Tyr Gln Glu Ile Phe Ala Tyr Glu Leu Ala Asp Gly Ser
        50                  55                  60

Val Ile Arg Ala Thr Lys Asp His Gln Phe Met Thr Glu Asp Gly Gln
65                  70                  75                  80

Met Phe Pro Ile Asp Glu Ile Trp Glu Lys Gly Leu Asp Leu Lys Lys
                85                  90                  95

Leu Pro Thr Val Gln Asp Val Lys Ile Val Arg Arg Gln Ser Leu Gly
            100                 105                 110

Val Gln Asn Val Tyr Asp Ile Gly Val Glu Lys Asp His Asn Phe Leu
        115                 120                 125

Leu Ala Ser Gly Glu Ile Ala Ser Asn
        130                 135

<210> SEQ ID NO 424
<211> LENGTH: 137
<212> TYPE: PRT
<213> ORGANISM: Unknown
<220> FEATURE:
<223> OTHER INFORMATION: Description of Unknown:
      Cyanobacterium endosymbiont of Epithemia turgida sequence

<400> SEQUENCE: 424

Cys Leu Ser Tyr Asp Thr Glu Val Leu Thr Val Glu Tyr Gly Ala Ile
1               5                   10                  15

Pro Ile Gly Arg Met Val Glu Glu Ser Leu Asp Cys Thr Val Tyr Thr
            20                  25                  30

Val Asp Lys Asn Gly Phe Val Tyr Thr Gln Ser Ile Gln Gln Trp His
        35                  40                  45

Ser Arg Gly Gln Gln Glu Ile Phe Glu Tyr Cys Phe Glu Asp Gly Ser
    50                  55                  60

Ile Ile Arg Ala Thr Lys Asp His Lys Phe Met Thr Ala Glu Gly Lys
65                  70                  75                  80

Met Ser Ser Ile His Asp Ile Phe Glu Gln Gly Leu Glu Leu Lys Lys
                85                  90                  95

Ile Ile Pro Trp Ser Gly Ala Lys Ile Ile Ser Cys Lys Ser Leu Gly
            100                 105                 110

Lys Gln Ser Val Tyr Asp Ile Gly Val Val Gln Asp His Asn Phe Leu
        115                 120                 125

Leu Ala Asn Gly Val Val Ala Ser Asn
    130                 135

<210> SEQ ID NO 425
<211> LENGTH: 133
<212> TYPE: PRT
<213> ORGANISM: Synechococcus sp.

<400> SEQUENCE: 425

Cys Leu Gly Tyr Asp Thr Pro Val Leu Thr Val Glu Tyr Gly Phe Met
1               5                   10                  15

Pro Ile Gly Lys Ile Val Glu Glu Lys Ile Gln Cys His Val Tyr Ser
            20                  25                  30

Val Asp Gln Asn Gly Leu Val Phe Thr Gln Ala Ile Ala Gln Trp His
        35                  40                  45

Asn Arg Gly Gln Gln Glu Val Trp Glu Tyr Asn Leu Asp Asn Gly Asp
```

```
                     50                  55                  60
Ile Val Arg Ala Thr Lys Asp His Lys Phe Met Thr Ile Asp Gly Gln
 65                  70                  75                  80

Met Leu Pro Ile Asn Gln Ile Phe Glu Gln Gly Leu Glu Leu Lys Val
                     85                  90                  95

Ile Ala Val Lys Ile Val Ser Cys Lys Pro Leu Arg Val Gln Thr Val
                100                 105                 110

Tyr Asp Ile Gly Val Glu Lys Asp His Asn Phe Ile Leu Asp Asn Gly
                115                 120                 125

Leu Val Ala Ser Asn
            130

<210> SEQ ID NO 426
<211> LENGTH: 134
<212> TYPE: PRT
<213> ORGANISM: Dactylococcopsis salina

<400> SEQUENCE: 426

Cys Leu Ser Tyr Asp Thr Glu Val Leu Thr Glu Tyr Gly Ala Ile
  1               5                  10                  15

Pro Ile Gly Lys Ile Val Glu Glu Arg Met Asn Cys His Val Tyr Ser
                 20                  25                  30

Val Asp Glu Asn Gly Phe Ile Tyr Ser Gln Pro Ile Ala Gln Trp His
             35                  40                  45

Pro Arg Gly Glu Gln Glu Val Val Glu Tyr Thr Leu Glu Asp Gly Lys
         50                  55                  60

Ile Ile Arg Ala Thr Ala Asp His Lys Met Met Thr Glu Thr Gly Glu
 65                  70                  75                  80

Met Leu Pro Ile Glu Gln Ile Phe Gln Gln Gln Leu Asp Leu Lys Ile
                     85                  90                  95

Ser Asn Gln Val Lys Ile Ile Asn Arg Gln Ser Leu Gly Lys Gln Thr
                100                 105                 110

Val Tyr Asp Ile Gly Val Glu Lys Asp His Asn Phe Ile Leu Gly Asn
                115                 120                 125

Gly Leu Val Ala Ser Asn
            130

<210> SEQ ID NO 427
<211> LENGTH: 137
<212> TYPE: PRT
<213> ORGANISM: Cylindrospermum stagnale

<400> SEQUENCE: 427

Cys Leu Ser Tyr Asp Thr Glu Ile Leu Thr Val Glu Tyr Gly Phe Ile
  1               5                  10                  15

Pro Ile Gly Glu Ile Val Glu Lys Arg Ile Glu Cys Ser Val Tyr Ser
                 20                  25                  30

Val Asp Asn His Gly Asn Val Tyr Thr Gln Pro Ile Ala Gln Trp His
             35                  40                  45

Asn Arg Gly Leu Gln Glu Val Phe Glu Tyr Cys Leu Glu Asp Gly Ser
         50                  55                  60

Thr Ile Arg Ala Thr Lys Asp His Lys Phe Met Thr Thr Asp Lys Glu
 65                  70                  75                  80

Met Leu Pro Ile Asp Glu Ile Phe Glu Arg Gly Leu Asp Leu Leu Arg
                     85                  90                  95

Val Glu Gly Leu Pro Ile Val Lys Ile Ile Met Arg Ser Tyr Val Gly
```

```
            100                 105                 110
Arg Glu Asn Val Tyr Asp Ile Gly Val Glu Arg Asp His Asn Phe Val
            115                 120                 125

Ala Lys Asn Gly Leu Ile Ala Ala Asn
            130                 135

<210> SEQ ID NO 428
<211> LENGTH: 137
<212> TYPE: PRT
<213> ORGANISM: Synechocystis sp.

<400> SEQUENCE: 428

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
            35                  40                  45

Asp Arg Gly Glu Gln Glu Val Leu Glu Tyr Glu Leu Glu Asp Gly Ser
        50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Val Lys Val Ile Gly Arg Arg Ser Leu Gly
            100                 105                 110

Val Gln Arg Ile Phe Asp Ile Gly Leu Pro Gln Asp His Asn Phe Leu
            115                 120                 125

Leu Ala Asn Gly Ala Ile Ala Ala Asn
            130                 135

<210> SEQ ID NO 429
<211> LENGTH: 137
<212> TYPE: PRT
<213> ORGANISM: Geitlerinema sp.

<400> SEQUENCE: 429

Cys Leu Ser Tyr Glu Thr Pro Val Met Thr Val Glu Tyr Gly Pro Leu
1               5                   10                  15

Pro Ile Gly Arg Ile Val Glu Glu Gln Leu Asp Cys Thr Val Tyr Ser
            20                  25                  30

Val Asp Glu Gln Gly His Val Tyr Thr Gln Pro Val Ala Gln Trp His
            35                  40                  45

His Arg Gly Leu Gln Glu Val Val Glu Tyr Glu Leu Glu Asp Gly Arg
        50                  55                  60

Arg Leu Arg Ala Thr Ala Asp His Arg Phe Met Thr Glu Thr Gly Glu
65                  70                  75                  80

Met Leu Pro Leu Ala Glu Ile Phe Glu Arg Gly Leu Glu Leu Arg Gln
                85                  90                  95

Val Ala Leu Arg Val Pro Val Lys Ile Val Ser Arg Arg Ser Leu Gly
            100                 105                 110

Met Gln Leu Val Tyr Asp Ile Gly Val Ala Ala Asp His Asn Phe Val
            115                 120                 125

Leu Ala Asp Gly Leu Ile Ala Ala Asn
            130                 135
```

<210> SEQ ID NO 430
<211> LENGTH: 137
<212> TYPE: PRT
<213> ORGANISM: Synechocystis sp.

<400> SEQUENCE: 430

Cys Leu Ser Phe Asp Ala Glu Ile Leu Thr Val Glu Tyr Gly Pro Leu
1               5                   10                  15

Ser Ile Gly Lys Ile Val Gly Glu Glu Ile Asn Cys Ser Val Tyr Ser
            20                  25                  30

Val Asp Pro Gln Gly Arg Ile Tyr Thr Gln Ala Ile Ala Gln Trp His
        35                  40                  45

Asp Arg Gly Val Gln Glu Val Phe Glu Tyr Glu Leu Glu Asp Gly Ser
    50                  55                  60

Val Ile Arg Ala Thr Pro Asp His Arg Phe Leu Thr Thr Asp Tyr Glu
65                  70                  75                  80

Leu Leu Ala Ile Glu Glu Ile Phe Ala Arg Gln Met Asp Leu Leu Thr
                85                  90                  95

Leu Thr Asn Leu Lys Leu Val Lys Val Val Arg Arg Ser Leu Gly
            100                 105                 110

Met His Arg Val Phe Asp Ile Gly Leu Ala Gln Asp His Asn Phe Leu
        115                 120                 125

Leu Ala Asn Gly Ala Ile Ala Ala Asn
    130                 135

<210> SEQ ID NO 431
<211> LENGTH: 135
<212> TYPE: PRT
<213> ORGANISM: Microcystis aeruginosa

<400> SEQUENCE: 431

Cys Leu Gly Gly Glu Thr Leu Ile Leu Thr Glu Glu Tyr Gly Leu Leu
1               5                   10                  15

Pro Ile Ala Lys Ile Val Ser Glu Glu Val Asn Cys Thr Val Tyr Ser
            20                  25                  30

Val Asp Lys Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Asn Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser Val Lys Ile Ile Ser Arg Gln Ser Leu Gly Arg Lys
            100                 105                 110

Pro Val Tyr Asp Ile Gly Val Glu Lys Asp His Asn Phe Leu Leu Gly
        115                 120                 125

Asn Gly Leu Ile Ala Ser Asn
    130                 135

<210> SEQ ID NO 432
<211> LENGTH: 135
<212> TYPE: PRT
<213> ORGANISM: Microcystis aeruginosa

<400> SEQUENCE: 432

Cys Leu Gly Gly Glu Thr Leu Ile Leu Thr Glu Glu Tyr Gly Leu Leu
1               5                   10                  15

```
Pro Ile Ala Lys Ile Val Ser Glu Glu Ile Asn Cys Thr Val Tyr Thr
            20                  25                  30

Val Asp Gln Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser Val Lys Ile Ile Gly Arg Gln Ser Leu Gly Arg Lys
            100                 105                 110

Pro Val Tyr Asp Ile Gly Val Glu Lys Asp His Asn Phe Leu Leu Gly
        115                 120                 125

Asn Gly Leu Ile Ala Ser Asn
    130                 135

<210> SEQ ID NO 433
<211> LENGTH: 137
<212> TYPE: PRT
<213> ORGANISM: Acaryochloris marina

<400> SEQUENCE: 433

Cys Leu Ser Tyr Asp Thr Pro Val Leu Thr Leu Glu Tyr Gly Trp Leu
1               5                   10                  15

Pro Ile Gly Gln Val Val Gln Glu Gln Ile Glu Cys Gln Val Phe Ser
            20                  25                  30

Ile Asn Glu Arg Gly His Leu Tyr Thr Gln Pro Ile Ala Gln Trp His
        35                  40                  45

His Arg Gly Gln Gln Glu Val Phe Glu Tyr Thr Leu Ala Asp Gly Ser
    50                  55                  60

Thr Ile Gln Ala Thr Ala Glu His Gln Phe Met Thr Thr Asp Gly Gln
65                  70                  75                  80

Met Tyr Pro Val Gln Gln Ile Phe Glu Glu Gly Leu Ser Leu Lys Gln
                85                  90                  95

Leu Pro Leu Pro Trp Gln Val Lys Ile Ile Gln Arg Arg Ser Leu Gly
            100                 105                 110

Leu Gln Ser Val Tyr Asp Ile Gly Leu Ala Gln Asp His Asn Phe Val
        115                 120                 125

Met Ala Asn Gly Trp Val Ala Ala Asn
    130                 135

<210> SEQ ID NO 434
<211> LENGTH: 137
<212> TYPE: PRT
<213> ORGANISM: Leptolyngbya sp.

<400> SEQUENCE: 434

Cys Leu Asp Gly Glu Thr Pro Ile Val Thr Val Glu Tyr Gly Val Leu
1               5                   10                  15

Pro Ile Arg Glu Ile Val Glu Lys Glu Leu Leu Cys Ser Val Tyr Ser
            20                  25                  30

Ile Asp Glu Asn Gly Phe Val Tyr Thr Gln Pro Val Glu Gln Trp His
        35                  40                  45

Gln Arg Gly Asp Arg Gln Met Phe Glu Tyr Gln Leu Asp Asn Gly Gly
    50                  55                  60
```

```
Val Ile Arg Ala Thr Pro Asp His Lys Phe Leu Thr Glu Gly Glu
 65                  70                  75                  80

Met Val Ala Ile Asp Glu Ile Phe Glu Lys Gly Leu Asn Leu Ala Glu
                 85                  90                  95

Phe Ala Pro Ala Asp Leu Val Lys Ile Leu Arg Arg His Ser Ile Gly
            100                 105                 110

Lys Ala Lys Thr Tyr Asp Ile Gly Val Ser Lys Asn His Asn Phe Leu
        115                 120                 125

Leu Ala Asn Gly Leu Phe Ala Ser Asn
        130                 135

<210> SEQ ID NO 435
<211> LENGTH: 137
<212> TYPE: PRT
<213> ORGANISM: Synechococcus elongatus

<400> SEQUENCE: 435

Cys Leu Ala Ala Asp Thr Glu Val Leu Thr Val Glu Tyr Gly Pro Ile
  1               5                  10                  15

Ala Ile Gly Lys Leu Val Glu Glu Asn Ile Arg Cys Gln Val Tyr Cys
                 20                  25                  30

Cys Asn Pro Asp Gly Tyr Ile Tyr Ser Gln Pro Ile Gly Gln Trp His
            35                  40                  45

Gln Arg Gly Glu Gln Glu Val Ile Glu Tyr Glu Leu Ser Asp Gly Arg
        50                  55                  60

Ile Ile Arg Ala Thr Ala Asp His Arg Phe Met Thr Glu Glu Gly Glu
 65                  70                  75                  80

Met Leu Ser Leu Asp Glu Ile Phe Glu Arg Ser Leu Glu Leu Lys Gln
                 85                  90                  95

Ile Pro Thr Pro Leu Leu Val Lys Ile Val Arg Arg Ser Leu Gly
            100                 105                 110

Val Gln Pro Val Tyr Asp Leu Gly Val Ala Thr Val His Asn Phe Val
        115                 120                 125

Leu Ala Asn Gly Leu Val Ala Ser Asn
        130                 135

<210> SEQ ID NO 436
<211> LENGTH: 137
<212> TYPE: PRT
<213> ORGANISM: Synechococcus sp.

<400> SEQUENCE: 436

Cys Leu Ser Ala Asp Thr Glu Leu Tyr Thr Val Glu Tyr Gly Trp Leu
  1               5                  10                  15

Pro Ile Gly Arg Leu Val Glu Glu Gln Ile Glu Cys Gln Val Leu Ser
                 20                  25                  30

Val Asn Ala His Gly His Val Tyr Ser Gln Pro Ile Ala Gln Trp His
            35                  40                  45

Arg Arg Ala Trp Gln Glu Val Phe Glu Tyr Gln Leu Glu Thr Gly Gly
        50                  55                  60

Thr Ile Lys Ala Thr Thr Asp His Gln Phe Leu Thr Asp Gly Gln
 65                  70                  75                  80

Met Tyr Arg Ile Glu Asp Ile Phe Gln Arg Gly Leu Asp Leu Trp Gln
                 85                  90                  95

Leu Pro Pro Asp Arg Phe Val Lys Ile Ile Ser Arg Cys Ser Leu Gly
            100                 105                 110
```

Ile Gln Pro Val Tyr Asp Ile Gly Val Ala Gln Asp His Asn Phe Val
            115                 120                 125

Ile Arg Gly Gly Leu Val Ala Ser Asn
        130                 135

<210> SEQ ID NO 437
<211> LENGTH: 137
<212> TYPE: PRT
<213> ORGANISM: Thermosynechococcus elongatus

<400> SEQUENCE: 437

Cys Leu Ser Gly Glu Thr Ala Val Met Thr Val Glu Tyr Gly Ala Val
1               5                   10                  15

Pro Ile Arg Arg Leu Val Gln Glu Arg Leu Ser Cys His Val Tyr Ser
            20                  25                  30

Leu Asp Gly Gln Gly His Leu Tyr Thr Gln Pro Ile Ala Gln Trp His
        35                  40                  45

Phe Gln Gly Phe Arg Pro Val Tyr Glu Tyr Gln Leu Glu Asp Gly Ser
    50                  55                  60

Thr Ile Cys Ala Thr Pro Asp His Arg Phe Met Thr Thr Arg Gly Gln
65                  70                  75                  80

Met Leu Pro Ile Glu Gln Ile Phe Gln Glu Gly Leu Glu Leu Trp Gln
                85                  90                  95

Val Ala Ile Ala Pro Arg Gly Lys Ile Val Gly Arg Arg Leu Met Gly
            100                 105                 110

Trp Gln Ala Val Tyr Asp Ile Gly Leu Ala Ala Asp His Asn Phe Val
        115                 120                 125

Leu Ala Asn Gly Ala Ile Ala Ala Asn
    130                 135

<210> SEQ ID NO 438
<211> LENGTH: 137
<212> TYPE: PRT
<213> ORGANISM: Thermosynechococcus sp.

<400> SEQUENCE: 438

Cys Leu Ser Gly Glu Thr Ala Val Met Thr Val Glu Tyr Gly Ala Val
1               5                   10                  15

Pro Ile Arg Arg Leu Val Gln Glu Arg Leu Thr Cys His Val Tyr Ser
            20                  25                  30

Leu Asp Ala Gln Gly His Leu Tyr Thr Gln Pro Ile Ala Gln Trp His
        35                  40                  45

Phe Gln Gly Phe Arg Pro Val Tyr Glu Tyr Gln Leu Glu Asp Gly Ser
    50                  55                  60

Thr Ile Trp Ala Thr Pro Asp His Arg Phe Met Thr Thr Arg Gly Gln
65                  70                  75                  80

Met Leu Pro Ile Glu Gln Ile Phe Gln Glu Gly Leu Glu Leu Trp Gln
                85                  90                  95

Gly Pro Ile Ala Pro Ser Cys Lys Ile Val Gly Arg Gln Leu Val Gly
            100                 105                 110

Trp Gln Ala Val Tyr Asp Ile Gly Val Ala Arg Asp His Asn Phe Leu
        115                 120                 125

Leu Ala Asn Gly Ala Ile Ala Ala Asn
    130                 135

<210> SEQ ID NO 439

```
<211> LENGTH: 137
<212> TYPE: PRT
<213> ORGANISM: Thermosynechococcus vulcanus

<400> SEQUENCE: 439

Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
            20                  25                  30

Leu Asp Pro Gln Gly His Leu Tyr Thr Gln Pro Ile Ala Gln Trp His
        35                  40                  45

Phe Gln Gly Phe Arg Pro Val Tyr Ala Tyr Gln Leu Glu Asp Gly Ser
    50                  55                  60

Thr Ile Cys Ala Thr Pro Asp His Arg Phe Met Thr Thr Ser Gly Gln
65                  70                  75                  80

Met Leu Pro Ile Glu Gln Ile Phe Arg Glu Gly Leu Glu Leu Trp Gln
                85                  90                  95

Val Ala Ile Ala Pro Pro Cys Lys Ile Val Gly Arg Arg Leu Val Gly
            100                 105                 110

Trp Gln Ala Val Tyr Asp Ile Gly Leu Ala Gly Asp His Asn Phe Leu
        115                 120                 125

Leu Ala Asn Gly Ala Ile Ala Ala Asn
    130                 135

<210> SEQ ID NO 440
<211> LENGTH: 137
<212> TYPE: PRT
<213> ORGANISM: Synechococcus sp.

<400> SEQUENCE: 440

Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Val Lys Ile Ile Arg Arg Lys Phe Ile Gly
            100                 105                 110

His Ala Pro Thr Tyr Asp Ile Gly Leu Ser Gln Asp His Asn Phe Leu
        115                 120                 125

Leu Gly Gln Gly Leu Ile Ala Ala Asn
    130                 135

<210> SEQ ID NO 441
<211> LENGTH: 136
<212> TYPE: PRT
<213> ORGANISM: Scytonema hofmanni

<400> SEQUENCE: 441

Cys Leu Ser Tyr Asp Thr Glu Val Leu Thr Ala Glu Tyr Gly Phe Leu
1               5                   10                  15
```

```
Pro Ile Gly Lys Ile Val Glu Lys Ala Ile Glu Cys Thr Val Tyr Ser
         20                  25                  30

Val Asp Asn Asp Gly Asn Ile Tyr Thr Gln Pro Ile Ala Gln Trp His
         35                  40                  45

Asp Arg Gly Gln Gln Glu Val Phe Glu Tyr Ser Leu Asp Asp Gly Ser
     50                  55                  60

Val Ile Arg Ala Thr Lys Asp His Lys Phe Met Thr Thr Gly Gly Gln
65                   70                  75                  80

Met Leu Pro Ile Asp Glu Ile Phe Glu Arg Gly Leu Asp Leu Met Arg
             85                  90                  95

Ile Asp Ser Leu Pro Val Lys Ile Leu Thr Arg Lys Ser Ile Gly Lys
                100                 105                 110

Gln Thr Val Tyr Asp Ile Gly Val Glu Arg Asp His Asn Phe Val Ile
            115                 120                 125

Lys Asn Gly Leu Val Ala Ser Asn
        130                 135

<210> SEQ ID NO 442
<211> LENGTH: 136
<212> TYPE: PRT
<213> ORGANISM: Westiella intricata

<400> SEQUENCE: 442

Cys Leu Ser Tyr Asp Thr Glu Ile Leu Thr Val Glu Tyr Gly Phe Leu
1               5                   10                  15

Pro Ile Gly Glu Ile Val Glu Lys Arg Ile Glu Cys Thr Val Tyr Thr
            20                  25                  30

Val Asp Thr Asn Gly Tyr Val Tyr Thr Gln Ala Ile Ala Gln Trp His
         35                  40                  45

Asn Arg Gly Glu Gln Glu Val Phe Glu Tyr Ala Leu Glu Asp Gly Ser
     50                  55                  60

Ile Ile Arg Ala Thr Lys Asp His Lys Phe Met Thr Ser Glu Gly Gln
65                   70                  75                  80

Met Leu Pro Ile Asp Glu Ile Phe Val Lys Gly Leu Asp Leu Leu Gln
             85                  90                  95

Val Gln Gly Leu Pro Val Lys Ile Ile Thr Arg Lys Phe Leu Gly Ile
                100                 105                 110

Gln Asn Val Tyr Asp Ile Gly Val Glu Gln Asn His Asn Phe Val Ile
            115                 120                 125

Lys Asn Gly Leu Val Ala Ser Asn
        130                 135

<210> SEQ ID NO 443
<211> LENGTH: 136
<212> TYPE: PRT
<213> ORGANISM: Fischerella sp.

<400> SEQUENCE: 443

Cys Leu Ser Tyr Asp Thr Glu Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Asn Asn Gly Asn Val Tyr Thr Gln Thr Ile Ala Gln Trp His
         35                  40                  45

Asn Arg Gly Gln Gln Glu Val Phe Glu Tyr Cys Leu Glu Asp Gly Ser
     50                  55                  60
```

Val Ile Arg Ala Thr Lys Asp His Lys Phe Met Thr Thr Asp Gly Gln
65                  70                  75                  80

Met Leu Pro Ile Asp Glu Ile Phe Ala Arg Gly Leu Asp Leu Leu Gln
                85                  90                  95

Val Lys Asn Leu Pro Val Lys Ile Val Thr Arg Arg Pro Leu Gly Thr
            100                 105                 110

Gln Asn Val Tyr Asp Ile Gly Val Glu Ser Asp His Asn Phe Val Ile
            115                 120                 125

Lys Asn Gly Leu Val Ala Ser Asn
130                 135

<210> SEQ ID NO 444
<211> LENGTH: 137
<212> TYPE: PRT
<213> ORGANISM: Mastigocladopsis repens

<400> SEQUENCE: 444

Cys Leu Ser Tyr Asp Thr Glu Val Leu Thr Val Glu Tyr Gly Phe Leu
1               5                   10                  15

Pro Ile Gly Glu Ile Val Glu Lys Ser Ile Glu Cys Ser Val Tyr Thr
            20                  25                  30

Val Asp Ser Asn Gly Asn Val Tyr Thr Gln Pro Ile Ala Gln Trp His
        35                  40                  45

Asn Arg Gly Gln Gln Glu Val Phe Glu Tyr Cys Leu Glu Asp Gly Ser
50                  55                  60

Ile Ile Arg Ala Thr Lys Asp His Lys Phe Met Thr Ile His Gly Gln
65                  70                  75                  80

Met Leu Pro Ile Asp Glu Ile Phe Glu Arg Gly Leu Glu Leu Met Lys
                85                  90                  95

Ile Gln Gly Leu Pro Glu Ala Lys Ile Ile Thr Arg Lys Ser Leu Gly
            100                 105                 110

Thr Gln Asn Val Tyr Asp Ile Gly Val Glu Arg Asp His Asn Phe Val
            115                 120                 125

Thr Arg Asp Gly Phe Ile Ala Ser Asn
130                 135

<210> SEQ ID NO 445
<211> LENGTH: 137
<212> TYPE: PRT
<213> ORGANISM: Scytonema hofmanni

<400> SEQUENCE: 445

Cys Leu Ser Tyr Asn Ser Glu Val Leu Thr Val Glu Tyr Gly Phe Leu
1               5                   10                  15

Pro Ile Gly Lys Ile Val Glu Lys Gly Ile Glu Cys Ser Val Tyr Ser
            20                  25                  30

Val Asp Ser Tyr Gly Lys Ile Tyr Thr Gln Val Ile Ala Gln Trp His
        35                  40                  45

Asn Arg Gly Gln Gln Glu Val Phe Glu Tyr Cys Leu Glu Asp Gly Thr
50                  55                  60

Ile Ile Gln Ala Thr Lys Asp His Lys Phe Met Thr Val Asp Gly Gln
65                  70                  75                  80

Met Leu Pro Ile Asp Glu Ile Phe Glu Arg Gly Leu Asp Leu Met Gln
                85                  90                  95

Val Gln Gly Leu Pro Asp Val Lys Ile Ile Thr Arg Lys Ser Leu Gly
            100                 105                 110

Thr Gln Asn Val Tyr Asp Ile Gly Val Ser Ser Asp His Asn Phe Val
            115                 120                 125

Met Lys Asn Gly Leu Ile Ala Ser Asn
    130                 135

<210> SEQ ID NO 446
<211> LENGTH: 137
<212> TYPE: PRT
<213> ORGANISM: Anabaena sp.

<400> SEQUENCE: 446

Cys Leu Ser Ser Asp Thr Glu Val Leu Thr Val Glu Tyr Gly Leu Ile
1               5                   10                  15

Pro Ile Gly Glu Ile Ile Glu Lys Arg Ile Asp Cys Ser Val Phe Ser
            20                  25                  30

Val Asp Lys Asn Gly Asn Ile Tyr Thr Gln Pro Ile Ala Gln Trp His
        35                  40                  45

Asp Arg Gly Ile Gln Glu Leu Tyr Glu Tyr Cys Leu Asp Asp Gly Ser
    50                  55                  60

Thr Ile Arg Ala Thr Lys Asp His Lys Phe Met Thr Thr Ala Gly Glu
65                  70                  75                  80

Met Leu Pro Ile Asp Glu Ile Phe Glu Arg Gly Leu Asp Leu Leu Lys
                85                  90                  95

Val His Asn Leu Pro Gln Val Lys Ile Ile Thr Arg Asn Tyr Val Gly
            100                 105                 110

Lys Glu Asn Val Tyr Asp Ile Gly Val Glu Arg Asp His Asn Phe Ala
        115                 120                 125

Ile Lys Asn Gly Leu Ile Ala Ser Asn
    130                 135

<210> SEQ ID NO 447
<211> LENGTH: 137
<212> TYPE: PRT
<213> ORGANISM: Fischerella sp.

<400> SEQUENCE: 447

Cys Leu Ser Tyr Asp Thr Glu Val Leu Thr Val Glu Tyr Gly Phe Leu
1               5                   10                  15

Pro Ile Gly Glu Ile Val Glu Lys Arg Ile Glu Cys Thr Val Tyr Thr
            20                  25                  30

Val Asp His Asn Gly Tyr Val Tyr Thr Gln Pro Ile Ala Gln Trp His
        35                  40                  45

Asn Arg Gly Tyr Gln Glu Val Phe Glu Tyr Gly Leu Glu Asp Gly Ser
    50                  55                  60

Val Ile Arg Ala Thr Lys Asp His Lys Phe Met Thr Ser Glu Gly Gln
65                  70                  75                  80

Met Leu Pro Ile Asp Glu Ile Phe Ala Arg Glu Leu Asp Leu Leu Gln
                85                  90                  95

Val Thr Gly Leu Val Asn Val Lys Ile Val Thr Arg Arg Leu Leu Gly
            100                 105                 110

Ile Gln Asn Val Tyr Asp Ile Gly Val Glu Gln Asn His Asn Phe Val
        115                 120                 125

Ile Lys Asn Gly Leu Val Ala Ser Asn
    130                 135

<210> SEQ ID NO 448
<211> LENGTH: 137

```
<212> TYPE: PRT
<213> ORGANISM: Calothrix sp.

<400> SEQUENCE: 448

Cys Leu Ser Tyr Asp Thr Glu Ile Phe Thr Val Glu Tyr Gly Phe Leu
1               5                   10                  15

Pro Ile Gly Glu Ile Val Glu Lys Arg Leu Glu Cys Thr Val Leu Thr
            20                  25                  30

Val Asp Asn His Gly Asn Ile Tyr Ser Gln Pro Ile Ala Gln Trp His
        35                  40                  45

His Arg Gly Gln Gln Gln Ile Tyr Glu Tyr Gly Leu Glu Asp Gly Ser
    50                  55                  60

Val Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Leu Gln
                85                  90                  95

Val Thr Asn Leu Asp Asn Val Lys Val Ile Thr Arg Lys Leu Ala Asp
            100                 105                 110

Thr Glu Asn Val Tyr Asp Ile Gly Val Glu Asn His His Asn Phe Leu
        115                 120                 125

Ile Lys Asn Gly Leu Val Ala Ser Asn
    130                 135

<210> SEQ ID NO 449
<211> LENGTH: 136
<212> TYPE: PRT
<213> ORGANISM: Fischerella thermalis

<400> SEQUENCE: 449

Cys Leu Ser Tyr Glu Thr Glu Ile Leu Thr Val Glu Tyr Gly Phe Leu
1               5                   10                  15

Pro Ile Gly Glu Ile Val Glu Lys Arg Ile Glu Cys Ser Val Tyr Thr
            20                  25                  30

Val Asp Asn Asn Gly Tyr Val Cys Thr Gln Pro Ile Ala Gln Trp His
        35                  40                  45

Asn Arg Gly Tyr Gln Glu Val Phe Glu Tyr Gly Leu Glu Asp Gly Ser
    50                  55                  60

Val Ile Arg Ala Thr Lys Asp His Lys Phe Met Thr Ile Asp Arg Gln
65                  70                  75                  80

Met Leu Pro Ile Asp Glu Ile Phe Ala Arg Gly Leu Asp Leu Leu Gln
                85                  90                  95

Val Thr Gly Leu Pro Val Lys Ile Ile Thr Arg Lys Ser Leu Gly Thr
            100                 105                 110

Gln Asn Val Tyr Asp Ile Gly Val Glu Gln Asn His Asn Phe Val Ile
        115                 120                 125

Lys Asn Gly Leu Val Ala Ser Asn
    130                 135

<210> SEQ ID NO 450
<211> LENGTH: 137
<212> TYPE: PRT
<213> ORGANISM: Unknown
<220> FEATURE:
<223> OTHER INFORMATION: Description of Unknown:
      cyanobacterium PCC 7702 Chl7702 sequence

<400> SEQUENCE: 450

Cys Leu Ser Tyr Asp Thr Glu Ile Leu Thr Val Glu Tyr Gly Phe Leu
```

-continued

```
              1               5                  10                 15
            Ser Ile Gly Glu Ile Val Glu Lys Glu Ile Glu Cys Thr Val Tyr Thr
                           20                 25                 30

Val Asp Ser Asn Gly Tyr Ile Tyr Thr Gln Pro Ile Ala Gln Trp His
                           35                 40                 45

Glu Gln Gly Glu Gln Glu Ile Phe Glu Tyr Ser Leu Glu Asp Gly Ser
                           50                 55                 60

Thr Ile Arg Ala Thr Lys Asp His Lys Phe Met Thr Ile Glu Gly Glu
             65                 70                 75                 80

Met Leu Pro Ile Asp Gln Ile Phe Ala Arg Gln Leu Asp Leu Met Gln
                           85                 90                 95

Ile Thr Gly Leu Pro Gln Val Lys Ile Ser Thr Lys Lys Ser Leu Gly
                          100                105                110

Lys Gln Lys Val Tyr Asp Ile Gly Val Val Arg Asp His Asn Phe Ile
                          115                120                125

Ile Lys Asn Gly Phe Val Ala Ser Asn
                          130                135

<210> SEQ ID NO 451
<211> LENGTH: 136
<212> TYPE: PRT
<213> ORGANISM: Fischerella sp.

<400> SEQUENCE: 451

Cys Leu Ser Tyr Asp Thr Glu Val Leu Thr Val Glu Tyr Gly Phe Leu
             1               5                  10                 15

Pro Ile Gly Glu Ile Val Glu Lys Arg Ile Glu Cys Thr Val Tyr Thr
                           20                 25                 30

Val Asp Thr Asn Gly Tyr Val Tyr Thr Gln Ala Ile Ala Gln Trp His
                           35                 40                 45

Asn Arg Asp Glu Gln Glu Val Phe Glu Tyr Ala Leu Glu Asp Gly Ser
                           50                 55                 60

Ile Ile Arg Ala Thr Lys Asp His Lys Phe Met Thr Ser Glu Gly Gln
             65                 70                 75                 80

Met Leu Pro Ile Asp Glu Ile Phe Ala Lys Gly Leu Asp Leu Leu Gln
                           85                 90                 95

Val Gln Gly Leu Pro Val Lys Ile Val Thr Arg Lys Phe Leu Gly Ile
                          100                105                110

Gln Asn Val Tyr Asp Ile Gly Val Glu Gln Asn His Asn Phe Val Ile
                          115                120                125

Lys Asn Gly Leu Val Ala Ser Asn
                          130                135

<210> SEQ ID NO 452
<211> LENGTH: 137
<212> TYPE: PRT
<213> ORGANISM: Fischerella muscicola

<400> SEQUENCE: 452

Cys Leu Ser Tyr Glu Thr Glu Ile Leu Thr Val Glu Tyr Gly Phe Leu
             1               5                  10                 15

Pro Ile Gly Glu Ile Val Glu Lys Arg Ile Glu Cys Ser Val Tyr Thr
                           20                 25                 30

Val Asp Asn Asn Gly Tyr Val Cys Thr Gln Thr Ile Ala Gln Trp His
                           35                 40                 45

Asn Arg Gly Tyr Gln Glu Val Phe Glu Tyr Gly Leu Glu Asp Gly Ser
```

```
Val Ile Arg Ala Thr Lys Asp His Lys Phe Met Thr Ile Asp Arg Gln
 65                  70                  75                  80

Met Leu Pro Ile Asp Glu Ile Phe Ala Arg Gly Leu Asp Leu Leu Gln
                 85                  90                  95

Val Lys Gly Leu Pro Glu Val Lys Ile Ile Thr Arg Gln Ser Leu Gly
            100                 105                 110

Thr Gln Asn Val Tyr Asp Ile Gly Val Glu Gln Asn His Asn Phe Val
        115                 120                 125

Ile Lys Asn Gly Leu Val Ala Ser Asn
        130                 135

<210> SEQ ID NO 453
<211> LENGTH: 137
<212> TYPE: PRT
<213> ORGANISM: Fischerella muscicola

<400> SEQUENCE: 453

Cys Leu Ser Tyr Asp Thr Glu Val Leu Thr Val Glu Tyr Gly Phe Leu
  1               5                  10                  15

Pro Ile Gly Glu Ile Val Glu Lys Thr Ile Glu Cys Asn Val Phe Thr
                 20                  25                  30

Val Asp Ser Asn Gly Tyr Val Tyr Thr Gln Pro Ile Ala Gln Trp His
            35                  40                  45

Asn Arg Gly Tyr Gln Glu Val Phe Glu Tyr Gly Leu Glu Asp Gly Ser
         50                  55                  60

Val Ile Arg Ala Thr Lys Asp His Lys Phe Met Thr Ser Glu Gly Lys
 65                  70                  75                  80

Met Leu Pro Ile Asp Glu Ile Phe Ala Arg Glu Leu Asp Leu Leu Gln
                 85                  90                  95

Val Thr Gly Leu Ile Asn Val Lys Ile Val Thr Arg Lys Phe Leu Gly
            100                 105                 110

Ile Gln Asn Val Tyr Asp Ile Gly Val Glu Gln Asn His Asn Phe Val
        115                 120                 125

Ile Lys Asn Gly Leu Val Ala Ser Asn
        130                 135

<210> SEQ ID NO 454
<211> LENGTH: 137
<212> TYPE: PRT
<213> ORGANISM: Lyngbya aestuarii

<400> SEQUENCE: 454

Cys Leu Ser Tyr Asp Thr Glu Ile Leu Thr Val Glu Tyr Gly Ala Ile
  1               5                  10                  15

Pro Ile Gly Lys Val Asp Glu Lys Ile Glu Cys Thr Val Tyr Ser
                 20                  25                  30

Val Asp Lys Asn Gly Leu Ile Tyr Thr Gln Pro Ile Ala Gln Trp His
            35                  40                  45

Asn Arg Gly Lys Gln Glu Val Phe Glu Tyr Ser Leu Glu Asp Gly Ser
         50                  55                  60

Thr Ile Arg Ala Thr Lys Asp His Lys Phe Met Thr Met Asp Asn Gln
 65                  70                  75                  80

Met Leu Pro Ile Asp Glu Ile Leu Glu Lys Gly Leu Glu Leu Lys Gln
                 85                  90                  95

Val Asn Ala Asp Ser Val Val Lys Ile Val Ser Arg Lys Ser Leu Asp
```

```
            100             105             110
Ser Gln Thr Val Tyr Asp Ile Gly Val Glu Thr Asp His Asn Phe Leu
        115             120             125
Leu Ala Asn Gly Ser Val Ala Ser Asn
        130             135
```

<210> SEQ ID NO 455
<211> LENGTH: 135
<212> TYPE: PRT
<213> ORGANISM: Microchaete sp.

<400> SEQUENCE: 455

```
Cys Leu Ser Tyr Lys Thr Gln Val Leu Thr Val Glu Tyr Gly Leu Leu
1               5                   10                  15
Ala Ile Gly Glu Ile Val Glu Lys Asn Ile Glu Cys Ser Val Phe Ser
            20                  25                  30
Val Asp Ile His Gly Asn Val Tyr Thr Gln Pro Ile Ala Gln Trp His
        35                  40                  45
His Arg Gly Gln Gln Glu Val Phe Glu Tyr Gly Leu Glu Asp Gly Ser
    50                  55                  60
Ile Ile Arg Ala Thr Lys Asp His Lys Phe Met Thr Thr Gln Gly Glu
65                  70                  75                  80
Met Leu Pro Ile Asp Glu Ile Phe Ala Arg Gly Leu Asp Leu Leu Gln
                85                  90                  95
Val Lys Gly Val Val Lys Ile Thr Arg Lys Tyr Ile Gly Lys Glu
            100             105             110
Asn Val Tyr Asp Ile Gly Val Glu Gln Asp His Asn Phe Ala Ile Lys
        115             120             125
Asn Gly Leu Ile Ala Ala Asn
        130             135
```

<210> SEQ ID NO 456
<211> LENGTH: 137
<212> TYPE: PRT
<213> ORGANISM: Leptolyngbya sp.

<400> SEQUENCE: 456

```
Cys Leu Ser Tyr Asp Thr Glu Ile Leu Thr Val Glu Tyr Gly Ala Leu
1               5                   10                  15
Pro Ile Gly Lys Ile Val Glu Asn Gln Met Ile Cys Ser Val Tyr Ser
            20                  25                  30
Ile Asp Asn Asn Gly Tyr Ile Tyr Ile Gln Pro Ile Ala Gln Trp His
        35                  40                  45
Asn Arg Gly Gln Gln Glu Val Phe Glu Tyr Ile Leu Glu Asp Gly Ser
    50                  55                  60
Ile Ile Arg Ser Thr Lys Asp His Lys Phe Met Thr Lys Gly Gly Glu
65                  70                  75                  80
Met Leu Pro Ile Asp Glu Ile Phe Glu Arg Gly Leu Glu Leu Ala Gln
                85                  90                  95
Val Thr Arg Leu Glu Gln Val Lys Ile Ser Arg Arg Ser Val Gly
            100             105             110
Val Gln Ser Val Tyr Asp Ile Gly Val Lys Gln Asp His Asn Phe Phe
        115             120             125
Leu Arg Asn Gly Leu Ile Ala Ser Asn
        130             135
```

```
<210> SEQ ID NO 457
<211> LENGTH: 137
<212> TYPE: PRT
<213> ORGANISM: Crocosphaera watsonii

<400> SEQUENCE: 457
```

Cys Leu Ser Tyr Asp Thr Glu Ile Leu Thr Val Glu Tyr Gly Ala Met
1               5                   10                  15

Tyr Ile Gly Lys Ile Val Glu Glu Asn Ile Asn Cys Thr Val Tyr Thr
            20                  25                  30

Val Asp Lys Asn Gly Phe Val Tyr Thr Gln Thr Ile Ala Gln Trp His
        35                  40                  45

Asn Arg Gly Glu Gln Glu Ile Phe Glu Tyr Asp Leu Glu Asp Gly Ser
    50                  55                  60

Lys Ile Lys Ala Thr Lys Asp His Lys Phe Met Thr Ile Asp Gly Glu
65                  70                  75                  80

Met Leu Pro Ile Asp Glu Ile Phe Glu Lys Asn Leu Asp Leu Lys Gln
                85                  90                  95

Val Val Ser His Pro Asp Val Lys Ile Ile Gly Cys Arg Ser Leu Gly
            100                 105                 110

Thr Gln Lys Val Tyr Asp Ile Gly Val Glu Lys Asp His Asn Phe Leu
        115                 120                 125

Leu Ala Asn Gly Ser Ile Ala Ser Asn
    130                 135

```
<210> SEQ ID NO 458
<211> LENGTH: 135
<212> TYPE: PRT
<213> ORGANISM: Coleofasciculus chthonoplastes

<400> SEQUENCE: 458
```

Cys Leu Ser Tyr Asp Thr Gln Ile Leu Thr Val Glu Tyr Gly Ala Val
1               5                   10                  15

Ala Ile Gly Glu Ile Val Glu Lys Gln Ile Glu Cys Thr Val Tyr Ser
            20                  25                  30

Val Asp Glu Asn Gly Tyr Val Tyr Thr Gln Pro Ile Ala Gln Trp His
        35                  40                  45

Asn Arg Gly Glu Gln Glu Val Phe Glu Tyr Leu Leu Glu Asp Gly Ala
    50                  55                  60

Thr Ile Arg Ala Thr Lys Asp His Lys Phe Met Thr Asp Glu Asp Gln
65                  70                  75                  80

Met Leu Pro Ile Asp Gln Ile Phe Glu Gln Gly Leu Glu Leu Lys Gln
                85                  90                  95

Val Glu Val Leu Val Lys Ile Ile Gly Arg Lys Pro Leu Gly Thr Gln
            100                 105                 110

Pro Val Tyr Asp Ile Gly Val Glu Arg Asp His Asn Phe Leu Leu Phe
        115                 120                 125

Asn Gly Ser Val Ala Ser Asn
    130                 135

```
<210> SEQ ID NO 459
<211> LENGTH: 133
<212> TYPE: PRT
<213> ORGANISM: Chroococcidiopsis sp.

<400> SEQUENCE: 459
```

Cys Leu Ser Tyr Asp Thr Glu Val Leu Thr Val Glu Tyr Gly Ala Ile
1               5                   10                  15

```
Pro Ile Gly Lys Ile Val Glu Lys Ile Ala Cys Asn Val Tyr Ser
            20                  25                  30

Val Asp Lys Asn Gly Phe Val Tyr Thr Gln Pro Ile Ala Gln Tyr His
        35                  40                  45

Asp Arg Gly Ile Gln Glu Val Phe Glu Tyr Arg Leu Glu Asn Gly Ser
50                  55                  60

Val Ile Arg Ala Thr Lys Asp His Lys Met Met Thr Ala Asp Gly Gln
65                  70                  75                  80

Met Leu Pro Ile Asp Glu Ile Phe Lys Gln Asn Leu Asp Leu Lys Gln
                85                  90                  95

Leu Asn Val Lys Ile Ile Ser Arg Gln Ser Leu Gly Lys Gln Ser Val
            100                 105                 110

Phe Asp Ile Gly Val Ala Lys Asp His Asn Phe Leu Leu Ala Asn Gly
        115                 120                 125

Leu Val Ala Ser Asn
    130

<210> SEQ ID NO 460
<211> LENGTH: 132
<212> TYPE: PRT
<213> ORGANISM: Aphanizomenon flos-aquae

<400> SEQUENCE: 460

Cys Leu Ser Tyr Asp Thr Glu Ile Leu Thr Val Glu Tyr Gly Phe Leu
1               5                   10                  15

Gln Ile Gly Glu Ile Val Glu Lys Gln Ile Glu Cys Lys Val Tyr Thr
            20                  25                  30

Val Asp Ser Asn Gly Ile Leu Tyr Thr Gln Ser Ile Ala Gln Trp His
        35                  40                  45

Asn Arg Gly Gln Gln Glu Val Tyr Glu Tyr Leu Leu Glu Asn Gly Ala
50                  55                  60

Ile Ile Arg Ala Thr Lys Asp His Lys Phe Met Thr Glu Glu Gly Gln
65                  70                  75                  80

Met Leu Pro Ile Asp Glu Ile Phe Ser Gln Gly Leu Asp Leu Leu Gln
                85                  90                  95

Val Val Lys Ile Ile Ser Arg Thr Tyr Val Gly Gln Ala Asn Val Tyr
            100                 105                 110

Asp Ile Gly Val Glu Asn Asp His Asn Phe Val Ile Lys Asn Gly Phe
        115                 120                 125

Ile Ala Ala Asn
    130

<210> SEQ ID NO 461
<211> LENGTH: 137
<212> TYPE: PRT
<213> ORGANISM: Raphidiopsis brookii

<400> SEQUENCE: 461

Cys Leu Ser Tyr Glu Thr Glu Val Leu Thr Leu Glu Tyr Gly Phe Leu
1               5                   10                  15

Pro Ile Gly Glu Ile Val Asp Lys Gln Met Val Cys Thr Val Phe Ser
            20                  25                  30

Val Asn Asp Ser Gly Asn Val Tyr Thr Gln Pro Ile Gly Gln Trp His
        35                  40                  45

Asp Arg Gly Val Gln Glu Leu Tyr Glu Tyr Cys Leu Asp Asp Gly Ser
50                  55                  60
```

Thr Ile Arg Ala Thr Lys Asp His Lys Phe Met Thr Thr Gln Gly Glu
65                  70                  75                  80

Met Val Pro Ile Asp Glu Ile Phe His Gln Gly Trp Glu Leu Val Gln
                85                  90                  95

Val Ser Gly Thr Met Asn Val Lys Ile Val Ser Arg Arg Tyr Leu Gly
            100                 105                 110

Lys Ala Asp Val Tyr Asp Ile Gly Val Ala Lys Asp His Asn Phe Ile
                115                 120                 125

Ile Lys Asn Gly Leu Val Ala Ser Asn
            130                 135

<210> SEQ ID NO 462
<211> LENGTH: 134
<212> TYPE: PRT
<213> ORGANISM: Cyanothece sp.

<400> SEQUENCE: 462

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Ser Val Tyr Thr
            20                  25                  30

Val Asn Lys Asn Gly Phe Val Tyr Thr Gln Ser Ile Ala Gln Trp His
            35                  40                  45

His Arg Gly Glu Gln Glu Val Phe Glu Tyr Tyr Leu Glu Asp Gly Glu
        50                  55                  60

Thr Ile Arg Ala Thr Lys Asp His Lys Phe Met Thr Thr Glu Gly Lys
65                  70                  75                  80

Met Leu Pro Ile Asp Glu Ile Phe Glu Asn Asn Leu Asp Leu Lys Lys
                85                  90                  95

Leu Thr Val Val Lys Ile Ile Glu Arg Arg Ser Leu Gly Lys Gln Asn
            100                 105                 110

Val Tyr Asp Ile Gly Val Glu Lys Asp His Asn Phe Leu Leu Ser Asn
            115                 120                 125

Asn Leu Ile Ala Ser Asn
            130

<210> SEQ ID NO 463
<211> LENGTH: 135
<212> TYPE: PRT
<213> ORGANISM: Xenococcus sp.

<400> SEQUENCE: 463

Cys Leu Ser Ala Asp Thr Glu Val Leu Thr Val Glu Tyr Gly Ala Ile
1               5                   10                  15

Ser Ile Gly Lys Ile Val Glu Glu Arg Ile Glu Cys Thr Val Tyr Ser
            20                  25                  30

Val Asp Ala Asn Gly Phe Val Tyr Thr Gln Glu Ile Ala Gln Trp His
            35                  40                  45

Asn Arg Gly Glu Gln Glu Val Phe Glu Tyr Met Leu Asp Asp Gly Ser
        50                  55                  60

Val Ile Arg Ala Thr Lys Asp His Lys Leu Met Thr Ile Asp Gly Gln
65                  70                  75                  80

Met Val Ala Ile Asp Glu Ile Phe Ser Gln Gly Leu Glu Leu Lys Gln
                85                  90                  95

Val Leu Gly Leu Val Lys Ile Val Ser Arg Lys Ser Leu Gly Thr Gln
            100                 105                 110

Thr Val Tyr Asp Leu Gly Val Ala Arg Asp His Asn Phe Leu Leu Ala
        115                 120                 125

Asn Gly Thr Val Ala Ser Asn
    130                 135

<210> SEQ ID NO 464
<211> LENGTH: 135
<212> TYPE: PRT
<213> ORGANISM: Pleurocapsa sp.

<400> SEQUENCE: 464

Cys Leu Ser Tyr Asp Thr Glu Ile Tyr Thr Val Glu Tyr Gly Ala Leu
1               5                   10                  15

Pro Ile Gly Lys Ile Val Glu Ser Arg Ile Lys Cys Thr Val Leu Thr
            20                  25                  30

Val Asp Lys Asn Gly Leu Val Tyr Ser Gln Pro Ile Val Gln Trp His
        35                  40                  45

Asp Arg Gly Ile Gln Glu Val Phe Glu Tyr Thr Leu Asp Asn Gly Ala
    50                  55                  60

Thr Ile Arg Ala Thr Lys Asp His Lys Phe Met Thr Val Glu Gly Gln
65                  70                  75                  80

Met Leu Pro Ile Asp Glu Ile Phe Glu Leu Gly Leu Glu Leu Lys Glu
                85                  90                  95

Ile Gln Gln Phe Val Lys Ile Ile Ser Arg Gln Ser Leu Gly Lys Gln
            100                 105                 110

Ser Val Tyr Asp Ile Gly Val Ala Lys Asp His Asn Phe Leu Leu Ala
        115                 120                 125

Asn Gly Met Val Ala Ser Asn
    130                 135

<210> SEQ ID NO 465
<211> LENGTH: 137
<212> TYPE: PRT
<213> ORGANISM: Cylindrospermopsis raciborskii

<400> SEQUENCE: 465

Cys Leu Ser Tyr Glu Thr Glu Val Leu Thr Leu Glu Tyr Gly Phe Val
1               5                   10                  15

Pro Ile Gly Glu Ile Val Asn Lys Gln Met Val Cys Thr Val Phe Ser
            20                  25                  30

Leu Asn Asp Ser Gly Asn Val Tyr Thr Gln Pro Ile Gly Gln Trp His
        35                  40                  45

Asp Arg Gly Val Gln Asp Leu Tyr Glu Tyr Cys Leu Asp Asp Gly Ser
    50                  55                  60

Thr Ile Arg Ala Thr Lys Asp His Lys Phe Met Thr Thr Gln Gly Glu
65                  70                  75                  80

Met Val Pro Ile Asp Glu Ile Phe His Gln Gly Trp Glu Leu Val Gln
                85                  90                  95

Val Ser Gly Ile Ser Lys Val Lys Ile Val Ser Arg Arg Tyr Leu Gly
            100                 105                 110

Lys Ala Asp Val Tyr Asp Ile Gly Val Ala Lys Asp His Asn Phe Ile
        115                 120                 125

Ile Lys Asn Gly Leu Val Ala Ser Asn
    130                 135

<210> SEQ ID NO 466

```
<211> LENGTH: 129
<212> TYPE: PRT
<213> ORGANISM: Spirulina major

<400> SEQUENCE: 466

Cys Leu Thr Tyr Asp Thr Leu Val Leu Thr Val Glu Tyr Gly Pro Val
1               5                   10                  15

Pro Ile Gly Lys Leu Val Glu Ala Gln Ile Asn Cys Gln Val Tyr Ser
            20                  25                  30

Val Asp Ala Asn Gly Phe Ile Tyr Thr Gln Ala Ile Ala Gln Trp His
        35                  40                  45

Asp Arg Gly Gln Arg Gln Val Tyr Glu Tyr Thr Leu Glu Asp Gly Ser
    50                  55                  60

Thr Ile Arg Ala Thr Pro Asp His Lys Phe Met Thr Ala Thr Gly Glu
65                  70                  75                  80

Met Leu Pro Ile Asp Gln Ile Phe Glu Gln Gly Leu Asp Leu Val Lys
                85                  90                  95

Ile Ile His Arg Arg Ala Leu Pro Pro Gln Ser Val Tyr Asp Ile Gly
            100                 105                 110

Val Glu Arg Asp His Asn Phe Leu Leu Pro Ser Gly Trp Val Ala Ser
        115                 120                 125

Asn

<210> SEQ ID NO 467
<211> LENGTH: 131
<212> TYPE: PRT
<213> ORGANISM: Spirulina subsalsa

<400> SEQUENCE: 467

Cys Leu Ser Tyr Asp Thr Lys Ile Ile Thr Val Glu Tyr Gly Ala Ile
1               5                   10                  15

Ala Ile Gly Thr Ile Val Glu Gln Gly Leu His Cys His Val Tyr Ser
            20                  25                  30

Val Asp Pro Asn Gly Phe Ile Tyr Thr Gln Pro Ile Ala Gln Trp His
        35                  40                  45

Gln Arg Gly Glu Gln Glu Val Phe Ala Tyr Thr Leu Glu Asn Gly Ser
    50                  55                  60

Ile Ile Gln Ala Thr Lys Asp His Lys Phe Met Thr Gln Gln Gly Lys
65                  70                  75                  80

Met Leu Pro Ile Asp Thr Ile Phe Glu Gln Gly Leu Asp Leu Leu Gln
                85                  90                  95

Val Lys Ile Ile Lys Arg Thr Ser Leu Gly Val Arg Pro Val Tyr Asp
            100                 105                 110

Ile Gly Val Ile Gln Asp His Asn Phe Leu Leu Glu Asn Gly Leu Val
        115                 120                 125

Ala Ser Asn
    130

<210> SEQ ID NO 468
<211> LENGTH: 135
<212> TYPE: PRT
<213> ORGANISM: Microcystis aeruginosa

<400> SEQUENCE: 468

Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Cys Thr Val Tyr Ser
```

```
            20                  25                  30
Val Asp Lys Asn Gly Phe Ile Tyr Ser Gln Pro Ile Ser Gln Trp His
            35                  40                  45

Glu Arg Gly Leu Gln Glu Val Phe Glu Tyr Thr Leu Glu Asn Gly Gln
        50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser Val Lys Ile Ser Arg Gln Phe Leu Gly Arg Lys
            100                 105                 110

Pro Val Tyr Asp Ile Gly Val Glu Lys Asp His Asn Phe Leu Leu Gly
            115                 120                 125

Asn Gly Leu Ile Ala Ser Asn
        130                 135
```

<210> SEQ ID NO 469
<211> LENGTH: 130
<212> TYPE: PRT
<213> ORGANISM: Myxosarcina sp.

<400> SEQUENCE: 469

```
Cys Leu Ser Tyr Asp Thr Glu Val Leu Thr Leu Lys Tyr Gly Ala Leu
1               5                   10                  15

Pro Ile Gly Glu Ile Val Glu Lys Arg Ile Asn Cys His Val Tyr Thr
            20                  25                  30

Arg Ala Glu Ser Gly Phe Phe Tyr Ile Gln Ser Ile Glu Gln Trp His
            35                  40                  45

Asp Arg Gly Glu Gln Glu Val Phe Glu Tyr Thr Leu Glu Asn Gly Ala
        50                  55                  60

Thr Ile Lys Ala Thr Lys Asp His Lys Phe Met Thr Ser Gly Gly Gln
65                  70                  75                  80

Met Leu Pro Ile Asp Glu Ile Phe Glu Arg Gly Leu Asp Leu Leu Val
                85                  90                  95

Lys Ile Val Ser Arg Lys Ser Leu Gly Lys Gln Pro Val Tyr Asp Leu
            100                 105                 110

Gly Val Ala Lys Asp His Asn Phe Leu Leu Ala Asn Gly Thr Val Ala
            115                 120                 125

Ser Asn
    130
```

<210> SEQ ID NO 470
<211> LENGTH: 136
<212> TYPE: PRT
<213> ORGANISM: Leptolyngbya sp.

<400> SEQUENCE: 470

```
Cys Leu Ser Ala Asp Thr Gln Leu Leu Thr Val Glu Tyr Gly Pro Leu
1               5                   10                  15

Glu Ile Gly Arg Ile Val Glu Gln Ile Ala Cys His Val Tyr Ser
            20                  25                  30

Val Asp Ala Asn Gly Phe Val Tyr Thr Gln Pro Ile Ala Gln Trp His
            35                  40                  45

Ser Arg Gly Glu Gln Glu Ile Phe Glu Tyr Gln Leu Glu Asp Gly Arg
        50                  55                  60

Thr Leu Arg Ala Thr Ala Asp His Lys Phe Met Thr Thr Thr Gly Glu
```

```
                65                  70                  75                  80
Met Gly Arg Ile Asn Asp Ile Phe Glu Gln Gly Leu Asp Leu Lys Gln
                    85                  90                  95

Ile Asp Leu Pro Gln Val Lys Val Ser Arg Gln Ser Leu Gly Val
                100                 105                 110

Gln Pro Val Tyr Asp Ile Gly Val Ala Thr Asp His Asn Phe Leu Leu
                115                 120                 125

Ala Asp Gly Leu Val Ala Ser Asn
            130                 135

<210> SEQ ID NO 471
<211> LENGTH: 132
<212> TYPE: PRT
<213> ORGANISM: Acaryochloris sp.

<400> SEQUENCE: 471

Cys Leu Ser Tyr Asp Thr Pro Val Leu Thr Leu Glu Tyr Gly Trp Leu
1               5                   10                  15

Pro Ile Gly Gln Val Val Gln Glu Gln Ile Glu Cys Gln Val Phe Ser
                20                  25                  30

Ile Asn Glu Arg Gly His Leu Tyr Thr Gln Pro Ile Ala Gln Trp His
            35                  40                  45

His Arg Gly Gln Gln Glu Val Phe Glu Tyr Thr Leu Thr Asp Gly Ser
        50                  55                  60

Thr Ile Gln Ala Thr Ala Glu His Gln Phe Met Thr Thr Asp Gly Gln
65                  70                  75                  80

Met Tyr Pro Ile Gln Gln Ile Phe Glu Glu Gly Leu Ser Leu Lys Gln
                85                  90                  95

Leu Val Lys Ile Thr Gln Arg Arg Ser Leu Gly Leu Gln Ser Val Tyr
                100                 105                 110

Asp Ile Gly Leu Ala Gln Asp His Asn Phe Val Ile Ala Asn Gly Trp
            115                 120                 125

Val Ala Ala Asn
            130

<210> SEQ ID NO 472
<211> LENGTH: 133
<212> TYPE: PRT
<213> ORGANISM: Geminocystis herdmanii

<400> SEQUENCE: 472

Cys Leu Ser Tyr Asp Thr Glu Val Leu Thr Val Glu Phe Gly Ala Ile
1               5                   10                  15

Pro Met Gly Lys Ile Val Glu Glu Arg Leu Asn Cys Gln Val Tyr Ser
                20                  25                  30

Val Asp Lys Asn Gly Phe Ile Tyr Thr Gln Asn Ile Ala Gln Trp His
            35                  40                  45

Asp Arg Gly Val Gln Glu Val Phe Glu Tyr Glu Leu Glu Asp Gly Arg
        50                  55                  60

Ile Ile Lys Ala Thr Lys Asp His Lys Met Met Ile Glu Asn Cys Glu
65                  70                  75                  80

Met Val Glu Ile Asp Arg Ile Phe Glu Glu Gly Leu Glu Leu Phe Glu
                85                  90                  95

Val Asn Val Lys Ile Leu Lys Arg Arg Ser Ile Ser Ser Gln Gln Val
                100                 105                 110

Tyr Asp Ile Gly Val Glu Lys Asp His Asn Phe Leu Leu Ala Asn Gly
```

Leu Val Ala Ser Asn
    130

<210> SEQ ID NO 473
<211> LENGTH: 133
<212> TYPE: PRT
<213> ORGANISM: Nodosilinea nodulosa

<400> SEQUENCE: 473

Cys Leu Ser Ala Asp Thr Glu Leu Leu Thr Leu Glu Tyr Gly Pro Leu
1               5                   10                  15

Thr Ile Gly Glu Ile Val Ala Lys Arg Ile Pro Cys His Val Phe Ser
            20                  25                  30

Val Asp Glu Ser Gly Tyr Val Tyr Thr Gln Pro Val Ala Gln Trp His
        35                  40                  45

Gln Arg Gly His Gln Glu Val Phe Glu Tyr Gln Leu Asp Asp Gly Thr
    50                  55                  60

Thr Ile Arg Ala Thr Ala Asp His Gln Phe Met Thr Glu Leu Gly Glu
65                  70                  75                  80

Met Met Ala Ile Asp Glu Ile Phe Gln Arg Gly Leu Glu Leu Lys Gln
                85                  90                  95

Val Glu Val Lys Ile Ile Ser Arg Gln Ser Leu Gly Val Gln Pro Val
            100                 105                 110

Tyr Asp Ile Gly Val Ala Arg Asp His Asn Phe Leu Leu Ala Asp Gly
        115                 120                 125

Gln Val Ala Ser Asn
    130

<210> SEQ ID NO 474
<211> LENGTH: 137
<212> TYPE: PRT
<213> ORGANISM: Rubidibacter lacunae

<400> SEQUENCE: 474

Cys Leu Ser Tyr Asp Thr Glu Val Leu Thr Val Glu Tyr Gly Pro Leu
1               5                   10                  15

Ala Ile Gly Thr Ile Val Ser Glu Arg Leu Ala Cys Thr Val Tyr Thr
            20                  25                  30

Val Asp Arg Ser Gly Phe Leu Tyr Ala Gln Ala Ile Ser Gln Trp His
        35                  40                  45

Glu Arg Gly Arg Gln Asp Val Phe Glu Tyr Ala Leu Asp Asn Gly Met
    50                  55                  60

Thr Ile Arg Ala Thr Lys Asp His Lys Leu Met Thr Ala Asp Gly Gln
65                  70                  75                  80

Met Val Ala Ile Asp Asp Ile Phe Thr Gln Gly Leu Thr Leu Lys Ala
                85                  90                  95

Ile Asp Thr Ala Ala Phe Met Lys Ile Val Ser Arg Lys Ser Leu Gly
            100                 105                 110

Val Gln His Val Tyr Asp Ile Gly Val Ala Arg Asp His Asn Phe Leu
        115                 120                 125

Leu Ala Asn Gly Ala Ile Ala Ser Asn
    130                 135

<210> SEQ ID NO 475
<211> LENGTH: 136
<212> TYPE: PRT

<213> ORGANISM: Chlorogloeopsis fritschii

<400> SEQUENCE: 475

Cys Leu Ser Tyr Asp Thr Ala Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Ser Asn Gly Tyr Ile Tyr Thr Gln Pro Ile Ala Gln Trp His
        35                  40                  45

Asn Arg Gly Glu Gln Glu Leu Phe Glu Tyr Ser Leu Glu Asp Gly Ser
    50                  55                  60

Ile Ile Arg Ala Thr Lys Asp His Lys Phe Met Thr Ile Asp Gly Gln
65                  70                  75                  80

Met Leu Pro Ile Asp Glu Ile Phe Ala Arg Lys Leu Glu Leu Met Gln
                85                  90                  95

Val Lys Gly Leu Pro Val Lys Ile Ile Ala Lys Lys Ser Leu Gly Thr
            100                 105                 110

Gln Asn Val Tyr Asp Ile Gly Val Glu Arg Asp His Asn Phe Val Ile
        115                 120                 125

Lys Asn Gly Leu Val Ala Ser Asn
    130                 135

<210> SEQ ID NO 476
<211> LENGTH: 137
<212> TYPE: PRT
<213> ORGANISM: Richelia intracellularis

<400> SEQUENCE: 476

Cys Leu Ser Tyr Asp Thr Gln Ile Leu Thr Val Glu His Gly Pro Met
1               5                   10                  15

Ser Ile Gly Glu Ile Val Glu Lys Cys Leu Glu Cys His Val Tyr Thr
            20                  25                  30

Val Asn Lys Asn Gly Asn Ile Cys Ile Gln Thr Ile Thr Gln Trp His
        35                  40                  45

Phe Arg Gly Glu Gln Glu Ile Phe Glu Tyr Glu Leu Glu Asp Gly Ser
    50                  55                  60

Phe Ile Gln Ala Thr Lys Asp His Lys Phe Met Thr Thr Thr Gly Glu
65                  70                  75                  80

Met Leu Pro Ile His Glu Ile Phe Thr Asn Gly Leu Glu Ile Leu Gln
                85                  90                  95

Leu Ser Lys Ser Leu Leu Val Lys Ile Leu Ala Arg Lys Ser Leu Gly
            100                 105                 110

Thr Gln Lys Val Tyr Asp Ile Gly Val Asn Asp Asp His Asn Phe Ala
        115                 120                 125

Leu Ser Asn Ser Phe Ile Ala Ser Asn
    130                 135

<210> SEQ ID NO 477
<211> LENGTH: 137
<212> TYPE: PRT
<213> ORGANISM: Synechococcus sp.

<400> SEQUENCE: 477

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys Gln Val Tyr Ser
            20                  25                  30

```
Val Asp Ala Gln Gly Leu Ile Tyr Thr Gln Pro Ile Glu Gln Trp His
        35                  40                  45

Asn Arg Gly Asp Arg Leu Leu Tyr Glu Tyr Glu Leu Glu Asn Gly Gln
    50                  55                  60

Met Ile Arg Ala Thr Pro Asp His Lys Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Val Lys Ile Ile Arg Arg Lys Phe Ile Gly
            100                 105                 110

His Ala Pro Thr Tyr Asp Ile Gly Leu Ser Gln Asp His Asn Phe Leu
        115                 120                 125

Leu Gly Gln Gly Leu Ile Ala Ala Asn
        130                 135

<210> SEQ ID NO 478
<211> LENGTH: 137
<212> TYPE: PRT
<213> ORGANISM: Synechococcus sp.

<400> SEQUENCE: 478

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys His Val Tyr Ser
                20                  25                  30

Val Asp Ala Gln Gly Leu Ile Tyr Thr Gln Pro Ile Glu Gln Trp His
        35                  40                  45

Gln Arg Gly Asp Arg Phe Leu Tyr Glu Tyr Glu Leu Glu Asn Gly Gln
    50                  55                  60

Met Ile Arg Ala Thr Pro Asp His Lys Phe Leu Thr Thr Thr Gly Lys
65                  70                  75                  80

Leu Leu Pro Ile Asp Glu Ile Phe Thr Gln Asn Leu Asp Leu Ala Ala
                85                  90                  95

Trp Ala Val Pro Asp Ser Val Lys Ile Ile Arg Arg Lys Phe Ile Gly
            100                 105                 110

His Ala Pro Thr Tyr Asp Ile Gly Leu Ser Gln Asp His Asn Phe Leu
        115                 120                 125

Leu Gly Gln Gly Phe Ile Ala Ala Asn
        130                 135

<210> SEQ ID NO 479
<211> LENGTH: 137
<212> TYPE: PRT
<213> ORGANISM: Synechococcus sp.

<400> SEQUENCE: 479

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys His Val Tyr Ser
                20                  25                  30

Val Asp Ala Gln Gly Leu Ile Tyr Thr Gln Pro Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Lys Phe Leu Thr Thr Thr Gly Glu
65                  70                  75                  80
```

```
Leu Leu Pro Ile Asp Glu Ile Phe Thr Gln Asn Leu Asp Leu Ala Ala
                85                  90                  95

Trp Ala Val Pro Asp Ser Val Lys Ile Leu Arg Arg Lys Phe Ile Gly
            100                 105                 110

Arg Ala Pro Thr Tyr Asp Ile Gly Leu Ser Gln Asp His Asn Phe Leu
        115                 120                 125

Leu Gly Gln Gly Leu Val Ala Ala Asn
130                 135
```

<210> SEQ ID NO 480
<211> LENGTH: 129
<212> TYPE: PRT
<213> ORGANISM: Synechococcus sp.

<400> SEQUENCE: 480

```
Cys Leu Ala Gly Asp Thr Pro Val Val Thr Val Glu Tyr Gly Val Leu
1               5                   10                  15

Pro Ile Arg Thr Ile Val Asp Gln Glu Leu Leu Cys His Val Tyr Ser
            20                  25                  30

Leu Asp Pro Gln Gly Phe Ile Tyr Ala Gln Pro Val Glu Gln Trp His
        35                  40                  45

Arg Arg Gly Asp Arg Leu Leu Tyr Glu Tyr Glu Leu Glu Thr Gly Ala
    50                  55                  60

Val Ile Arg Ala Thr Pro Asp His Lys Phe Leu Thr Ala Thr Gly Glu
65                  70                  75                  80

Met Leu Pro Ile Asp Glu Ile Phe Val Arg Asn Leu Asp Leu Val Lys
                85                  90                  95

Ile Ile Arg Arg Asn Leu Ile Gly Glu Ala Ala Thr Tyr Asp Ile Gly
            100                 105                 110

Leu Gly Lys Asp His Asn Phe Leu Leu Gly Gln Gly Leu Ile Ala Ser
        115                 120                 125

Asn
```

<210> SEQ ID NO 481
<211> LENGTH: 130
<212> TYPE: PRT
<213> ORGANISM: Synechococcus sp.

<400> SEQUENCE: 481

```
Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Thr Gln Pro Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Lys Phe Leu Thr Thr Thr Gly Glu
65                  70                  75                  80

Leu Leu Pro Ile Asp Glu Ile Phe Thr Gln Asn Leu Asp Leu Val
                85                  90                  95

Lys Ile Ile Arg Arg Lys Phe Ile Gly His Ala Pro Thr Tyr Asp Ile
            100                 105                 110

Gly Leu Ser Gln Asp His Asn Phe Leu Leu Gly Gln Gly Leu Ile Ala
        115                 120                 125
```

Ala Asn
    130

<210> SEQ ID NO 482
<211> LENGTH: 130
<212> TYPE: PRT
<213> ORGANISM: Synechococcus sp.

<400> SEQUENCE: 482

Cys Leu Ala Gly Asp Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Thr Gln Pro Ile Glu Gln Trp His
        35                  40                  45

Lys Arg Gly Asp Arg Leu Leu Tyr Glu Tyr Glu Leu Glu Asn Gly Gln
    50                  55                  60

Ile Ile Arg Ala Thr Pro Asp His Lys Phe Leu Thr Thr Thr Gly Glu
65                  70                  75                  80

Met Arg Pro Ile Asp Glu Ile Phe Ala Lys Asn Leu Ser Leu Leu Val
                85                  90                  95

Lys Ile Ile Arg Arg Lys Phe Val Gly His Ala Pro Thr Tyr Asp Ile
            100                 105                 110

Gly Leu Ser Gln Asp His Asn Phe Leu Leu Gly Gln Gly Leu Ile Ala
        115                 120                 125

Ala Asn
    130

<210> SEQ ID NO 483
<211> LENGTH: 134
<212> TYPE: PRT
<213> ORGANISM: Cyanothece sp.

<400> SEQUENCE: 483

Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
            20                  25                  30

Val Asp Lys Asn Gly Phe Val Tyr Thr Gln Asn Ile Ala Gln Trp His
        35                  40                  45

Leu Arg Gly Gln Gln Glu Val Phe Glu Tyr Tyr Leu Asp Asp Gly Ser
    50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Arg Gly Leu Glu Leu Lys Lys
                85                  90                  95

Ile Lys Ile Val Lys Ile Val Ser Tyr Arg Ser Leu Gly Lys Gln Phe
            100                 105                 110

Val Tyr Asp Ile Gly Val Ala Gln Asp His Asn Phe Leu Leu Ala Asn
        115                 120                 125

Gly Ser Ile Ala Ser Asn
    130

<210> SEQ ID NO 484
<211> LENGTH: 137
<212> TYPE: PRT
<213> ORGANISM: Synechococcus elongatus

<400> SEQUENCE: 484

Cys Leu Ala Ala Asp Thr Glu Val Leu Thr Val Glu Tyr Gly Pro Ile
1               5                   10                  15

Ala Ile Gly Lys Leu Val Glu Glu Asn Ile Arg Cys Gln Val Tyr Cys
            20                  25                  30

Cys Asn Pro Asp Gly Tyr Ile Tyr Ser Gln Pro Ile Gly Gln Trp His
        35                  40                  45

Gln Arg Gly Glu Gln Glu Val Ile Glu Tyr Glu Leu Ser Asp Gly Arg
    50                  55                  60

Ile Ile Arg Ala Thr Ala Asp His Arg Phe Met Thr Glu Gly Glu
65                  70                  75                  80

Met Leu Ser Leu Asp Glu Ile Phe Glu Arg Ser Leu Glu Leu Lys Gln
                85                  90                  95

Ile Pro Thr Pro Leu Leu Val Lys Ile Val Arg Arg Ser Leu Gly
            100                 105                 110

Val Gln Pro Val Tyr Asp Leu Gly Val Ala Thr Val His Asn Phe Val
        115                 120                 125

Leu Ala Asn Gly Leu Val Ala Ser Asn
    130                 135

<210> SEQ ID NO 485
<211> LENGTH: 137
<212> TYPE: PRT
<213> ORGANISM: Chlorogloeposis fritschii

<400> SEQUENCE: 485

Cys Leu Ser Tyr Asp Thr Ala Ile Leu Thr Val Glu Tyr Gly Phe Leu
1               5                   10                  15

Pro Ile Gly Glu Ile Val Glu Lys Gly Ile Glu Cys Thr Val Tyr Thr
            20                  25                  30

Val Asp Ser Asn Gly Tyr Ile Tyr Thr Gln Pro Ile Ala Gln Trp His
        35                  40                  45

Asn Arg Gly Glu Gln Glu Leu Phe Glu Tyr Ser Leu Glu Asp Gly Ser
    50                  55                  60

Ile Ile Arg Ala Thr Lys Asp His Lys Phe Met Thr Ile Asp Gly Gln
65                  70                  75                  80

Met Leu Pro Ile Asp Glu Ile Phe Ala Arg Lys Leu Glu Leu Met Gln
                85                  90                  95

Val Lys Gly Leu Pro Glu Val Lys Ile Ala Lys Lys Ser Leu Gly
            100                 105                 110

Thr Gln Asn Val Tyr Asp Ile Gly Val Glu Arg Asp His Asn Phe Val
        115                 120                 125

Ile Lys Asn Gly Leu Val Ala Ser Asn
    130                 135

<210> SEQ ID NO 486
<211> LENGTH: 132
<212> TYPE: PRT
<213> ORGANISM: Cyanothece sp.

<400> SEQUENCE: 486

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Thr Val Tyr Thr
            20                  25                  30

Val Asp Pro Asn Gly Phe Val Tyr Thr Gln Ala Ile Ala Gln Trp His

```
                35                  40                  45
Tyr Arg Gly Glu Gln Glu Ile Phe Glu Tyr Tyr Leu Glu Asp Gly Ala
 50                  55                  60
Thr Ile Arg Ala Thr Lys Asp His Lys Phe Met Thr Met Glu Gly Lys
 65                  70                  75                  80
Met Leu Pro Ile Asp Glu Ile Phe Glu Asn Asn Leu Asp Leu Lys Gln
                 85                  90                  95
Leu Val Lys Ile Ile Gly Arg Gln Ser Leu Gly Val Gln Lys Val Tyr
                100                 105                 110
Asp Ile Gly Val Glu Lys Glu His Asn Phe Leu Leu His Asn Gly Leu
            115                 120                 125
Ile Ala Ser Asn
        130

<210> SEQ ID NO 487
<211> LENGTH: 132
<212> TYPE: PRT
<213> ORGANISM: Lyngbya majuscula

<400> SEQUENCE: 487

Cys Leu Ser Tyr Asp Thr Glu Ile Ile Thr Val Glu Tyr Gly Pro Ile
 1               5                  10                  15
Ala Ile Gly Glu Ile Val Glu Lys Gly Ile Pro Cys Thr Val Tyr Ser
                 20                  25                  30
Val Asp Ser Asn Gly Tyr Val Tyr Thr Gln Pro Ile Ala Gln Trp His
             35                  40                  45
Asn Arg Gly Glu Gln Glu Val Phe Glu Tyr Thr Leu Asp Asp Gly Ser
 50                  55                  60
Val Ile Arg Ala Thr Lys Asp His Lys Phe Met Thr Ile Asp Gly Gln
 65                  70                  75                  80
Met Leu Pro Ile Asp Glu Ile Phe Glu Gly Gly Leu Glu Leu Lys Gln
                 85                  90                  95
Leu Val Lys Ile Ile Ser Arg Lys Ser Leu Gly Thr Gln Pro Val Tyr
                100                 105                 110
Asp Ile Gly Val Lys Asp Asp His Asn Phe Ile Leu Ala Asn Gly Met
            115                 120                 125
Val Ala Ser Asn
        130

<210> SEQ ID NO 488
<211> LENGTH: 137
<212> TYPE: PRT
<213> ORGANISM: Unknown
<220> FEATURE:
<223> OTHER INFORMATION: Description of Unknown: filamentous
      cyanobacterium ESFC-1 sequence

<400> SEQUENCE: 488

Cys Leu Ser Tyr Asp Thr Glu Val Leu Thr Val Glu Tyr Gly Ala Val
 1               5                  10                  15
Pro Ile Gly Lys Leu Val Glu Lys Leu Asn Cys Ser Val Tyr Thr
                 20                  25                  30
Val Asp Pro Asn Gly Tyr Ile Tyr Thr Gln Ala Ile Ala Gln Trp His
             35                  40                  45
Asp Arg Gly Ile Gln Glu Val Phe Glu Tyr Gln Leu Glu Asp Asn Thr
 50                  55                  60
Ile Ile Arg Ala Thr Lys Asp His Lys Phe Met Thr Glu Asp His Gln
```

```
                65                  70                  75                  80
Met Leu Pro Ile Asp Glu Ile Phe Arg Gly Leu Glu Leu Lys Lys
                    85                  90                  95

Cys Pro Gln Pro Gln Val Lys Ile Ile Arg Arg Arg Ser Leu Gly
                100                 105                 110

Phe Gln Pro Val Tyr Asp Ile Gly Leu Glu Gln Asp His Asn Phe Leu
                115                 120                 125

Leu Asn Gln Gly Ala Ile Ala Ser Asn
            130                 135
```

<210> SEQ ID NO 489
<211> LENGTH: 129
<212> TYPE: PRT
<213> ORGANISM: Synechococcus sp.

<400> SEQUENCE: 489

```
Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
                20                  25                  30

Val Asp Ala Gln Gly Leu Ile Tyr Ala Gln Leu Ile Glu Gln Trp His
            35                  40                  45

Gln Arg Gly Asp Arg Leu Leu Tyr Glu Tyr Glu Leu Glu Asn Gly Gln
        50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Val Lys
                    85                  90                  95

Ile Ile Arg Arg Lys Phe Ile Gly His Ala Pro Thr Tyr Asp Ile Gly
                100                 105                 110

Leu Ser Gln Asp His Asn Phe Leu Leu Gly Gln Gly Leu Ile Ala Ala
            115                 120                 125

Asn
```

<210> SEQ ID NO 490
<211> LENGTH: 132
<212> TYPE: PRT
<213> ORGANISM: Acaryochloris marina

<400> SEQUENCE: 490

```
Cys Leu Ser Tyr Asp Thr Pro Val Leu Thr Leu Glu Tyr Gly Trp Leu
1               5                   10                  15

Pro Ile Gly Gln Val Val Gln Glu Gln Ile Glu Cys Gln Val Phe Ser
                20                  25                  30

Ile Asn Glu Arg Gly His Leu Tyr Thr Gln Pro Ile Ala Gln Trp His
            35                  40                  45

His Arg Gly Gln Gln Glu Val Phe Glu Tyr Thr Leu Ala Asp Gly Ser
        50                  55                  60

Thr Ile Gln Ala Thr Ala Glu His Gln Phe Met Thr Thr Asp Gly Gln
65                  70                  75                  80

Met Tyr Pro Val Gln Gln Ile Phe Glu Glu Gly Leu Ser Leu Lys Gln
                    85                  90                  95

Leu Val Lys Ile Ile Gln Arg Arg Ser Leu Gly Leu Gln Ser Val Tyr
                100                 105                 110

Asp Ile Gly Leu Ala Gln Asp His Asn Phe Val Met Ala Asn Gly Trp
            115                 120                 125
```

Val Ala Ala Asn
    130

<210> SEQ ID NO 491
<211> LENGTH: 129
<212> TYPE: PRT
<213> ORGANISM: Microcystis aeruginosa

<400> SEQUENCE: 491

Cys Leu Gly Gly Glu Thr Leu Ile Leu Thr Glu Glu Tyr Gly Leu Leu
1               5                   10                  15

Pro Ile Ala Lys Ile Val Ser Glu Glu Val Asn Cys Thr Val Tyr Ser
            20                  25                  30

Val Asp Lys Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Asn Asp Gly Glu
65                  70                  75                  80

Met Leu Ala Ile Asp Thr Ile Phe Glu Arg Gly Leu Asp Leu Val Lys
                85                  90                  95

Ile Ile Ser Arg Gln Ser Leu Gly Arg Lys Pro Val Tyr Asp Ile Gly
            100                 105                 110

Val Glu Lys Asp His Asn Phe Leu Leu Gly Asn Gly Leu Ile Ala Ser
        115                 120                 125

Asn

<210> SEQ ID NO 492
<211> LENGTH: 125
<212> TYPE: PRT
<213> ORGANISM: Anabaena circinalis

<400> SEQUENCE: 492

Cys Leu Ser Tyr Asp Thr Glu Ile Leu Thr Val Glu Tyr Gly Phe Leu
1               5                   10                  15

Glu Ile Gly Glu Ile Val Glu Lys Gln Ile Glu Cys Lys Val Tyr Thr
            20                  25                  30

Val Asp Ser Asn Gly Ile Leu Tyr Thr Gln Pro Ile Ala Gln Trp His
        35                  40                  45

His Arg Gly Gln Gln Glu Val Tyr Glu Tyr Leu Leu Glu Asn Gly Ala
    50                  55                  60

Ile Ile Arg Ala Thr Lys Asp His Lys Phe Met Thr Glu Ala Gly Glu
65                  70                  75                  80

Met Leu Pro Ile Asp Asp Ile Phe Thr Gln Val Lys Ile Ile Ser Arg
                85                  90                  95

Thr Tyr Val Gly Gln Ala Asn Val Tyr Asp Ile Gly Val Glu Asn Asp
            100                 105                 110

His Asn Phe Val Ile Lys Asn Gly Phe Val Ala Ala Asn
        115                 120                 125

<210> SEQ ID NO 493
<211> LENGTH: 125
<212> TYPE: PRT
<213> ORGANISM: Anabaena circinalis

<400> SEQUENCE: 493

Cys Leu Ser Tyr Asp Thr Glu Ile Leu Thr Val Glu Tyr Gly Phe Leu

```
           1               5                  10                 15
         Glu Ile Gly Glu Ile Val Glu Lys Gln Ile Glu Cys Arg Val Tyr Thr
                       20                 25                 30

Val Asp Ser Asn Gly Ile Leu Tyr Thr Gln Pro Ile Ala Gln Trp His
                       35                 40                 45

Tyr Arg Gly Gln Gln Glu Val Tyr Glu Tyr Leu Leu Glu Asn Gly Ala
                       50                 55                 60

Ile Ile Arg Ala Thr Lys Asp His Asn Phe Met Thr Glu Ala Gly Glu
         65                70                 75                 80

Met Leu Pro Ile Asp Asp Ile Phe Thr Gln Ile Lys Ile Ile Ser Arg
                            85                 90                 95

Lys Tyr Val Gly Gln Ala Asn Val Tyr Asp Ile Gly Val Glu Asn Asp
                           100                105                110

His Asn Phe Val Ile Lys Asn Gly Phe Val Ala Ala Asn
                           115                120                125
```

<210> SEQ ID NO 494
<211> LENGTH: 124
<212> TYPE: PRT
<213> ORGANISM: Cyanobacterium sp.

<400> SEQUENCE: 494

```
         Cys Leu Ser Tyr Asp Thr Lys Val Leu Thr Val Glu Tyr Gly Pro Leu
         1               5                  10                 15

Pro Ile Gly Lys Val Gln Glu Asn Ile Arg Cys Arg Val Tyr Thr
                       20                 25                 30

Thr Asn Asp Gln Gly Leu Ile Tyr Thr Gln Pro Ile Ala Gln Trp His
                       35                 40                 45

Asn Arg Gly Lys Gln Glu Ile Phe Glu Tyr His Leu Asp Asp Lys Thr
                       50                 55                 60

Ile Ile Arg Ala Thr Lys Glu His Gln Phe Met Thr Val Asp His Val
         65                70                 75                 80

Met Met Pro Ile Asp Glu Ile Phe Glu Gln Lys Ile Ile Arg Arg Lys
                            85                 90                 95

Ser Leu Gly Met His Glu Val Phe Asp Ile Gly Leu Glu Lys Asp His
                           100                105                110

Asn Phe Val Leu Ser Asn Gly Leu Ile Ala Ser Asn
                           115                120
```

<210> SEQ ID NO 495
<211> LENGTH: 129
<212> TYPE: PRT
<213> ORGANISM: Planktothrix sp.

<400> SEQUENCE: 495

```
         Cys Leu Ser Tyr Asp Thr Glu Val Leu Thr Val Glu Tyr Gly Leu Ile
         1               5                  10                 15

Pro Ile Ser Lys Ile Val Glu Glu Lys Ile Glu Cys Thr Val Tyr Thr
                       20                 25                 30

Val Asn Asn Gln Gly Tyr Val Tyr Thr Gln Pro Ile Ala Gln Trp His
                       35                 40                 45

Asn Arg Gly Glu Gln Glu Val Phe Glu Tyr Tyr Leu Glu Asp Gly Ser
                       50                 55                 60

Val Ile Arg Ala Thr Lys Asp His Lys Phe Met Thr Val Glu Gly Gln
         65                70                 75                 80

Met Leu Pro Ile Asp Glu Ile Phe Glu Lys Glu Leu Asp Leu Val Lys
```

```
                    85                  90                  95

Ile Ile Ser Arg Lys Ser Leu Gly Thr Gln Pro Val Tyr Asp Ile Gly
            100                 105                 110

Val Gln Glu Asp His Asn Phe Val Leu Asn Asn Gly Leu Val Ala Ser
        115                 120                 125

Asn

<210> SEQ ID NO 496
<211> LENGTH: 129
<212> TYPE: PRT
<213> ORGANISM: Planktothrix sp.

<400> SEQUENCE: 496

Cys Leu Ser Tyr Asp Thr Glu Ile Leu Thr Val Glu Tyr Gly Leu Met
1               5                   10                  15

Pro Ile Gly Lys Ile Val Lys Glu Lys Ile Glu Cys Thr Val Tyr Thr
            20                  25                  30

Val Asn Asn Gln Gly Tyr Val Tyr Thr Gln Pro Ile Ala Gln Trp His
        35                  40                  45

His Arg Gly Glu Gln Glu Val Phe Glu Tyr Cys Leu Glu Asp Gly Ser
    50                  55                  60

Val Ile Arg Ala Thr Lys Asp His Lys Phe Met Thr Val Gln Gly Gln
65                  70                  75                  80

Met Leu Pro Ile Asp Glu Ile Phe Glu Lys Leu Asp Leu Val Lys
                85                  90                  95

Ile Ile Ser Arg Lys Ser Leu Gly Thr Gln Pro Val Tyr Asp Ile Gly
            100                 105                 110

Val Gln Glu Asp His Asn Phe Leu Leu Asn Asn Gly Leu Val Ala Ser
        115                 120                 125

Asn

<210> SEQ ID NO 497
<211> LENGTH: 137
<212> TYPE: PRT
<213> ORGANISM: Fremyella diplosiphon

<400> SEQUENCE: 497

Cys Leu Ser Tyr Asp Thr Glu Val Leu Thr Val Glu Tyr Gly Leu Ile
1               5                   10                  15

Pro Ile Gly Glu Ile Val Glu Lys Arg Leu Glu Cys Ser Val Tyr Ser
            20                  25                  30

Val Asp Ile Asn Gly Asn Val Tyr Thr Gln Pro Ile Ala Gln Trp His
        35                  40                  45

His Arg Gly Gln Gln Glu Val Phe Glu Tyr Ala Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Leu Gln
                85                  90                  95

Val Pro His Leu Pro Glu Val Lys Ile Val Thr Arg Arg Ala Ile Gly
            100                 105                 110

Ala Ala Asn Val Tyr Asp Ile Gly Val Glu Gln Asp His Asn Phe Ala
        115                 120                 125

Ile Lys Asn Gly Leu Ile Ala Ala Asn
        130                 135
```

```
<210> SEQ ID NO 498
<211> LENGTH: 129
<212> TYPE: PRT
<213> ORGANISM: Planktothrix sp.

<400> SEQUENCE: 498

Cys Leu Ser Tyr Asp Thr Glu Ile Leu Thr Val Glu Tyr Gly Leu Ile
1               5                   10                  15

Pro Ile Ser Lys Ile Val Glu Glu Lys Ile Glu Cys Thr Val Tyr Thr
            20                  25                  30

Val Asn Asn Gln Gly Tyr Val Tyr Thr Gln Pro Ile Ala Gln Trp His
        35                  40                  45

Asn Arg Gly Glu Gln Glu Val Phe Glu Tyr Tyr Leu Glu Asp Gly Ser
    50                  55                  60

Val Ile Arg Ala Thr Lys Asp His Lys Phe Met Thr Val Asp Gly Gln
65                  70                  75                  80

Met Leu Pro Ile Asp Glu Ile Phe Glu Lys Glu Leu Asp Leu Val Lys
                85                  90                  95

Ile Ile Ser Arg Lys Ser Leu Gly Thr Gln Pro Val Tyr Asp Ile Gly
            100                 105                 110

Val Gln Glu Asp His Asn Phe Val Leu Asn Asn Gly Leu Val Ala Ser
            115                 120                 125

Asn

<210> SEQ ID NO 499
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 499

His His His His His His
1               5
```

SPLIT INTEINS WITH EXCEPTIONAL SPLICING ACTIVITY

CROSS-REFERENCE OF RELATED APPLICATION

This application is a continuation of U.S. patent application Ser. No. 16/073,602, filed Jul. 27, 2018, which claims priority to International Application No. PCT/US2017/015455 filed Jan. 27, 2017, which claims priority to U.S. Provisional Application No. 62/288,661 filed Jan. 29, 2016, which is hereby incorporated by reference in its entirety.

STATEMENT OF GOVERNMENT SUPPORT

This invention was made with government support under Grant No. GM086868 awarded by the National Institutes of Health. The government has certain rights in the invention.

INCORPORATION BY REFERENCE

The present application incorporates by reference a sequence listing, in electronic format, entitled SEQ_LISTING.txt, created Jul. 25, 2018, which is 425 kb in size. The information in the electronic format of the sequence listing is incorporated herein by reference in its entirety.

BACKGROUND

1. Technical Field

The field of the currently claimed embodiments of the present invention relate to inteins, split inteins, compositions comprising inteins and methods for use of the like for protein engineering.

2. Discussion of Related Art

Protein splicing is a posttranslational auto-processing event in which an intervening protein domain called an intein excises itself from a host protein in a traceless manner such that the flanking polypeptide sequences (exteins) are ligated together via a normal peptide bond.[1] While protein splicing typically occurs spontaneously following translation of a contiguous polypeptide, some inteins exist naturally in a split form.[1] The two pieces of the split intein are expressed separately and remain inactive until encountering their complementary partner, upon which they cooperatively fold and undergo splicing in trans. This activity has been harnessed in a host of protein engineering methods that provide control over the structure and activity of proteins both in vitro and in vivo.[1] The first two split inteins to be characterized, from the cyanobacteria Synechocystis Species PCC6803 (Ssp) and Nostoc puminciforme PCC73102 (Npu), are orthologs naturally found inserted in the alpha subunit of DNA Polymerase III (DnaE).[2-4] Npu is especially notable due its remarkably fast rate of protein trans-splicing (PTS) ($t_{1/2}$=50 s at 30° C.).[5] This half-life is significantly shorter than that of Ssp ($t_{1/2}$=80 min at 30° C.).[5] an attribute that has expanded the range of applications open to PTS.[1]

Despite the ongoing discovery of new fast inteins,[6,7] little is known about what separates them from their slower homologues. Such an understanding should help identify new inteins that are likely to splice rapidly and potentially allow for the engineering of split inteins with superior PTS properties.

SUMMARY

Embodiments of the invention include a split intein N-fragment including an amino acid sequence of at least 80%, 85%, 90%, 95%, 98%, 99%, or 100% sequence identity to (SEQ ID NO: 1)
CLSYDTEILTVEYGFLPIGKIVEERIECTVYTVDKNGFVYTQPIAQWHNR

GEQEVFEYCLEDGSIIRATKDHKFMTTDGQMLPIDEIFERGL.

Embodiments of the invention include a split intein N-fragment including an amino acid sequence, wherein said amino acid sequence comprises an amino acid sequence of at least 80%, 85%, 90%, 95%, 98%, 99%, or 100% sequence identity to (SEQ ID NO: 2)
CLSYDTEILTVEYGFLPIGKIVEERIECTVYTVDKNGPVYTQPIAQWHN

RGEQEVFEYCLEDGSIIRATKDHKFMTTDGQMLPIDEIFERGLDLKQVD

GLP.

Embodiments of the invention include a split intein C-fragment including an amino acid sequence of at least 80%, 85%, 90%, 95%, 98%, 99%, or 100% sequence identity to (SEQ ID NO: 3)
VKIISRKSLGTQNVYDIGVEKDHNFLLKNGLVASN.

Embodiments of the invention include a split intein C-fragment including an amino acid sequence, wherein said amino acid sequence of said C-fragment comprises an amino acid sequence of at least 80%, 85%, 90%, 95%, 98%, 99%, or 100% sequence identity to (SEQ ID NO: 4)
MVKIISRKSLGTQNVYDIGVEKDHNFLLKNGLVASN.

Embodiments of the invention include a split intein C-fragment including an amino acid sequence, wherein said amino acid sequence of said C-fragment comprises an amino acid sequence of at least 80%, 85%, 90%, 95%, 98%, 99%, or 100% sequence identity to (SEQ ID NO: 389)
VKIISRKSLGTQNVYDIGVGEPHNFLLKNGLVASN.

Embodiments of the invention include a composition including a split intein N-fragment comprising an amino acid sequence of at least 80%, 85%, 90%, 95%, 98%, 99%, or 100% sequence identity to (SEQ ID NO: 1)
CLSYDTEILTVEYGFLPIGKIVEERIECTVYTVDKNGFVYTQPIAQWHN RGEQEVFEYCLEDGSIIRATKDHKFMTTDGQMLPIDEIFERGL
or (SEQ ID NO: 2)
CLSYDTEILTVEYGFLPIGKIVEERIECTVYTVDKNGFVYTQPIAQWHN

RGEQEVFEYCLEDGSIIRATKDHKFMTTDGQMLPIDEIFERGLDLKQVD

GLP and a split intein C-fragment comprising an amino acid sequence of at least 80%, 85%, 90%, 95%, 98%, 99%, or 100% sequence identity to (SEQ ID NO: 3)
VKIISRKSLGTQNVYDIGVEKDHNFLLKNGLVASN, (SEQ ID NO: 4)
MVKIISRKSLGTQNVYDIGVEKDHNFLLKNGLVASN,
or (SEQ ID NO: 389)
VKIISRKSLGTQNVYDIGVGEPHNFLLKNGLVASN.

Embodiments of the invention include a nucleotide plasmid including a nucleotide sequence encoding for a split intein N-fragment comprising an amino acid sequence of at least 80%, 85%, 90%, 95%, 98%, 99%, or 100% sequence identity to (SEQ ID NO: 1)
CLSYDTEILTVEYGFLPIGKIVEERIECTVYTVDKNGFVYTQPIAQWHN RGEQEVFEYCLEDGSIIRATKDHKFMTTDGQMLPIDEIFERGL
or (SEQ ID NO: 2)
CLSYDTEILTVEYGFLPIGKIVEERIECTVYTVDKNGFVYTQPIAQWHN

RGEQEVFEYCLEDGSIIRATKDHKFMTTDGQMLPIDEIFERGLDLKQVD

GLP.

Embodiments of the invention include a nucleotide plasmid comprising a nucleotide sequence encoding for a split intein C-fragment including an amino acid sequence of at least 80%, 85%, 90%, 95%, 98%, 99%, or 100% sequence identity to (SEQ ID NO: 3)
VKIISRKSLGTQNVYDIGVEKDHNFLLKNGLVASN, (SEQ ID NO: 4)
MVKIISRKSLGTQNVYDIGVEKDHNFLLKNGLVASN,
or (SEQ ID NO: 389)
VKIISRKSLGTQNVYDIGVGEPHNFLLKNGLVASN.

Embodiments of the invention include a method for splicing two complexes including the following: contacting a first complex comprising a first compound and a split intein N-fragment with a second complex comprising a second compound and a split intein C-fragment, with contacting performed under conditions that permit binding of the split intein N-fragment to the split intein C-fragment to form an intein intermediate; and reacting the intein intermediate to form a conjugate of the first compound with the second compound. The split intein N-fragment includes an amino acid sequence of at least 80%, 85%, 90%, 95%, 98%, 99%, or 100% sequence identity to CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1) or CLSYDTEILTVEYGFLPIGKIVEE-RIECTVYTVDKNGFVYTQPI-AQWHNRGEQEVFEYCLED GSII-RATKDHKFMTTDGQMLPIDEIFERGLDLKQVDGLP (SEQ ID NO: 2), and the split intein C-fragment comprises an amino acid sequence of at least 80%, 85%, 90%, 95%, 98%, 99%, or 100% sequence identity to (SEQ ID NO: 3)
VKIISRKSLGTQNVYDIGVEKDHNFLLKNGLVASN, (SEQ ID NO: 4)
MVKIISRKSLGTQNVYDIGVEKDHNFLLKNGLVASN,
or (SEQ ID NO: 389)
VKIISRKSLGTQNVYDIGVGEPHNFLLKNGLVASN.

Embodiments of the invention include a method including the following: contacting a first complex comprising a first compound and a split intein N-fragment with a second complex comprising a second compound and a split intein C-fragment, with the contacting performed under conditions that permit binding of the split intein N-fragment to the split intein C-fragment to form an intein intermediate; and reacting the intein intermediate with a nucleophile to form a conjugate of the first compound with the nucleophile. The split intein N-fragment includes an amino acid sequence of at least 80%, 85%, 90%, 95%, 98%, 99%, or 100% sequence identity to CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1) or CLSYDTEILTVEYGFLPIGKIVEE-RIECTVYTVDKNGFVYTQPIAQWHNRGEQEVFEYCL EDGSIIRATKDHKFMTTDGQMLPIDEIFERGLD-LKQVDGLP (SEQ ID NO: 2), and the split intein C-fragment includes an amino acid sequence of at least 80%, 85%, 90%, 95%, 98%, 99%, or 100% sequence identity to (SEQ ID NO: 3)
VKIISRKSLGTQNVYDIGVEKDHNFLLKNGLVASN, (SEQ ID NO: 4)
MVKIISRKSLGTQNVYDIGVEKDHNFLLKNGLVASN,
or (SEQ ID NO: 389)
VKIISRKSLGTQNVYDIGVGEPHNFLLKNGLVASN.

In some embodiments, the compound, first compound, or second compound is or includes a peptide or a polypeptide. In some embodiments, the compound, first compound, or second compound is or includes an antibody, antibody chain, or antibody heavy chain. In some embodiments, the compound, first compound, or second compound is or includes a peptide, oligonucleotide, drug, or cytotoxic molecule.

Embodiments of the invention include an intein comprising an amino acid sequence of at least 80%, 85%, 90%, 95%, 98%, 99%, or 100% sequence identity to (SEQ ID NO: 390)
CLSYDTEILTVEYGFLPIGKIVEERIECTVY

TVDKNGFVYTQPIAQWHNRGEQEVFEYCLED

GSIIRATKDHKFMTTDGQMLPIDEIFERGLD

LRQVDGLPVKIISRKSLGTQNVYDIGVEKDH

NFLLKNGLVASN.

Embodiments of the invention include a kit for splicing two complexes together including the following: a split intein N-fragment including an amino acid sequence of at least 80%, 85%, 90%, 95%, 98%, 99%, or 100% sequence identity to

```
                                              (SEQ ID NO: 1)
CLSYDTEILTVEYGFLPIGKIVEERIECTVY

TVDKNGFVYTQPIAQWHNRGEQEVFEYCLED

GSIIRATKDHKFMTTDGQMLPIDEIFERGL
or (SEQ ID NO: 2)
CLSYDTEILTVEYGFLPIGKIVEERIECTVY

TVDKNGFVYTQPIAQWHNRGEQEVFEYCLED

GSIIRATKDHKFMTTDGQMLPIDEIFERGLD

LKQVDGLP;
``` a split intein C-fragment comprising an amino acid sequence of at least 80%, 85%, 90%, 95%, 98%, 99%, or 100% sequence identity to

```
                                              (SEQ ID NO: 3)
VKIISRKSLGTQNVYDIGVEKDHNFLLKNGLVASN, (SEQ ID NO: 4)
MVKIISRKSLGTQNVYDIGVEKDHNFLLKNGLVASN,
or (SEQ ID NO: 389)
VKIISRKSLGTQNVYDIGVGEPHNFLLKNGLVASN.
``` reagent(s) for permitting the binding of the split intein N-fragment to the split intein C-fragment to form an intein intermediate; and a nucleophilic agent.

Embodiments of the invention include a method for generating a synthetic consensus intein peptide sequence including the following: generating a population of a plurality of homologous intein peptide sequences; identifying amino acids associated with fast splicing within the population of a plurality of homologous intein peptide sequences; generating a subpopulation of a second plurality of homologous intein peptide sequences, with the second plurality of homologous intein peptide sequences including amino acids associated with fast splicing; creating an alignment of at least three peptide sequences of the subpopulation; determining a most frequently occurring amino acid residue at each position of the at least three peptide sequences; and generating a synthetic consensus intein peptide sequence based on the most frequently occurring amino acid residue at each position of the at least three peptide sequences.

Embodiments of the invention include a method including the following: fusing a first nucleotide sequence encoding an amino acid sequence of a first intein fragment (split intein N-fragment) including with a second nucleotide sequence encoding an amino acid sequence of a second intein fragment (split intein C-fragment), so that the fusion of the first nucleotide sequence and the second nucleotide sequence codes for a contiguous intein. The split intein N-fragment includes an amino acid sequence of at least 80%, 85%, 90%, 95%, 98%, 99%, or 100% sequence identity to CLSYDTEILTVEYGFLPIGKIVEERIECTVYTVDKNGFVYTQPI-AQWHNRGEQEVFEYCLED GSII-RATKDHKFMTTDGQMLPIDEIFERGL (SEQ ID NO: 1) or CLSYDTEILTVEYGFLPIGKIVEERIECTVYTVDKNGFVYTQPIAQWHNRGEQEVFEYCLEDGSIIRATKDHKFMTTDGQMLPIDEIFERGLD-LKQVDGLP (SEQ ID NO: 2), and the split intein C-fragment includes an amino acid sequence of at least 80%, 85%, 90%, 95%, 98%, 99%, or 100% sequence identity to

```
                                              (SEQ ID NO: 3)
VKIISRKSLGTQNVYDIGVEKDHNFLLKNGLVASN, (SEQ ID NO: 4)
MVKIISRKSLGTQNVYDIGVEKDHNFLLKNGLVASN,
or (SEQ ID NO: 389)
VKIISRKSLGTQNVYDIGVGEPHNFLLKNGLVASN.
```

Embodiments of the invention include a method including the following: fusing a first nucleotide sequence encoding an amino acid sequence of a first intein fragment (split intein N-fragment) including CLSYDTEILTVEYGFLPIG-KIVEERIECTVYTVDKNGFVYTQPI-AQWHNRGEQEVFEYCLED GSII-RATKDHKFMTTDGQMLPIDEIFERGL (SEQ ID NO: 1) with a second nucleotide sequence encoding an amino acid sequence of a second intein fragment (split intein C-fragment) including VKIISRKSLGTQNVYDIGVEKDHN-FLLKNGLVASN (SEQ ID NO: 3), so that the fusion of the first nucleotide sequence and the second nucleotide sequence codes for a contiguous intein.

Embodiments of the invention include a gene fusion including the following: a first nucleotide sequence encoding an amino acid sequence of a first intein fragment (split intein N-fragment) with a second nucleotide sequence encoding an amino acid sequence of a second intein fragment (split intein C-fragment). The split intein N-fragment includes an amino acid sequence of at least 80%, 85%, 90%, 95%, 98%, 99%, or 100% sequence identity to CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1) or CLSYDTEILTVEYGFLPIGKIVEE-RIECTVYTVDKNGFVYTQPIAQWHNRGEQEVFEYCLEDGSIIRATKDHKFMTTDGQMLPIDEIFERGLD-LKQVDGLP (SEQ ID NO: 2), and the split intein C-fragment includes an amino acid sequence of at least 80%, 85%, 90%, 95%, 98%, 99%, or 100% sequence identity to

```
                                              (SEQ ID NO: 3)
VKIISRKSLGTQNVYDIGVEKDHNFLLKNGLVASN, (SEQ ID NO: 4)
MVKIISRKSLGTQNVYDIGVEKDHNFLLKNGLVASN,
or (SEQ ID NO: 389)
VKIISRKSLGTQNVYDIGVGEPHNFLLKNGLVASN.
```

Embodiments of the invention include a gene fusion including the following: a first nucleotide sequence encoding an amino acid sequence of a first intein fragment (split intein N-fragment) including CLSYDTEILTVEYGFLPIG-KIVEERIECTVYTVDKNGFVYTQPI-AQWHNRGEQEVFEYCLED GSII-RATKDHKFMTTDGQMLPIDEIFERGL (SEQ ID NO: 1) fused with a second nucleotide sequence encoding an amino acid sequence of a second intein fragment (split intein C-fragment) including VKIISRKSLGTQNVY-DIGVEKDHNFLLKNGLVASN (SEQ ID NO: 3).

Embodiments of the invention include a complex (e.g., a fusion protein) comprising a split intein N-fragment and a compound. For example, the compound can be or include a peptide, a polypeptide or an antibody chain, such as an antibody heavy chain. For example, the compound can include a peptide, oligonucleotide, drug, or cytotoxic molecule. For example, the compound can be a 1,2-amino thiol or a 1,2-amino alcohol bonded to a peptide, oligonucleotide, drug, or cytotoxic molecule. The split intein N-fragment includes an amino acid sequence of at least 80%, 85%, 90%, 95%, 98%, 99%, or 100% sequence identity to CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1) or an amino acid sequence of at least 80%, 85%, 90%, 95%, 98%, 99%, or 100% sequence identity to

```
                                        (SEQ ID NO: 2)
CLSYDTEILTVEYGFLPIGKIVEERIECTVY

TVDKNGFVYTQPIAQWHNRGEQEVFEYCLED

GSIIRATKDHKFMTTDGQMLPIDEIFERGLD

LKQVDGLP;
```

Embodiments of the invention include a complex (e.g., a fusion protein) comprising a split intein C-fragment and a compound. For example, the compound can be or include a dendrimer, peptide or polypeptide. For example, the compound can include a peptide, an oligonucleotide, a drug, or a cytotoxic molecule. For example, the compound can be a 1,2-amino thiol or a 1,2-amino alcohol bonded to a peptide, oligonucleotide, drug, or cytotoxic molecule. The split intein C-fragment includes an amino acid sequence of at least 80%, 85%, 90%, 95%, 98%, 99%, or 100% sequence identity to VKIISRKSLGTQNVYDIGVEKDHNFLLKNGLVASN (SEQ ID NO: 3), an amino acid sequence of at least 80%, 85%, 90%, 95%, 98%, 99%, or 100% sequence identity to MVKIISRKSLGTQNVYDIGVEKDHNFLLKNGLVASN (SEQ ID NO: 4), or an amino acid sequence of at least 80%, 85%, 90%, 95%, 98%, 99%, or 100% sequence identity to VKIISRKSLGTQNVYDIGVGEPHNFLLKNGLVASN (SEQ ID NO: 389). The dendrimer can be a compound having the structure

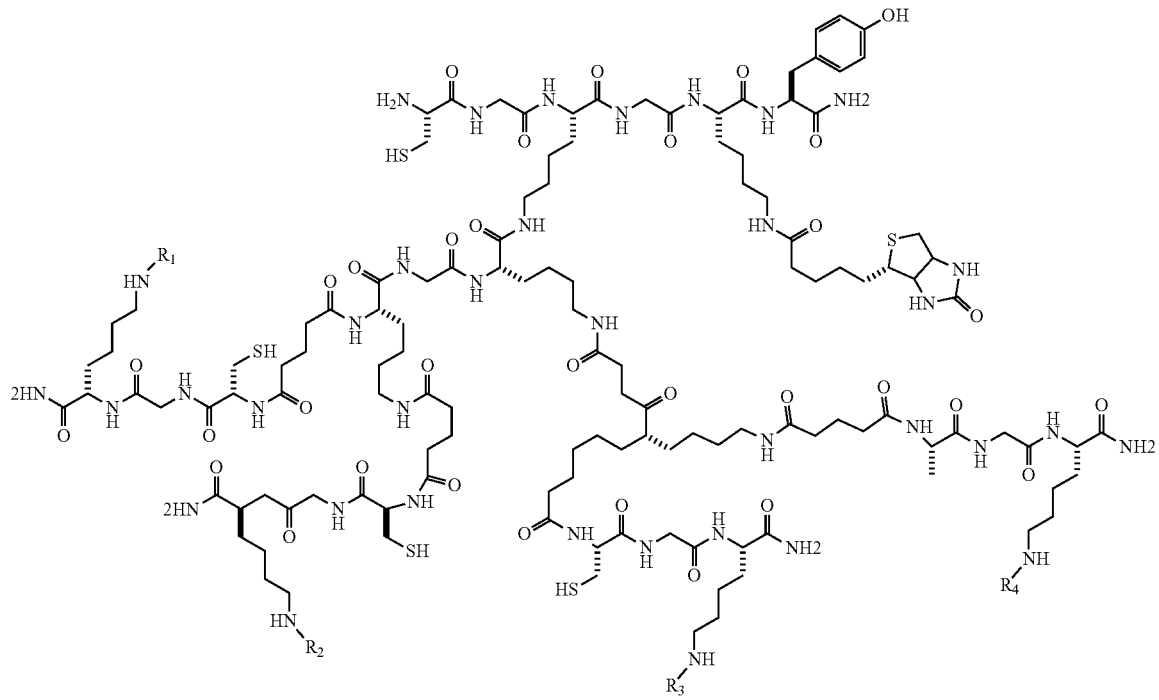

wherein R1, R2, R3, and R4 are each (independently) hydrogen (H) or a cargo molecule (the cargo molecules on R1, R2. R3, and R4 can be different from each other). R1, R2, R3, and R4 can each be a dye molecule. For example, R1, R2, R3, and R4 can each be a fluorescein derivative having the structure Embodiments of the invention include a complex of the structure

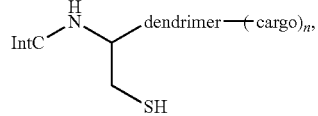

with IntC being a split intein C-fragment and n being from 0 to 8.

Embodiments of the invention include a complex of the structure

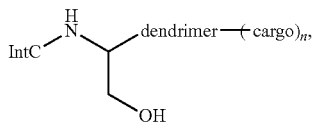

with IntC being a split intein C-fragment and n being from 0 to 8.

Embodiments of the invention include a complex of the structure

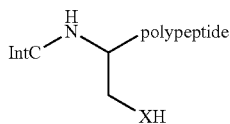

with IntC being a split intein C-fragment and X being sulfur (S) or oxygen (O). The split intein C-fragment comprises an amino acid sequence of at least 80%, 85%, 90%, 95%, 98%, 99%, or 100% sequence identity to VKIISRKSLGTQNVY-DIGVEKDHNFLLKNGLVASN (SEQ ID NO: 3), an amino acid sequence of at least 80%, 85%, 90%, 95%, 98%, 99%, or 100% sequence identity to MVKIISRKSLGTQNVY-DIGVEKDHNFLLKNGLVASN (SEQ ID NO: 4), or an amino acid sequence of at least 80%, 85%, 90%, 95%, 98%, 99%, or 100% sequence identity to VKIISRKSLGTQNVY-DIGVGEPHNFLLKNGLVASN (SEQ ID NO: 389).

Embodiments of the invention include a contiguous intein that can be used, for example, in traditional semi-synthesis applications such as Expressed Protein ligation.

BRIEF DESCRIPTION OF THE DRAWINGS

FIGS. 7A.1 to 7A.3, 7B.1 to 7B.3, 7C.1 to 7C.3, 7D.1 to 7D.3, 7E.1 to 7E.3, 7F.1 to 7F.3, 7G.1 to 7G.3, and 7H.1 to 7H.3 show an alignment and refinement of the DnaE intein family according to an embodiment of the invention, where:

FIGS. 7A.1, 7B.1, 7C.1, 7D.1, 7E.1, 7F.1, 7G.1, and 7H.1 correspond to amino acids 1-50 of the indicated sequences of split intein N-fragments, FIGS. 7A.2, 7B.2, 7C.2, 7D.2, 7E.2, 7F.2, 7G.2, and 7H.2 correspond to the amino acids 51-100 of the indicated sequences of split intein N-fragments, and FIGS. 7A.3, 7B.3, 7C.3, 7D.3, 7E.3, 7F.3, 7G.3, and 7H.3 correspond to the amino acids 101-102 of the indicated sequences of split intein N-fragments, followed by the sequences of the split intein C-fragments, FIGS. 7A.1 and 7A.2 correspond to the sequences of SEQ ID NO: 5, 7, 9, 11, 13, 15, 17, 19, 21, 23, 25, 27, 29, 31, 33, 35, 37, 39, 41, 43, 45 and 47;

FIG. 7A.3 corresponds to the last two amino acids of the sequences of FIGS. 7A.1 and 7A.2 followed by the sequences of SEQ ID NO: 6, 8, 10, 12, 14, 16, 18, 20, 22, 24, 26, 28, 30, 32, 34, 36, 38, 40, 42, 44, 46 and 48;

FIGS. 7B.1 and 7B.2 correspond to the sequences of SEQ ID NO: 49, 51, 53, 55, 57, 59, 61, 63, 65, 67, 69, 71, 73, 75, 77, 79, 81, 83, 85, 87, 89 and 91;

FIG. 7B.3 corresponds to the last two amino acids of the sequences of FIGS. 7B.1 and 7B.2 followed by the sequences of SEQ ID NO: 50, 52, 54, 56, 58, 60, 62, 64, 66, 68, 70, 72, 74, 76, 78, 80, 82, 84, 86, 88, 90 and 92;

FIGS. 7C.1 and 7C.2 correspond to the sequences of SEQ ID NO: 93, 95, 97, 99, 101, 103, 105, 107, 109, 111, 113, 115, 117, 119, 121, 123, 125, 127, 129, 131, 133 and 135;

FIG. 7C.3 corresponds to the last two amino acids of the sequences of FIGS. 7C.1 and 7C.2 followed by the sequences of SEQ ID NO: 94, 96, 98, 100, 102, 104, 106, 108, 110, 112, 114, 116, 118, 120, 122, 124, 126, 128, 130, 132, 134 and 136;

FIGS. 7D.1 and 7D.2 correspond to the sequences of SEQ ID NO: 137, 139, 141, 143, 145, 147, 149, 151, 153, 155, 157, 159, 161, 163, 165, 167, 169, 171, 173, 175, 177 and 179;

FIG. 7D.3 corresponds to the last two amino acids of the sequences of FIGS. 7D.1 and 7D.2 followed by the sequences of SEQ ID NO: 138, 140, 142, 144, 146, 148, 150, 152, 154, 156, 158, 160, 162, 164, 166, 168, 170, 172, 174, 176, 178 and 180;

FIGS. 7E.1 and 7E.2 correspond to the sequences of SEQ ID NO: 181, 183, 185, 187, 189, 191, 193, 195, 197, 199, 201, 203, 205, 207, 209, 211 and 213;

FIG. 7E.3 corresponds to the last two amino acids of the sequences of FIGS. 7E.1 and 7E.2 followed by the sequences of SEQ ID NO: 182, 184, 186, 188, 190, 192, 194, 196, 198, 200, 202, 204, 206, 208, 210, 212 and 214;

FIGS. 7F.1 and 7F.2 correspond to the sequences of SEQ ID NO: 215, 217, 219, 221, 223, 225, 227, 229, 231, 233, 235, 237, 239, 241, 243, 245, 247, 249, 251, 253, 255, 257, 259 and 261;

FIG. 7F.3 corresponds to the last two amino acids of the sequences of FIGS. 7F.1 and 7F.2 followed by the sequences of SEQ ID NO: 216, 218, 220, 222, 224, 226, 228, 230, 232, 234, 236, 238, 240, 242, 244, 246, 248, 250, 252, 254, 256, 258, 260 and 262;

FIGS. 7G.1 and 7G.2 correspond to the sequences of SEQ ID NO: 263, 265, 267, 269, 271, 273, 275, 277, 279, 281, 283, 285, 287, 289, 291, 293, 295, 297, 299, 301, 303, 305, 307, 309 and 311;

FIG. 7G.3 corresponds to the last two amino acids of the sequences of FIGS. 7G.1 and 7G.2 followed by the sequences of SEQ ID NO: 264, 266, 268, 270, 272, 274, 276, 278, 280, 282, 284, 286, 288, 290, 292, 294, 296, 298, 300, 302, 304, 306, 308, 310 and 312;

FIGS. 7H.1 and 7H.2 correspond to the sequences of SEQ ID NO: 313, 315, 317, 319, 321, 323, 325, 327, 329, 331, 333, 335, 337, 339, 341, 343, 345, 347, 349, 351, 353, 355, 357 and 359; and FIG. 7H.3 corresponds to the last two amino acids of the sequences of FIGS. 7H.1 and 7H.2 followed by the sequences of SEQ ID NO: 314, 316, 318, 320, 322, 324, 326, 328, 330, 332, 334, 336, 338, 340, 342, 344, 346, 348, 350, 352, 354, 356, 358 and 360;

DETAILED DESCRIPTION

Figure 1:
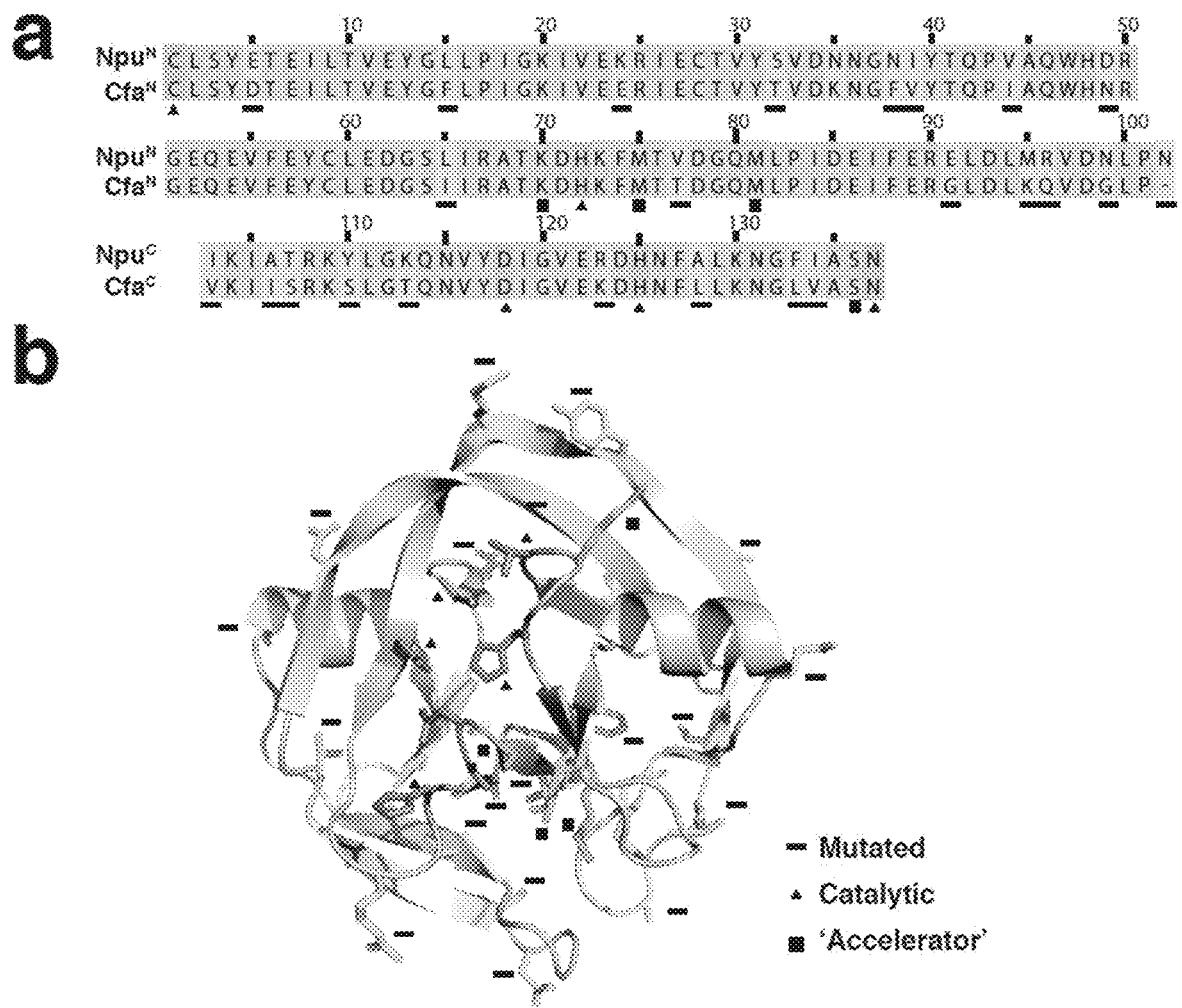
FIG. 1 shows an alignment and a computer-generated model of the design of the Cfa split intein according to an embodiment of the invention, where, in Panel a of FIG. 1, NpuN corresponds to SEQ ID NO: 5, NpuC corresponds to SEQ ID NO: 6, CfaN corresponds to SEQ ID NO: 2, and CfaC corresponds to SEQ ID NO: 3.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are hereby incorporated by reference in their entirety as if each had been individually incorporated.

Embodiments of the invention include a split intein N-fragment comprising an amino acid sequence of at least 80%, 85%, 90%, 95%, 98%, 99%, or 100% sequence identity to (SEQ ID NO: 1)
CLSYDTEILTVEYGFLPIGKIVEERIECTVY

TVDKNGFVYTQPIAQWHNRGEQEVFEYCLED

GSIIRATKDHKFMTTDGQMLPIDEIFERGL

Embodiments of the invention include a split intein N-fragment comprising an amino acid sequence, wherein said amino acid sequence comprises an amino acid sequence of at least 80%, 85%, 90%, 95%, 98%, 99%, or 100% sequence identity to (SEQ ID NO: 2)
CLSYDTEILTVEYGFLPIGKIVEERIECTVY

TVDKNGFVYTQPIAQWHNRGEQEVFEYCLED

GSIIRATKDHKFMTTDGQMLPIDEIFERGLD

LKQVDGLP;

Embodiments of the invention include a split intein C-fragment comprising an amino acid sequence of at least 80%, 85%, 90%, 95%, 98%, 99%, or 100% sequence identity to VKIISRKSLGTQNVYDIGVEKDHNFLLKNGLVASN (SEQ ID NO: 3).

Embodiments of the invention include a split intein C-fragment comprising an amino acid sequence, wherein said amino acid sequence of said C-fragment comprises an amino acid sequence of at least 80%, 85%, 90%, 95%, 98%, 99%, or 100% sequence identity to (SEQ ID NO: 4)
MVKIISRKSLGTQNVYDIGVEKDHNFLLKNGLVASN.

Embodiments of the invention include a composition comprising the following: a split intein N-fragment comprising an amino acid sequence of at least 80%, 85%, 90%, 95%, 98%, 99%, or 100% sequence identity to CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1); and a split intein C-fragment comprising an amino acid sequence of at least 80%, 85%, 90%, 95%, 98%, 99%, or 100% sequence identity to VKIISRKSLGTQNVY-DIGVEKDHNFLLKNGLVASN (SEQ ID NO: 3).

Embodiments of the invention include a nucleotide plasmid comprising a nucleotide sequence encoding for a split intein N-fragment comprising an amino acid sequence of at least 80%, 85%, 90%, 95%, 98%, 99%, or 100% sequence identity to (SEQ ID NO: 1)
CLSYDTEILTVEYGFLPIGKIVEERIECTVY

TVDKNGFVYTQPIAQWHNRGEQEVFEYCLED

GSIIRATKDHKFMTTDGQMLPIDEIFERGL

Embodiments of the invention include a nucleotide plasmid comprising a nucleotide sequence encoding for a split intein C-fragment comprising an amino acid sequence of at least 80%, 85%, 90%, 95%, 98%, 99%, or 100% sequence identity to (SEQ ID NO: 3)
VKIISRKSLGTQNVYDIGVEKDHNFLLKNGLVASN.

Embodiments of the invention include a method for splicing two complexes comprising: contacting a first complex comprising a first compound and a split intein N-fragment and a second complex comprising a second compound and a split intein C-fragment, wherein contacting is performed under conditions that permit binding of the split intein N-fragment to the split intein C-fragment to form an intein intermediate; and reacting the intein intermediate to form a conjugate of the first compound with the second compound, wherein said split intein N-fragment comprises an amino acid sequence of at least 80%, 85%, 90%, 95%, 98%, 99%, or 100% sequence identity to CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1), and wherein said split intein C-fragment comprises an amino acid sequence of at least 80%, 85%, 90%, 95%, 98%, 99%, or 100% sequence identity to VKIISRKSLGTQNVY-DIGVEKDHNFLLKNGLVASN (SEQ ID NO: 3). In some embodiments, reacting the intein intermediate comprises contacting the intein intermediate with a nucleophile. In some embodiments, said first compound is a polypeptide. In some embodiments, said first compound is an antibody.

Embodiments of the invention include an intein comprising an amino acid sequence of at least 80%, 85%, 90%, 95%, 98%, 99%, or 100% sequence identity to (SEQ ID NO: 390)
CLSYDTEILTVEYGFLPIGKIVEERIECTVY

TVDKNGFVYTQPIAQWHNRGEQEVFEYCLED

GSIIRATKDHKFMTTDGQMLPIDEIFERGLD

LRQVDGLPVKIISRKSLGTQNVYDIGVEKDH

NFLLKNGLVASN.

Embodiments of the invention include a kit for splicing two complexes together comprising the following: a split intein N-fragment comprising an amino acid sequence of at least 80%, 85%, 90%, 95%, 98%, 99%, or 100% sequence identity to CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1); a split intein C-fragment comprising an amino acid sequence of at least 80%, 85%, 90;%, 95%/6, 98%, 99%, or 100% sequence identity to VKIISRKSLGTQNVYDIGVEKDHN-FLLKNGLVASN (SEQ ID NO: 3); reagents for permitting the binding of the split intein N-fragment to the split intein C-fragment to form an intein intermediate; and a nucleophilic agent.

Embodiments of the invention include a method for generating a synthetic consensus intein peptide sequence comprising: generating a population of a plurality of homologous intein peptide sequences: identifying amino acids associated with fast splicing within said population of a plurality of homologous intein peptide sequences; generating a subpopulation of a second plurality of homologous intein peptide sequences, wherein said second plurality of homologous intein peptide sequences comprise amino acids associated with fast splicing; creating an alignment of at least three peptide sequences of said subpopulation: determining a most frequently occurring amino acid residue at each position of said at least three peptide sequences; and generating a synthetic consensus intein peptide sequence based on said most frequently occurring amino acid residue at each position of said at least three peptide sequences.

Embodiments of the invention include a method comprising: fusing a first nucleotide sequence encoding an amino acid sequence of a first intein fragment comprising CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1) with a second nucleotide sequence encoding an amino acid sequence of a second intein fragment comprising VKIIS-RKSLGTQNVYDIGVEKDHNFLLKNGLVASN (SEQ ID NO: 3), so that the fusion of the first nucleotide sequence and second nucleotide sequence codes for a contiguous intein.

Embodiments of the invention include a gene fusion comprising a first nucleotide sequence encoding an amino acid sequence of a first intein fragment comprising CLSYDTEILTVEYGFLPIGKIVEE-RIECTVYTVDKNGFVYTQPI-AQWHNRGEQEVFEYCLED GSII-RATKDHKFMTTDGQMLPIDEIFERGL (SEQ ID NO: 1) fused with a second nucleotide sequence encoding an amino acid sequence of a second intein fragment comprising (SEQ ID NO: 3)
VKIISRKSLGTQNVYDIGVEKDHNFLLKNGLVASN.

Embodiments of the invention include a contiguous intein that can be used, for example, in traditional semi-synthesis applications such as Expressed Protein ligation.

In some embodiments, the various intein fragments described are linked, fused, chemically bonded, complexed or coupled by conventional methods known in the art to polymers, peptides, polypeptides, oligopeptides, small molecules, nucleotides, polynucleotides, oligonucleotides, drugs, cytotoxic molecules or combinations thereof.

Example 1

In some embodiments, the basis of rapid protein splicing through a comparative study of the first two characterized split inteins, Npu and Ssp was investigated. The substantial difference in splicing rate between these two proteins is especially puzzling given their highly similar sequences (63% identity) and near superimposable active site structures. Previous mutagenesis studies on Npu and Ssp suggest that the difference in activity between the two is likely due to the combined effects of several residues, rather than a single site.[6,8] However, it remains unclear just how many residues are responsible for the fast versus slow reaction rates and by extension, whether these 'accelerator' residues contribute equally to the individual chemical steps in the overall protein splicing process. Consequently, we began our study by exploring these questions, in the hope that this would provide a starting point for developing an improved PTS system.

The high level of conservation within the active sites of Npu and Ssp suggests that more distal amino acid differences account for the disparity in splicing rate between the two. Thus, attention was focused on 'second shell' residues, those directly adjacent to the active site. To simplify this analysis, a batch mutagenesis strategy was employed in conjunction with a previously reported in vitro PTS assay.[5] This assay uses split intein constructs with short native extein sequences and allows the rates of branched intermediate formation ($k_1$, $k_2$) and its resolution to final splice products ($k_3$) to be determined using a three state kinetic model.

The known cross-reactivity of Npu and Ssp intein fragments served as a convenient platform on which to assess which half of the split intein contributes most significantly to the difference in activity.[3] Both the $Ssp^N$-$Npu^C$ (chimera 1) and $Npu^N$-$Ssp^C$ (chimera 2) chimeras show a decrease in the rates of branch formation and resolution compared to that of native Npu (FIG. 4C, 4D). This indicates that residues on both the N- and C-intein fragments of Npu and Ssp contribute to the difference in their splicing rate. Next, four groups of second shell positions on each of these chimeras were chosen based on their proximity to the active site, and the corresponding Ssp residues were mutated to those in Npu (FIGS. 4A and 4B). From the chimera 1 mutants. Batch 2 (L56F, S70K, A83P, E85D) completely restored branch formation activity to that of native Npu (FIG. 4C), while Batch 1 (R73K, L75M, Y79G, L81M) restored the majority of branch resolution activity (FIG. 4D). The effects of mutations on the chimera 2 background were more prosaic, with no single batch able to restore splicing activity to that of native Npu (FIGS. 4C and 4D). Lastly, the A136S mutation on Ssp$^C$ has previously been shown to accelerate protein splicing and was examined separately.[8] This A136S mutation increases the rate of branch resolution two fold, but has no impact on branch formation (FIGS. 4C and 4D).

Figure 4:
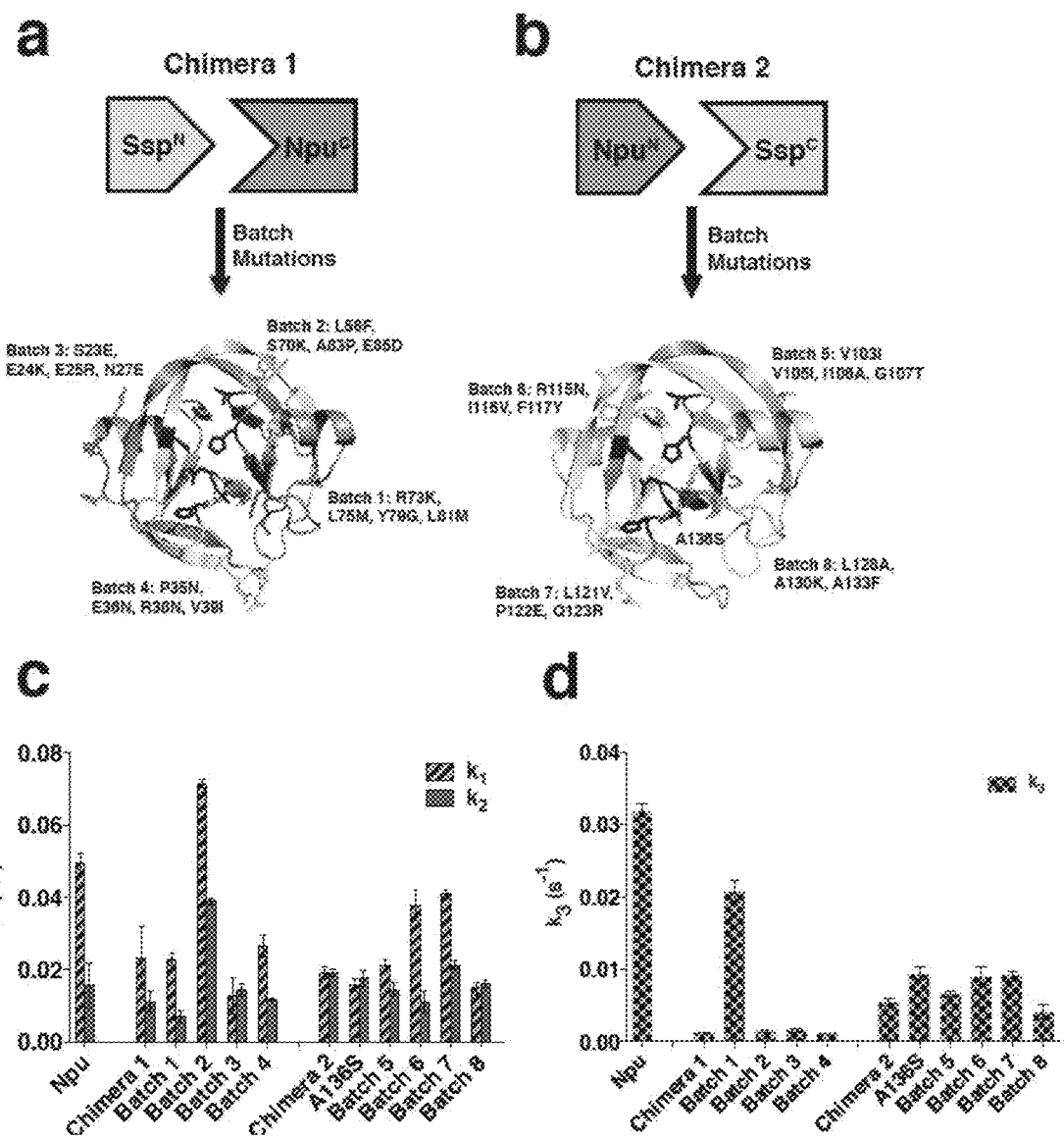
FIG. 4 shows the identification of second shell 'accelerator' residues important for rapid protein trans-splicing according to an embodiment of the invention.

FIG. 4 shows the identification of second shell 'accelerator' residues important for rapid protein trans-splicing according to an embodiment of the invention. In Panels A and B, design of second shell batch mutants on chimera 1 (SspN-NpuC) and chimera 2 (NpuN-SspC) is shown. In each case, the location of the mutants (rendered as sticks) is shown using the crystal structure of Npu (pdb=4kl15). Catalytic residues are shown in black (rendered as sticks). Panel C shows forward (k1) and reverse (k2) rates of branched intermediate formation from starting materials for the various constructs described in this study (error=SD (n=3)). Panel D shows the rate of branch resolution (k3) of the various constructs (error=SD (n=3)).

Next the individual contributions of residues within batch mutants 1 and 2 was investigated, since these had the most profound effect on splicing activity. For Batch 2, further mutagenesis shows that the interaction between F56, K70, and D85 is likely responsible for the increased rate of branch formation in Npu$^N$ (FIG. 5A). Structural evidence supports this data, as K70 is a part of the highly conserved TXXH block B loop in Npu$^N$ (residues 69-72) that catalyzes the initial N-to-S acyl shift in protein splicing.[9] Thus, the position and dynamics of K70 (packed against F56 and D85) should directly impact the catalytic residues T69 and H72 (FIG. 5B).[10-12] From Batch 1. K73, M75, and M81 are responsible for the faster rate of branch resolution in Npu$^N$ (FIG. 6A). These residues pack around the terminal asparagine of the C-intein, which must undergo succinimide formation in the final step of protein splicing (FIG. 6B). Taken together, the mutagenesis data points to the key role that second shell 'accelerator' residues play in tuning the activity of split inteins.

Figure 5:
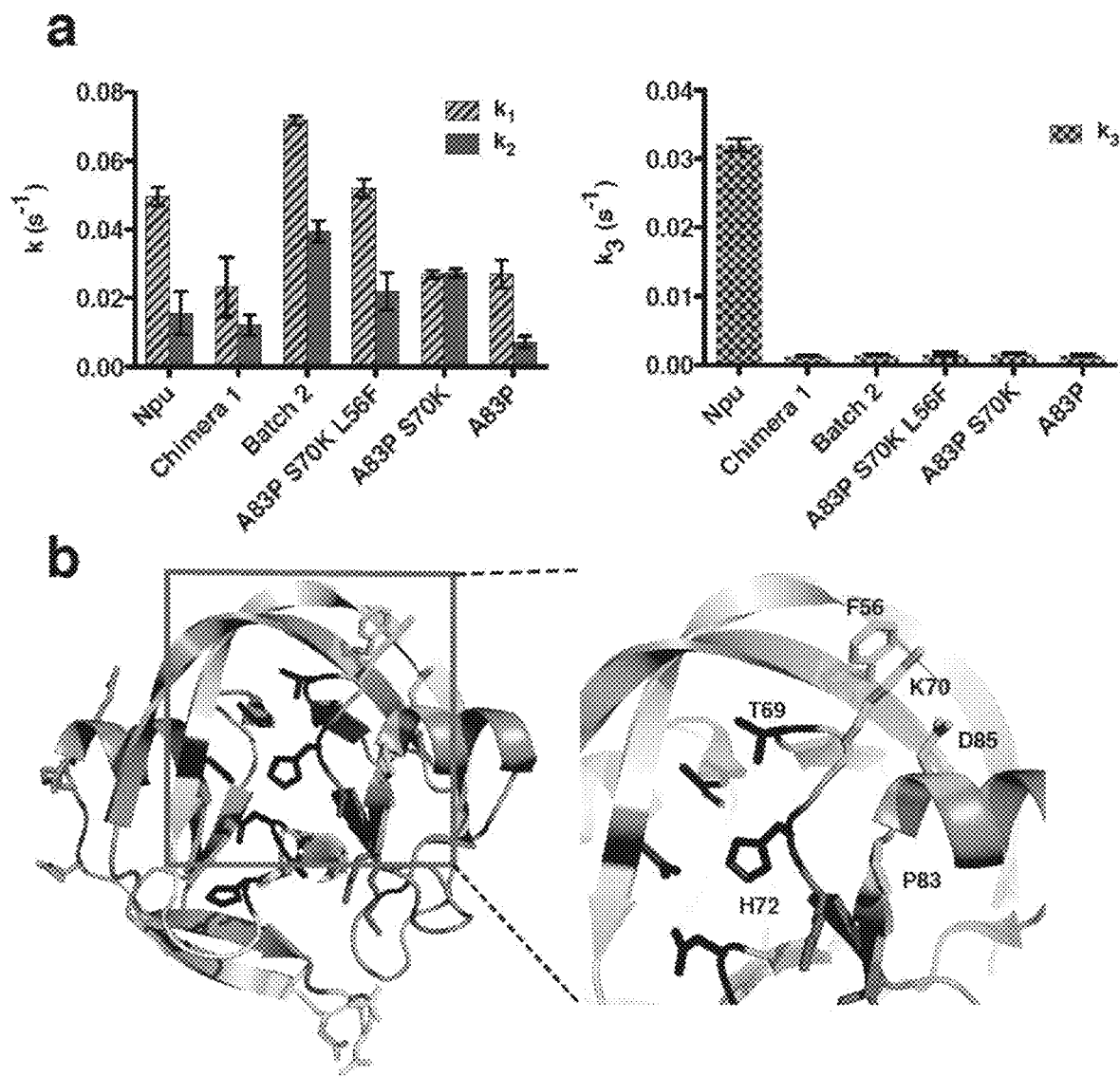
FIG. 5 shows kinetic analysis of Batch 2 mutations and computer generated models according to an embodiment of the invention.

FIG. 5 shows kinetic analysis of Batch 2 mutations and computer generated models according to an embodiment of the invention Panel A shows the equilibrium rates of branch formation (k1, k2) and rates of branch resolution (k3) for the single (A83P), double (A83P, S70K), and triple (L56F, S70K, A83P) point mutants of SspN that comprise Batch 2 (L56F, S70K, A83P, E85D) (error=SD (n=3)). Panel B shows a zoom view of Batch 2 (sticks next to labels F56, K70, P83, and D85) in the Npu active site (pdb=4kl5). Catalytic residues are rendered as black sticks.

Figure 6:
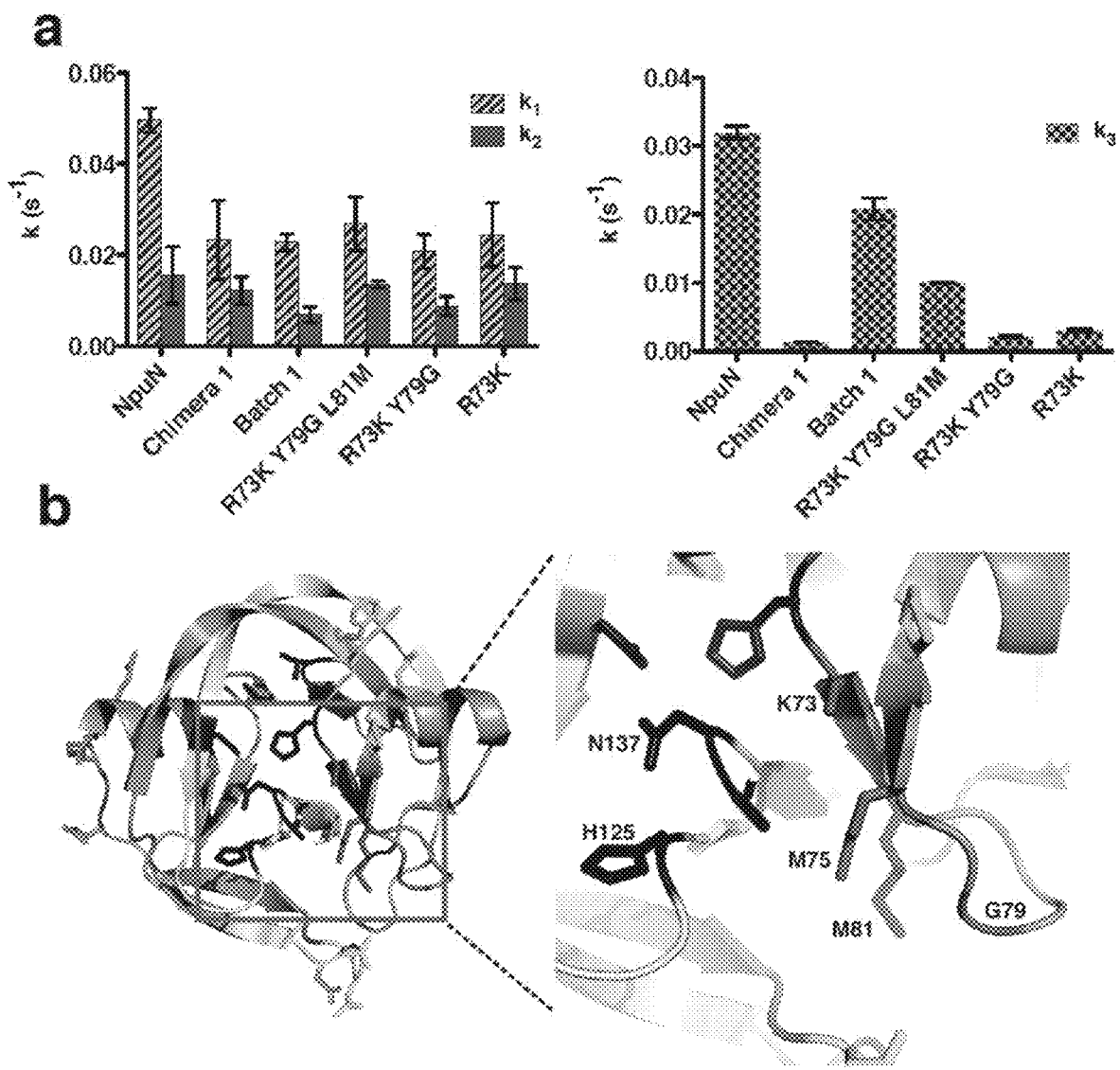
FIG. 6 shows an analysis of Batch 1 mutations and computer generated models according to an embodiment of the invention.

FIG. 6 shows an analysis of Batch 1 mutations and computer generated models according to an embodiment of the invention. Panel A shows the equilibrium rates of branch formation (k1, k2) and rates of branch resolution (k3) for the single (R73K), double (R73K, Y79G), and triple (R73K. Y79G. L81M) point mutants comprising Batch 1 (error=SD (n=3)). Panel B shows a zoom view of Batch 1 (sticks next to labels K73, M75, G79, and M81) in the Npu structure (pdb=4kl5). Catalytic residues are rendered as black sticks.

The 'accelerator' residues found to affect the splicing rate allow for an activity-guided approach to engineer a consensus DnaE intein. Consensus protein engineering is a tool applied to a homologous set of proteins in order to create a thermostable variant derived from the parent family.[13,14] A multiple sequence alignment (MSA) is first generated from homologues of a particular protein, from which the most statistically frequent residue at each position is chosen as the representative in the consensus sequence. For the DnaE inteins, 105 sequences were identified through a BLAST[15] search of the JGI[16] and NCBI[17] databases (FIGS. 7A.1 to 7A.3, 7B.1 to 7B.3, 7C.1 to 7C.3, 7D.1 to 7D.3, and 7E.1 to 7E.3). Next, the alignment was filtered to only contain sequences bearing the second shell indicators of fast splicing: K70, M75, M81, and S136. The 73 theoretically fast inteins left in the MSA (FIGS. 7F.1 to 7F.3, 7G.1 to 7G.3, and 7H.1 to 7H.3) were then used to generate a consensus fast DnaE intein sequence (Cfa) (FIG. 1). The various sequences disclosed in FIGS. 7A.1 to 7A.3, 7B.1 to 7B.3, 7C.1 to 7C.3, 7D.1 to 7D.3, 7E.1 to 7E.3, 7F.1 to 7F.3, 7G.1 to 7G.3, and 7H.1 to 7H.3 are presented below:

>NpuPCC73102/1-137
(SEQ ID NO: 5)
CLSYETEILTVEYGLLPIGKIVEKRIECTVYSVDNNGNIYTQP

VAQWHDRGEQEVFEYCLEDGSLIRATKDHKFMTVDGQMLPIDE

IFERELDLMRVDNLPN (SEQ ID NO: 6)
IKIATRKYLGKQNVYDIGVERDHNFALKNGFIASN

>CthPCC7203:/1-137 Chroococcidiopsis
thermalis PCC 7203
(SEQ ID NO: 7)
CLSYDTEILTVEYGAIPIGKIVEERIECTVYSVDNNGFIYTQP

IAQWHNRGQQEVFEYCLEDGSURATKDHKFMTFEGKMLPIDEI

FEQELDLKQVKSIQN (SEQ ID NO: 8)
VKIISRKSLGIQPVYDIGVERDHKFVLKNGLVASN

>NspCCY9414:/1-137 Nodularia spumigena
CCY9414 genome
(SEQ ID NO: 9)
CLSYDTEILTVEYGYIPIGEIVEKAIECSVYSVDNNGNVYTQP

IAQWIINRGEQEVFEYSLEDGSTIRATKDHKFMTTDGQMLPID

EIFAQELDLLQVHGLPK (SEQ ID NO: 10)
VKITARKFVGRENVYDIGVERYHNFAIKNGLIASN

>AcyPCC7122:/1-137 Anabaena cylindrica PCC
7122
(SEQ ID NO: 11)
CLSYDTEVLTVEYGFIPIGEIVEKRIECSIFSVDKNGNVYTQPI

AQWHNRGRQEIYEYCLDDGSKIRATKDHKFMTTAGEMLPIDEIF

ERDLDLLKVEGLPE (SEQ ID NO: 12)
VKIISRQYLGQADVYDIGVEEDHNFAIKNGFIASN

>CspPCC7507:/1-137 Calothrix sp. PCC 7507,
complete genome
(SEQ ID NO: 13)
CLSYDTEVLTVEYGLLPIGEIVEKGIECRVFSVDNHGNVYTQP

IAQWHNRGQQEVFEYGLDDGSVIRATKDHKFMTTDGKMLPIDE

IFERGLDLLQVQGLPE (SEQ ID NO: 14)
VKVITRKYIGKENVYDIGVELDHNFAIRNGLVASN

>NspPCC7524:/1-137 *Nostoc* sp. PCC 7524

(SEQ ID NO: 15)
CLSYDTEILTVEYGFLPIGEIVEKGIECTVFSVASNGIVYTQP

IAQWHNRGQQEIFEYCLEDGSIIRATKDHKFMTQDGQMLPIDE

IFACELDLLQVQGLPE (SEQ ID NO: 16)
VKVVTRRYIGKENVYDIGVERDHNFVIRNGLVASN

>Naz0708:/1-137 'Nostoc azollae' 0708

(SEQ ID NO: 17)
CLSYKTEVLIVEYGLIPIGEIVEKRIECSLFSVDENGNIYTQP

IAQWHHRGVQEVYEYCLDDGTIIRATKDHKFMTTIGEMLPIDE

IFERDLNLLQVNGLPT (SEQ ID NO: 18)
VKIISRQFLGPANVYDIGVAQDHNFAIKNGLIASN

>NspPCC7120:/1-137 *Nostoc* sp. PCC 7120 DNA (SEQ ID NO: 19)
CLSYDTEVLTVEYGFVPIGEIVEKGIECSVFSINNNGIVYTQP

IAQWHHRGKQEVFEYCLEDGSIIKATKDHKFMTQDGKMLPIDE

IFEQELDLLQVKGLPE (SEQ ID NO: 20)
IKIASRKFLGVENVYDIGVRRDHNFFIKNGLIASN

>AvaATCC29413/1-137 *Anabaena variabilis* ATCC 29413

(SEQ ID NO: 21)
CLSYDTEVLTVEYGFVPIGEIVDKGIECSVFSIDSNGIVYTQP

IAQWHHRGKQEVFEYCLEDGSIIKATKDHKFMTQDGKMLPIDE

IFEQELDLLQVKGLPE (SEQ ID NO: 22)
IKIASRKFLGVENVYDIGVGRDHNFFVKNGLIASN

>PspPCC7327:/1-135 *Pleurocapsa* sp. PCC 7327.

(SEQ ID NO: 23)
CLSYDTKILTVEYGAMPIGKIVEEQIDCTVYTVNQNGFVYTQP

IAQWHDRGKQEIFEYCLEDGSHRATKDHRFMTTDGQMLPIDKI

FEKGLDLKTINCD (SEQ ID NO: 24)
VKILSRKSLG1QSVYD1GVEKDHNFLLANGLVASN

>CspPCC7424:/1-135 *Cyanothece* sp. PCC 7424

(SEQ ID NO: 25)
CLSYETQIMTVEYGLMPIGKIVEEQIDCTVYTVNKNGFVYTQP

IAQWHYRGEQEVFEYCLEDGSTRATKDHKFMTTDGQMLPIDEI

FEQGLELKQIHLS (SEQ ID NO: 26)
VKIISRQSLGIQPVYDIGVEKDHNFLISDGLIASN

>CspPCC7822:/1-134 *Cyanothece* sp. PCC 7822

(SEQ ID NO: 27)
CLSYDTEILTVEYGPMPIGKIVEEQIECTVYTVDKNGLVYTQP

IAQWHHRGQQEVFEYCLEDGSIIRATKDIIKFMTDDGQIVILP

IEEIFEKGLELKQIIL (SEQ ID NO: 28)
VKIISRQLAGNQTVYDLGVEKDHNFLLANGLIASN

>NspPCC7107:/1-137 *Nostoc* sp. PCC 7107

(SEQ ID NO: 29)
CLSYDTQVLTVEYGLVPIGEIVEKQLECSVFTIDGHGYVYTQA

IAQWHNRGQQEVFEYGLEDGSVIRATKDIIKFMTTDGQMLPID

EIFERELDLLQVQGLRW (SEQ ID NO: 30)
VKIITRKYIGQANVYDIGVAQDHNFVIENRLIASN

>TboIicb1/1-136 *Tolypothrix bouteillei* Iicb1

(SEQ ID NO: 31)
CLSYDTEILTVEYGFLPIGKIVEKGIECNVYSVDKNGNIYTQP

IAQWHDRGEQEVFEYCLENGSVIRATKDHKFMTTSGEMLPIDE

IFERGLDLIRVEDLP (SEQ ID NO: 32)
VKILTRKSIGKQTVYDIGVERDHNFVIKNGSVASN

>Aov:/1-136 *Aphanizomenon ovalisporum* DnaE precursor (dnaE) gene (SEQ ID NO: 33)
CLSADTEILTVEYGFLPIGEIVGKAIECRVYSVDGNGNGYTQS

IAQWHNRGEQEVFEYTLEDGSIIRATKDHKFMTTDGEMLPIDE

XFARQLDLMQVQGLH (SEQ ID NO: 34)
VKITARKFVGRENVYDIGVEHHHNFAIKNGLIASN

>OnvPCC7112:/1-137 *Oscillatoria nigro-viridis* PCC 7112

(SEQ ID NO: 35)
CLSYDTKILTVEYGPMAIGKIVEEKIECTVYSVDSNGYIYTQS

IAQWHRRGQQEVFEYCLEDGSIIRATKDHKFMTVGGQMLPIDE

IFEQGLDLKQINSSSD (SEQ ID NO: 36)
VKHSRKSLGTQEVYDIGVEREHNFILENSLVASN

>RspPCC7116:/1-135 *Rivularia* sp. PCC 7116, complete genome (SEQ ID NO: 37)
CLSYDTEVLTEEFGLIPIGKIVEEKIDCTVYSVDVNGNVYSQP

IAQWHNRGMQEVFEYELEDGSTIRATKDHKFMTVDGEMLAIDE

IFEKGLELKRVGIY (SEQ ID NO: 38)
VKIISRKVLKTENVYDIGLEGDHNFHKDGLIASN

>TerIMS101:/1-137 *Trichodesmium erythraeum* IMS 101

(SEQ ID NO: 39)
CLTYETEIMTVEYGPLPIGKIVEYRIECTVYTVDKNGYIYTQP

IAQWHNRGMQEVYEYSLEDGTVIRATPEHKFMTEDGQMLPIDE

IFERNLDLKCLGTLEL (SEQ ID NO: 40)
VKIVSRKLAKTENVYDIIVTKDHNFVLANGLIASN

>MspPCC7113.71-137 *Microcoleus* sp. PCC 7113, (SEQ ID NO: 41)
CLSYDSEILTVEYGLMPIGKIVEEGIECTVYSVDSHGYLYTQP

IAQWHHRGQQEVFEYDLEDGSVIRATKDHKFMTSEGQMLAIDEI

FERGLELKQVKRSQP (SEQ ID NO: 42)
VKIVRRKSEGIQTVYDIGVERDHNFLLANGLVASN

>ScyPCC7437:/1-137 *Stanieria cyanosphaera* PCC 7437

(SEQ ID NO: 43)
CLSYDTEILTVEYGAMPIGKIVKEQIECNVYTVNQNGFIYP

QAIAQWHERGKQEIFEYTLDNGLVIRATKDHKFMTIDGQML

PIDEIFERGLELQRINDYSN (SEQ ID NO: 44)
VKIVSRKSLGKQPVYDIGVTKDHNFLLSNGVVASN

>CspPCC6303:/1-137 *Calothrix* sp. PCC 6303

(SEQ ID NO: 45)
CLSYDTEILTWEYGFLKIGEIVEKQILCSVFSVDEQGNVYT

QPIAQWHNRGLQELFAYQLEDGGVIRATKDHKFMTTDGQML

AIDEIFERQLDLFQVKGLPE (SEQ ID NO: 46)
VKIISRKVLKTENVYDIGLEGDHNFIIKDGLIASN

>Cst/1-134 PCC7202: *Cyanobacterium stameri* PCC 7202

(SEQ ID NO: 47)
CLSYDTEVLTVEYGVLPIGKIVEEQIQCTVYSVDQYGFVYT

QAIAQWHDRGEQEVFEYELENGATIKATKDHKMMTSDGQML

PIDQIFEQGLDLFMVSF (SEQ 3D NO: 48)
VKIVKRRSHGIQKVYDIGVAKDHNFLLHNGLVASN

>CspATCC51142:/1-134 *Cyanothece* sp. ATCC 51142

(SEQ ID NO: 49)
CLSYDTEILTVEYGPMPIGKIVEENINCTYTTVDPNGFVYT

QAIAQWHYRGEQEIFEYYLEDGATIRATKDHKFMTMEGKML

PIDEIFENNLDLKQLTL (SEQ ID NO: 50)
VKIIGRQSLGVQKVYDIGVEKEHNFLLHNGLIASN

>CspPCC8801:/1-134 *Cyanothece* sp. PCC 8801

(SEQ ID NO: 51)
CLSYDTEILTVEYGAIPIGKVVEENIDCTVYTVDKNGFVYT

QNIAQWHLRGQQEVFEYYLDDGSTLRATKDHQFMTLEGEML

PIHEIFERGLELKKIKI (SEQ ID NO: 52)
VKIVSYRSLGKQFVYDIGVAQDHNFLLANGSIASN

>Asp:/1-136 *Anabaena* sp. 90 chromosome (SEQ ID NO: 53)
CLSYDTEILTVEYGFLEIGEIVEKQIECKVYTIDSNGMLYT

QSIAQWHNRGQQEVYEYLLENGAIIRATKDHKFMTEAGQML

PIDEIFAQGLDLLQVGVAE (SEQ ID NO: 54)
VKIVSRTYVGQANVYDIGVESDHNFVIKNGFIASN

>Aha:/1-137 *Aphanothece halophytica*

(SEQ ID NO: 55)
CLSYDTEIWTVEYGAMPIGKIVEEKIECSVYTVDENGFVYT

QPIAQWHPRGQQEIIEYTLEDGRKIRATKDHKMMTESGEML

PIEEIFQRELDLKVETFHEM (SEQ ID NO: 56)
VKIIKRQSLGRQNVYDVCVHDIANFVLANGCVASN

>HspPCC7418:/1-137 *Halothece* sp. PCC 7418

(SEQ ID NO: 57)
CLSYDTEIWTVEYGAMPIGKIVEEKTECSVYTVDENGFVYTQP

IAQWHPRGQQEIIEYTLEDGRKIRATKDHKMMTESGEMLPIEE

IFQRELDLKVETFHEM (SEQ ID NO: 58)
VKHKRQSLGRQNVYDIGVETDIINFVLANGCVASN

>CapPCC 10605 71-137 *Cyanobacterium aponinum* PCC 10605

(SEQ ID NO: 59)
CLSYDTEILIYEYGAISIGKIVEEKINCQVYSVDKNGFIYTQN

IAQWHDRGSQELFEYELEDGRIIKATKDHKMMTKDGQMLAIND

IFEQELELYSVDDMGV (SEQ ID NO: 60)
VKIVKRRSLGVQPVYDIGVEKDHNFILANGLVASN

>Cat:/1-133 Candidate *Atelocyanobacterium thalassa* isolate (SEQ ID NO: 61)
CLSYDTKVLTVEYGPLPIGKVVQENIRCRVYTTNDQGLIYTQ

PIAQWHNRGKQEIFEYHLDDKTIIRATKEHQFMTVDHVMMPI

DEIFEQGEELKKIK (SEQ ID NO: 62)
LKIIRRKSLGMHEVFDIGLEKDHNFVLSNGLIASN

>Ol171-137 *Oscillaloria limnetica* 'Solar Lake' Dna Eprecursor (SEQ ID NO: 63)
CLSYNTEVLTVEYGPLPIGKIVDEQIHCRVYSVDENGFVYTQ

AIAQWHDRGYQEIFAYELADGSVIRATKDHQFMTEDGQMFPI

DEIWEKGLDLKKLPTVQD (SEQ ID NO: 64)
VKIVRRQSLGVQNVYDIGVEKDHNFLLASGEIASN

-continued

\>Cen:/1-137 *Cyanobacterium endosymbiont of Epithemia turgida*
(SEQ ID NO: 65)
CLSYDTEVLTVEYGAIPIGRMVEESLDCTVYTVDKNGFVYTQ

SIQQWHSRGQQEIFEYCFEDGSHRATKDHKFMTAEGKMSSIH

DIFEQGLELKKIIPWSG (SEQ ID NO: 66)
AKIISCKSLGKQSVYDIGVVQDHNFLLANGVVASN

\>SspPCC7502:/1-133 *Synechococcus sp. PCC 7502*
(SEQ ID NO: 67)
CLGYDTPVLTVEYGFMPIGKIVEEKIQCHVYSVDQNGLVFTQ

AIAQWHNRGQQEVWEYNLDNGDIVRATKDHKFMTIDGQMLPI

NQIFEQGLELKVIA (SEQ ID NO: 68)
VKIVSCKPLRVQTVYDIGVEKDHNFILDNGLVASN

\>DsaPCC8305:/1-134 *Dactylococcopsis salina PCC 8305*
(SEQ ID NO: 69)
CLSYDTEVLTEEYGAIPIGKIVEERMNCHVYSVDENGFIYSQP

IAQWHPRGEQEWEYTLEDGKIIRATADHKMMTETGEMLPTEQI

FQQQLDLKISNQ (SEQ ID NO: 70)
VKIINRQSLGKQTVYDIGVEKDHNFILGNGLVASN

\>CstPCC7417:/1-337 *Cylindrospermum stagnale PCC 7417*
(SEQ ID NO: 71)
CLSYDTEILTVEYGFIPIGEIVEKRIECSVYSVDNHGNVYTQP

IAQWHNRGLQEVFEYCLEDGSTIRATKDHKFMTTDKEMLPIDE

IFERGLDLLRVEGLPI (SEQ ID NO: 72)
VKHMRSYVGRENYYDIGVERDHNFVAKNGLIAAN

\>SspPCC6803:/1-137 *Synechocystis sp. PCC 6803*
(SEQ ID NO: 73)
CLSFGTEILTVEYGPLPIGKIVSEEINCSVYSVDPEGRVYTQ

AIAQWHDRCEQEVLEYELEDGSVIRATSDHRFLTTDYQLLAI

EEIFARQLDLLTLENIKQ (SEQ ID NO: 74)
VKYTGRRSLGVQRIFDIGLPQDHNFLLANGAIAAN

\>GspPCC7401:/1-137 *Geitlerinema sp. PCC 7407*
(SEQ ID NO: 75)
CLSYETPVMTVEYGPLPIGRIVEEQLDCTVYSVDEQGHVYTQ

PVAQWHRGLQEWEYELEDGRRLRATADHRFMTETGEMLPLA

EIFERGLELRQVALRVP (SEQ ID NO: 76)
VKIVSRRSLGMQLVYDIGVAADHNFVLADGLIAAN

\>SspPCC6714:/1-137 *Synechocystis sp. PCC 6714*
(SEQ ID NO: 77)
CLSFDAEILTVEYGPLSIGKIVGEEINCSVYSVDPQGRIYTQ

AIAQWHDRGVQEVFEYELEDGSVIRATPDHRFLTTDYELLAI

EEIFARQMDLLTLTNLKL (SEQ ID NO: 78)
VKVVRRRSLGMHRVFDIGLAQDHNFLLANGAIAAN

\>MaePCC7806:/1-135 *Microcystis aeruginosa PCC 7806*
(SEQ ID NO: 79)
CLGGETLILTEEYGLLPIAKIVSEEVNCTVYSVDKNGFVYSQ

PISQWHERGLQEVFEYTLENGQTIQATKDHKFMTNDGEMLAI

DTIFERGLDLKSSDFS (SEQ ID NO: 80)
VKIISRQSLGRKPVYDIGVEKDIINFLLGNGLIASN

\>MaeNIES843:/1-135 *Microcystis aemginosa NIES-843 DNA*
(SEQ ID NO: 81)
CLGGETLILTEEYGLLPIAKIVSEEINCTVYTVDQNGFVYSQI

MSQWHERGLQHVFEYTLENGQTIQATKDHKFMTSDGEMLAIDT

IFERGLDLKSSDFS (SEQ ID NO: 82)
VKTTGRQSLGRKPVYDIGVEKDHNFLLGNGLIASN

\>AmaMBIC11017:/1-137 *Acaryochloris marina MBIC11017.*
(SEQ ID NO: 83)
CLSYDIPVLTLEYGWLPIGQVVQEQIECQVFSINERGHLYTQP

IAQWHHRGQQEVFEYTLADGSTIQATAEHQFMTTDGQMYPVQQ

IFEEGLSLKQLPLPWQ (SEQ ID NO: 84)
VKIIQRRSLGLQSVYDIGLAQDHNFVMANGWVAAN

\>LspPCC7376:/1-137 *Leptolyngbya sp. PCC 7376*
(SEQ ID NO: 85)
CLDGETPIVTVEYGVLPIREIVEKELLCSVYSIDENGFVYTQP

VEQWHQRGDRQMFEYQLDNGGVIRATPDHKFLTTEGEMVAIDE

IFEKGLNLAEFAPADL (SEQ ID NO: 86)
VKILRRHSIGKAKTYDIGVSKNHNFLLANGLFASN

\>SelPCC6301:/1-137 *Synechococcus elongatus PCC 6303*
(SEQ ID NO: 87)
CLAADTEVLTVEYGPIAIGKLVEENIRCQVYCCNPDGYIYSQ

PICQWHQRGEQEVIEYELSDGRHRATADHRFMTEEGEMLSLD

EIFERSLELKQIPTPLL (SEQ ID NO: 88)
VKFVRRRSLGVQPVYDLGVATVHNFVLANGLVASN

\>SspPCC6312:/1-137 *Synechococcus sp. PCC 6312*
(SEQ ID NO: 89)
CLSADTELYTVEYGWLPICRLVEEQIECQVLSVNAHGHVYSQ

PIAQWHRRAWQEVFEYQLETGGTIKATTDHQFLTTDGQMYRI

EDIFQRGLDLWQLPPDRF (SEQ ID NO: 90)
VKIISRCSLGIQPVYDIGVAQDHNFVIRGGLVASN

\>Tel:/1-137 *Thermosynechococcus elongatus* BP-1 DNA
(SEQ ID NO: 91)
CLSGETAVMTVEYGAVPIRRLVQERLSCHVYSLDGQGHLYTQ

PIAQWHFQGFRPVYEYQLEDGSTICATPDHRFMTTRGQMLPI

EQIFQEGLELWQVAIAPR (SEQ ID NO:92)
GKIVGRRLMGWQAVYDIGLAADHNFVLANGAIAAN

\>Tsp:/1-137 *Thermosynechococcus sp.* NK55 genome
(SEQ ID NO: 93)
CLSGETAVMTVEYGAVPIRRLVQERLTCHVYSLDAQGHLYT

QPIAQWHFQGFRPVYEYQLEDGSTIWATPDHRFMTTRGQML

PIEQIFQEGLELWQGPIAPS (SEQ ID NO: 94)
CKIVGRQLVGWQAVYDIGVARDHNFLLANGAIAAN

\>Tvu:/1-137 *Thermosynechococcus vulcanus* DnaE precursor
(SEQ ID NO: 95)
CLSGETAVMTVEYGAIPIRRLVQERLICQYYSLDPQ

GHLYTQPIAQWHFQGFRPVYAYQLEDGSTICATPDH

RFMTTSGQMLPIEQIFREGLELWQVAIAPP (SEQ ID NO: 96)
CKIVGRRLVGWQAVYDIGLAGDHNFLLANGAIAAN

\>SspPCC7002:/1-137 *Synechococcus* sp. PCC 7002
(SEQ ID NO: 97)
CLAGGTPVVTVEYGVLPIQITVEQELLCHVYSVDA

QGLIYAQLIEQWHQRGDRLLYEYELENGQMIRATP

DIIRFLTTFGELLPIDEIFTQNLDLAAWAVPDS (SEQ ID NO: 98)
VKIIRRKFIGHAPTYDIGLSQDHNFLLGQGLIAAN

\>ShoPCC7110:/1-136 *Scytonema hofmanni* PCC 7110 contig00136
(SEQ ID NO: 99)
CLSYDTEVLTAEYGFLPIGKIVEKAIECTVYSVDN

DGNIYTQPIAQWHDRGQQEVFEYSLDDGSVIRATK

DHKFMTTGGQMLPIDEIFERGLDLMRIDSLP (SEQ ID NO: 100)
VKILTRKSIGKQTVYDIGVERDHNFVIKNGLVASN

\>WinUHHT291/1-136 *Westiella intricata* UHHT-29-1
(SEQ ID NO: 101)
CLSYDTEILTVEYGFLPIGEIVEKRIECTVYTVDT

NGYVYTQAIAQWHNRGEQEVFEYALEDGSURATKD

HKFMTSEGQMLPIDEIFVKGLDLLQVQGLP (SEQ ID NO: 102)
VKIITRKFLGIQNVYDIGVEQNHNFVIKNGLVASN

\>FspPCC9605:/1-136 *Fischerella* sp. PCC 9605 FIS9605DRAFT
(SEQ ID NO: 103)
CLSYDTEILTVEYGFLPIGEIVEKGIECTVYTVDN

NGNVYTQTIAQWHNRGQQEVFEYCLEDGSVIRATK

DHKFMTTDGQMLPIDEIFARGLDLLQVKNLP (SEQ ID NO: 104)
VKIVTRRPLGTQNVYDIGVESDHNFVIKNGLVASN

\>MrePCC10914:/1-137 *Mastigocladopsis repens* PCC 10914
(SEQ ID NO: 105)
CLSYDTEVLTVEYGFLPIGEIVEKSIECSVYTVDS

NGNVYTQPIAQWHNRGQQEVFEYCLEDGSIIRATK

DHKFMTIHGQMLPIDEIFERGLELMKIQGLPE (SEQ ID NO:106)
AKIITRKSLGTQNVYDlGVERDHNFVTRDGFIASN

\>ShoUTEX2349:/1-137 [*Scytonema hofmanni*] UTEX 2349
(SEQ ID NO: 107)
CLSYNSEVETVEYGFLPIGKIVEKGIECSVYSVDS

YGKIYTQVIAQWHNRGQQEVFEYCLEDGTHQATKD

HKFMTVDGQMLPIDEIFERGLDLMQVQGLPD (SEQ ID NO: 108)
VKNTRKSLGTQNVYDIGVSSDIINFVMKNGLIASN

\>AspPCC7108:/1-137 *Anabaena* sp. PCC 7108 Ana7108scaffold_2_Cont3
(SEQ ID NO: 109)
CLSSDTEVLTVEYGLIPIGEIIEKRIDCSVFSVDK

NGNIYTQPIAQWHDRGIQELYEYCLDDGSTIRATK

DHKFMTTAGEMLPIDEIFERGLDLLKVHNLPQ (SEQ ID NO: 110)
VKHTRNYVGKENVYDIGVERDHNFAIKNGLIASN

\>FspPCC9339:/1-137 *Fischerella* sp. PCC 9339 PCC9339DRAFT
(SEQ ID NO: 111)
CLSYDTEVLTVEYGFLPIGEIVEKRIECTVYTVDH

NGYVYTQPIAQWHNRGYQEVFEYGLEDGSVIRATK

DHKFMTSEGQMLPIDEIFARELDLLQVTGLVN (SEQ ID NO: 112)
VKIVTRRLLGIQNVYDIGVEQNHNFVIKNGLVASN

\>Csp336:/1-137 *Calothrix* sp. 336/3
(SEQ ID NO: 113)
CLSYDTEIFTVEYGFLPIGEIVEKRLECTVLTVDN

HGNTYSQPIAQWHHRGQQQIYEYGLEDCSVIRATK

DHKFMTTDGQMEPIDEIFERGLDLLQVTNLDN (SEQ ID NO: 114)
VKVITRKLADTENVYDIGVENHHNFLIKNGLVASN

\>FthPCC7521:/1-136 *Fischerella thennalis* PCC 7521
(SEQ ID NO: 115)
CLSYETEILTVEYGFLPIGEIVEKRIECSVYTVDN

NGYVCTQPIAQWHNRGYQEVFEYGLEDGSVIRATK

DHKFMTIDRQMLPIDEIFARGLDLLQVTGLP (SEQ ID NO: 116)
VKIITRKSLGTQNVYDIGVEQNHNFVIKNGLVASN

>CyaPCC7702/1-137 cyanobacterium PCC 7702 Chl7702

(SEQ ID NO: 117)
CLSYDTEILTVEYGFLSIGEIVEKEIECTVYTVDS

NGYIYTQPIAQWHEQGEQEIFEYSLEDGSTIRATK

DHKFMTIEGEMLPIDQIFARQLDLMQITGLPQ (SEQ ID NO: 118)
VKISTKKSLGKQKVYDIGVVRDHNFIIKNGFVASN

>FspPCC9431:/1-136 Fischerella sp. PCC 9431

(SEQ ID NO: 119)
CLSYDTEVLTVEYGFLPIGEIVEKRIECTVYTVDT

NGYVYTQAIAQWHNRDEQEVFEYALEDGSIIRATK

DHKFMTSEGQMLPIDEIFAKGLDLLQVQGLP (SEQ ID NO: 120)
VKIVTRKFLGIQNYYDIGVEQNHNFVIKNGLVASN

>FmuPCC7414:/1-37 Fischerella muscicola PCC 7414

(SEQ ID NO: 121)
CLSYETEILTVEYGFLPIGEIVEKRIECSVYTVDN

NGYVCTQTIAQWHNRGYQEVFEYGLEDGSVIRATK

DHKFMTIDRQMLPIDEIFARGLDLLQVKGLPE (SEQ ID NO: 122)
VKIITRQSLGTQNVYDIGVEQNHNFVIKNGLVASN

>FmuPCC73103:/1-137 Fischerella muscicola SAG 1427-1 = PCC 73103

(SEQ ID NO: 123)
CLSYDTEVLTVEYGFLPIGEIVEKTIECNVFTVDS

NGYVYTQPIAQWHNRGYQEVFEYGLEDGSVIRATK

DHKFMTSEGKMIPIDETFARELDLLQVTGLIN (SEQ ID NO: 124)
VKIVFRKFLGIQNVYDIGVEQNHNFVIKNGLVASN

>Lae:/1-137 Lyngbya aestuarii BL J laest3 contig.3

(SEQ ID NO: 125)
CLSYDTEILTVEYGAIPIGKVVDEKIECTVYSVDK

NGLIYTQPIAQVVHNRGKQEVFEYSLEDGSTIRAT

KDHKFMTMDNQMLPIDEILEKGLELKQVNADSV (SEQ ID NO: 126)
VKIVSRKSLDSQTVYDIGVETDFINFLLANGSVASN

>MspPCC7126:/1-135 Microchaete sp. PCC 7126

(SEQ ID NO: 127)
CLSYKTQVLTVEYGLLAIGEIVEKNIECSVFSVDI

HGNVYTQPIAQWHHRGQQEVFEYGLEDGSIIRATK

DHKFMTTQGEMLPIDEIFARGLDLLQVKGV (SEQ ID NO: 128)
VKIITRKYIGKENVYDIGVEQDHNFAIKNGLIAAN

>Lsp:/1-137 Leptolyngbya sp. JSC-1

(SEQ ID NO: 129)
CLSYDTEILTVEYGALPIGKIVENQMICSVYSIDN

NGYIYIQPIAQWHNRGQQEVFEYILEDGSIIRSTK

DHKFMTKGGEMEPIDEIFERGLELAQVTRLEQ (SEQ ID NO: 130)
VKIISRRSVGVQSVYDIGVKQDHNFFLRNGLIASN

>CwaWH8501:/1-137 Crocosphaera watsonii WH8501

(SEQ ID NO: 131)
CLSYDTEILTVEYGAMYIGKIVEENINCTVYTVDK

NGFVYTQTIAQWHNRGEQEIFEYDLEDGSKIKAT

KDHKFMTIDGEMLPIDEIFEKNLDLKQVVSHPD (SEQ ID NO: 132)
VKIIGCRSLGTQKVYDIGVEKDHNFLLANGSIASN

>CchPCC7420:/1-135 Coleofasciculus chthonoplastes PCC 7420 (Mcht)

(SEQ ID NO: 133)
CLSYDTQILTVEYGAVAIGEIVEKQIECTVYSVDE

NGYVYTQPIAQWHNRGEQEVFEYLLEDGATIRATK

DHKFMTDEDQMLPIDQIFEQGLELKQVEVL (SEQ ID NO: 134)
VKIIGRKPLGTQPVYDIGVERDHNFLLFNGSVASN

>CspPCC6712/1-133

(SEQ ID NO: 135)
CLSYDTEVLTVEYGAIPIGKIVEEKIACNVYSVDK

NGFVYTQPIAQYHDRGIQEVFEYRLENGSVIRATK

DHKMMTADGQMLPIDEIFKQNLDLKQLN (SEQ ID NO: 136)
VKIISRQSLGKQSVFDIGVAKDFINFLLANGLVASN

>AflNIES81:/1-132 Aphanizomenon flos-aquae NIES-81

(SEQ ID NO: 137)
CLSYDTEILTVEYGFLQIGEIVEKQIECKVYTVDS

NGILYTQSIAQWHNRGQQEVYEYLLENGAIIRATK

DHKFMTEEGQMLPIDEIFSQGLDLLQV (SEQ ID NO: 138)
VKIISRTYVGQANVYDIGVENDHNFVIKNGFIAAN

>Rbr:/1-137 Raphidiopsis brookii D9 D9_5, (SEQ ID NO: 139)
CLSYETEVLTLEYGFLPIGEIVDKQMVCTVFSVND

SGNVYTQPIGQWHDRGVQELYEYCLDDGSTIRATK

DHKFMTIQGEMVPIDEIFHQGWELVQVSGTMN (SEQ ID NO: 140)
VKIVSRRYLGKADVYDIGVAKDHNFHKNGLVASN

>CspCCy0110:/1-134 Cyanothece sp. CCY0110 1101676644604

(SEQ ID NO: 141)
CLSYDTEILTVEYGPMPIGKIVEENINCSVYTVNK

NGFVYTQSIAQWHHRGEQEVFEYYLEDGETIRATK

DHKFMTTEGKMLPIDEIFENNLDLKKLTV (SEQ ID NO: 142)
VKIIERRSLGKQNVYDIGVEKDHNFLLSNNLIASN

>XspPCC7305:/1-135 *Xenococcus* sp. PCC 7305

(SEQ ID NO: 143)

CLSADTEVLTVEYGAISIGKIVEERIECTVYSVDA

NGFVYTQEIAQWHNRGEQEVFEYMLDDGSVIRATK

DHKLMTIDGQMVAIDEIFSQGLELKQVLGL (SEQ ID NO: 144)

VKIVSRKSLGTQTVYDLGVARDHNFLLANGTVASN

>PspPCC7319:/1-135 *Pleurocapsa* sp. PCC 7319

(SEQ ID NO: 145)

CLSYDTEIYTVFYGALPIGKIVESRIKCTVLTVDK

NCLVYSQPIVQWHDRGIQEVFEYTLDNGATIRATK

DHKFMTVEGQMLPIDEIFELGLELKEIQQF (SEQ ID NO: 146)

VKIISRQSLGKQSVYDIGVAKDHNFLLANGMVASN

>CraCS505:/1-137 *Cylindrospermopsis raciborskii* CS-505

(SEQ ID NO: 147)

CESYETEVLTLEYGFVPIGEIVNKQMVCTVFSLN

DSGNVYTQPIGQWHDRGVQDLYEYCLDDGSTIRA

TKDHKFMTTQGEMVPIDEIFHQGWELVQVSGISK (SEQ ID NO: 148)

VKIVSRRYLGKADVYDIGVAKDHNFIIKNGLVASN

>SmaPCC6313/1-129 *Spirulina* major PCC 6313

(SEQ ID NO: 149)

CLTYDTLVLTVEYGPVPIGKLVEAQINCQVYSV

DANGFIYTQAIAQWHDRGQRQVYEYTLEDGSTI

RATPDHKFMTATGEMLPIDQIFEQGLDL (SEQ ID NO: 150)

VKIIHRRALPPQSVYDIGVERDHNFLLPSGWVASN

>SsuPCC9445:/1-131 *Spirulina subsalsa* PCC 9445

(SEQ ID NO: 151)

CLSYDTKIITVEYGAIAICTTVEQGLHCFWYSVD

PNGFIYTQPIAQWHQRGEQEVFAYTLENGSIIQA

TKDHKFMTQQGKMLPIDTIFEQGLDLLQ (SEQ ID NO: 152)

VKIIKRTSLGVRPVYDIGVIQDHNFLLENGLVASN

>MaePCC9807:/1-135 *Microcystis aeruginosa* 9807

(SEQ ID NO: 153)

CLGGETLILTEEYGLLPIAKIVSEEINCTVYSVD

KNGFIYSQPTSQWHERGLQEVFEYTLENGQTIQA

TKDHKFMTSDGEMLAIDTIFERGLDLKSSDFS (SEQ ID NO: 154)

VKUSRQFLGRKPVYDIGVEKDHNFLLGNGLIASN

>MspGI1:/1-130 *Myxosarcina* sp. GI1 contig_13

(SEQ ID NO: 155)

CLSYDTEVLTLKYGALPIGEIVEKRINCHVYTRA

ESGFFYIQSIEQWHDRGEQEVFEYTLENGATIKA

TKDHKFMTSGGQMLPIDEIFERGLDLL (SEQ ID NO: 156)

VKIVSRKSLGKQPVYDLGVAKDHNFLEANGTVASN

>LspPCC6406:/1-136 *Leptolyngbya* sp. PCC 6406

(SEQ ID NO: 157)

CLSADTQLLTVEYGPLEIGRIVEEQIACHVYSVDA

NGFVYTQPIAQWHSRGEQEIFEYQLEDGRTLRATA

DHKFMTTTGEMGRINDIFEQGLDLKQIDLPQ (SEQ ID NO: 158)

VKWSRQSLGVQPVYDIGVATDHNFLLADGLVASN

>AspCCMEE5410:/1-132 *Acaryochloris* sp. CCMEE 5410

(SEQ ID NO: 159)

CLSYDTPVLTLEYGWLPIGQVVQEQIECQVFSIN

ERGHLYTQPIAQWHHRGQQEVFEYTLTDGSTIQA

TAEHQFMTTDGQMYPIQQIFEEGLSLKQL (SEQ ID NO: 160)

VKITFQRRSLGLQSVYDIGLAQDHNFVIANGWVAAN

>GhePCC6308:/1-133 *Geminocystis herdmanii* PCC 6308

(SEQ ID NO: 161)

CLSYDTEVETVEFGAIPMGKIVEERLNCQVYSVD

KNGFIYTQNIAQWHDRGVQEVFEYELEDGRIIKA

TKDHKMMIENCEMVEIDRIFEEGLELFEVN (SEQ ID NO: 162)

VKILKRRSISSQQVYD1GVEKDHNFLLANGLVASN

>NnoPCC7104:/1-133 *Nodosilinea nodulosa* PCC 7104

(SEQ ID NO: 163)

CLSADTELLLTEYGPLTIGEIVAKRIPCHVFSVDE

SGYVYTQPVAQWHQRGHQEVFEYQLDDGTTIRATA

DHQFMTELGEMMAIDEIFQRGLELKQVE (SEQ ID NO: 164)

VKIISRQSLGVQPVYDIGVARDHNFLLADGQVASN

>RlaKORDI51-2:/1-137 *Rubidibacter lacunae* KORDI 51-2

(SEQ ID NO 165)

CLSYDTEVLTVEYGPLAIGTIVSERLACTVYTVDR

SGFLYAQAISQWHERGRQDVFEYALDNGMTIRATK

DHKLMTADGQMVAIDDIFTQGLTLKAIDTAAF (SEQ ID NO: 166)

MKIVSRKSLGVQHVYDIGVARDHNFLLANGAIASN

>CfrPCC9212/1-136 *Chlorogloeopsis fritschii* PCC 9212

(SEQ ID NO: 167)

CLSYDTAILTVEYGPLPIGEIVEKGIECTVYTVDS

NGYIYTQPIAQWHNRGEQELFEYSLEDGSIIRATK

DHKFMTIDGQMLPIDEIFARKLELMQVKGLP

>RinHH01:/1-137 Richelia intracellularis HH01 WGS project (SEQ ID NO: 169)
CLSYDTQILTVEHGPMSIGEIVEKCLECHVYTVN
KNGNICIQTITQWHFRGEQEIFEYELEDGSFIQA
TKDHKFMTTTGEMLPIHEIFTNGLEILQLSKSLL (SEQ ID NO: 170)
VKILARKSLGTQKVYDIGVNDDHNFALSNSFIASN >SspPCC7117/1-137

(SEQ ID NO: 171)
CLAGDTPVVTVEYGVLPIQTIVEQELLCQVYSVDA
QGLIYTQPIEQWHNRGDRLLYEYELENGQMIRATP
DHKFLTITGELLPIDEIFTQNLDLAAWAVPDS (SEQ ID NO: 172)
VKIIRRKFIGHAPTYDIGLSQDHNFLLGQGLIAAN

>SspPCC8807/1-137

(SEQ ID NO: 173)
CLAGDIPVVTVEYGVLPIQTIVEQELLCHVYSVDA
QGLIYTQPIEQWHRGDRFLYEYELENGQMIRATP
DHKFLTTTGKLLPIDEIFTQNLDLAAWAVPDS (SEQ ID NO: 174)
VKHRRKFIGHAPTYDIGLSQDHNFLLGQGFIAAN

>SspNKBG042902:/1-137 Synechococcus sp. NKBG042902

(SEQ ID NO: 175)
CLAGDTPVVTVEYGVLPIQTIVEQELLCHVYSVDA
QGLIYTQPIEQWHRGDRLLYEYELENGQMIRATP
DHKFLTTTGELLPIDEIFTQNLDLAAWAVPDS (SEQ ID NO: 176)
VKILRRKFIGRAPTYDIGLSQDHNFLLGQGLVAAN

>SspNKBG15041:/1-129 Synechococcus sp. NKBG15041

(SEQ ID NO: 177)
CLAGDTPVVTVEYGVLPIRTIVDQELLCHVYSLDP
QGFIYAQPVEQWHRRGDRLLYEYELETGAVIRATP
DHKFLTATGEMLPIDEIFVRNLDL (SEQ ID NO: 178)
VKIIRRNLIGEAATYDIGLGKDHNFLLGQGLIASN

>SspPCC73109/1-130

(SEQ ID NO: 179)
CLAGGTPVVTVEYGVLPIQTIVEQELLCHVYSVDA
QGLIYTQPIEQWHRGDRLLYEYELENGQMIRATP
DHKFLTTTGELLPIDEIFTQNLDLL (SEQ ID NO: 180)
VKIIRRKFIGHAPTYDIGLSQDHNFLLGQGLIAAN

>SspPCC7003/1-130

(SEQ ID NO: 181)
CLAGDTPVVTVEYGVLPIQTIVEQELLCHVYSVDA
QGLIYTQPIEQWHKRGDRLLYEYELENGQHRATPD
HKFLTTTGEMRPIDEIFAKNLSLL (SEQ ID NO: 182)
VKIIRRKFVGHAPTYDIGLSQDHNFLLGQGLIAAN

>CspPCC8802/1-134: Cyanothece sp. PCC 8802

(SEQ ID NO: 183)
CLSYDTEILTVEYGAIPIGKVVEENIDCTVYTVDKN
GFVYTQNIAQWHLRGQQEVFEYYLDDGSILRATKDI
IQFMTLEGEMLPTHEIFERGLELKKTKI (SEQ ID NO: 184)
VKIVSYRSLGKQFVYDIGVAQDHNFLLANGSIASN

>SelPCC7942:/1-137 Synechococcus elongate PCC 7942

(SEQ ID NO: 185)
CLAADTEVLTVEYGPIAIGKLVEENIRCQVYCCNPD
GYIYSQPIGQWHQRGEQEVIEYELSDGRIIRATADH
RFMTEEGEMLSLDEIFERSLELKQIPTPLL (SEQ ID NO: 186)
VKIVRRRSLGVQPVYDLGVATVHNFVLANGLVASN

>CfrPCC6912:/1-137 Chlorogloeposis Fritschii PCC 6912

(SEQ ID NO: 187)
CLSYDTAILTVEYGFLPIGEIVEKGIECTVYTVDSN
GYIYTQPIAQWHNRGEQELFEYSLEDGSIIRATKDH
KFMTIDGQMLPIDEIFARKLELMQVKGLPE (SEQ ID NO: 188)
VKHAKKSLGTQNVYDIGVERDHNFVIKNGLVASN

>CspATC51472:/1-132 Cyanothece sp ATCC 51472

(SEQ ID NO: 189)
CLSYDTEILTVEYGPMPIGKIVEENINCTVYTVDPN
GFVYTQAIAQWHYRGEQEIFEYYLEDGATIRATKDH
KFMTMEGKMLPIDEIFENNLDLKQL (SEQ ID NO: 190)
VKHGRQSLGVQKVYDIGVEKEHNFLLHNGLIASN

>Lma:/1-132 Lyngbya majuscula (SEQ ID NO: 191)
CLSYDTEIITVEYGPIAIGEIVEKGIPCTVYSVDSN
GYVYTQPIAQWHNRGEQEVFEYTLDDGSVIRATKDH
KFMTIDGQMLPIDEIFEGGLELKQL (SEQ ID NO: 192)
VKIISRKSLGTQPVYDIGVKDDHNFILANGMVASN >CspESFC/1-137

(SEQ ID NO: 193)
CLSYDTEVLTVEYGAVPIGKLVEEKLNCSVYTVDPN
GYIYTQAIAQWHDRGIQEVFEYQLEDNTIIRATKDH
KFMTEDHQMLPIDEIFERGLELKKCPQPQQ (SEQ ID NO: 194)
VKIIRRRSLGFQPVYDIGLEQDHNFLLNQGAIASN

>SspPCC7002:/1-129 *Synechococcus* sp. PCC 7002

(SEQ ID NO: 195)
CLAGGTPVVTVEYGVLPIQTIVEQELLCHVYSVDAQ

GLIYAQLIEQWHQRGDRLLYEYELENGQMIRATPDH

RFLTTTGELLPIDEIFTQNLDL (SEQ ID NO: 196)
VKIIRRKFIGHAPTYDIGLSQDMNFLLGQGLIAAN

>AmaMBIC11017:/1-132 *Acaryochloris marina* MBIC11017

{SEQ ID NO: 197)
CLSYDTPVLTLEYGWLPIGQVVQEQIECQVFSINER

GHLYTQPIAQWHHRGQQEVFEYTLADGSTIQATAEH

QFMTTDGQMYPVQQIFEEGLSLKQL (SEQ ID NO: 198)
VKIIQRRSLGLQSVYDIGLAQDHNFVMANGWVAAN

>Mae905:/1-129 *Microcystis aeruginosa* DIANCHI905

(SEQ ID NO: 199)
CLGGETLILTEEYGLLPIAKIVSEEVNCTVYSVDKN

GFVYSQPISQWHERGLQEVFEYTLENGQTIQATKDH

KFMTNDGEMLAIDTIFERGLDL (SEQ ID NO: 200)
VKIISRQSLGRKPVYDIGVEKDHNFLLGNGLIASN

>AciAWQC310F:/1-125 AWQC: *Anabaena circinalis* AWQC310F (SEQ ID NO: 201)
CLSYDTEILTVEYGFLEIGEIVEKQIECKVYTVDSN

GILYTQPIAQWHHRGQQEVYEYLLENGAIIRATKDH

KFMTEAGEMLPIDDIFTQ (SEQ ID NO: 202)
VKIISRTYVGQANVYD1GVENDHNFVIKNGFVAAN

>AciAWQC131C:/1-125 *Anabaena circinalis* AWQC 131C (SEQ ID NO: 203)
CLSYDTEILTVEYGFLEIGEIVEKQIECRVYTVDSN

GILYTQPIAQWHYRGQQEVYEYLLENGAIIRATKDH

NFMTEAGEMLPIDDIFTQ (SEQ ID NO: 204)
IKHSRKYVGQANVYDIGYENDHNFVIKNGFVAAN

>CspUCYN:/1-124 *Cyanobacterium* sp. UCYN-A2

(SEQ ID NO: 205)
CLSYDTKVLTVEYGPLPIGKVVQENIRCRVYTTNDQ

GLIYTQPIAQVVHNRGKQEIFEYHLDDKTIIRATKE

HQFMTVDHVMMPIDEIFEQ (SEQ ID NO: 206)
KI1RRKSLGMHEVFD1GLEKDHNFVLSNGLIASN

Pst:/1-129 *Planktothrix* St147: st147_cleanDRAFT_c6

(SEQ ID NO: 207)
CLSYDTEVLTVEYGLIPISKIVEEKIECTVYTVNNQ

GYVYTQPIAQWHNRGEQEVFEYYLEDGSVIRATKDH

KFMTVEGQMLPIDEIFEKELDL (SEQ ID NO: 208)
VKIISRKSLGTQPVYDIGVQEDHNFVLNNGLVASN

>PlaCYA98/1-129: *Planktothrix* NIVA-CYA 98

(SEQ ID NO: 209)
CLSYDTEILTVEYGLMPIGKIVKEKIECTVYTVNN

QGWYTQPIAQWHHRGEQEVFEYCLEDGSVIRATKD

HKFMTVQGQMLPIDEIFEKELDL (SEQ ID NO: 210)
VKIISRKSLGTQPVYDIGVQEDHNFLLNNGLVASN

>FdiUTEX481:/1-137 *Fremyella diplosiphon* UTEX 481

(SEQ ID NO: 211)
CLSYDTEVLTVEYGLIPIGEIVEKRLECSVYSVDI

NGNVYTQPIAQWHHRGQQEVFEYALEDGSIIRATK

DHKFMTTDGQMLPIDEIFERGLDLLQVPHLPE (SEQ ID NO: 212)
VKIVTRRAIGAANYTDIGVEQDHNFAIKNGLIAAN

> Pst585:/1-129 *Planktothrix* sp. 585: Length = 1586997

(SEQ ID NO: 213)
CLSYDTEILTVEYGLIPISKIVEEKIECTVYTVNN

QGYVYTQPIAQWHNRGEQEVFEYYLEDGSVIRATK

DHKFMTVDGQMLPIDEIFEKELDL (SEQ ID NO: 214)
VKIISRKSLGTQPVYDIGVQEDHNFVLNNGLVASN

>NpuPCC73102/1-137

(SEQ ID NO: 215)
CLSYETEILTVEYGLLPIGKIVEKRIECTVYSVDN

NGNTYTQPVAQWHDRGEQEVFEYCLEDGSLIRATK

DHKFMTVDGQMLPIDEIFERELDLMRVDNLPN (SEQ ID NO: 216)
IKIATRKYLGKQNVYDIGVERDHNFALKNGFIASN

>CthPCC7203:/1-137 *Chroococcidiopsis thermalis* PCC 7203

(SEQ ID NO: 217)
CLSYDTEILTVEYGAIPIGKIVEERIECTVYSVDN

NGFIYTQPIAQWHNRGQQEVFEYCLEDGSIIRATK

DHKFMTFEGKMLPIDEIFEQELDLKQVKSIQN (SEQ ID NO: 218)
VKIISRKSLGIQPVYDIGVERDHKFVLKNGLVASN

-continued

>NspCCY9414:/1-337 *Nodularia spumigena*
CCY9414 genome (SEQ ID NO: 219)
CLSYDTEILTVEYGYIPIGEIVEKAIECSVYSVDN

NGNVYTQPIAQWHNRGEQEVFEYSIEDGSTIRATK

DHKFMTTDGQMLPIDEIFAQELDLLQVHGLPK (SEQ ID NO: 220)
VKITARKFVGRENVYDIGVERYHNFAIKNGLIASN

>AcyPCC7122:/1-137 *Anabaena cyliridrica*
PCC 7122

(SEQ ID NO: 221)
CLSYDTEVLTVEYGFIPIGEIVEKRIECSIFSVDK

NGNVYTQPIAQWHNRGRQEIYEYCLDDGSKIRATK

DHKFMTTAGEMLPIDEIFERDLDLLKVEGLPE (SEQ ID NO: 222)
VKITSRQYLGQADVYDIGVEEDITKFAIKNGFIASN

>CspPCC7507:/1-137 *Calothrix* sp.
PCC 7507, complete genome (SEQ ID NO: 223)
CLSYDTEVLTVEYGLLPIGEIVEKGIECRVFSVDN

HGNVYTQPTAQWHNRGQQEVFEYGLDDGSVIRATK

DHKFMTTDGKMLPIDEIFERGLDLLQVQGLPE (SEQ ID NO: 224)
VKVITRKYIGKENVYDIGVELDHNFAIRNGLVASN

>NspPCC7524:/1-137 *Nostoc* sp
PCC 7524

(SEQ ID NO: 225)
CLSYDTEDLTVEYGFLPIGEIVEKGIECTVFSVAS

NGIVYTQPIAQWHNRGQQEIFEYCLEDGSIIRATK

DHKFMTQDGQMLPIDEIFACELDLLQVQGLPE (SEQ ID NO: 226)
VKVVTRKYIGKENVYDIGVERDHNFVIRNGLVASN

>Naz0708:/1-137 'Nostoc azollae'
0708

(SEQ ID NO: 227)
CLSYKTEVLTVEYGLIPIGEIVEKRIECSLFSVDE

NGNIYTQPIAQWHRGVQEVYEYCLDDGTIIRATK

DFIKFMTTIGEMLPIDEIFERDLNLLQVNGLPT (SEQ ID NO: 228)
VKIISRQFLGPANVYDIGVAQDHNFAIKNGLIASN

>NspPCC7120:/1-137 *Nostoc* sp.
PCC 7120 DNA (SEQ ID NO: 229)
CLSYDTEVLTVEYGFVPIGEIVEKGIECSVFSINN

NGIVYTQPIAQWHHRGKQEVFEYCLEDGSIIKATK

DHKFMTQDGKMLPIDEIFEQELDLLQVKGLPE (SEQ ID NO: 230)
IKIASRKFLGVENVYDIGVRRDHNFFIKNGLIASN

>AvaATCC29413:/1-137 *Anabaena variabilis*
ATCC 29413

(SEQ ID NO: 231)
CLSYDTEVLTVEYGFVPTGEIVDKGTFCSVFSIDS

NGIVYTQPTAQWHHRGKQEVFEYCLEDGSIIKATK

DHKFMTQDGKMLPIDEIFEQELDLLQVKGLPE (SEQ ID NO: 232)
IKIASRKFLGVENVYDIGVGRDHNFFVKNGLIASN

>PspPCC7327:/1-135 *Pleurocapsa* sp.
PCC 7327.

(SEQ ID NO: 233)
CLSYDTKILTVEYGAMPIGKIVEEQIDCTVYTVNQ

NGFVYTQPIAQWHDRGKQEIFEYCLEDGSIIRATK

DHKFMTTDGCEMLPIDKIFEKGLDLKTINCD (SEQ ID NO: 234)
VKILSRKSLGIQSVYDIGVEKDHNFLLANGLVASN

>CspPCC7424:/1-135 *Cyanothece* sp.
PCC 7424

(SEQ ID NO: 235)
CLSYETQIMTVEYGLMPIGKIVEEQIDCTVYTVNK

NGFVYTQPIAQWHYRGEQEVFEYCLEDGSTIRATK

DMKFMTTDGQMLPIDEIFEQGLELKQIHLS (SEQ ID NO: 236)
VKIISRQSLGIQPVYDIGVEKDHNFLISDGLIASN

>CspPCC7822:/1-134 *Cyanothece* sp.
PCC 7822

(SEQ ID NO: 237)
CLSYDTEILTVEYGPMPIGKTVEEQIECTVYTVDKN

GLVYTQPIAQWHHRGQQEVFEYCLEDGSIIRATKDH

KFMTDDGQMLPIEEIFEKQLELKQIIL (SEQ ID NO: 238)
VKIISRQLAGNQTVYDLGVEKDHNFLLANGLIASN

>NspPCC7107:/1-137 *Nostoc* sp.
PCC 7107

(SEQ ID NO: 239)
CLSYDTQVLTVEYGLVPIGEIVEKQLECSVFTIDG

HGYVYTQAIAQWHNRGQQEVFEYGLEDGSVIRATK

DHKFMTTDGQMLPIDEIFERELDLLQVQGLRW (SEQ ID NO: 240)
VKIITRKYIGQANVYDIGVAQDHNFVIENRLIASN

>TboIicb1/1-136 *Tolypothrix bouteillei*
Iicb1

(SEQ ID NO: 241)
CLSYDTEILTVEYGFLPIGKIVEKGIECNVYSVDK

NGNIYTQPIAQWHDRGEQEVFEYCLENGSVIRATK

DHKFMTTSGEMLPIDEIFERGLDLIRVEDLP (SEQ ID NO: 242)
VKILTRKSIGKQTVYDIGVERDHNFVIKNGSVASN

>Aov:/1-136 *Aphanizomenon ovalisporum*
DnaE precursor (dnaE) gene (SEQ ID NO: 243)
CLSADTEILTVEYGFLPIGEIVGKAIECRVYSVDG

NGNIYTQSFAQWHRGEQEVFEYTLEDGSIIRATK

DFIKFMTTDGEMLPIDEXFARQLDLMVQGLH (SEQ ID NO: 244)
VKITARKFVGRENVYDIGVEHHHNFAIKNGLIASN

>OnvPCC7112:/1-137
*Oscillatoria nigro-viridis*
PCC 7112

(SEQ ID NO: 245)
CLSYDIKILTVEYGPMAIGKIVEEKIECTVYSVDS

NGYIYIQSIAQWHRRGQQEVFEYCLEDGSIIRATK

DHKFMTVGGQMLPIDESFEQGLDLKQINSSSD (SEQ ID NO: 246)
VKHSRKSLGTQEVYDIGVEREHNFILENSLVASN

>RspPCC7116:/1-135 *Rivularia* sp.
PCC 7116, complete genome (SEQ ID NO: 247)
CLSYDTEVLTFEFGLUPIGKIVEEKUDCTVYSVD

VNGNVYSQPSAQWHNRGMQEVFEYELEDGSTIRA

TKDHKFMTVDGEMLAIDEIFEKGLELKRVGIY (SEQ ID NO: 248)
VKESRKVLKTENVYDIGLEGDHNFIIKDGLIASN

>MspPCC7113:/1-137 *Microcoleus* sp.
PCC 7113, (SEQ ID NO: 249)
CLSYDSEILTVEYGLMPIGKIVEEGIECTVYSVD

SHGYLYTQPIAQWHHRGQQEVFEYDLEDGSVIRA

TKDHKFMTSEGQMLAIDEIFERGLELKQVKRSQP (SEQ ID NO: 250)
VKIVRRKSLGIQTVYDIGVERDHNFLLANGLVASN

>ScyPCC7437:/1-137 *Stanieria cyanosphaera*
PCC 7437

(SEQ ID NO: 251)
CLSYDTEILTVEYGAMPIGKIVKEQIECNVYTVN

QNGFIYPQAIAQWHERGKQEIFEYTLDNGLVIRA

TKDHKFMTIDGQMLPIDEIFERGLELQRINDYSN (SEQ ID NO: 252)
VKIVSRKSLGKQPVYDIGVTKDHNFLLSNGWASN

>CspPCC6303:/1-137 *Calothrix* sp.
PCC 6303

(SEQ ID NO: 253)
CLSYDTEILTWEYGFLKIGEIVEKQILCSVFSVDE

QGNVYTQPIAQWHNRGLQELFAYQLEDGGVIRATK

DHKFMTTDGQMLAIDEIFERQLDLFQVKGLPE (SEQ ID NO: 254)
VKIISRKVLKTENVYDIGLEGDHNFIIKDGLIASN

>Cst:/1-134 PCC7202:
*Cyanobacterium stanieri*
PCC 7202

(SEQ ID NO: 255)
CLSYDTEVLTVEYGVLPIGKIVEEQIQCTVYSVDQ

YGFVYTQAIAQWHDRGEQEVFEYELENGATIKATK

DHKMMTSDGQMLPIDQIFEQGLDLFMVSF (SEQ ID NO: 256)
VKIVKRRSHGIQKVYDIGVAKDHNFLLHNGLVASN

>CspATCC51142:/1-134 *Cyanothece* sp.
ATCC 51142

(SEQ ID NO: 257)
CLSVDTEILTVEYGPMPIGKIVEENINCTVYTVDP

NGFVYTQAIAQWHYRGEQEIFEYTLEDGATIRATK

DHKFMTMEGKMLPIDEIFENNLDLKQLTL (SEQ ID NO: 258)
VKIIGRQSLGVQKVYDIGVEKEHNFLLHNGLIASN

>CspPCC8801:/1-134 *Cyanothece* sp.
PCC 8801

(SEQ ID NO: 259)
CLSYDTEILTVEYGAIPIGKVVEENIDCTVYTVDK

NGFVYTQNIAQWHLRGQQEVFEYYLDDGSILRATK

DHQFMTLEGEMLPIHEIFERGLELKKIKI (SEQ ID NO: 260)
VKIYSYRSLGKQFVYDIGVAQDHNFLLANGSIASN

>Asp:/1-136 *Anabaena* sp.
90 chromosome (SEQ ID NO: 261)
CLSYDTEILTVEYGFLEIGEIVEKQIECKVYTIDS

NGMLYTQSIAQWHNRGQQEVYEYLLENGAIIRATK

DHKFMTEAGQMLPIDEIFAQGLDLLQVGVAE (SEQ ID NO: 262)
VKIVSRTYVGQANVYDIGVESDHNFVIKNGFIASN

>Aha:/1-137 *Aphanothece halophytica*

(SEQ ID NO: 263)
CLSYDTEIWTVEYGAMPIGKIVEEKIECSVYTVDE

NGFVYTQPIAQWHPRGQQEIIEYTLEDGRKIRATK

DHKMMTESGEMLPIEEIFQRELDLKVETFHEM (SEQ ID NO: 264)
VKIIKRQSLGRQNVYDVCVETDHNFVLANGCVASN

>HspPCC7418:/1-137 *Halothece* sp.
PCC 7418

(SEQ ID NO: 265)
CLSYDTEIWTVEYGAMPIGKIVEEKIECSVYTVDE

NGFVYTQPIAQWHPRGQQEIIEYTLEDGRKIRATK

DHKMMTESGEMLPIEEIFQRELDLKVETFHEM (SEQ ID NO: 266)
VKIIKRQSLGRQNVYDIGVETDHNFVLANGCVASN

>CapPCC10605:/1-137 *Cyanobacterium aponinum*
PCC 10605

(SEQ ID NO: 267)
CLSYDTEILTVEYGAISIGKIVEEKINCQVYSVDK

NGFIYTQNIAQWHDRGSQELFEYELEDGRIIKATK

DHKMMTKDGQMLAINDIFEQELELYSVDDMGV (SEQ ID NO: 268)
VKIVKRRSLGVQPVYDIGVEKDHNFILANGLVASN

>Cat.:/1-133 Candidatus Atelocyanobacterium thalassa isolate (SEQ ID NO: 269)
CLSYDTKVLTVEYGPLPIGKVVQENIRCRVYTTND

QGLTYTQPIAQWHNRGKQEIFEYHLDDKTORATKE

HQFMTVDHVMMPIDEIFEQGLELKKIK (SEQ ID NO: 270)
LKIIRRKSLGMHEVFDIGLEKDIINFVLSNGLIASN

>Oli.:/1-137 Oscillatoria limnetica 'Solar Lake' DnaE precursor (SEQ ID NO: 271)
CLSYNTEVLTVEYGPLPTGKLIVDEQIHCRVYSVD

ENGFVYTQAIAQWHDRGYQEIFAYELADGSVIRAT

KDHQFMTEDGQMFPIDEIWEKGLDLKKLFIVQD (SEQ ID NO: 272)
VKIVRRQSLGVQNVYDIGVEKDHNFLLASGEIASN

>Cen:/1-137 Cyanobacterium endosymbiont of Epithemia turgida (SEQ ID NO: 273)
CLSYDTEVLTVEYGAIPIGRMVEESLDCTVYTVDK

NGFVYTQSIQQWMSRGQQEIFEYCFEDGSTIRATK

DHKFMTAEGKMSSTITDIFEQGLELKKIIPWSG (SEQ ID NO: 274)
AKIISCKSLGKQVYDIGVVQDHNFLLANGVVASN

>SspPCC7502:/1-133 Synechococcus sp. PCC 7502

(SEQ ID NO: 275)
CLGYDTPVLTVEYGFMPIGKIVEEKIQCHVYSVDQ

NGLVFTQAIAQWHNRGQQEVWEYNLDNGDIVRATK

DHKFMTIDGQMLPINQIFEQGLELKVIA (SEQ ID NO: 276)
VKIVSCKPLRVQTVYDIGVEKDHNFILDNGLVASN

>CspUCYN.:/1-124 Cyanobacterium sp. UCYN-A2

(SEQ ID NO: 277)
CLSYDTKVLTVEYGPLPIGKVVQENIRCRVYTTNDQ

GLIYTQPIAQWHNRGKQEIFEYHLDDKTIIRATKEH

QFMTVDHVMMPIDEIFEQ (SEQ ID NO: 278)
KIIRRKSLGMHEVFDIGLEKDHNFVLSNGLIASN

>Pst.:/1-129 Planktothrix st147: st_147_cleanDRAFT_c6

(SEQ ID NO: 279)
CLSYDTEVLTVEYGLIPISKIVEEKIECTVYTVNNG

YVYTQPIAQWHNRGEQEVFEYYLEDGSVIRATKDHK

FMTVEGQMLPIDEIFEKELDL (SEQ ID NO: 280)
VKIISRKSLGTQPVYDIGVQEDHNFVLNNGIVASN

>PlaCYA98/1-129: Planktothrix NIVA-CYA 98

(SEQ ID NO: 281)
CLSYDTEILTVEYGLMPIGKIVKEKIECTVYTVNN

QGYVYTQPIAQWHHRGEQEVFEYCLEDGSVIRATK

DHKFMTVQGQMLPIDEIFEKELDL (SEQ ID NO: 282)
VKIISRKSLGTQPVYDIGVQEDHNFLLNNGLVASN

>Pst585:/1-129 Planktothrix sp. 585: Length = 1586997

(SEQ ID NO: 283)
GLSYDTEILTVEYGLIPISKIVEEKIECTVYTVNN

QGYVYTQPIAQWHNRGEQEVFEYYLEDGSVIRATK

DHKFMTVDGQMLPIDEIFEKELDL (SEQ ID NO: 284)
VKIISRKSLGTQPVYDIGVQEDHNFVLNNGLVASN

>CspPCC8802:/1-134: Cyanothece sp. PCC 8802

(SEQ ID NO: 285)
CLSYDTEILTVEYGAIPIGKVVEENIDCTYYTVDK

NGFVYTQNIAQWHLRGQQEVFEYYLDDGSILRATK

DHQFMTLEGEMLPIHEIFERGLELKKIKI (SEQ ID NO: 286)
VKIVSYRSLGKQFVYDIGVAQDHNFLLANGSIASN

>CfrPCC6912.:/1-137 Chlorogloeposis fritschii PCC 6912

(SEQ ID NO: 287)
CLSYDTAILTVEYGFLPIGEIVEKGIECTVYTVDS

NGYIYTQPIAQWHNRGEQELFEYSLEDGSIIRATK

DHKFMTIDGQMLPIDEIFARKLELMQVKGLPE (SEQ ID NO: 288)
VKIIAKKSLGTQNYYDIGVERDHNFVIKNGLVASN

>CspATC51472:/1-132 Cyanothece sp. ATCC 51472

(SEQ ID NO: 289)
CLSYDTEILTVEYGPMPIGKIVEENINCTVYTVDP

NGFVYTQAIAQWHYRGEQEIFEYYLEDGATIRATK

DHKFMTMEGKMLPIDEIFENNLDLKQL (SEQ ID NO: 290)
VKHGRQSLGVQKVYDIGVEKEHNFLLHNGLIASN

>Lma.:/1-132 Lyngbya majuscula (SEQ ID NO: 291)
CLSYDTEIITVEYGPIAIGEIVEKGIPCTVYSVDS

NGYVYTQPIAQWHNRGEQEVFEYTLDDGSVIRATK

DHKFMTIDGQMLPIDEIFEGGLELKQL (SEQ ID NO: 292)
VKIISRKSLGTQPVYDIGVKDDHNFILANGMVASN

>CspESFC/1-137

(SEQ ID NO: 293)
CLSYDTEVLTVEYGAVPIGKLVEEKLNCSVYIVDP

NGYIYTQAIAQWHDRGIQEVFEYQLEDNTIIRATK

DHKFMTEDHQMLPIDEIFERGLELKKCPQPQQ (SEQ ID NO: 294)
VKIIRRRSLGFQPVYDSGLEQDHNFLLNQGAIASN

-continued

>Mae905:/1-129 *Alicrocystis aeruginosa* DIANCHI905

(SEQ ID NO: 295)
CLGGETLILTEEYGLLPIAKIVSEEVNCTVYSVDK

NGFVYSQPISQWHERGLQEVFEYTLENGQTIQATK

DHKFMTNDGEMLAIDTIFERGLDL (SEQ ID NO: 296)
VKIISRQSLGRKPVYDIGVEKDHNFLLGNGLIASN

>RlaKORDI51-2:/1-137 *Rubidibacter lacunae* KORDI 51-2

(SEQ ID NO: 297)
CLSYDTEVLIYEYGPLAIGTIVSERLACTVYIVDR

SGFLYAQAISQWHERGRQDVFEYALDNGMTIRATK

DHKLMTADGQMVAIDDIFTQGLTLKAIDTAAF (SEQ ID NO: 298)
MKIVSRKSLGVQHVYDIGVARDHNFLLANGAIASN

>CfrPCC9212/1-136 *Chlorogloeopsis fritschii* PCC 9212

(SEQ ID NO: 299)
CLSYDTAILTVEYGFLPIGEIVEKGIECTVYTVDS

NGYIYTQPIAQWHNRGEQELFEYSLEDGSIIRATK

DHKFMTIDGQMLPIDEIFARKLELMQVKGLP (SEQ ID NO: 300)
VKDAKKSLGTQNVYDIGVERDHNFVIKNGLVASN

>RinHH01:/1-137 *Richelia intracellularis* HH0.1 WGS project (SEQ ID NO: 301)
CLSYDTQILTVEHGPMS1GEIVEKCLECHVYTVNK

NGNICIQTITQWHFRGEQEIFEYELEDGSFIQATK

DHKFMTTTGEMLPIHEIFTNGLEILQLSKSLL (SEQ ID NO: 302)
VKILARKSLGTQKVYDIGVNDDHNFALSNSFIASN

>GhePCC6308:/1-133 *Geminocystis herdmanii* PCC 6308

(SEQ ID NO: 303)
CLSYDTEVLTVEFGAIPMGKIVEERLNCQVYSVDK

NGFIYTQNIAQWHDRGVQEVFEYELEDGRIIKATK

DHKMMIENCEMVEIDRIFEEGLELFEVN (SEQ ID NO: 304)
VKILKRRSISSQQVYDIGVEKDHNFLLANGLVASN

>SsuPCC9445:/1-131 *Spirulina subsalsa* PCC 9445

(SEQ ID NO: 305)
CLSYDTKIITVEYGAIAIGTIVEQGLHCHVYSVDP

NGFIYTQPIAQWHQRGEQEVFAYTLENGSIIQATK

DHKFMTQQGKMLPIDTIFEQGLDLLQV (SEQ ID NO: 306)
KIIKRTSLGVRPVYDIGVIQDHNFLLENGLVASN

>MaePCC9807:/1-135 *Microcystis aeruginosa* 9807

(SEQ ID NO: 307)
CLGGETLILTEEYGLLPIAKIVSEEINCTVYSVDK

NGFIYSQPISQWHERGLQEVFEYTLENGQTIQATKD

HKFMTSDGEMLAIDTIFERGLDLKSSDFS (SEQ ID NO: 308)
VKIISRQFLGRKPVYDIGVEKDHNFLLGNGLIASN

>MspGII:/1-130 *Myxosarcina* sp. GI1 contig_13

(SEQ ID NO: 309)
CLSYDTEVLTLKYGALPIGEIVEKRINCHVYTRAE

SGFFYIQSIEQWHDRGEQEVFEYTLENGATIKATK

DHKFMTSGGQMLPIDEIFERGLDLL (SEQ ID NO: 310)
VKIVSRKSLGKQPVYDLGVAKDHNFLLANGTVASN

>ShoPCC7110:/1-136 *Scytonema hofmanni* PCC 7110 contig00136

(SEQ ID NO: 311)
CLSYDTEVLTAEYGFLPIGKIVEKAIECTVYSVD

NDGNIYTQPIAQWMDRGQQEVFEYSLDDGSVIRA

TCDHKFMTTCGQMLPIDEFFERCLDLMRIDSLP (SEQ ID NO: 312)
VKILTRKSIGKQTVYDIGVERDHNFVIKNGLVASN

>WinUHHT291/1-136 *Westiella intricata* UHHT-29-1

(SEQ ID NO: 313)
CLSYDTEILTVEYGFLPIGEIVEKRIECTVYTVD

TNGYVYTQAIAQWHNRGEQEVFEYALEDGSMRAT

KDHKFMTSEGQMLPIDEIFVKGLDLLQVQGLP (SEQ ID NO: 314)
VKIITRKFLGIQNVYD1GVEQNHNFVIKNGLVASN

>FspPCC9605:/1-136 *Fischerella* sp. PCC 9605 FIS9605DRAFT (SEQ ID NO: 315)
CLSYDTETLTVEYGFLPIGEIVEKGIECTVYTVDN

NGNVYTQTIAQWHNRGQQEVFEYCLEDGSVIRATK

DHKFMTTDGQMLPIDEIFARGLDLLQVKNLP (SEQ ID NO: 316)
VKIVTRRPLGTQNVYDIGVESDHNFVIKNGLVASN

>MrePCC10914:/1-137 *Mastigocladopsis repens* PCC 10914

(SEQ ID NO: 317)
CLSYDTEVLTVEYGFLPIGEIVEKSIECSVYTVDS

NGNVYTQPIAQWHNRGQQEVFEYCLEDGSIIRATK

DHKFMTEIGQMLPIDEIFERGLELMKIQGLPE (SEQ ID NO: 318)
AKIITRKSLGTQNVYDIGVERDHNFVTRDGFIASN

-continued

>ShoUTEX2349:/1-137 [*Scytonema hofmanni*] UTEX 2349

(SEQ ID NO: 319)
CLSYNSEVLTVEYGFLPIGKIVEKGIECSVYSVDS
YGKIYTQVIAQWHNRGQQEVFEYCLEDGTIIQAT
KDHKFMTVDGQMLPIDEIFERGLDLMQVQGLPD (SEQ ID NO: 320)
VKIITRKSLGTQNVYDIGVSSDHNFVMKNGLIASN

>AspPCC7108:/1-137 *Anabaena sp.* PCC 7108 Ana7108scaffold_2_Cont3

(SEQ ID NO: 321)
CLSSDTEVLTVEYGLIPIGEHEKRIDCSVFSVDKN
GNIYTQPIAQWHDRGIQELYEYCLDDGSTIRATKD
HKFMTTAGEMLPIDEIFERGLDLLKVMNLPQ (SEQ ID NO: 322)
VKIITRNYVGKENVYDIGVERDHNFAIKNGLIASN

>FspPCC9339:/1-137 *Fischerella sp.* PCC 9339 PCC9339DRAFT (SEQ ID NO: 323)
CLSYDTEVLTVEYGFLPIGEIVEKRIECTVYTVD
HNGYVYTQPIAQWHNRGYQEVFEYGLEDSVIRAT
KDHKFMTSEGQMLPIDEIFARELDLLQVTGLVN (SEQ ID NO: 324)
VKIVTRRLLGIQNVYDIGVEQNHNFVIKNGLVASN >Csp336:/1-137 *Calothrix sp.* 336/3

(SEQ ID NO: 325)
CLSYDIEIFTVEYGFLPIGEIVEKRLECTVLTVD
NHGNIYSQPIAQWHHRGQQQIYEYGLEDGSVIRA
TKDHKFMTTDGQMLPIDEIFERGLDLLQVTNLDN (SEQ ID NO: 326)
VRVITRKLADTENVTDIGVENHHNFLIKNGLVASN

>FthPCC7521:/1-136 *Fischerellai hermalis* PCC 7521

(SEQ ID NO: 327)
CLSYETEILTVEYGFLPIGEIVEKRIECSVYTVDN
NGYVCTQPIAQWHNRGYQEVFEYGLEDGSVIRATK
DHKFMTIDRQMLPIDEIFARGLDLLQVTGCP (SEQ ID NO: 328)
VKIITRKSLGTQNVYDIGVEQNHNFVIKNGLVASN

>CyaPCC7702/1-137 *cyanobacterium* PCC 7702 CH17702

(SEQ ID NO: 329)
CLSYDTEILTVEYGFLSIGEIVEKEIECTVYIYDS
NGYIYTQPIAQWHEQGEQEIFEYSLEDGSTIRATK
DHKFMTIECEMLPIDQIFARQLDLMQITGLPQ (SEQ ID NO: 330)
VKISTKKSLGKQKVYDIGVVRDHNFIIKNGFVASN

>FspPCC9431:/1-136 *Fischerella sp.* PCC 9433

(SEQ ID NO: 331)
CLSYDTEVLTVEYGFLPIGEIVEKRIECTVYTVDT
NGYVYTQAIAQWHNRDEQEVFEYALEDGSTIRATR
DHKFMTSEGQMLPIDEIFAKGLDLLQVQGLP (SEQ ID NO: 332)
VKIVTRKFLGIQNVYDTGVEQNHNFVTKNGLVASN

>FmuPCC7414:/1-137 *Fischerella muscicola* PCC 7414

(SEQ ID NO: 333)
CLSYETEILTVEYGFLPIGEIVEKRIECSVYTVDN
NGYVCTQTIAQWHNRGYQEVFEYGLEDGSVIRATK
DHKFMTIDRQMLPIDEIFARGLDLLQVKGLPE (SEQ ID NO: 334)
VKHTRQSLGTQNVYDIGVEQNHNFVIKNGLVASN

>FmuPCC73103:/1-137 *Fischerella muscicola* SAG 1427-1 = PCC 73103

(SEQ ID NO: 335)
CLSYDTEVLTCEYGFLPIGEIVEKTIECNVFTVDS
NCYVYTQPIAQWHNRGYQEVFEYGLEDGSVIRATK
DHKFMTSEGKMLPIDEIFARELDLLQVTGLIN (SEQ ID NO: 336)
VKIVTRKFLGIQNVYDIGVEQNHNFVIKNGLVASN

>Lae:/1-137 *Lyngbya aestuarii* BL J laest3.contig.3

(SEQ ID NO: 337)
CLSYDTEILTVEYGAIPIGKVVDEKIECTVYSVDK
NGLIYTQPIAQWHNRGKQEVFEYSLEDGSTIRATK
DHICFMTMDNQMLPIDEILEKGLELKQVNADSV (SEQ ID NO: 338)
VKIVSRKSLDSQTVYDIGVETDHNFLLANGSVASN

>Lsp:/1-137 *Leptolyngbya sp.* JSC-1

(SEQ ID NO: 339)
CLSYDTEILTVEYGALPIGKIVENQMICSVYSIDN
NGYIYIQPIAQWHNRGQQEVFEYILEDGSIIRSTK
DHKFMTKGGEMLPIDEIFERGLELAQVTRLEQ (SEQ ID NO: 340)
VKHSRRSVGVQSYTDIGVKQDHNFFLRNGLIASN

>CwaWH8501:/1-137 *Crocosphaera watsonii* WH8501

(SEQ ID NO: 341)
CLSYDTEILTVEYGAMYIGKIVEENINCTVYTVDK
NGFVYTQTIAQWHNRGEQEIFEYDLEDGSKIKATK
DHKFMTIDGEMLPIDEIFEKNLDLKQVVSHPD (SEQ ID NO: 342)
VKIIGCRSLGTQKVYDIGVEKDHNFLLANGSIASN

>CchPCC7420:/1-135 *Coleofasciculus chthonoplastes* PCC 7420

(SEQ ID NO: 343)
CLSYDTQILTVEYGAVAIGEIVEKQIECTVYSVDE
NGYVYTQPIAQWHNRGEQEVFEYLLEDGATIRATK
DHKFMTDEDQMLPIDQIFEQGLELKQVEVL (SEQ ID NO: 344)
VKIIGRKPLGTQPVYDIGVERDHNFLLFNGSVASN

>CspPCC6712/1-133

(SEQ ID NO: 345)
CLSYDTEVLTVEYGAIPIGKIVEEKIACNVYSVDK
NGFVYTQPIAQYHDRCHQEVFEYRLENGSVIRATK
DHKMMTADGQMLPIDEIFKQNLDLKQLN

-continued

VKIISRQSLGKQSVFDIGVAKDHNFLLANGLVASN (SEQ ID NO: 346)

>Rbr:/1-137 Raphidiopsis brookii D9 D9_5,

CSYETEVLTLEYGFLPIGFIVDKQMVCTVFSVND (SEQ ID NO: 347)

SGNVYTQPIGQWHDRGVQELYEYCLDDGSTIRAT

KDHKFMTTQGEMVPIDEIFHQGWELVQVSGTMN

VKIVSRRYLGKADVYDIGVAKDHNFIIKNGLVASN (SEQ ID NO: 348)

>CspCCy0110:/1-134 Cyanothece sp. CCY0110 1101676644604

CLSYDTEILTVEYGPMPIGKIVEENINCSVYTVN (SEQ ID NO: 349)

KNGFWTQSIAQWHHRGEQEVFEYYLEDGETIRAT

KDHKFMTTEGKMLPIDEIFENNLDLKKLTV

VKIIERRSLGKQNVYDIGVERDHNFLLSNNLIASN (SEQ ID NO: 350)

>XspPCC7305:/1-135 Xenococcus sp. PCC 7305

CLSADTEVLTVEYGAISIGKIVEERIECTVYSVDA (SEQ ID NO: 351)

NGFVYTQEIAQWHNRGEQEVFEYMLDDGSV1RATK

DHKLMTIDGQMVAIDEIFSQGLELKQVLGL

VKIVSRKSLGTQTVYDLGVARDHNFLLANGTVASN (SEQ ID NO: 352)

>PspPCC7319:/1-135 Pleurocapsa sp. PCC 7319

CLSYDTEIYTVEYGALPIGKIVESRIKCTVLTVDK (SEQ ID NO: 353)

NGLVYSQPIVQWHDRGIQEVFEYTLDNGATIRATK

DHKFMTVEGQMLPIDEIFELGLELKEIQQF

VKIISRQSLGKQSVYDIGVAKDHNFLLANGMVASN (SEQ ID NO: 354)

>CraCS505:/1-137 Cylindrospermopsis raciborskii CS-505

CLSYETEVITLEYGFVPIGEIVNKQMVCTVFSLNDS (SEQ ID NO: 355)

GNVYTQPSGQWMDRGVQDLYEYCLDDGSTIRATKDH

KFMTTQGEMVPIDEIFHQGWELVQVSGISK

VKIVSRRYLGKADVYDIGVAKDHNFIIKNGLVASN (SEQ ID NO: 356)

>MaePCC7806:/1-135 Microcystis aeruginosa PCC 7806

CLGGETLILTEEYGLLPIAKIVSEEVNCTVYSVDK (SEQ ID NO: 357)

NGFVYSQPISQWHERGLQEVFEYTLENGQTIQATK

DHKFMTNDGEMLAIDTIFERGLDLKSSDFS

VKIISRQSLGRKPVYDIGVEKDHNFLLGNGLIASN (SEQ ID NO: 358)

>MaeNIES843:/1-135 Microcystis aeruginosa NIES-843 DNA

CLGGETLILTEFYGLLPIAKIVSEEINCTVYTVDQN (SEQ ID NO: 359)

GFVTSQPISQWHERGLQEVFEYTLENGQTIQATKDH

KFMTSDGEMLAIDTIFERGLDLKSSDFS

VKHGRQSLGRKPVYDIGVEKDHNFLLGNGLIASN (SEQ ID NO: 360)

FIG. 1 shows an alignment and a computer-generated model of the design of the Cfa split intein according to an embodiment of the invention. Panel A shows a sequence alignment of Npu DnaE and Cfa DnaE. The sequences share 82% identity with the differences (underlined, cyan) evenly distributed through the primary sequence. Catalytic residues and second shell 'accelerator' residues are shown in caret, orange and asterisk, green, respectively. Panel B shows the same residues highlighted in panel a mapped on to the Npu structure (pdb=4kl5).

The Cfa intein has high sequence similarity to Npu (82%), and the non-identical residues are spread throughout the 3D structure of the protein.

Figure 2:
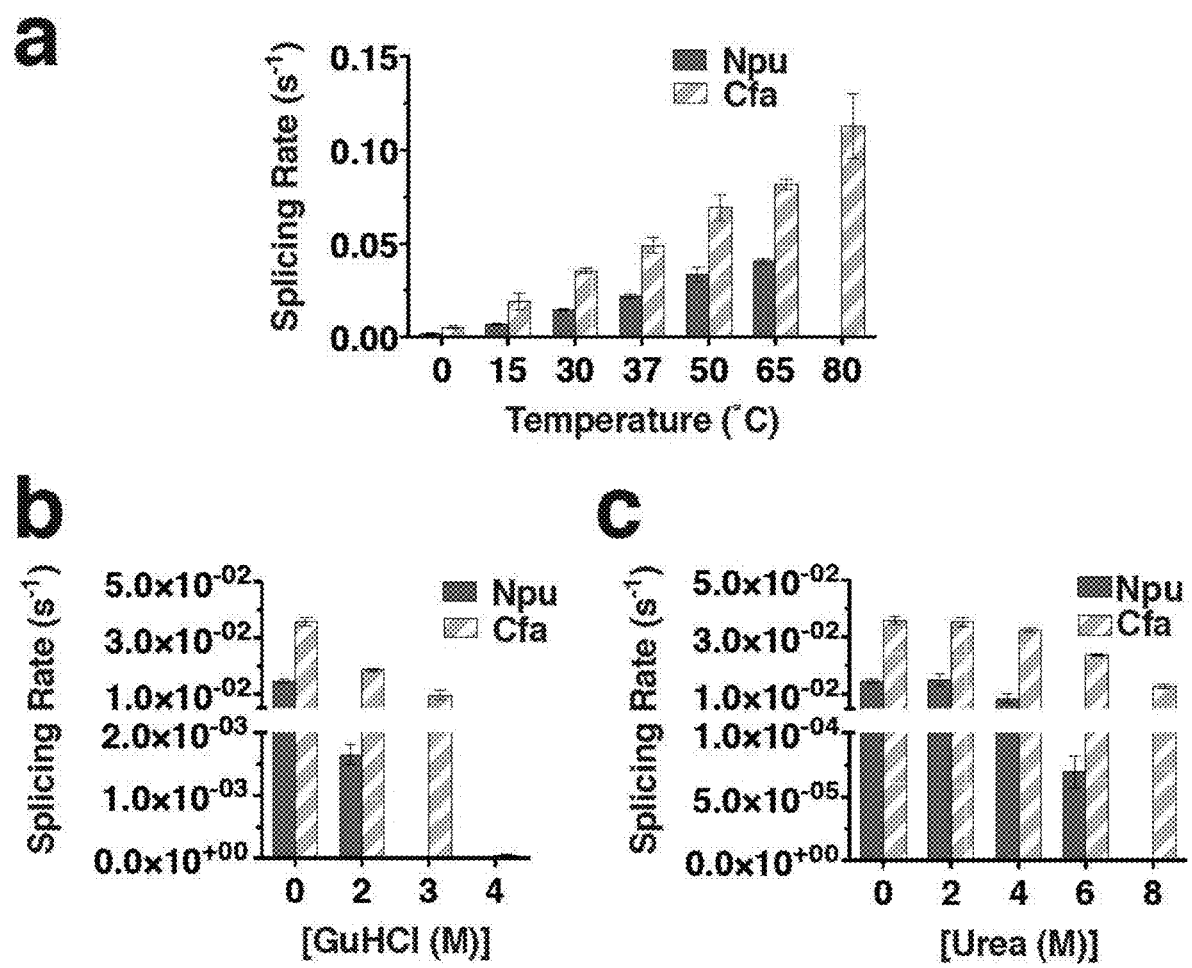
FIG. 2 shows graphs showing the characterization of the Cfa intein according to an embodiment of the invention.

Cfa intein fragments fused to model exteins were generate and their PTS activity was measured using the aforementioned in vitro assay (FIG. 2). This revealed that the Cfa intein splices 2.5 fold faster at 30° C. than Npu ($t_{1/2}$ 20 s vs. 50 s), a notable enhancement in activity since the latter is the fastest characterized DnaE split intein (FIG. 2A). This accelerated rate manifests itself both in branch formation (3-fold increase) and branch resolution (2-fold increase). In line with parent DnaE inteins. Cfa retains the preference for a bulky hydrophobic residue at the +2 position of the C-extein. Strikingly, Cfa shows an increased splicing rate as a function of temperature and is consistently faster than Npu (FIG. 2A). The Cfa intein even maintains activity at 80° C., albeit with reduced yield of splice products, while Npu is inactive at this temperature. These results demonstrate that consensus engineering is effective in producing an intein that is highly active across a broad range of temperatures.

Applications of PTS typically require fission of a target protein and fusion of the resulting fragments to the appropriate split intein segments.[1] As a consequence, the solubility of these fusion proteins can sometimes be poor. Because protein denaturants such as guanidine hydrochloride (GuHCl) and urea are frequently used to keep these less soluble fragments in solution, the ability of Cfa to splice in the presence of these chaotropic agents was tested. Cfa intein was found to splice in the presence of up to 4M GuHCl (with little decrease in activity seen up to 3M), while no activity was observed for Npu in ≥3M GuHCl (FIG. 2B). Remarkably, the splicing of Cfa is largely unaffected up to 8M urea, while splicing of Npu falls off dramatically above 4M urea (FIG. 2C).

FIG. 2 shows graphs showing the characterization of the Cfa intein according to an embodiment of the invention. In Panel A, splicing rates for Cfa and Npu as a function of temperature are shown. Npu is inactive at 80° C. (error=SD (n=3)). In Panels B and C, splicing rates for Cfa and Npu as a function of added chaotrope are shown. Npu is inactive in 3M GuHCl or 8M Urea. Note, Cfa has residual activity in 4M GuHCl ($k=7\times10^5$)(error=SD (n=3)).

The unprecedented and unexpected tolerance of Cfa to high concentrations of GuHCl and urea suggests the intein might retain activity directly following chaotropic extraction of insoluble proteins from bacterial inclusion bodies, thereby expediting PTS-based studies. Accordingly, the model fusion protein, $His_6$-Sumo-$Cfa^N$, was overexpressed in *E. coli* cells and extracted the protein from inclusion bodies with 6M urea. The protein was purified from this extract by nickel affinity chromatography and then directly, and efficiently, modified by PTS under denaturing conditions, i.e. without the need for any intervening refolding steps. In general, it is expected that the robust activity of Cfa in the presence of chaotropic agents will prove useful when working with protein fragments that demonstrate poor solubility under native conditions.

Figure 3A:
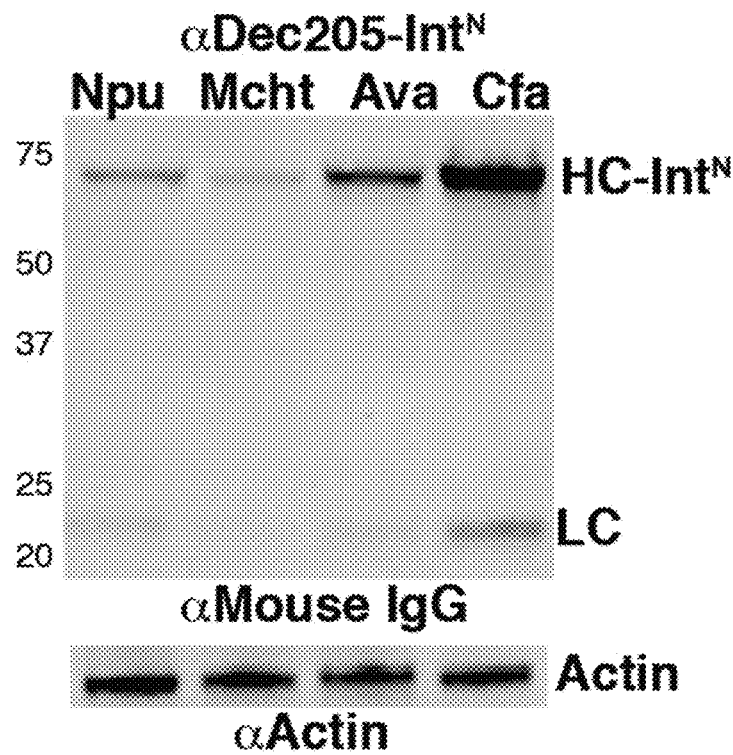
FIGS. 3A to 3E show expression and modification of a mouse monoclonal antibody using the Cfa intein according to an embodiment of the invention.
Figure 3B:
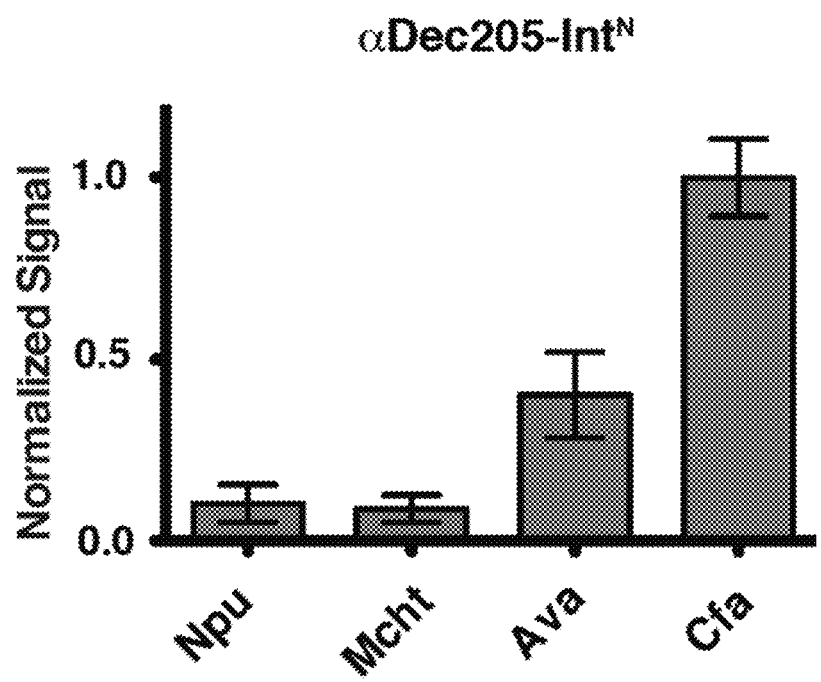
Figure 8:
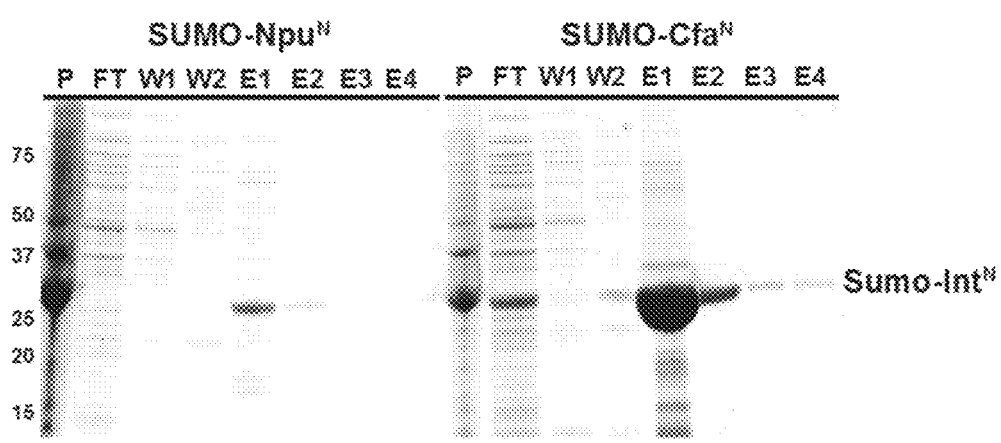
FIG. 8 is an image of an SDS-PAGE analysis of test expression of His$_6$-SUMO-Npu$^N$ and His$_6$-SUMO-Cfa$^N$ according to an embodiment of the invention.

Fusing a protein of interest to a split intein can result in a marked reduction in cellular expression levels compared to the protein alone.[6] This situation is more frequently encountered for fusions to N-inteins than to C-inteins, which is likely due to the larger size of the former and their partially folded state.[18] It was therefore investigated whether the improved thermal and chaotropic stability of Cfa would translate to increased expression levels of $Cfa^N$ fusions. Indeed, model studies in *E. coli* revealed a significant (30-fold) increase in soluble protein expression for a $Cfa^N$ fusion compared to the corresponding $Npu^N$ fusion (FIG. 8). Given this result, it was investigated whether $Cfa^N$ fusions would also exhibit increased protein expression levels in mammalian cells. In particular, intein fusions to the heavy chain (HC) of monoclonal antibodies (mAbs) have emerged as a powerful tool for site-specific conjugation of synthetic cargoes.[19-21] The expression levels in HEK293 cells of a mAb (αDec205) as a function of the N-intein fused to its HC was explored. Consistent with the bacterial expression results, production of the HC-$Cfa^N$ fusion was significantly higher than for the other inteins examined; for example, the secreted levels of the mAb-Cfa construct were ~10-fold higher than for the corresponding Npu fusion (FIGS. 3A and 3B). Importantly, mAb-Cfa retained PTS activity and could be site-specifically modified with a synthetic peptide by splicing directly in the growth medium following the four-day expression at 37° C.

FIG. 8 is an SDS-PAGE analysis of test expression of $His_6$-SUMO-$Npu^N$ and $His_6$-SUMO-$Cfa^N$. Coomassie brilliant blue stained gel from a 4 mL column volume (CV) Ni-NTA purification of the soluble fraction of 1 L of *E. coli* culture. Lanes correspond to (P) the inclusion body pellet, (FT) flow through of batch bound Ni-NTA solution, (W1) a 5 CV wash with 5 mM imidazole, (W2) a 5 CV wash of 25 mM imidazole, (E1-E4) and four 1.5 CV elutions of 250 mM imidazole.

Figure 3C:
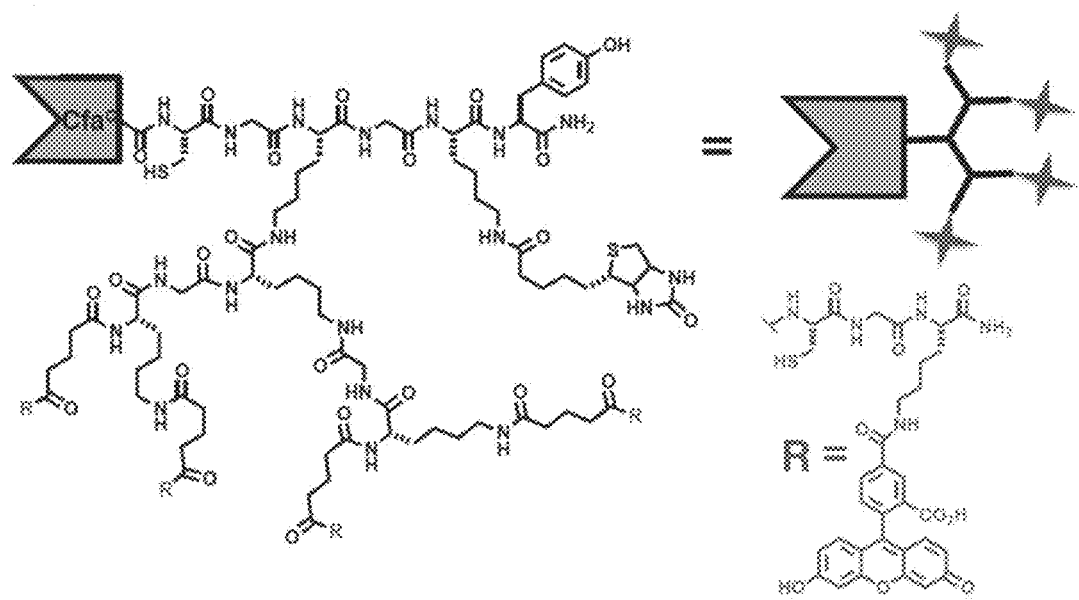
Figure 3D:
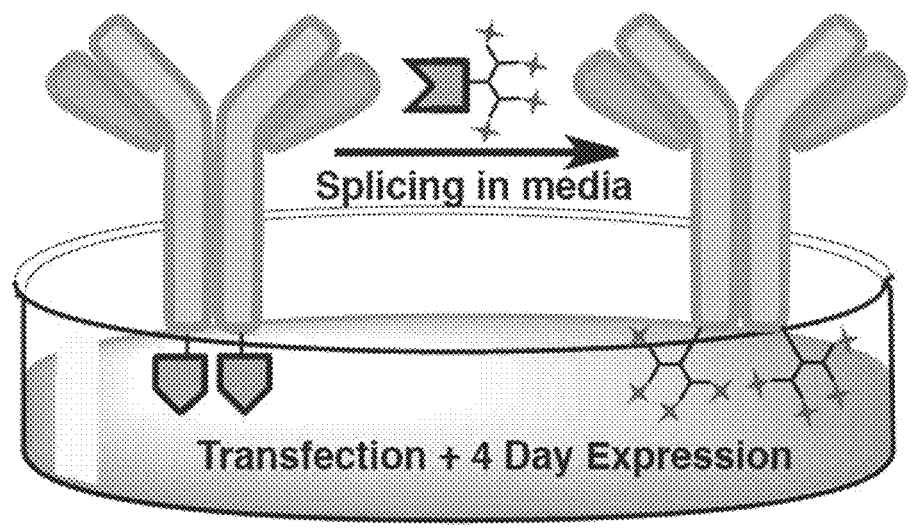
Figure 3E:
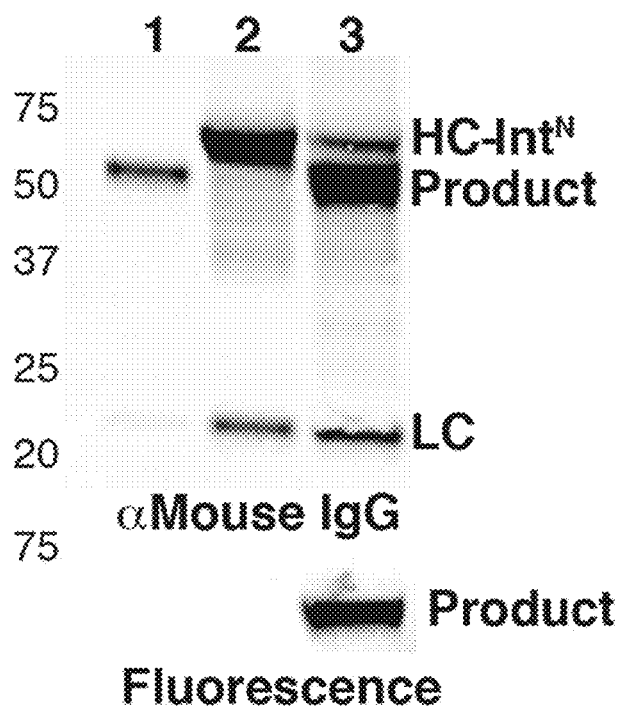

Finally, to further explore the utility of the Cfa intein in the context of antibody conjugation, whether the PTS system could be used to attach multiple copies of a synthetic cargo to the heavy chain of the mAb was investigated. Accordingly, semisynthesis was used to prepare a construct in which the C-terminal half of Cfa ($Cfa^C$) was fused to a C-extein containing a dendrimeric scaffold allowing multimeric attachment of cargo, in this case fluorescein (FIG. 3C). This dendritic cargo was successfully linked to the αDec205 antibody via Cfa-mediated PTS, again performed directly in situ within the cellular growth medium (FIGS. 3D and 3E). This represents the first time that PTS has been used to attach a branched extein construct to a target protein, highlighting the potential of the system for manipulating the payload quantity of antibody drug conjugates.[22]

FIGS. 3A to 3E show expression and modification of a mouse monoclonal antibody using the Cfa intein according to an embodiment of the invention. FIG. 3A shows test expression in HEK293T cells of various IntN homologues (Npu, Mcht, Ava and Cfa) fused to the C-terminus of the heavy chain of a mouse αDec205 monoclonal antibody. Top: Western blot analysis (αMouse IgG) of antibody levels present in the medium following the 96 hour expression. Bottom: α-actin western blot of cell lysate as a loading control. FIG. 3B shows quantification of normalized expression yield by densitometry of αDEC205 HC-IntN signal in panel A (error=SD (n=4)). FIG. 3C shows the structure of the CfaC-dendrimer construct used in PTS reactions with the αDEC205 HC-IntN fusion. For simplicity, the CfaC peptide sequence is depicted symbolically in green (as a rectangle with a triangular cut-out on the left). FIG. 3D is a schematic of the in situ PTS approach used to modify the HC of a mAb with a multivalent cargo. FIG. 3E is an SDS-PAGE analysis of PTS reaction. Lane 1: Wild type mouse αDEC205 mAB. Lane 2: Mouse αDEC205-CfaN mAB fusion. Lane 3: addition of the CfaC-dendrimer to the media containing the αDEC205-CfaN mAB. The splicing reaction was analyzed by fluorescence (bottom) and western blot (top, αMouse IgG).

The discovery of fast split inteins has revolutionized the applications of protein trans splicing. The remarkable robustness of the Cfa intein described in this study should extend the utility of many of these technologies by allowing PTS to be performed in a broader range of reaction conditions. Moreover, the ability of Cfa to increase the expression yields of N-intein fusions should encourage further use of split inteins for protein semisynthesis. The activity-guided approach we use to engineer this intein may be applied to other intein families or act as a general strategy for the refinement of multiple sequence alignments used for consensus engineering.

Materials and Methods

Materials

Oligonucleotides and synthetic genes were purchased from Integrated DNA Technologies (Coralville, IA). The QuickChange XL II site directed mutagenesis kit and Pfu Ultra II Hotsart fusion polymerase were purchased from Agilent (La Jolla, CA). All restriction enzymes and 2× Gibson Assembly Master Mix were purchased from New England Biolabs (Ipswich, MA). "In-house" high-competency cells used for cloning and protein expression were generated from One Shot Bl21 (DE3) chemically competent *E. coli* and sub-cloning efficiency DH5α competent cells purchased from Invitrogen (Carlsbad, CA). Dulbecco's Modified Eagle Medium (DMEM), Lipofectamine 2000, and low IgG fetal bovine serum were purchased from Invitrogen as well. DNA purification kits were purchased from Qiagen (Valencia, CA). All plasmids were sequenced by GENEWIZ (South Plainfield, NJ). N,N-diisopropylethylamine (DIPEA), Luria Bertani (LB) media, and all buffering salts were purchased from Fisher Scientific (Pittsburgh, PA). Dimethylformamide (DMF), dichloromethane (DCM), Coomassie brilliant blue, triisopropylsilane (TIS), β-Mercaptoethanol (BME), DL-dithiothreitol (DTT), sodium 2-mercaptoethanesulfonate (MESNa), tetrakis(triphenylphosphine)palladium(0) ($Pd(PPh_3)_4$), and 5(6)-carboxyfluorescein were purchased from Sigma-Aldrich (Milwaukee, WI) and used without further purification. Tris(2-carboxyethyl)phosphine hydrochloride (TCEP) and isopropyl-β-D-thiogalaetopyranoside (IPTG) were purchased from Gold Biotechnology (St. Louis, MO). The protease inhibitor used was the Roche Complete Protease Inhibitor (Roche, Branchburg, NJ). Nickel-nitrilotriacetic acid (Ni-NTA) resin was purchased from Thermo scientific (Rockford, IL). Fmoc amino acids were purchased from Novabiochem (Darmstadt, Germany) or Bachem (Torrance, CA). (7-Azabenzotriazol-1-yloxy)tripyrrolidinophosphonium hexafluorophosphate (PyAOP) and O-(Benzotriazol-1-yl)-N,N,N',N'-tetramethyluronium hexafluorophosphate (HBTU) were purchased from Genscript (Piscataway, NJ). Rink Amide-ChemMatrix resin was purchased from Biotage (Charlotte, NC). Trifluoroacetic acid (TFA) was purchased from Halocarbon (North Augusta, SC). Immun-blot PVDF membrane (0.2 μm) and Criterion XT Bis-Tris gels (12% polyacrylamide) were purchased from Bio-Rad (Hercules, CA). MES-SDS running buffer was purchased from Boston Bioproducts (Ashland, MA). Anti-Mouse IgG secondary antibody (Licor mouse 800) and Mouse αActin primary antibody were purchased from Li-COR biotechnology (Lincoln, NE).

Equipment

Analytical RP-HPLC was performed on Hewlett-Packard 1100 and 1200 series instruments equipped with a Cis Vydac column (5 μm, 4.6×150 mm) at a flow rate of 1 mL/min. Preparative RP-HPLC was performed on a Waters prep LC system comprised of a Waters 2545 Binary Gradient Module and a Waters 2489 UV detector. Purifications were carried out on a $C_{18}$ Vydac 218TP1022 column (10 μM; 22×250 mm) at a flow rate of 18 mL/min. All runs used 0.1% TFA (trifluoroacetic acid) in water (solvent A) and 90% acetonitrile in water with 0.1% TFA (solvent B). Unless otherwise stated, peptides and proteins were analyzed using the following gradient: 0% B for 2 minutes (isocratic) followed by 0-73% B over 30 minutes. Electrospray ionization mass spectrometric analysis (ESI-MS) was performed on a Bruker Daltonics MicroTOF-Q II mass spectrometer. Size-exclusion chromatography was carried out on an AKTA FPLC system (GE Healthcare) using a Superdex S75 16/60 (CV=125 mL) column. Coomassie-stained gels and western blots were imaged using a LI-COR Odyssey Infrared Imager. Fluorescent gels were imaged using a GE ImageQuant LAS 4000 Imager. The splicing-dependent E. coli growth assay was performed on a VersaMax tunable microplate reader from Molecular Devices. Cell lysis was carried out using a S-450D Branson Digital Sonifier.

Cloning of DNA Plasmids

All N-intein constructs for E. coli expression were cloned into previously used pET and pTXB1 vectors.[1] Plasmids encoding for WT pet30-His$_6$-SUMO-AEY-Ssp$^N$, pet30-His$_6$-SUMO-AEY-Npu$^N$, pTXB1-Ssp$^C$-MxeGyrA-His$_6$, and pTXB1-Npu$^C$-MxeGyrA-His$_6$ plasmids were cloned as previously described[1] and encode for the following protein sequences. Protein products after either SUMO cleavage (N-inteins) or thiolysis (C-inteins) are shown in bold for all plasmids.

```
Plasmid 1:
WT Ssp^N: pet30-His_6-SUMO-AEY-Ssp^N
                                           (SEQ ID NO: 361)
MGSSHHHHHHGSGLVPRGSASMSDSEVNQEAKPEVKPETHINLKV

SDGSSEIFFKIKKTTPLRRLMEAFAKRQGKEMDSLRFLYDGIRIQADQT

PEDLDMEDNDIIEAHREQIGGAEYCLSFGTEILTVEYGPLPIGKIVSEE

INCSVYSVDPEGRVVTQAIAQWHDRGEQEVLEYELEDGSVIRATSDHRF

LTTDYQLLAIEEIFARQLDLLTLENIKQTEEALDNHRLPFPLLDAGTIK
```

```
Plasmid 2:
WT Npu^N: pet30-His_6-SUMO-AEY-Npu^N
                                           (SEQ ID NO: 362)
MGSSHHHHHHGSGLVPRGSASMSDSEVNQEAKPEVKPETHINLKV

SDGSSEIFFKIKKTTPLRRLMEAFAKRQGKEMDSLRFLYDGIRIQADQT

PEDLDMEDNDIIEAHREQIGGAEYALSYETEILTVEYGLLPIGKIVEKR

IECTVYSVDNNGNIYTQPVAQWHDRGEQEVFEYCLEDGSLIRATKDHKF

MTVDGQMLPIDEIFERELDLMRVDNLPN
```

```
Plasmid 3:
WT Ssp^C: pTXB1-Ssp^C-MxeGyrA-His_6
                                           (SEQ ID NO: 363)
MVKVIGRRSLGVQRIFDIGLPQDHNFLLANGAIAANCITGDALVALPEG

ESVRIADIVPGARPNSDNAIDLKVLDRHGNPVLADRLFHSGEHPVYTVR

TVEGLRVTGTANHPLLCLVDVAGVPTLLWKLIDEIKPGDYAVIQRSAFS

VDCAGFARGKPEFAPTTYTVGVPGLVRFLEAHHRDPDAQAIADELTDGR

FYYAKVASVTDAGVQPVYSLRVDTADHAFITNGFVSHAHHHHHH
```

```
Plasmid 4:
WT Npu^C: pTXB1-Npu^C-MxeGyrA-His_6
                                           (SEQ ID NO: 364)
MIKIATRKYLGKQNVYDIGVERDHNFALKNGFIASNCITGDALVALPEG

ESVRIADIVPGARPNSDNAIDLKVLDRHGNPVLADRLFHSGEHPVYTVR

TVEGLRVTGTANHPLLCLVDVAGVPTLLWKLIDEIKPGDYAVIQRSAFS

VDCAGFARGKPEFAPTTYTVGVPGLVRFLEAHHRDPDAQAIADELTDGR

FYYAKVASVTDAGVQPVYSLRVDTADHAFITNGFVSHAHHHHHH
```

All Ssp$^N$ batch mutants were cloned using the QuikChange site directed mutagenesis kit using plasmid 1 as a template and encode for the protein sequences shown below. The N-intein sequence is shown in bold with the residues corresponding to the batch mutation underlined.

```
Plasmid 5:
Batch 1: Pet30-His_6-SUMO-AEY-Ssp^N (R73K, L75M,
Y79G, L81M)
                                           (SEQ ID NO: 365)
MGSSHHHHHHGSGLVPRGSASMSDSEVNQEAKPEVKPETHINLKVS

DGSSEIFFKIKKTTPLRRLMEAFAKRQGKEMDSLRFLYDGIRIQADQTPE

DLDMEDNDIIEAHREQIGGAEYCLSFGTEILTVEYGPLPIGKIVSEEINC

SVYSVDPEGRVYTQAIAQWHDRGEQEVLEYELEDGSVIRATSDHKFMTTD

GQMLAIEEIFARQLDLLTLENIKQTEEALDNHRLPFPLLDAGTIK
```

```
Plasmid 6:
Ssp^N R73K: Pet30-His_6-SUMO-AEY-Ssp^N (R73K)
                                           (SEQ ID NO: 366)
MGSSHHHHHHGSGLVPRGSASMSDSEVNQEAKPEVKPETHINLKVS

DGSSEIFFKIKKTTPLRRLMEAFAKRQGKEMDSLRFLYDGIRIQADQTPE

DLDMEDNDIIEAHREQIGGAEYCLSFGTEILTVEYGPLPIGKIVSEEINC

SVYSVDPEGRVYTQAIAQWHDRGEQEVLEYELEDGSVIRATSDHKFLTTD

YQLLAIEEIFARQLDLLTLENIKQTEEALDNHRLPFPLLDAGTIK
```

Plasmid 7:
Ssp$^N$ R73K Y79G: Pet30-His$_6$-SUMO-AEY-Ssp$^N$ (R73K, Y79G)
(SEQ ID NO: 367)
MGSSHHHHHHGSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDIIEAHREQIGGAEYCLSFGTEILTVEYGPLPIGKIVSEEINC

SVYSVDPEGRVYTQAIAQWHDRGEQEVLEYELEDGSVIRATSDHKFLTTD

GQLLAIEEIFARQLDLLTLENIKQTEEALDNHRLPFPLLDAGTIK

Plasmid 8:
Ssp$^N$ R73K Y79G L81M: Pet30-His$_6$-SUMO-AEY-Ssp$^N$ (R73K, Y79G, L81M)
(SEQ ID NO: 368)
MGSSHHHHHHGSGLVPRGSASMSDSEVNQEAKPEVKPEVKPETHINLKVS

DGSSEIFFKIKKTTPLRRLMEAFAKQGKEMDSLRFLYDGIRIQADQTPED

LDMEDNDIIEAHREQIGGAEYCLSFGTEILTVEYGPLPIGKIVSEEINCS

VYSVDPEGRVYTQAIAQWHDRGEQEVLEYELEDGSVIRATSDHKFLTTDG

QMLAIEEIFARQLDLLTLENIKQTEEALDNHRLPFPLLDAGTIK

Plasmid 9:
Batch 2: Pet30-His$_6$-SUMO-AEY-Ssp$^N$ (L56F, S70K, A83P, E85D)
(SEQ ID NO: 369)
MGSSHHHHHHGSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDIIEAHREQIGGAEYCLSFGTEILTVEYGPLPIGKIVSEEINC

SVYSVDPEGRVYTQAIAQWHDRGEQEVFEYELEDGSVIRATKDHRFLTTD

YQLLPIDEIFARQLDLLTLENIKQTEEALDNHRLPFPLLDAGTIK

Plasmid 10:
Ssp$^N$ A83P: Pet30-His$_6$-SUMO-AEY-Ssp$^N$ (A38P)
(SEQ ID NO: 370)
MGSSHHHHHHGSGLVPRGSASMSDSEVNQEAKPEVKPEVKPETHINLKVS

DGSSEIFFKIKKTTPLRRLMEAKFAKRQGKEMDSLRFLYDGIRIQADQTP

EDLDMEDNDIIEHREQIGGAEYCLSFGTEILTVEYGPLPIGKIVSEEINC

SVYSVDPEFRVYTQAIAQWHDRGEQEVLEYELEDGSVIRATSDHRFLTTD

YQLLPIEEIFARQLDLLTLENIKQTEEALDNHRLPFPLLDAGTIK

Plasmid 11:
Ssp$^N$ S37K A83P: Pet30-His$_6$-SUMO-AEY-Ssp$^N$ (S70K, A83P)
(SEQ ID NO: 371)
MGSSHHHHHHGSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDIIEAHREQIGGAEYCLSFGTEILTVEYGPLPIGKIVSEEINC

SVYSVDPEGRVYTQAIAQWHDRGEQEVLEYELEDGSVIRATKDHRFLTTD

YQLLPIEEIFARQLDLLTLENIKQTEEALDNHRLPFPLLDAGTIK

Plasmid 12:
Ssp$^N$ L56, S70K, A83P: Pet30-His$_6$-SUMO-AEY-Ssp$^N$ (L56F, S70K, A83P)
(SEQ ID NO: 372)
MGSSHHHHHHGSGLVPRGSASMSDSEVNQEAKPEVKPEVKPETHINLKVS

DGSSEIFFKIKKTTPLRRLMEAKAKRQGKEMDSLRFLYDGIRIQADQTPE

DLDMEDNDIIEAHREQIGGAEYCLSFGTEILTVEYGPLPIGKIVSEEINC

SVYSVDPEGRVYTQAIAQWHDRGEQEVFEYELEDGSVIRATKDHRFLTTD

YQLLPIEEIFARQLDLLTLENIKQTEEALDNHRLPFPLLDAGTIK

Plasmid 13:
Batch 3: Pet30-His$_6$-SUMO-AEY-Ssp$^N$ (S23E, E24K, E25R, N27E)
(SEQ ID NO: 373)
MGSSHHHHHHGSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDIIEAHREQIGGAEYCLSFGTEILTVEYGPLPIGKIVEKRIEC

SVYSVDPEGRVYTQAIAQWHDRGEQEVLEYELEDGSVIRATSDHRFLTTD

YQLLAIEEIFARQLDLLTLENIKQTEEALDNHRLPFPLLDAGTIK

Plasmid 14:
Batch 4: Pet30-His$_6$-SUMO-AEY-Ssp$^N$ (P35N, E36N, R38N, V39I)
(SEQ ID NO: 374)
MGSSHHHHHHGSGLVPRGSASMSDSEVNQEAKPEVKPEVKPETHINLKVS

DGSSEIFFKIKKTTPLRRLMEAKAKRQGKEMDSLRFLYDGIRIQADQTPE

DLDMEDNDIIEAHREQIGGAEYCLSFGTEILTVEYGPLPIGKIVSEEINC

SVYSVDNNGNIYTQAIAQWHDRGEQEVLEYELEDGSVIRATSDHRFLTTD

YQLLAIEEIFARQLDLLTLENIKQTEEALDNHRLPFPLLDAGTIK

The four batch mutants (Batches 5-8) and A136S point mutant on the Ssp$^C$ intein were cloned by inverse PCR using Pfu Ultra 11 HS Polymerase (Agilent) using plasmid 3 as a template and code the protein sequences shown below:

Plasmid 15:
Batch 5: pTXB1-Ssp$^C$-MxeGyrA-His$_6$ (V103I, V105I, I106A, G107T)
(SEQ ID NO: 375)
MIKIATRRSLGVQRIFDIGLPQDHNFLLANGAIAANCITGDALVALPEGE

SVRIADIVPGARPNSDNAIDLKVLDRHGNPLVLADRLFHSGEHPVYTVRT

VEGLRVTGTANHPLLCLVDVAGVPTLLWKLIKEIKPGDYAVIQRSAFSVD

CAGFARGKPEEAPTTYTVGVPGLVRFLEAHHRDPDAQAIADELTDGRFYY

AKVASVTDAGVQPVYSLRVDTADHAFITNGFVSHAHHHHHH

Plasmid 16:
Batch 6: pTXB1-Ssp$^C$-MxeGyrA-His$_6$ (R115N, I116V, F117Y)
(SEQ ID NO: 376)
MVKVIGRRSLGVQNVYDIGLPQDHNFLLANGAIAANCITGDALVALPEGE

SVRIADIVPGARPNSDNAIDLKVLDRHGNPVLADRLFHSGEHPVYTVRTV

EGLRVTGTANHPLLCLVDVAGVPTLLWKLIKEIKPGDYAVIQRSAFSVDC

AGFARGKPEFAPTTYTVGVPGLVRFLEAHHRDPDAQAIADELTDGRFYYA

KVASVTDAGVQPVYSLRVDTADHAFITNGFVSHAHHHHHH

Plasmid 17:
Batch 7 pTXB1-Ssp$^C$-MxeGyrA-His$_6$ (L121V, P122E, Q123R)
(SEQ ID NO: 377)
MVKVIGRRSLGVQRIFDIGVERDHNFLLANGAIAANCITGDALVALPEGE

SVRIADIVPGARPNSDNAIDLKVLDRHGNPVLADRLFHSGEHPVYTVRTV

EGLRVTGTANHPLLCLVDVAGVPTLLWKLIKEIKPGDYAVIQRSAFSVDC

AGFARGKPEFAPTTYTVGVPGLVRFLEAHHRDPDAQAIADELTDGRFYYA

KVASVTDAGVQPVYSLRVDTADHAFITNGFVSHAHHHHHH

-continued

Plasmid 18:
Batch 8: pTXB1-Ssp$^C$-MxeGyrA-His$_6$ (L128A, A130K, A133F)
(SEQ ID NO: 378)
MVKVIGRRSLGVQRIFDIGLPQDHNFALKNGFIAANCITGDALVALPEGE

SVRIADIVPGARPNSDNAIDLKVLDRHGNPVLADRLFHSGEHPVYTVRTV

EGLRVTGTANHPLLCLVDVAGVPTLLWKLIKEIKPGDYAVIQRSAFSVDC

AGFARGKPEFAPTTYTVGVPGLVRFLEAHHRDPDAQAIADELTDGRFYYA

KVASVTDAGVQPVYSLRVDTADHAFITNGFVSHAHHHHHH

Plasmid 19:
Ssp$^C$ A136S: pTXB1-Ssp$^C$-MxeGyrA-His$_6$ (A136S)
(SEQ ID NO: 379)
MVKVIGRRSLGVQRIFDIGLPQDHNFLLANGAIASNCITGDALVALPEGE

SVRIADIVPGARPNSDNAIDLKVLDRHGNPVLADRLFHSGEHPVYTVRTV

EGLRVTGTANHPLLCLVDVAGVPTLLWKLIDEIKPGDYAVIQRSAFSVDC

AGFARGKPEFAPTTYTVGVPGLVRFLEAHHRDPDAQAIADELTDGRFYYA

KVASVTDAGVQPVYSLRVDTADHAFITNGFVSHAHHHHHH

The gene for the fused Consensus DnaE sequence was codon-optimized for *E. coli* expression through IDT DNA and purchased as a gBlock. The DNA gBlock sequence is shown below:

(SEQ ID NO: 380)
TGCCTGTCTTACGACACAGAGATTCTGACCGTTGAATATGGATTCCTTCC

TATCGGTAAGATCGTGGAGGAACGGATTGAATGCACAGTCTATACGGTAG

ATAAAAATGGCTTTGTGTATACACAACCTATTGCTCAGTGGCATAACCGG

GGAGAACAGGAAGTTTTCGAATACTGCTTAGAAGACGGTTCGATTATCCG

TGCAACGAAAGATCACAAATTTATGACGACCGACGGTCAGATGTTACCGA

TTGATGAGATTTTCGAACGGGGGTTAGACCTGAAACAAGTTGATGGTTTG

CCGATGGTCAAGATCATTAGTCGTAAGAGTCTGGGCACTCAAAACGTCTA

CGATATTGGAGTAGAAAAAGATCATAATTTTTTGCTGAAGAATGGGCTGG

TGGCCTCTAAC

The expression plasmid for Cfa$^N$ was cloned using Gibson assembly into plasmid 1, yielding a vector coding for the following protein shown below:

Plasmid 20:
Cfa$^N$: pET3-His$_6$-SUMO-AEY-Cfa$^N$
(SEQ ID NO: 381)
MGSSHHHHHHGSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDIIEAHREQIGGAEYCLSYDTEILTVEYGFLPIGKIVEERIEC

TVYTVDKNGFVYTQPIAQWHNRGEQEVFEYCLEDGSIIRATKDHKFMTTD

GQMLPIDEIFERGLDLKQVDGLP

The expression plasmid for the Consensus C-intein was cloned using Gibson Assembly into plasmid 3, yielding a vector coding for the following gene:

Plasmid 21:
Cfa$^C$: pTXB1-Cfa$^C$-MxeGyrA-H6
(SEQ ID NO: 382)
MVKIISRKSLGTQNVYDIGVEKDHNFLLKNGLVASNCITGDALVALPEGE

SVRIADIVPGARPNSDNAIDLKVLDRHGNPVLADRLFHSGEHPVYTVRTV

EGLRVTGTANHPLLCLVDVAGVPTLLVKLIDEIKPGDYAVIQRSAFSVDC

AGFARGKPEFAPTTYTVGVPGLVRFLEAHHRDPDAQAIADELTDGRFYYA

KVASVTDAGVQPVYSLRVDTADHAFITNGFVSHAHHHHHH

Cfa constructs used for *E. coli* growth screen.
Cfa plasmids used to screen the dependency of splicing at the +2 position of the C-extein were generating using restriction cloning into a previously generated plasmid[2] containing a dual expression system of the split aminoglycoside phosphotransferase (Kan$^R$) gene. The Cfa dual expression construct is shown below:
Plasmids 22-25
[KanR Promoter]-[RBS]-[KanR$^N$]-[Cfa$^N$]-[iRBS]-Cfa$^C$[CXN-KanR$^C$]

Following the promoter sequence, there are two separate *E. coli* ribosomal binding sites in this vector (RBS and iRBS). Each RBS is followed by one half of the split KanR-Intein construct, whose protein sequences are shown below (the Cfa intein is highlighted in bold).

KanR$^N$-Cfa$^N$:
(SEQ ID NO: 384)
MEQKLISEEDLSHIQRETSCSRPRLNSNMDADLYGYKWARDNVGQSGATI

YRLYGKPDAPELFLKHGKGSVANDVTDEMVRLNWLTEFMPLPTIKHFIRT

PDDAWLLTTAIPGKTAFQVLEEYPDSGENIVDALAVFLRRLHSIPVCNCP

FNSDRVFRLAQAQSRMNNGLVDASDFDDERNGWPVEQVWKEMHKLLPFCL

SYDTEILTVEYGFLPIGKIVEERIECTVYTVDKNGFVYTQPIAQWHNRGE

QEVFEYCLEDGSIIRATKDHKFMTTDGQMLPIDEIFERGLDLKQVDGLP

Cfa$^C$-KanR$^C$
(SEQ ID NO: 385)
MVKIISRKSLGTQNVYDIGVEKDHNFLLKNGLVASNCXNSVVTHGDFSLD

NLIFDEGKLIGCIDVGRVGIADRYQDLAILWNCLGEFSPSLQKRLFQKYG

IDNPDMNKLQFHLMLDEFF

The +2 position of the C-extein is underlined, and is either phenylalanine, glycine, arginine, or glutamate.
αDEC205-HC-Cfa$^N$
pCMV Plasmids containing the αDEC205 antibody light chain (LC), heavy chain (HC), and HC-intein fusions (HC-Npu$^N$, HC-Mcht$^N$-Ava$^N$) were obtained as previously described.[3] A codon-optimized Cfa DnaE sequence for mammalian cell expression was generated using JCAT[4] and purchased as a gBlock through IDT DNA. The sequence is shown below:

(SEQ ID NO: 386)
TGCCTGAGCTACGACACCGAGATCCTGACCGTGGAGTACGGCTTCCTGCC

CATCGGCAAGATCGTGGAGGAGCGCATCGAGTGCACCGTGTACACCGTGG

-continued

ACAAGAACGGCTTCGTGTACACCCAGCCCATCGCCCAGTGGCACAACCGC

GGCGAGCAGGAGGTGTTCGAGTACTGCCTGGAGGACGGCAGCATCATCCG

CGCCACCAAGGACCACAAGTTCATGACCACCGACGGCCAGATGCTGCCCA

TCGACGAGATCTTCGAGCGCGGCCTGGACCTGAAGCAGGTGGACGGCCTG

CCCGTGAAGATCATCAGCCGCAAGAGCCTGGGCACCCAGAACGTGTACGA

CATCGGCGTGGAGAAGGACCACAACTTCCTGCTGAAGAACGGCCTGGTGG

CCAGCAAC

The mammalian codon-optimized Cfa$^N$ sequence was then cloned into the pCMV HC-Npu$^N$ plasmid using restriction cloning to give a sequence coding for the following protein:

```
Plasmid 26:
HC-Cfa^N: pCMV-HC-Cfa^N
                                               (SEQ ID NO: 387)
MGWSCIILFLVATATGVHSEVKLLESGGGLVQPGGSLRLSCAASGFTFND

FYMNWIRQPPGQAPEWLGVIRNKGNGYTTEVNTSVKGRFTISRDNTQNIL

YLQMNSLRAEDTAIYYCARGGPYYYSGDDAPYWGQGVMVTVSSATTKGPS

VYPLAPSGSAAQTNSMVTLGCLVKGYFPEPVTVTWNSGLSLSSGVHTFPA

VLQSDLYTLSSSVTVPSSTWPSETVTCNVAHPASSTKVDKKIVPRDCGCK

PCICTVPEVSSVFIFPPKPKDVLTITLTPKVTCVVVAISKDDPEVQFSWF

VDDVEVHTAQTQPREEQFNSTFRSVSELPIMHQDWLNGKEFKCRVNSAAF

PAPIEKTISKTKGRPKAPQVYTIPPPKEQMAKDKVSLTCMITDFFPEDIT

VEWQWNGQPAENYKNTQPIMDTDGSYFVYSKLNVQKSNWEAGNTFTCSVL

HEGLHNHHTEKSLSHSPGKASGGCLSYDTEILTVEYGFLPIGKIVEERIE

CTVYTVDKNGFVYTQPIAQWHNRGEQEVFEYCLEDGSIIRATKDHKFMTT

DGQMLPIDEIFERGLDLKQVDGLPGHHHHHHG
```

Cfa$^C$ Intein for Ligation of Dendrimer:

A plasmid containing the Cfa C-intein with a C-extein linker was cloned by inverse PCR into plasmid 21 and codes for the protein sequence shown below:

```
Plasmid 27:
Cfa^C-link: pTXB1-H6-Cfa^C-CFNSGG-MxeGyrA-H6
                                               (SEQ ID NO: 388)
MGHHHHHHSGVKIISRKSLGTQNVYDIGVEKDHNFLLKNGLVASNCFNSG

GCITGDALVALPEGESVRIADIVPGARPNSDNAIDLKVLDRHGNPVLADR

LFHSGEHPVYTVRTVEGLRVTGTANHPLLCLVDVAGVPTLLWKLIKEIKP

GDYAVIQRSAFSVDCAGFARGKPEFAPTTYTVGVPGLVRFLEAHHRDPDA

QAIADELTDGRFYYAKVASVTDAGVQPVYSLRVDTADHAFITNGFVSHAH

HHHHH
```

The expression and purification protocols of all His$_6$-SUMO-AEY-Int$^N$ (plasmids 1, 2, 5-14, 20) and Int$^C$-GyrA-His$_6$ (plasmids 3, 4, 15-19, 21 27) constructs were adapted from previously described methods.[1]

Expression of all His$_6$-SUMO-AEY-Int$^N$ Constructs

E. coli BL21(DE3) cells were transformed with an N-intein plasmid and grown at 37° C. in 1 L of LB containing 50 μg/mL of kanamycin. Once the culture had reached an OD$_{600}$=0.6, 0.5 mM IPTG was added to induce expression (0.5 mM final concentration, 3 hr at 37° C.). The cells were pelleted via centrifugation (10,500 ref, 30 min) and stored at −80° C.

Purification of all His$_6$-SUMO-AEY-Int$^N$ Constructs
Purification of N-Intein Constructs for Batch Mutagenesis The cell pellets (from expression of plasmids 1, 2, 5-14) were resuspended in 30 mL of lysis buffer (50 mM phosphate, 300 mM NaCl, 5 mM imidazole, pH 8.0) containing Roche Complete protease inhibitor cocktail. The resuspended cells were then lysed by sonication on ice (35% amplitude, 8×20 second pulses on/30 seconds off). The insoluble inclusion body containing the N-intein was recovered by centrifugation (35,000 rcf, 30 min). The supernatant was discarded and the pellet was resuspended in 30 mL of Triton wash buffer (lysis buffer with 0.1% triton X-100) and incubated at room temperature for 30 minutes. The Triton wash was then centrifuged at 35,000 rcf for 30 minutes. The supernatant was discarded, the inclusion body pellet was resuspended in 30 mL of lysis buffer containing 6M Urea, and the suspension was incubated overnight at 4° C. to extract and resolubilize the protein. This mixture was then centrifuged at 35,000 rcf for 30 minutes.

The supernatant was then mixed with 4 mL of Ni-NTA resin (for affinity purification using the His$_6$ tag) and incubated at 4° C. for 30 minutes to batch bind the protein. This mixture was loaded on a fritted column, the flow through was collected, and the column was washed with 5 column volumes (CV) of lysis buffer with 6M Urea and 5 CV of lysis buffer with 25 mM imidazole and 6M urea. The protein was then eluted in four 1.5 CV fractions of lysis buffer with 250 mM imidazole and 6M Urea. The first two elution fractions were generally found by SDS-PAGE (12% Bis-Tris gel, run for 50 minutes at 170V) to contain the expressed protein and were combined for refolding.

The N-inteins were refolded by stepwise dialysis into lysis buffer with 0.5 mM DTT at 4° C. This refolded protein was then treated with 10 mM TCEP and Ulp1 protease (overnight, RT) to cleave the His$_6$-SUMO expression tag. The solution was then mixed with 4 mL Ni-NTA resin and incubated for 30 minutes at 4° C. The slurry was applied to a fritted column and the flow through was collected together with a 3 CV wash with lysis buffer. The protein us then treated with 10 mM TCEP, concentrated to 10 mL, and further purified by size exclusion chromatography using an S75 16/60 gel filtration column employing degassed splicing buffer (100 mM sodium phosphate, 150 mM NaCl, 1 mM EDTA, pH 7.2) as the mobile phase. Fractions were analyzed by SDS-PAGE, analytical RP-HPLC, and ESI-MS. Pure protein was stored by flash-freezing in liquid N$_2$ following the addition of glycerol (20% v/v). Note: during the refolding step, significant protein precipitation was observed for Batch 3, suggesting it is prone to aggregation.

Purification of Cfa$^N$:

The cell pellet (from expression of plasmid 20) was first resuspended in 30 mL of lysis buffer (50 mM phosphate, 300 mM NaCl, 5 mM imidazole. pH 8.0) containing the Roche Complete protease inhibitor cocktail. The cells were then lysed by sonication (35% amplitude, 8×20 second pulses on/30 seconds off), and the lysate was pelleted by centrifugation (35,000 rcf, 30 min). The supernatant was incubated with 4 mL of Ni-NTA resin for 30 minutes at 4° C. to enrich for the soluble Cfa$^N$ protein. The slurry was then loaded onto a fritted column, and the column was washed with 20 mL of wash buffer 1 (lysis buffer) followed by 20 mL of wash buffer 2 (lysis buffer with 25 mM imidazole). Finally, the protein was eluted from the column with 4×1.5 CV of elution buffer (lysis buffer +250 mM imidazole).

The desired protein, which was present in elution fractions 1 and 2 as determined by SDS-PAGE (12% bis-tris gel run in MES-SDS running buffer at 170V for 50 minutes), was then dialyzed into lysis buffer for 4 hours at 4° C. Following dialysis, the protein was treated with 10 mM TCEP and Ulp1 protease overnight at room temperature to cleave the $His_6$-SUMO expression tag. The solution was then incubated with 4 mL Ni-NTA resin for 30 minutes at 4° C. The slurry was applied to a fritted column and the flow through was collected together with a 3 CV wash with lysis buffer. The protein was then treated with 10 mM TCEP, concentrated to 10 mL, and purified over an S75 16/60 gel filtration column employing degassed splicing buffer (100 mM sodium phosphate, 150 mM NaCl, 1 mM EDTA, pH 7.2) as the mobile phase. Fractions were analyzed by SDS-PAGE (12% bis-tris gel run in MES-SDS running buffer at 170V for 60 minutes), analytical RP-HPLC, and ESI-MS. Pure Protein was stored in glycerol (20% v/v) and flash-frozen in liquid $N_2$.

Semisynthesis of $Int^C$-CFN Constructs

E. coli BL21 (DE3) cells were transformed with the appropriate pTXB1-$Int^C$-GyrA-$H_6$ plasmid (plasmids 3, 4, 15-19, 21) and grown in 2 L of LB media containing ampicillin (100 µg/mL) at 37° C. Once the culture had reached an $OD_{600}$=0.6, expression was induced by the addition of IPTG (0.5 mM, 3 hours, 37° C.). Cell pellets were harvested by centrifugation (10,500 rcf, 30 min), resuspended in lysis buffer, and lysed by sonication on ice (35% amplitude, 10×20 second pulses on/30 seconds off). The protein in the soluble fraction was isolated by centrifugation (35,000 rcf, 30 min) and then enriched by Ni-NTA purification (4 mL beads, carried out as described for N-intein constructs). Following elution in lysis buffer with 250 mM imidazole, the imidazole was removed by dialysis into fresh lysis buffer. The ligation was then carried out overnight at room temperature with the addition of 10 mM TCEP, the Roche Complete protease inhibitor cocktail, 100 mM MESNa, 5 mM EDTA, and 5 mM CFN—$NH_2$ (pH 7.0). The ligated $Int^C$-CFN peptide was acidified with 0.5% TFA and purified via RP-HPLC on a $C_{18}$ preparative column: Gradient=10% B for 10 minutes (isocratic) followed by 20-60% B over 60 minutes. The purity of each protein was determined by analytical RP-HPLC and its identity was confirmed by ESI-MS.

Isolation of $Cfa^C$-link-MESNa

The $Cfa^C$-link-MESNa peptide used for the semisynthesis of the Intein-dendrimer fusion was expressed and purified exactly as described above for the $Int^C$-CFN constructs (expression from plasmid 27). However, no tripeptide was added during the final ligation step, instead resulting in thiolysis of the intein and formation of an α-thioester. This $Cfa^C$-MESNa α-thioester was then purified by preparative RP-HPLC. Fractions were analyzed by ESI-MS, combined, and lyophilized.

Analysis of protein trans-splicing by RP-HPLC and ESI-MS for Batch Mutants.

Splicing reactions were carried out as adapted from a previously described protocol.[1] Briefly, N- and C-inteins (15 µM $Int^N$, 10 µM $Int^C$) were individually preincubated in splicing buffer (100 mM sodium phosphates, 150 mM NaCl, 1 mM EDTA, pH 7.2) with 2 mM TCEP for 15 minutes. All splicing reactions were carried out at 30° C. unless otherwise indicated. Splicing reactions comparing the tolerance of Npu and Cfa to chaotropic agents were carried out with the indicated concentration of either Urea or guanidine hydrochloride. Splicing was initiated by mixing equal volumes of N- and C-inteins with aliquots removed at the indicated times and quenched by the addition of 8M guanidine hydrochloride, 4% TFA (3:1 v/v). For all splicing reactions containing either $Npu^C$-CFN or $Cfa^C$-CFN, reaction progress was monitored by RP-HPLC. For all splicing reactions containing $Ssp^C$-CFN, reaction progress was monitored by ESI-MS (samples desalted with ZipTip prior to injection) due to poor chromatographic resolution of each state as seen previously.[1] Splicing for Batch 3 and for Cfa at 80° C. (15 minute preincubation) were both observed to be inefficient, reaching ~50% completion. This is likely due to aggregation (and inactivation) of the N-intein. Note, shorter preincubations of Cfa at 80° C. led to more efficient splicing.

Kinetic analysis of trans-splicing reactions of Batch Mutants:

Kinetic analysis was carried out as previously described.[1] Briefly, five species (1-5) are separated by RP-HPLC, and peak areas are determined. For ESI-MS, peak areas are calculated for species 1-4. Each individual peak was normalized against the total area of all peaks combined and reaction progress curves were plotted (n=3). The data were then fit in ProFit to the analytical solution to the coupled differential rate equation for the three state kinetic splicing model. Because the starting material cannot be separated from the linear thioester using this assay, the three state kinetic model collapses the binding step and the first two steps of the splicing reaction into one equilibrium. Each splicing reaction was carried out in triplicate with each replicate analyzed separately. The mean and standard deviation for all values (n=3) are reported.

Kinetic Analysis of Overall Trans-Splicing Reactions for Npu and Cfa

All splicing reactions comparing Npu and Cfa were separated by RP-HPLC with peak areas once again calculated using the manufacturer's software. For these reactions, peak areas for the starting material and branched intermediate (species 1 and 2) and product (species 3, 4, 5) were calculated. The data was then fit to the first order rate equation using the GraphPad Prism software.

$$[P](t)=[P]_{max} \cdot (1-e^{-kt})$$

Where [P] is the normalized intensity of product, $[P]_{max}$ is this value at t=∞ (the reaction plateau), and k is the rate constant ($s^{-1}$). The mean and standard deviation (n=3) are reported.

Generation and refinement of the DnaE Intein Multiple Sequence alignment.

Homologues of Npu DnaE were identified through a BLAST[5] search of the NCBI[6] (nucleotide collection) and JGI[7] databases using the Npu DnaE protein sequences. This led to the identification of 105 proteins with >60% sequence identity. For N-inteins with long C-terminal tails, the proteins were truncated to 102 residues, the length of Npu. For N-inteins from the JGI database, the point of truncation was determined by the results of the BLAST program (the last residue identified in the Blast search was selected as the truncation point). Next, a multiple sequence alignment (MSA) was generated of the fused sequence (i.e. the N-intein connected to the C-intein) of all 105 inteins in Jalview (FIGS. 7A.1 to 7A.3, 7B.1 to 7B.3, 7C.1 to 7C.3, 7D.1 to 7D.3, and 7E.1 to 7E.3).[8] To refine the MSA for inteins predicted to splice quickly, all sequences not containing K70, M75, M81, and S136 (the 'accelerator' residues) were removed from the alignment, leaving behind 73 inteins predicted to have fast splicing kinetics (7F.1 to 7F.3, 7G.1 to 7G.3, and 7H.1 to 7H.3). The consensus sequence of this refined alignment of fast inteins (Cfa) was calculated in Jalview by determining the amino acid that appeared most frequently at each position. A consensus residue was not identified at positions 98 and 102 due to lack of homology in the alignment, and thus the consensus sequence was truncated to 101 amino acids and position 98 was fixed to the residue found in Npu DnaE. This consensus sequence was then aligned with Npu DnaE in Jalview to calculate its percent identity. Non-identical residues were mapped onto the crystal structure of Npu DnaE (pdb=4K15) (FIG. 1).

FIGS. 7A.1 to 7A.3, 7B.1 to 7B.3, 7C.1 to 7C.3, 7D.1 to 7D.3, 7E.1 to 7E.3, 7F.1 to 7F.3, 7G.1 to 7G.3, and 7H.1 to 7H.3 show an alignment and refinement of the DnaE intein family. FIGS. 7A.1 to 7A.3, 7B.1 to 7B.3, 7C.1 to 7C.3, 7D.1 to 7D.3, and 7E.1 to 7E.3 show the multiple sequence alignment (MSA) of the 105 members of the DnaE intein family found from a BLAST search of the JGI and NCBI sequences databases. The locations of the 'accelerator' residues used to filter the alignment are indicated with black arrows. 7F.1 to 7F.3, 7G.1 to 7G.3, and 7H.1 to 7H.3 show MSA of the 73 DnaE inteins predicted to demonstrate fast splicing kinetics due to the presence of all four accelerator residues.

E. coli $Kan^R$ screen for Cfa extein dependency.

The protein splicing coupled kanamycin resistance ($Kan^R$) assay was carried out as previously described.[2,9] Briefly, a plasmid coding for a fragmented aminoglycoside phosphotransferase fused to a split intein (Cfa) with either F, G, R, or E present at the +2 position of the C-extein (plasmids 22-25) was transformed into DH5α competent cells and grown in starter cultures overnight (LB Broth, 100 µg/mL ampicillin, 18 hrs). These cultures were then diluted twenty-fold into a 96 well plate, and E. coli growth was measured at various concentrations of kanamycin (2.5, 10, 25, 50, 100, 250, 1000 µg/mL kanamycin with 100 µg/mL ampicillin). The cell optical density at 650 nm ($OD_{600}$) at the 24-hour end point was fit to a dose response curve with variable slope.

$$OD_{obs} = OD_{min} + \frac{(OD_{Max} - OD_{min})}{1 + 10^{[(logIC_{50} - lo\,[Kan])\cdot HillSlope]}}$$

Where $OD_{min}$ was fixed to background absorbance at 650 nm. Each assay was carried out in triplicate, fit separately, and ICs values are reported as the mean and standard deviation of $IC_{50}$ for these three separate measurements.

Protein Trans Splicing of Extracted Inclusion Body

E. coli inclusion bodies containing His-Sumo-$Cfa^N$ expression (plasmid 20) were resuspended and extracted overnight at 4° C. in lysis buffer containing 6M urea. Following centrifugation (35,000 ref, 30 min), the supernatant was removed and the protein enriched by Ni-NTA under denaturing conditions (as described above). However, instead of refolding the protein, trans-splicing was directly initiated by the addition of $Cfa^C$-CFN (10 µM $Cfa^C$, 2 mM TCEP, 2 mM EDTA, 2 hrs, RT). Reaction progress was monitored by SDS-PAGE.

αDec205-HC-$Int^N$ Test Expression and Splicing

Test Expression of HC-$Npu^N$, HC-$Mcht^N$, HC-$Ave^N$, HC-$Cfa^N$

Expression of all mAb constructs was carried out as previously described.[3] Briefly, plasmids encoding the αDec205-LC and the αDec205-HC-IntN were co-transfected into HEK293T cells and incubated for 96 hr (5% $CO_2$). The cells were spun down (5 minutes, 1,000 rcf), 15 µL of media for each intein fusion was mixed with 5 µL of 4× loading dye, and run on a 12% Bis-Tris gel in MES-SDS running buffer (170V for 50 minutes). The protein was then analyzed by western blot (transferred to a PVDF membrane, blotting against αMouse IgG). Expression yield was measured as the amount of HC-$Int^N$ in the media as determined by densitometry. To account for varying cell growth and survival, the yield was normalized using an α-actin blot of the HEK293T cell lysate (5 s sonication, 35% amplitude, in 1× loading dye) and then represented relative to the expression of HC-$Cfa^N$. Four replicates of this test expression were carried out, and the mean was calculated with error represented as the standard deviation.

Protein Trans-Splicing in Growth Media

Following the 96 hr expression at 37° C. of the mAB-$Ava^N$ and mAB-$Cfa^N$ constructs described above, the media was spun down (1,000 rcf, 5 minutes). The supernatant was then mixed with the $Cfa^C$-CFN peptide (semisynthesis of expressed plasmid 21) and incubated for 2 hours at room temperature (1 µM $Cfa^C$-CFN, 2 mM TCEP, 2 mM EDTA). The splicing reactions were analyzed by SDS-PAGE (12% Bis-Tris run in MES-SDS running buffer at 170V for 50 minutes) followed by western blot (αMouse IgG).

Peptide and Dendrimer Synthesis

Cys-Gly-Lys(Fluorescein). This peptide was synthesized by manual addition of reagents on the Rink Amide resin according to a previously published procedure.[2]

Supplemental Scheme 1

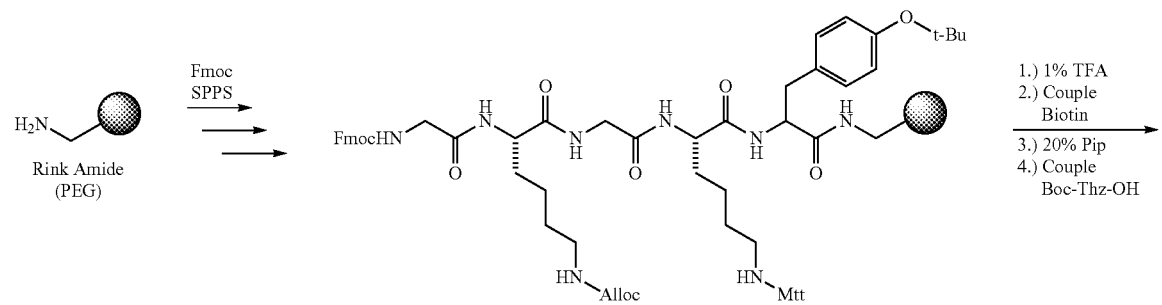

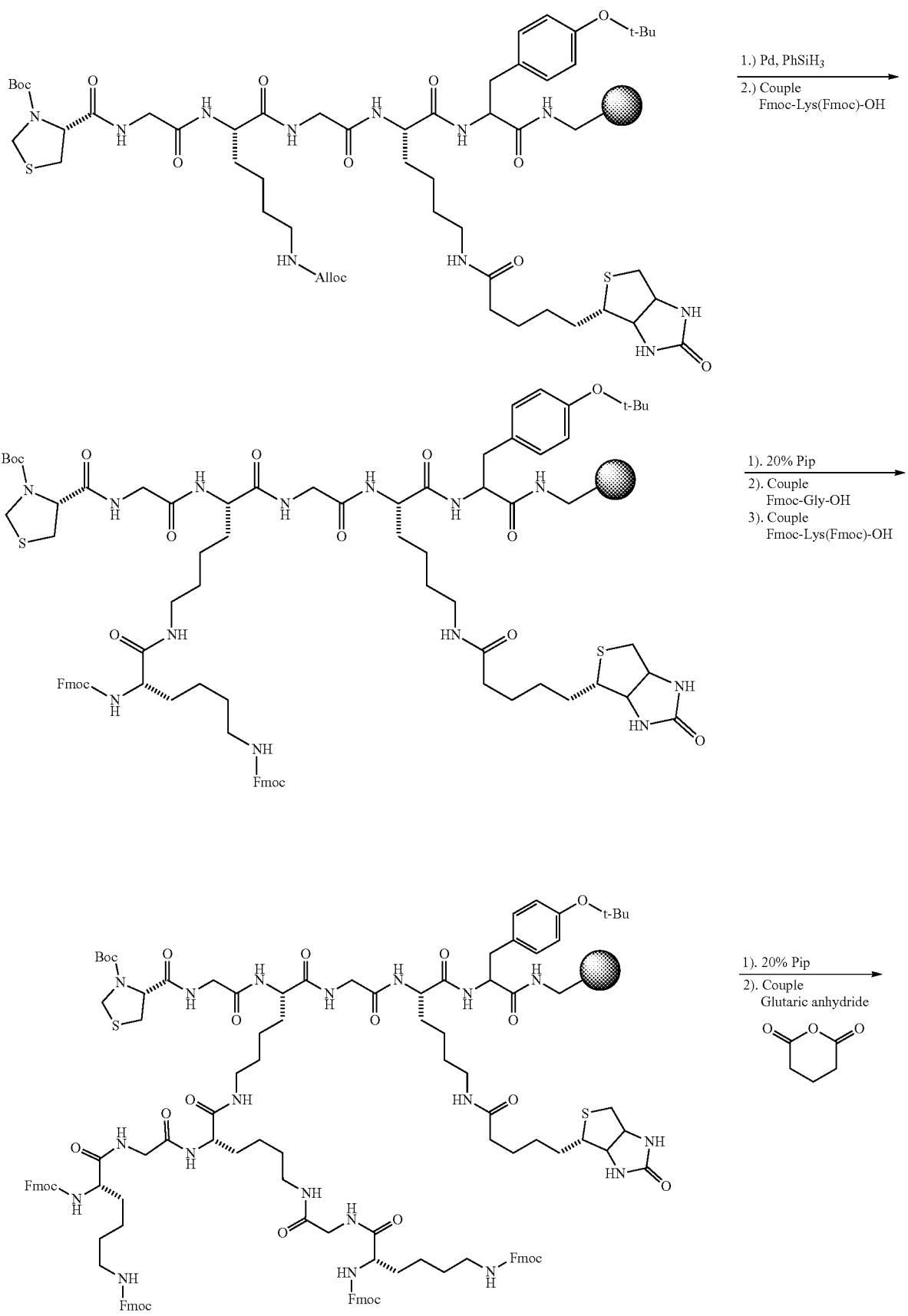

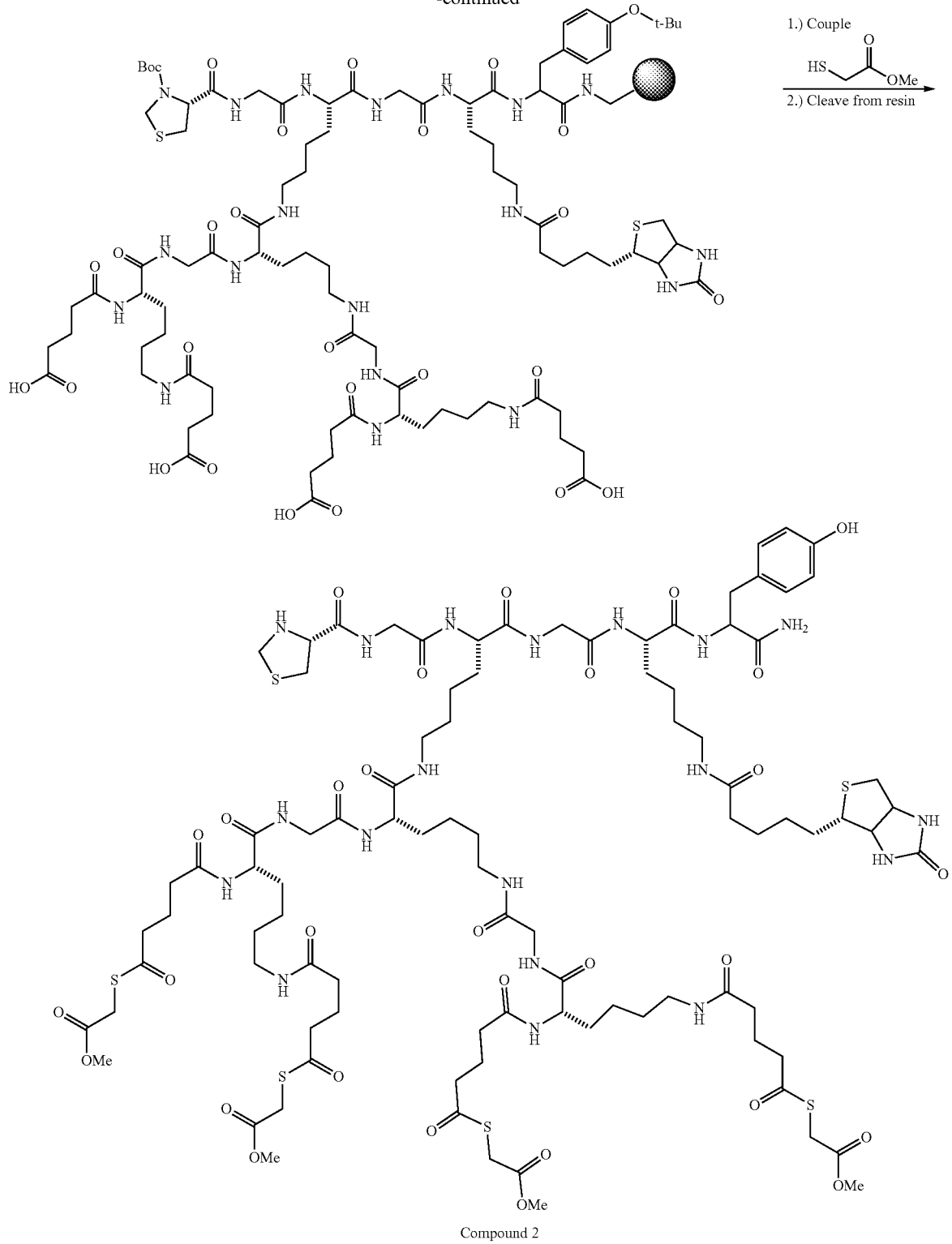

Compound 2

Compound 2 (dendrimer thioester). This compound was synthesized on the solid phase using the route outlined in Supplemental Scheme 1 on a scale of 400 mg of Rink Amide resin (substitution: 0.47 mmol/g, 188 μmol). General procedures are given first, followed by any specific methods for this peptide. The Fmoc group was removed with 3 mL of 20% piperidine in DMF and performed twice (one deprotection for 30 sec followed by an additional deprotection for 15 min). After each deprotection step, as well as all subsequent synthetic steps, flow washes were used (3×5 sec. with ~5 mL of DMF each). Coupling was performed using 4 eq. of monomer, 4 eq. of either HBTU and 8 eq. of DIPEA with no pre-activation unless otherwise stated. Double couplings were used for all residues to ensure complete acylation.

The Trityl protecting group was selectively removed using 1% TFA, 5% TIS in DCM using a total of 30 mL (10×3 mL) of deprotection cocktail. Thorough washing of the resin with DCM both during and after these cycles ensured the removal of any liberated Trityl species. The resin was also neutralized with 5% DIPEA in DMF before the next coupling was undertaken. The Alloc group was deprotected using 0.1 eq of tetrakis(triphenylphosphine) palladium(0), 20 eq of phenylsilane in DCM for 3×45 min each. Thorough washing of the resin with DCM during and after these cycles was used, as well as a 5% DIPEA in DMF wash before the next coupling. The glutaric anhydride monomer was used as a preactivated dicarboxylic acid to allow the formation of the thioesters (i.e. to have a free resin-bound carboxylic acid to functionalize). 20 eq of glutaric anhydride and 10 eq of DIPEA (relative to the number of amines to be acylated) was added to the resin and allowed to react for one hour. The resin was then washed and the coupling was repeated to ensure complete reaction of the resin bound primary amines. To form the resin bound thioesters, 30 eq of methyl thioglycolate, 5 eq of PyAOP and 10 eq of DIPEA (relative to the number of carboxylates) in DMF was added to the resin and allowed to react for one hour. The resin was washed with excess DMF and the coupling procedure was repeated an additional two times.

Cleavage was performed with 95% TFA, 2.5% TIS and 2.5% $H_2O$ for two hours at room temperature. The peptide was then precipitated with diethyl ether, dissolved in water with 0.1% TFA and analyzed via RP-HPLC. The crude material was purified via semi-preparative scale RP-HPLC, and the desired fractions were analyzed, pooled and lyophilized. RP-HPLC characterization: gradient 0-73% B, $t_r$=18.4 min. Expected Mass: 2198.86 Da. Found: 2198.82 Da.

Compound 3 (endrimer Fluorescein).

Compound 3 was synthesized by native chemical ligation (scheme 2). Compound 2 was dissolved in ligation buffer and mixed with five eq. of Cys-Gly-Lys(Fluorescein)(1 mM 2, 5 mM peptide, 4M Guanidine, 100 mM phosphate, 150 mM NaCl, 100 mM MPAA, 20 mM TCEP, pH 7.0) and allowed to react overnight at room temperature. Deprotection of the thiazolidine was then accomplished by the addition of 0.1M methoxyamine (final concentration) and decreasing the pH of the ligation buffer to 4.0 (overnight. RT).

When attempting to purify compound 3 by RP-HPLC, we noticed that it displayed poor solubility when acidified and diluted in water. However, Cys-Gly-Lys(Fluorescein), MPAA, and methoxyamine all remained in solution. From this observation, we purified 3 by selective precipitation following 10-fold dilution in water with 0.1% TFA. The precipitated powder was isolated by centrifugation (17,000 rcf, 5 min), and then redissolved (100 mM phosphate, 150 mM NaCl, pH 7.2) to wash away any remaining contaminants. Once again, the solution was precipitated by acidification and isolated by centrifugation (17.000 rcf, 5 min). This isolated powder was then lyophilized. Expected mass: 4417.8 Da. Found: 4417.5 Da.

Supplemental Scheme 2. Native chemical ligation was used to elaborate tetrathioester-containing compound 2 with a fluorescent tripeptide. Subsequent deprotection using methoxylamine was used to expose the N-terminal cysteine for further ligations yielded tetra-functionalized dendrimer, compound 3.

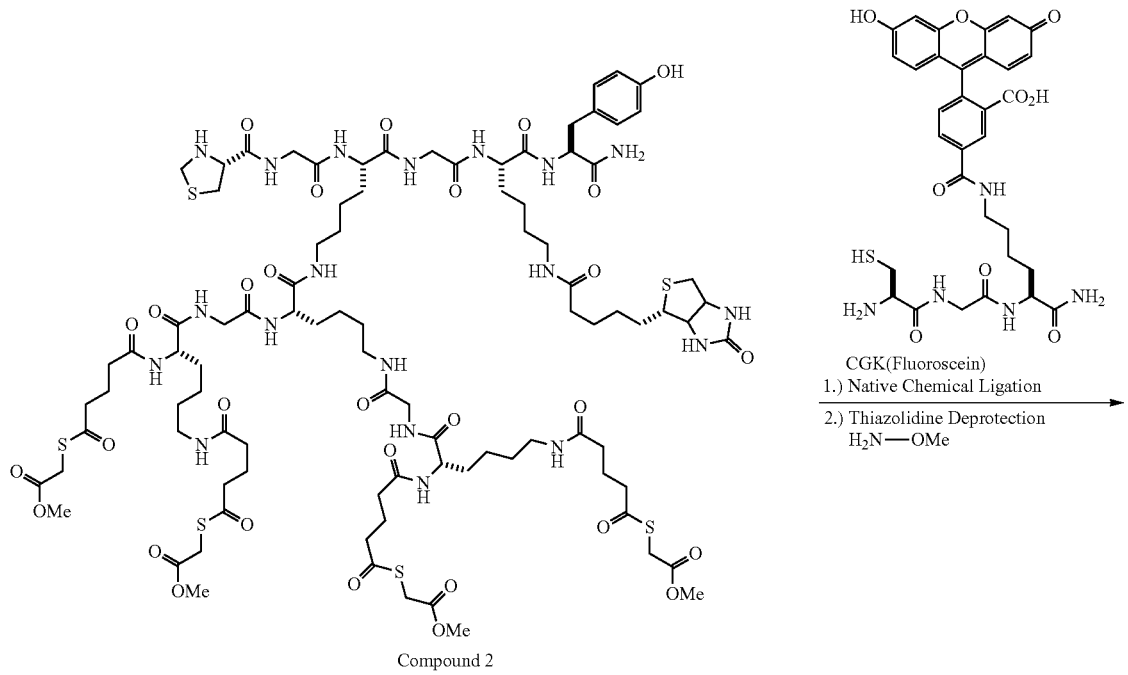

-continued

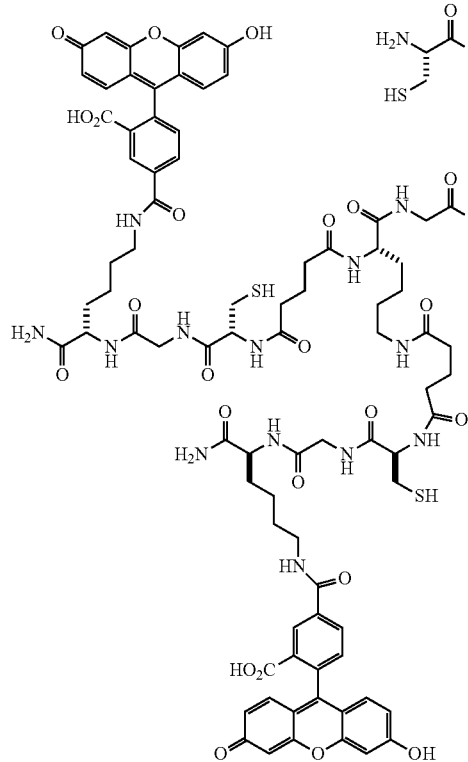
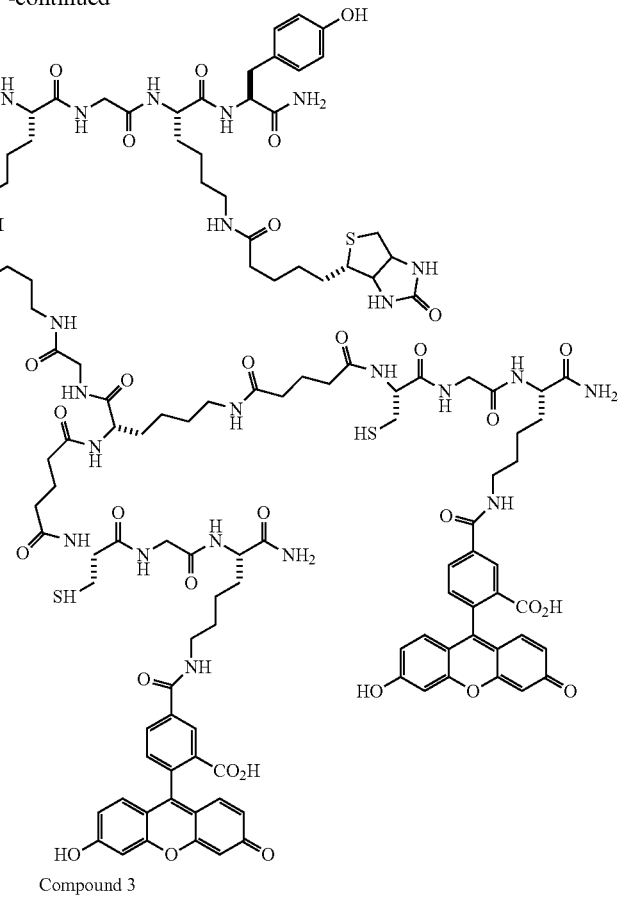

Compound 3

Compound 1: (Cfa$^C$-Dendrimer)

Compound 1 was synthesized by expressed protein ligation. Compound 3 was dissolved in ligation buffer and mixed with 1.5 eq of the Cfa$^C$-MESNa thioester (100 μM 3, 150 μM Cfa$^C$-MESNa, 4M Guanidine, 100 mM phosphate, 150 mM NaCl, 20 mM TCEP, 100 mM MPAA). The reaction was allowed to proceed overnight at room temperature. The ligated product was then purified by semi-preparative RP-HPLC. Desired fractions were pooled and lyophilized. Expected mass: 9860.8 Da. Found: 9860.3 Da.

Protein Trans-Splicing of dendrimer with αDec205 mAb.

The αDec205 mAb with Cfa$^N$ fused to its C-terminus was expressed as described above. Following the 96 hr expression, the media was concentrated 10-fold in an Amicon 30K concentrator (0.5 mL). Compound 1 was dissolved in splicing buffer (100 mM phosphate, 150 mM NaCl, 1 mM EDTA, pH 7.2) and then mixed with the concentrated media (2 μM compound 1, 2 mM TCEP, 1 mM EDTA) and the reaction allowed to proceed for 2 hrs at room temperature. The splicing mixture was then analyzed by SDS-PAGE (12% Bis-Tris run in MES-SDS running buffer at 170V for 50 minutes) and imaged on a fluorescence imager. This was followed by transfer to a PVDF membrane and western blot analysis (αMouse IgG).

Figure 11:
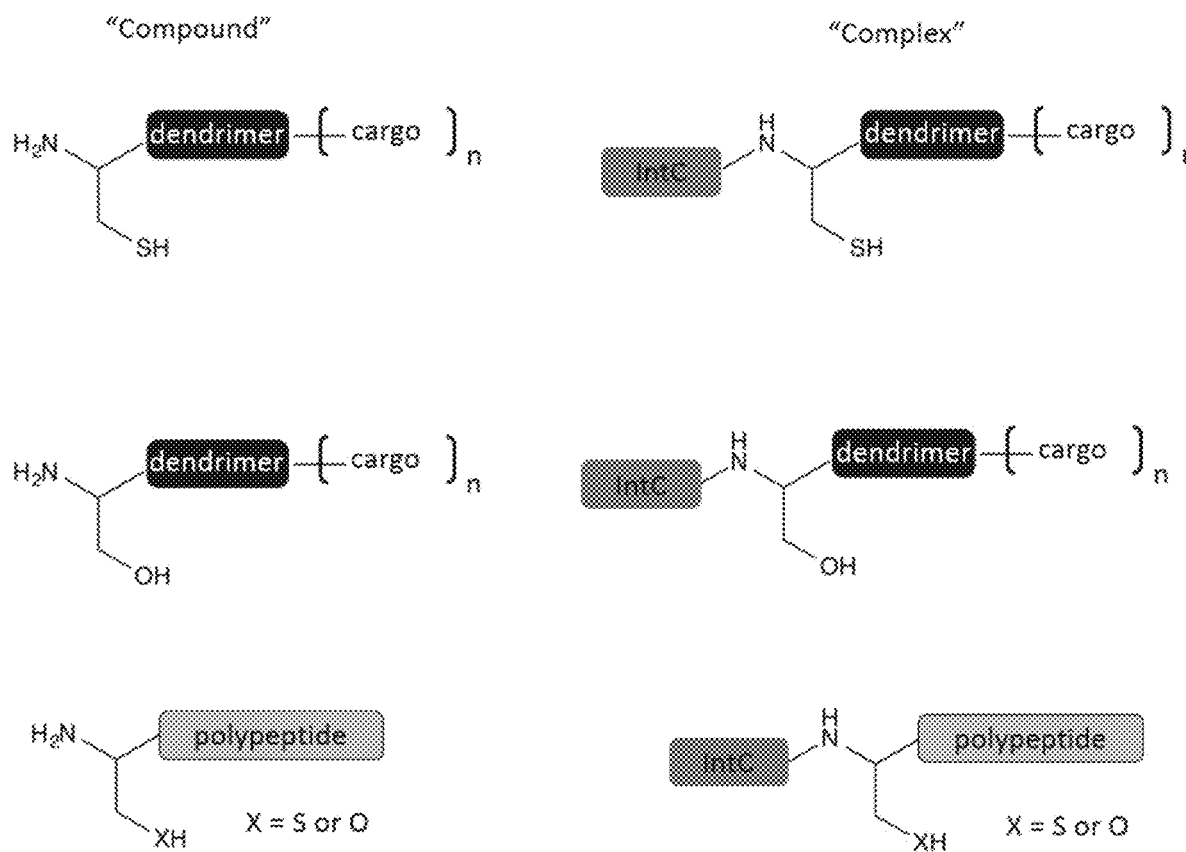
FIG. 11 shows a table illustrating several complexes and compounds according to an embodiment of the invention.

The invention allows for the formation of various complexes between a split intein fragment and a compound. Several such complexes and compounds are illustrated in the table of FIG. 11. IntC is a split intein fragment, for example, a split intein C-fragment. For example, the dendrimer can have the form of Compound 2, Compound 3, or portions of these. For example, the cargo can be a dye (e.g., fluorescein), another marker molecule, a drug (e.g., a cytotoxic molecule, such as used in the treatment of cancer), or a nucleotide. For example, the polypeptide can be a wholly or partially synthetic or a naturally occurring polypeptide or portion thereof. A dendrimer can be a molecule having a branched chemical structure onto which one or more "cargo" molecules can be "loaded". A "cargo" molecule can be a synthetic of naturally occurring molecule. The cargo molecule can be structured to have no free 1,2-amino thiols or 1,2-amino alcohols. When the intein is bonded through an amino thiol or amino alcohol to a polypeptide, as shown in row 3 of the table of FIG. 11, the complex formed can be considered to be a recombinant fusion protein.

Example 2

A major caveat to splicing-based methods is that all characterized inteins exhibit a sequence preference at extein residues adjacent to the splice site. In addition to a mandatory catalytic Cys, Ser, or Thr residue at position +1 (i.e., the first residue within the C-extein), there is a bias for residues resembling the proximal N- and C-extein sequence found in the native insertion site. Deviation from this preferred sequence context leads to a marked reduction in splicing activity, limiting the applicability of PTS-based methods.[23, 24] Accordingly, there is a need for split inteins whose activities are minimally affected by local sequence environment. For DnaE inteins, extein sequence preferences are largely confined to the catalytic cysteine at the +1 position and large hydrophobic residues that are preferred at the +2 position.[25]

Figure 9:
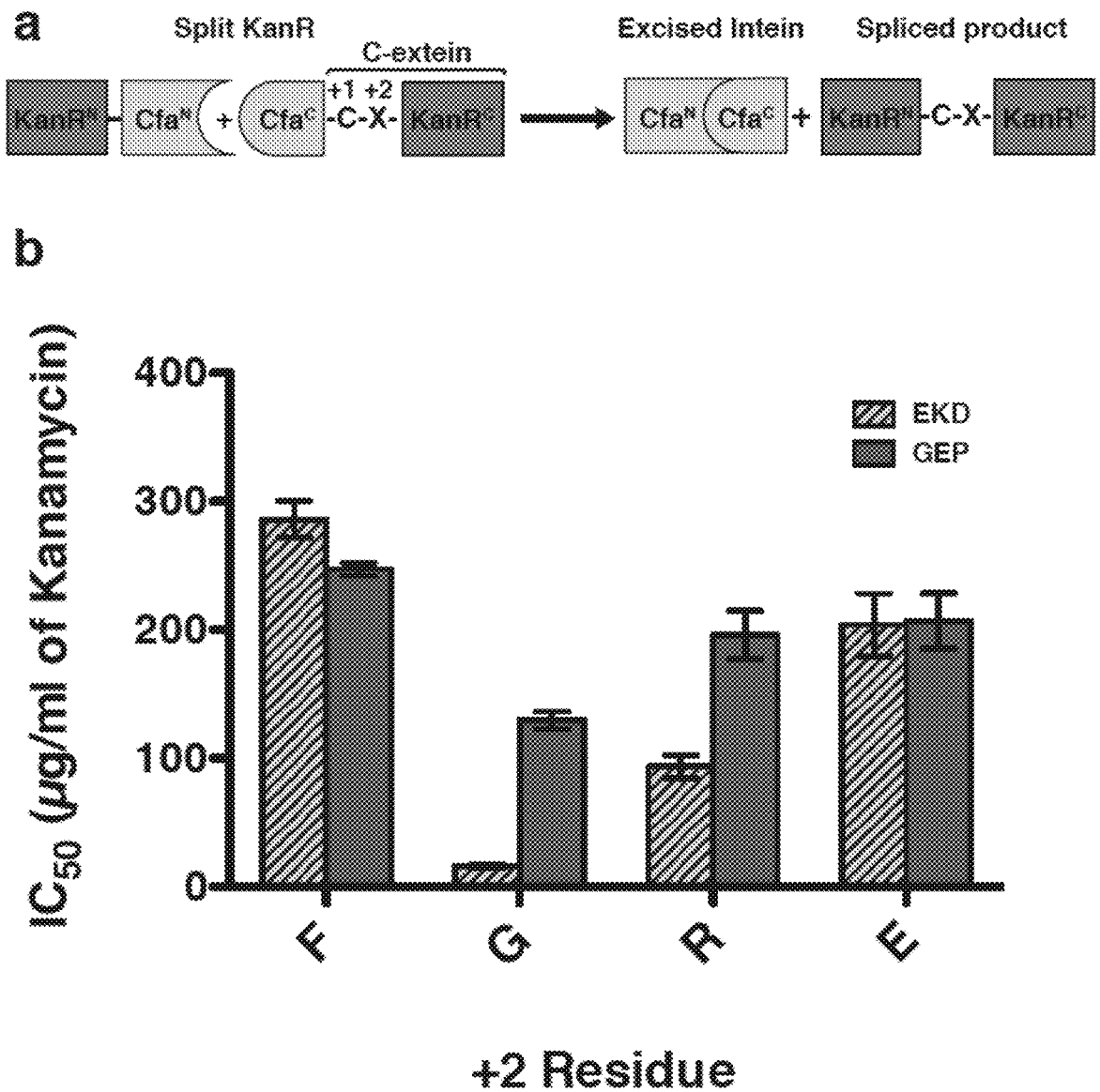
FIG. 9 shows a schematic and graph showing increased promiscuity of Cfa$_{GEP}$ according to an embodiment of the invention.

In this example, a "EKD" to "GEP" loop mutation into residues 122-124 of Cfa (Cfa$_{GEP}$) was engineered and resulted in increased promiscuity at the +2 position of the C-extein in a kanamycin resistance assay (FIG. 9). The EKD→EP mutation increases the activity of Cfa under a wide range of extein contexts. In addition, it can be reasonably expected that these same (or similar) mutations will increase promiscuity among other members of the DnaE intein family (including Npu and those listed in FIGS. 7A.1 to 7A.3, 7B.1 to 7B.3, 7C.1 to 7C.3, 7D.1 to 7D.3, 7E.1 to 7E.3, 7F.1 to 7F.3, 7G.1 to 7G.3, and 7H.1 to 7H.3).

The following sequences represent the engineered inteins:

The Cfa C-intein with the "GEP" mutation that imparts more "promiscuous" activity according to an embodiment of the invention is:

(SEQ ID NO: 389)
VKIISRKSLGTQNVYDIGVGEPHNFLLKNGLVASN.

An example of a fusion intein of the Cfa N-intein and Cfa C-intein with the "GEP" mutation of SEQ ID: 389) is:

(SEQ ID NO: 390)
CLSYDTEILTVEYGFLPIGKIVEERIECTVYTVDKNGFVYTQPIAQWHN

RGEQEVFEYCLEDGSIIRATKDHKFMTTDGQMLPIDEIFERGLDLKQVD

GLPVKIISRKSLGTQNVYDIGVGEPHNFLLKNGLVASN.

FIG. 9 shows a schematic and a table showing the increased promiscuity of Cfa$_{CEP}$. Panel A shows a schematic depicting the PTS-dependent *E. coli* selection system with the Cfa split intein. The kanamycin resistance protein, KanR, is split and fused to N- and C-intein fragments (Cfa$^N$ and Cfa$^C$). The +2 C-extein residue (red X) is varied in the system. In Panel B, IC$_{50}$ values for kanamycin resistance of the Cfa$_{EKD}$ (WT) and Cfa$_{GEP}$ (GEP) inteins with indicated +2 C-extein residue are shown (error=standard error (n=3)).

Figure 10:
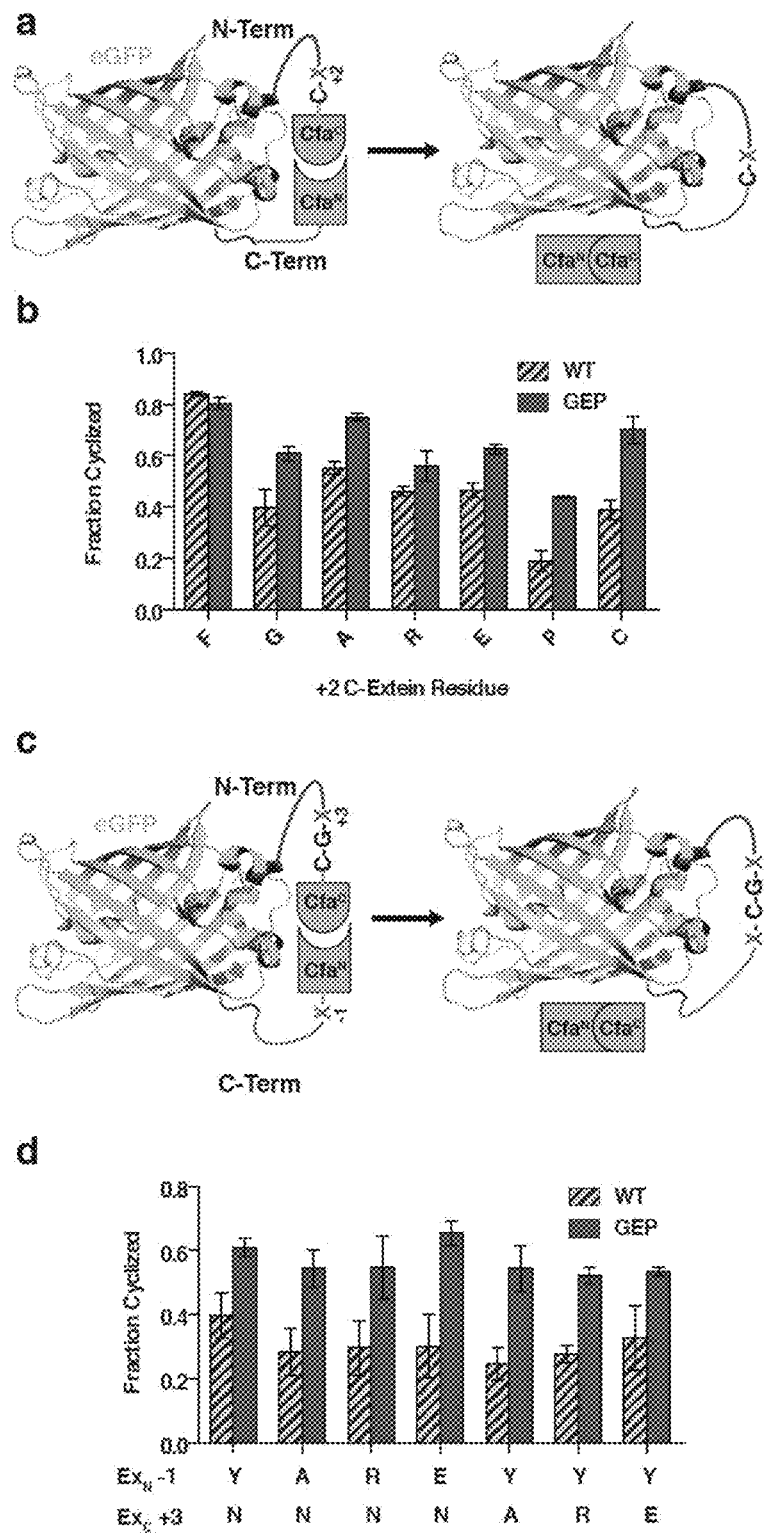
FIG. 10 shows graphs and schematics showing cyclization of eGFP in E. coli with variable residues according to an embodiment of the invention.

Furthermore, this same tolerance for varying extein sequences was also observed in the cyclization of eGFP in *E. coli* (FIG. 10). The Cfa$_{GEP}$ intein demonstrated improved yields of cyclized product in all unfavorable +2 C-extein contexts tested (FIG. 10 panel A, FIG. 10 panel B). In addition, Cfa$_{GEP}$ maintains this improved cyclization activity even when the −1 and +3 extein positions are varied (FIG. 10 panel C, FIG. 10 panel D). This engineered "GEP" loop sequence, which has not been identified in a wild type naturally split DnaE intein, should thus expand the breadth of proteins and peptides accessible to PTS-based technologies.

FIG. 10 shows schematics and graphs showing eGFP Cyclization with the Cfa$_{GEP}$ split intein. Panel A is a schematic depicting cyclization of eGFP in *E. coli* with variable residues at the +2 C-extein position (red X). In panel B, the fraction of cyclized eGFP formed after overnight expression in *E. coli* for Cfa$_{EKD}$ (WT) and Cfa$_{GEP}$ (GEP) with the indicated +2 C-extein residue is shown (mean±standard deviation, n=3). Panel C is a schematic depicting the cyclization of eGFP in *E. coli* with variable residues at the +3 C-extein position (blue X) and −1 N-extein position (red X). Panel D shows a fraction of cyclized eGFP formed after overnight expression in *E. coli* for Cfa$_{EKD}$ (WT) and Cfa$_{GEP}$ (GEP) with the indicated +3 C-extein and −1 N-extein residues (mean±standard deviation, n=3).

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES (1) Shah, N. H., Muir, T. W. *Chem. Sci.* 2014, 5, 15.

(2) Wu, H.; Hu, Z.; Liu, X. Q. *Proc. Natl. Acad Sci. U.S.A.* 1998, 95, 9226.

(3) Iwai, H.; Zuger, S.; Jin, J.; Tam, P. H. *FEBS Lett.* 2006, 580, 1853.

(4) Zettler, J.; Schutz, V.; Mootz, H. D. *FEBS Lett.* 2009, 583, 909.

(5) Shah, N. H.; Eryilmaz, E.; Cowburn, D.; Muir, T. W. *J. Am. Chem. Soc.* 2013, 135, 5839.

(6) Shah, N. H.; Dann, G. P.; Vila-Perello, M.; Liu, Z.; Muir, T. W. *J. Am. Chem. Soc.* 2012, 134, 11338.

(7) Carvajal-Vallejos, P.; Pallisse, R.; Mootz, H. D., Schmidt, S. R. *J. Biol. Chem* 2012, 287, 28686.

(8) Wu. Q.; Gao, Z.; Wei, Y.; Ma. G.; Zheng, Y.; Dong, Y.; Liu, Y. *Biochem. J.* 2014, 461, 247.

(9) Aranko, A. S.; Oeemig, J. S.; Kajander, T.; Iwai, H. *Nat. Chem. Biol.* 2013, 9, 616.

(10) Pietrokovski, S. *Protein Sci.* 1994, 3, 2340.

(11) Dearden, A. K.; Callahan, B.; Roey, P. V.; Li, Z.; Kumar, U.; Belfort, M.; Nayak, S. K. *Protein Sci.* 2013, 22, 557.

(12) Du, Z.; Shemella, P. T.; Liu, Y.; McCallum, S. A.; Pereira, B.; Nayak, S. K.; Belfort, G.; Belfort, M.; Wang, C. *J. Am. Chem. Soc.* 2009, 131, 11581.

(13) Lehmann, M.; Kostrewa, D.; Wyss, M.; Brugger, R.; D'Arcy, A.; Pasamontes, L.; van Loon, A. P. *Protein Eng.* 2000, 13, 49.

(14) Steipe, B. *Methods Enymol.* 2004, 388, 176.

(15) Altschul, S. F.; Gish, W.; Miller, W.; Myers, E. W.; Lipman, D. J. *J. Mol. Biol.* 1990, 215, 403.

(16) Grigoriev, I. V.; Nordberg, H.; Shabalov, I.; Aerts, A.; Cantor, M.; Goodstein, D.; Kuo, A.; Minovitsky, S.; Nikitin, R.; Ohm, R. A.; Otillar, R.; Poliakov, A.; Ratnere, I; Riley, R.; Smimova, T.; Rokhsar, D.; Dubchak, I. *Nucleic Acid Res.* 2012, 40, D26.

(17) Tatusova, T.; Ciufo, S.; Fedorov, B.; O'Neill, K.; Tolstoy, I. *Nucleic Acids Res.* 2014, 42, D553.

(18) Shah, N. H.; Eryilmaz, E.; Cowburn, D.; Muir, T. W. *J. Am. Chem. Soc.* 2013, 135, 18673.

(19) Mohlmann, S.; Bringmann, P.; Greven, S.; Harrenga, A. *BMC Biotechnol.* 2011, 11, 76.

(20) Barbuto, S.; Idoyaga, J.; Vila-Perello, M., Longhi, M. P.; Breton, G.; Steinman, R. M.; Muir, T. W. *Nat. Chem. Biol.* 2013, 9, 250.
(21) Vila-Perello, M.; Liu, Z.; Shah, N. H.; Willis, J. A.; Idoyaga, J.; Muir, T. W. *J. Am. Chem. Soc.* 2013, 135, 286.
(22) Shah, N. D.; Parekh, H. S.; Steptoe, R. J. *Pharm. Res.* 2014, 31, 3150.
(23) Iwai, H.; Zuger, S.; Jin, J.; Tam, P. H. *FEBS Lett.* 2006, 580, 1853.
(24) Amitai, G.; Callahan, B. P.; Stanger, M. J.; Belfort, G.; Belfort, M. *Proc Nat Acad Sci USA* 2009, 106, 11005.
(25) Cheriyan, M.; Pedamallu, C. S.; Tori, K.; Perler, F. *J Biol Chem* 2013, 288, 6202.

What is claimed is:

1. A split intein N-fragment comprising an amino acid sequence having from 95% to less than 98% sequence identity to (SEQ ID NO: 1)
CLSYDTEILTVEYGFLPIGKIVEERIECTVYTVDKNGFVYTQPIAQWHN

RGEQEVFEYCLEDGSIIRATKDHKFMTTDGQMLPIDEIFERGL or to (SEQ ID NO: 2)
CLSYDTEILTVEYGFLPIGKIVEERIECTVYTVDKNGFVYTQPIAQWHN

RGEQEVFEYCLEDGSIIRATKDHKFMTTDGQMLPIDEIFERGLDLKQVD

GLP, wherein:
said split intein N-fragment is able to form a split intein intermediate with a split intein C-fragment comprising the amino acid sequence of SEQ ID NO: 3 or SEQ ID NO: 4.

2. A complex comprising the split intein N-fragment of claim 1 and a compound.

3. The complex of claim 2, wherein the compound is selected from the group consisting of:
  (i) a peptide or a polypeptide,
  (ii) an antibody chain,
  (iii) an antibody heavy chain, and
  (iv) a compound comprising a peptide, an oligonucleotide, a drug or a cytotoxic molecule.

4. A split intein C-fragment comprising an amino acid sequence having from 95% to less than 98% sequence identity to (SEQ ID NO: 3)
VKIISRKSLGTQNVYDIGVEKDHNFLLKNGLVASN or to (SEQ ID NO: 4)
MVKIISRKSLGTQNVYDIGVEKDHNFLLKNGLVASN;

wherein said split intein C-fragment is able to form a split intein intermediate with a split intein N-fragment comprising the amino acid sequence of SEQ ID NO: 1 or SEQ ID NO: 2.

5. A complex comprising the split intein C-fragment of claim 4 and a compound.

6. The complex of claim 5, wherein the compound is selected from the group consisting of:
(i) a peptide or a polypeptide,
(ii) a compound comprising a peptide, an oligonucleotide, a drug, or a cytotoxic molecule,
(iii) a 1,2-amino thiol bonded to a peptide, an oligonucleotide, a drug, or a cytotoxic molecule,
(iv) a 1,2-amino alcohol bonded to a peptide, an oligonucleotide, a drug, or a cytotoxic molecule and
(v) a dendrimer.

7. The complex of claim 5, wherein the compound is a dendrimer having the structure

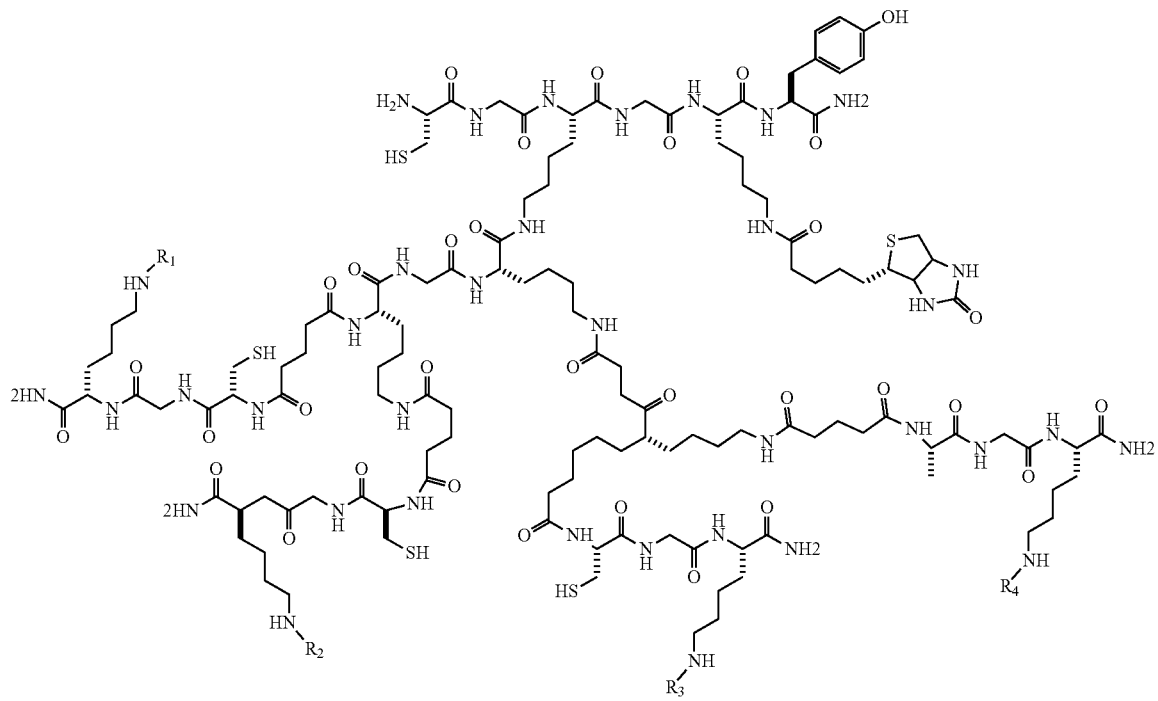

wherein R1, R2, R3, and R4 are independently selected from the group consisting of hydrogen (H) and cargo molecules.

8. The complex of claim 7, wherein R1, R2, R3, and R4 are each a dye molecule or wherein R1, R2, R3, and R4 are each a fluorescein derivative having the structure

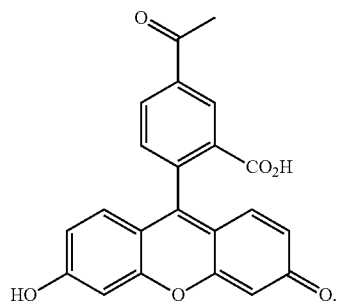 [SMILES: CC(=O)c1ccc(-c2c3ccc(=O)cc-3oc3cc(O)ccc23)c(C(=O)O)c1]

9. A complex selected from the group consisting of:
(i) a complex of the structure

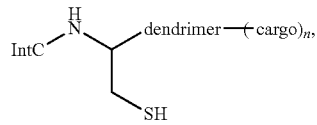

wherein IntC is the split intein C-fragment of claim 4 and
wherein n is from 0 to 8;
(ii) a complex of the structure

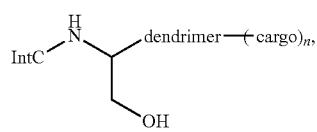

wherein IntC is the split intein C-fragment of claim 4 and
wherein n is from 0 to 8; and
(iii) a complex of the structure

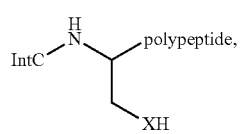

wherein IntC is the split intein C-fragment of claim 4 and wherein X is sulfur (S) or oxygen (O).

10. A composition comprising:

a split intein N-fragment comprising an amino acid sequence having from 95% to less than 98% sequence identity to SEQ ID NO: 1 or SEQ ID NO: 2, wherein said split intein N-fragment is able to form a split intein intermediate with a split intein C-fragment comprising the amino acid sequence of SEQ ID NO: 3 or SEQ ID NO: 4; and the split intein C-fragment of claim 4.

11. A nucleotide plasmid comprising a nucleotide sequence encoding the split intein N-fragment of claim 1.

12. A nucleotide plasmid comprising a nucleotide sequence encoding the split intein C-fragment of claim 4.

13. A method for splicing two complexes comprising:

contacting:

a first complex comprising a first compound and a split intein N-fragment comprising an amino acid sequence having from 95% to less than 98% sequence identity to SEQ ID NO: 1 or SEQ ID NO: 2, wherein said split intein N-fragment is able to form a split intein intermediate with a split intein C-fragment comprising the amino acid sequence of SEQ ID NO: 3 or SEQ ID NO: 4; and a second complex comprising a second compound and the split intein C-fragment of claim 4, wherein the contacting is performed under conditions that permit binding of the split intein N-fragment to the split intein C-fragment to form an intein intermediate; and reacting the intein intermediate to form a conjugate of the first compound with the second compound.

14. A method comprising:

contacting:

a first complex comprising a first compound and a split intein N-fragment comprising an amino acid sequence having from 95% to less than 98% sequence identity to SEQ ID NO: 1 or SEQ ID NO: 2, wherein said split intein N-fragment is able to form a split intein intermediate with a split intein C-fragment comprising the amino acid sequence of SEQ ID NO: 3 or SEQ ID NO: 4; and a second complex comprising a second compound and the split intein C-fragment of claim 4, wherein the contacting is performed under conditions that permit binding of the split intein N-fragment to the split intein C-fragment to form an intein intermediate; and reacting the intein intermediate with a nucleophile to form a conjugate of the first compound with the nucleophile.

15. A method comprising:

fusing:

a first nucleotide sequence encoding an amino acid sequence of a split intein N-fragment comprising an amino acid sequence having from 95% to less than 98% sequence identity to SEQ ID NO: 1 or SEQ ID NO: 2, wherein said split intein N-fragment is able to form a split intein intermediate with a split intein C-fragment comprising the amino acid sequence of SEQ ID NO: 3 or SEQ ID NO: 4; with a second nucleotide sequence encoding an amino acid sequence of the split intein C-fragment of claim 4, so that the fusion of the first nucleotide sequence and the second nucleotide sequence encodes for a contiguous intein.

16. The method of claim 13, wherein the first compound is a polypeptide or an antibody and/or wherein the second compound is a dendrimer or a polypeptide.

17. A kit for splicing two complexes together comprising:

a split intein N-fragment comprising an amino acid sequence having from 95% to less than 98% sequence identity to SEQ ID NO: 1 or SEQ ID NO: 2, wherein said split intein N-fragment is able to form a split intein intermediate with a split intein C-fragment comprising the amino acid sequence of SEQ ID NO: 3 or SEQ ID NO: 4;

the split intein C-fragment of claim 4;

a reagent for binding the split intein N-fragment to the split intein C-fragment to form an intein intermediate; and a nucleophilic agent.

18. A gene fusion comprising:

a first nucleotide sequence encoding an amino acid sequence of a split intein N-fragment comprising an amino acid sequence having from 95% to less than 98% sequence identity to SEQ ID NO: 1 or SEQ ID NO: 2, wherein said split intein N-fragment is able to form a split intein intermediate with a split intein C-fragment comprising the amino acid sequence of SEQ ID NO: 3 or SEQ ID NO: 4, fused with a second nucleotide sequence encoding an amino acid sequence of the split intein C-fragment of claim 4.

19. A polynucleotide encoding the split intein N-fragment of claim 1.

20. A polynucleotide encoding the split intein C-fragment of claim 4.

21. The split intein N-fragment according to claim 1, wherein the amino acid sequence comprises conservative amino acid substitutions.

22. A split intein C-fragment comprising an amino acid sequence having from 95% to less than 98% sequence identity to (SEQ ID NO: 389)
VKIISRKSLGTQNVYDIGVEKDHNFLLKNGLVASN, wherein the residues GEP are conserved, and wherein said split intein C-fragment is able to form a split intein intermediate with a split intein N-fragment comprising the amino acid sequence of SEQ ID NO: 1 or SEQ ID NO: 2.

23. The split intein C-fragment according to claim 22, wherein the amino acid sequence comprises conservative amino acid substitutions.

* * * * *